US012466883B1

(12) United States Patent
Roberts et al.

(10) Patent No.: US 12,466,883 B1
(45) Date of Patent: Nov. 11, 2025

(54) LEPTIN COMPOSITIONS AND METHODS OF MAKING AND USING THE SAME TO SUPPORT WEIGHT LOSS AND/OR MAINTENANCE

(71) Applicant: Lumen Bioscience, Inc., Seattle, WA (US)

(72) Inventors: James Michael Roberts, Seattle, WA (US); Mesfin Mulugeta Gewe, Bothell, WA (US); Uland Lau, Redmond, WA (US); Mark Heinnickel, Seattle, WA (US); Michael Dodds, Normandy Park, WA (US); David Bolick, Whitewater, CO (US); Nhi Yen Khuong, Kenmore, WA (US); Hannah Tabakh, Seattle, WA (US); Brian Finrow, Seattle, WA (US); Jennifer Lynn Wierman, Ithaca, NY (US)

(73) Assignee: LUMEN BIOSCIENCE, INC., Seattle, WA (US)

( * ) Notice: Subject to any disclaimer, the term of this patent is extended or adjusted under 35 U.S.C. 154(b) by 0 days.

(21) Appl. No.: 19/207,094

(22) Filed: May 13, 2025

Related U.S. Application Data

(60) Provisional application No. 63/646,354, filed on May 13, 2024.

(51) Int. Cl.

| | |
|---|---|
| ***C07K 16/26*** | (2006.01) |
| ***A61K 9/00*** | (2006.01) |
| ***A61P 3/04*** | (2006.01) |
| *A61K 38/00* | (2006.01) |

(52) U.S. Cl.
CPC ............ *C07K 16/26* (2013.01); *A61K 9/0053* (2013.01); *A61P 3/04* (2018.01); *A61K 38/00* (2013.01)

(58) Field of Classification Search
CPC .......... C07K 16/26; A61P 3/04; A61K 9/0053
See application file for complete search history.

(56) References Cited

U.S. PATENT DOCUMENTS

| | | | |
|---|---|---|---|
| 5,831,017 A * | 11/1998 | Hoffmann | C07K 14/5759 530/324 |
| 10,131,870 B2 | 11/2018 | Takeuchi et al. | |
| 10,336,982 B2 | 7/2019 | Takeuchi et al. | |
| 10,415,012 B2 | 9/2019 | Takeuchi et al. | |
| 10,415,013 B2 | 9/2019 | Takeuchi et al. | |
| 2021/0213124 A1 | 7/2021 | Roberts et al. | |
| 2021/0338751 A1 | 11/2021 | Roberts et al. | |
| 2024/0002481 A1 | 1/2024 | Roberts | |

FOREIGN PATENT DOCUMENTS

| | | | |
|---|---|---|---|
| EP | 849276 A1 * | 6/1998 | C07K 14/575 |
| WO | WO-0113935 A2 * | 3/2001 | A61K 31/517 |
| WO | WO-2012050930 A2 * | 4/2012 | A61P 3/06 |

OTHER PUBLICATIONS

Bendayan & Cammissotto, "Control of Food Intake and Body Weight Through Oral Administration of Leptin," J. Endocrinology and Diabetes 3(3):1049, pp. 1-6 (2016).

Bendayan & Cammissotto, "Control of Food Intake by Oral Administration of Leptin to Dogs," J. Endocrinology and Diabetes 3(3):1050, pp. 1-4 (2016).

Berger et al., "Intranasal leptin relieves sleep-disordered breathing in mice with diet-induced obesity," Am J Respir Crit Care Med, Issue 6:773-783 (Mar. 15, 2019).

Courbage, Sophie, et al. "Implication of heterozygous variants in genes of the leptin-melanocortin pathway in severe obesity." The Journal of Clinical Endocrinology & Metabolism 106(10)2991-3006. (Sep. 27, 2021).

FDA Label for Myalept®, Reference ID: 3534419 (Approval 2014), 56 pages, https://www.accessdata.fda.gov/drugsatfda_docs/label/2014/125390s004lbl.pdf.

Flier and Ahima, Leptin physiology and pathophysiology: knowns and unknowns 30 years after its discovery, J Clin Invest. 2024;134(1):el 74595, pp. 1-3 ( Jan. 2024).

Hebebrand et al., "The role of leptin in rodent and human sleep: a transdiagnostic approach with a particular locus on anorexia nervosa," Neuroscience and Biobehavioral Reviews 149:105164, pp. 1-13 ( Epub Apr. 7, 2023).

Hernandez-Lepe et al., Hypolipidemic effect of Arthrospira (Spirulina) maxima supplementation and a systematic physical exercise program in overweight and obese men: a double-blind, randomized, and crossover controlled trial, Marine Drugs, 17:270, 13 pages. (May 7, 2019).

Ip, M. and Mokhlesi, B., "Activating leptin receptors in the central nervous system using intranasal leptin," American Journal of Respiratory and Critical Care Medicine, vol. 199, No. 6, pp. 689-690 (2019).

Jester et al., "Development of Spirulina for the manufacture and oral delivery of protein therapeutics," Nature Biotechnology, vol. 40: 956-964 (Jun. 2022). Epub (Mar. 22, 2022).

Masuda et al., "Multiple micronutrient supplementation using Spirulina platensis during the first 1000 days is positively associated with development in children under five years: a follow up of a randomized trial in Zambia," Nutrients, 11(4):730 (Mar. 29, 2019), 10 pages.

(Continued)

*Primary Examiner* — Amber D Steele
(74) *Attorney, Agent, or Firm* — COOLEY LLP

(57) ABSTRACT

Provided are compositions comprising leptin and methods of using the same to support weight loss. Also provided are modified leptins, including recombinant leptins, and methods of making and using the same.

29 Claims, 50 Drawing Sheets

Specification includes a Sequence Listing.

(56) References Cited

OTHER PUBLICATIONS

Moradi et al., “Effects of Spirulina supplementation on obesity: a systematic review and meta-analysis of randomized clinical trials,” Complement TherMed, 47:102211, 7 pages (Oct. 2019).
Obradovic et al., “Leptin and Obesity: Role and Clinical Implication,” Frontiers in Endocrinology, vol. 12, Article 585887, 14 pages. (May 18, 2021).
Oramed Press Release, Dec. 23, 2020, “Oramed Reports Positive First in Human Data from Oral Leptin Study,” 3 pages. Retrieved online at https://www.prnewswire.com/news-releases/oramed-reports-positive-first-in-human-data-from-oral-leptin-study-301198022.html.
Schulz et al. “Intranasal leptin reduces appetite and induces weight loss in rats with diet-induced obesity (DIO),” Endocrinology 153(1): 143-153 (2012).

* cited by examiner

FIG. 6A

pCPC600
MBP
G4S-K-G4S
Human leptin 22-167AA V94M
6xHis

SEQ ID NO: 88

SEQ ID NO: 89

FIG. 6B

SEQ ID NO: 1

GTGTTGGGGCTGACTTTTGCTGCCTTGTTGGGGGGGGCGATTTTAACTGAGGTCACTTTTTCTTGGCCGGGATTGGCTAA
TCGCTTGTATGAGGCTATCCGTCTGCGGGATTATCCCACGGTTCAAGGGGTGGTGGTATTTTTGGCCGTTATTGTGGTGG
CGGCTAGTTTGGCGATCGATATTTTGAATGCTTGTATTGACCCACGGATTCGCTATTAATTCCCTGTCAGAAAATATACT
TAGTTATTAATACTTAGTTATTTTTCTTAATAAATTTTAACAAACCAAAGGGCGTTGGCAGTGTATAAAGGATATTTGAA
GGGGTGAGAAGGAAGGCGAATGTTGATTTATGAAGTTTGATTAACATTTGTATCAAAATATAAAATTCTTCTCATAAACC
CTGTACAATCTTTTAAGATTTCGGAAAGTGTTCTAGGATACTGAAGAAATGAACCACGGGGCAATTGTTAAAAGCCTTTG
TCGATGGTTCGCCCCGGAAGGGGTCTTAGGAGGTGACACCGATGGATTGATTGTCGTGATCATTCATGGTGTGTCCAATC
CCAACTCAACTCTAAGCAAGTCAACAAGTAGGAGATAAATCTATGAAAATCGAAGAAGGTAAACTGGTAATCTGGATTAA
CGGCGATAAAGGCTATAACGGACTCGCTGAAGTCGGTAAGAAATTCGAGAAAGATACCGGAATTAAAGTCACCGTTGAGC
ATCCGGATAAACTGGAAGAGAAATTCCCACAGGTTGCGGCAACTGGCGATGGCCCTGACATTATCTTCTGGGCACACGAC
CGCTTTGGTGGCTACGCTCAATCTGGCCTGTTGGCTGAAATCACCCCGGACAAAGCGTTCCAGGACAAGCTGTATCCGTT
TACCTGGGATGCCGTACGTTACAACGGCAAGCTGATTGCTTACCCGATCGCTGTTGAAGCGTTATCGCTGATTTATAACA
AAGATCTGCTGCCGAACCCGCCAAAAACCTGGGAAGAGATCCCGGCGCTGGATAAAGAACTGAAAGCGAAAGGTAAGAGC
GCGCTGATGTTCAACCTGCAAGAACCGTACTTCACCTGGCCGCTGATTGCTGCTGACGGGGGTTATGCGTTCAAGTATGA
AAACGGCAAGTACGACATTAAAGACGTGGGCGTGGATAACGCTGGCGCGAAAGCGGGTCTGACCTTCCTGGTTGACCTGA
TTAAAAACAAACACATGAATGCAGACACCGATTACTCCATCGCAGAAGCTGCCTTTAATAAAGGCGAAACAGCGATGACC
ATCAACGGCCCGTGGGCATGGTCCAACATCGACACCAGCAAAGTGAATTATGGTGTAACGGTACTGCCGACCTTCAAGGG
TCAACCATCCAAACCGTTCGTTGGCGTGCTGAGCGCAGGTATTAACGCCGCCAGTCCGAACAAAGAGCTGGCAAAAGAGT
TCCTCGAAAACTATCTGCTGACTGATGAAGGTCTGGAAGCGGTTAATAAAGACAAACCGCTGGGTGCCGTAGCGCTGAAG
TCTTACGAGGAAGAGTTGGCGAAAGATCCACGTATTGCCGCCACTATGGAAAACGCCCAGAAAGGTGAAATCATGCCGAA
CATCCCGCAGATGTCCGCTTTCTGGTATGCCGTGCGTACTGCGGTGATCAACGCCGCCAGCGGTCGTCAGACTGTCGATG
AAGCCCTGAAAGACGCGCAGACTTCCGGCGGAGGTGGAGGCTCAAAAGGCGGTGGAGGTAGCGCTGGAGGCGTACCGATC
CAGAAAGTGCAGGACGACACCAAGACGCTGATTAAAACAATTGTCACTCGTATTAATGACATTTCACACACCCAGTCCGT
GAGCTCGAAACAGAAAGTAACCGGTCTGGATTTTATCCCGGGCCTACATCCAATACTGACGCTCTCGAAGATGGATCAGA
CTCTTGCAGTGTATCAGCAGATTCTTACCTCCATGCCTTCTCGTAACATGATCCAAATTTCTAATGATCTTGAAAACCTG
CGCGACTTACTGCATGTTCTGGCGTTCTCAAAAAGCTGTCACTTGCCGTGGGCCAGTGGTTTAGAAACGCTGGATAGTCT
GGGAGGCGTGTTGGAGGCGAGCGGCTACAGCACCGAAGTCGTTGCTCTGTCGCGCTTGCAAGGGAGCTTACAGGATATGC
TCTGGCAACTGGATCTGAGCCCCGGCTGCTCAAGCGGCGGTAGTCACCATCACCACCATCACTAA

| Name | Mutations |
|---|---|
| 7Z3Q_001 | (12/146) = 8% |
| 7Z3Q_002 | (13/146) = 9% |
| 7Z3Q_003 | (29/146) = 20% |
| 7Z3Q_004 | (76/146) = 52% |
| 7Z3Q_005 | (85/146) = 58% |
| 7Z3Q_006 | (82/146) = 56% |

| Name | Mutations |
|---|---|
| 8DHA_001 | (24/146) = 16% |
| 8DHA_002 | (16/146) = 11% |
| 8DHA_003 | (34/146) = 23% |
| 8DHA_004 | (74/146) = 51% |
| 8DHA_005 | (81/146) = 55% |
| 8DHA_006 | (71/146) = 49% |

FIG. 7E

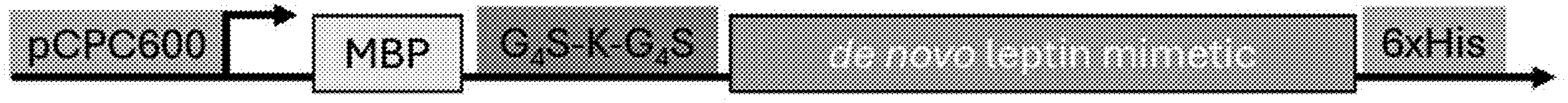

GTGTTGGGGCTGACTTTTGCTGCCTTGTTGGGGGGGCGATTTAACTGAGGTCACTTTTTCTTGGCCGGGATTGGCTAA
TCGCTTGTATGAGGCTATCCGTCTGCGGGATTATCCCACGGTTCAAGGGGTGGTGGTATTTTTGGCCGTTATTGTGGTGG
CGGCTAGTTTGGCGATCGATATTTTGAATGCTTGTATTGACCCACGGATTCGCTATTAATTCCCTGTCAGAAAATATACT
TAGTTATTAATACTTAGTTATTTTTCTTAATAAATTTTAACAAACCAAAGGGCGTTGGCAGTGTATAAAGGATATTTGAA
GGGGTGAGAAGGAAGGCGAATGTTGATTTATGAAGTTTGATTAACATTTGTATCAAAATATAAAATTCTTCTCATAAACC
CTGTACAATCTTTTAAGATTTCGGAAAGTGTTCTAGGATACTGAAGAAATGAACCACGGGGCAATTGTTAAAAGCCTTTG
TCGATGGTTCGCCCCGGAAGGGGTCTTAGGAGGTGACACCGATGGATTGATTGTCGTGATCATTCATGGTGTGTCCAATC
CCAACTCAACTCTAAGCAAGTCAACAAGTAGGAGATAAATCTATGAAAATCGAAGAAGGTAAACTGGTAATCTGGATTAA
CGGCGATAAAGGCTATAACGGACTCGCTGAAGTCGGTAAGAAATTCGAGAAAGATACCGGAATTAAAGTCACCGTTGAGC
ATCCGGATAAACTGGAAGAGAAATTCCCACAGGTTGCGGCAACTGGCGATGGCCCTGACATTATCTTCTGGGCACACGAC
CGCTTTGGTGGCTACGCTCAATCTGGCCTGTTGGCTGAAATCACCCCGGACAAAGCGTTCCAGGACAAGCTGTATCCGTT
TACCTGGGATGCCGTACGTTACAACGGCAAGCTGATTGCTTACCCGATCGCTGTTGAAGCGTTATCGCTGATTTATAACA
AAGATCTGCTGCCGAACCCGCCAAAAACCTGGGAAGAGATCCCGGCGCTGGATAAAGAACTGAAAGCGAAAGGTAAGAGC
GCGCTGATGTTCAACCTGCAAGAACCGTACTTCACCTGGCCGCTGATTGCTGCTGACGGGGGTTATGCGTTCAAGTATGA
AAACGGCAAGTACGACATTAAAGACGTGGGCGTGGATAACGCTGGCGCGAAAGCGGGTCTGACCTTCCTGGTTGACCTGA
TTAAAAACAAACACATGAATGCAGACACCGATTACTCCATCGCAGAAGCTGCCTTTAATAAAGGCGAAACAGCGATGACC
ATCAACGGCCCGTGGGCATGGTCCAACATCGACACCAGCAAAGTGAATTATGGTGTAACGGTACTGCCGACCTTCAAGGG
TCAACCATCCAAACCGTTCGTTGGCGTGCTGAGCGCAGGTATTAACGCCGCCAGTCCGAACAAAGAGCTGGCAAAAGAGT
TCCTCGAAAACTATCTGCTGACTGATGAAGGTCTGGAAGCGGTTAATAAAGACAAACCGCTGGGTGCCGTAGCGCTGAAG
TCTTACGAGGAAGAGTTGGCGAAAGATCCACGTATTGCCGCCACTATGGAAAACGCCCAGAAAGGTGAAATCATGCCGAA
CATCCCGCAGATGTCCGCTTTCTGGTATGCCGTGCGTACTGCGGTGATCAACGCCGCCAGCGGTCGTCAGACTGTCGATG
AAGCCCTGAAAGACGCGCAGACTTCCGGCGGAGGTGGAGGCTCAAAAGGCGGTGGAGGTAGCGCNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNGGCGGTAGTCACCATCACCACCATCACTAA

SEQ ID NO: 2

FIG. 7F

```
Gen1 1     VPIQKVQDDTKTLIKTIVTRINDISHTQSVSSKQKVTGLDFIPGLHPILT
Gen2 1     VPVEQIRKDLETLIRTVITRIDTIPYVKEVSPKQKVTGLEFIPGTKEKIT

Gen1 51    LSKMDQTLAVYQQILTSMPSRNMIQISNDLENLRDLLHVLAFSKSCHLPW
Gen2 51    YTDADETLAIYQEILSLLPEPELQQIALDLDNIRDLIRELAATKNCPLPR

Gen1 101   ASGLETLDSLGGVLEASGYSTEVVALSRLQGSLQDMLWQLDLSPGC (SEQ ID NO: 63)
Gen2 101   ASGLPDREKLLEAIKESGYSVAVTTATKLKEFLEKLIEELKKDPGC (SEQ ID NO: 56)
```

Alignment Matrix = BLOSUM62
Identity = 43.84 %
Similarity = 69.18 %

Black = identical amino acids
Bold = Similar biochemical property amino acids
Grey = not similar biochemical property amino acids

SDS-PAGE analysis.

| Lane | Description |
|---|---|
| 1 | Molecular marker |
| 2 | Gen1 leptin, no fusion tag |
| 3 | Gen2 leptin, no fusion tag |

FIG. 9C

| | KD (nM) | KD Error | ka (1/Ms) | ka Error | kdis (1/s) | kdis Error |
|---|---|---|---|---|---|---|
| **wild-type leptin** | 0.93 | 7.6E-12 | 4.87±05 | 1.97±03 | 4.52E-04 | 3.255E-06 |
| **Gen2 leptin** | 1.41 | 1.42E-11 | 6.44±05 | 4.83±03 | 9.07E-04 | 6.142E-06 |

| | Expression | | Activity | Protease resistance % of untreated (37°C 60 min) | |
|---|---|---|---|---|---|
| | Receptor binding ELISA, % TDW | Western blot % SDW | $IC_{50}$ Cell-based assay | Trypsin | Chymotrypsin |
| **Wild-type human leptin (Gen1)** | 0.2-0.3 | 0.3-0.5 | 0.4 | 0.09 | 0 |
| **Leptin redesign (Gen2)** | 2.53 | 4.51 | 0.28 | 9.81 | 43.48 |

Heat treated wild type leptin heat treated generation 2 leptin

FIG. 11C

| Temperature | IC50 (nM) wild-type | IC50 (nM) Gen2 |
|---|---|---|
| 4°C | 0.04406 | 0.0397 |
| 25°C | 0.05614 | 0.05229 |
| 50°C | 0.5219 | 0.04285 |
| 70°C | 40.76 | 0.04073 |
| 90°C | | 0.04455 |

| Sample | IC50 (nM) |
|---|---|
| PP5867-117 | 0.04991 |
| PP8709-001 (N82K) | 19.04 |
| PP8710-001 (S120A) | 1.314 |
| PP8711-001 (N82K/S120A) | 108 |

Non-binding Gen2 Regions

| Sample | IC50 (nM) |
|---|---|
| PP5867-117 | 0.04991 |
| PP8712-001 | 51.76 |
| PP8713-001 | 91.12 |
| PP8714-001 | 104.2 |
| PP8715-001 | 15.87 |
| PP8716-001 | 71.83 |

LEPTIN COMPOSITIONS AND METHODS OF MAKING AND USING THE SAME TO SUPPORT WEIGHT LOSS AND/OR MAINTENANCE

CROSS-REFERENCE TO RELATED APPLICATIONS

This application claims the benefit of priority to U.S. provisional application No. 63/646,354 filed on May 13, 2024, which is hereby incorporated by reference in its entirety.

TECHNICAL FIELD

The disclosure relates to compositions comprising leptin and methods of making the same and methods of using the same to support weight loss and/or weight maintenance.

REFERENCE TO AN ELECTRONIC SEQUENCE LISTING

The contents of the electronic sequence listing (LUBI_039_01US_SeqList_ST26.xml; Size: 196,828 bytes; and Date of Creation: Aug. 20, 2025) are herein incorporated by reference in their entirety.

BACKGROUND

Leptin was one of the first identified satiety-inducing hormones. It is constitutively synthesized by adipose tissue to maintain whole-body energy homeostasis and episodically secreted by gastric epithelial cells as an acute response to food intake.

Publication of early data showing that parenterally delivered leptin decreases food intake and induces weight loss in lean rodents sparked enormous interest in the use of injected leptin to treat obesity in humans. Subsequent research showed that parenterally administered leptin signals via specific receptors located in the central nervous system. Unfortunately, these studies demonstrated that obese individuals—both rodents and humans—are resistant to circulating leptin, rendering parenteral administration ineffective. The percent weight loss from leptin injections in obese humans is substantially less than the weight loss seen with glucagon-like peptide-1 (GLP-1) incretin mimetics (Wadden, Thomas A., et al. "Tirzepatide after intensive lifestyle intervention in adults with overweight or obesity: the SURMOUNT-3 phase 3 trial." *Nature Medicine* 29.11 (2023): 2909-2918), the current top-of-the-line treatment for obesity. The efficacy of parenteral leptin monotherapy is far too low for commercial viability.

Moreover, systemically administered leptin had other drawbacks, including the induction of neutralizing anti-drug antibodies in certain individuals. This raised the possibility that parenteral leptin therapy might cause lipodystrophy (a disease of leptin deficiency) in individuals without congenital leptin deficiency. As a result, although parenteral leptin was approved by the FDA in 2014, the label came with a black-box warning. It is only indicated for use in individuals with congenital leptin deficiency. It is also costly to manufacture and requires inconvenient daily injections. All of these are barriers to broad usage, a key requirement for any product to make a significant impact on the prevalence of overweight and obesity, maladies that together afflict more than two-thirds of the population in some areas of the world. Leptin was therefore abandoned by commercial drug developers for other targets, most notably incretin mimetics such as analogues of glucagon-like peptide-1 (GLP-1).

Incretin-based therapies have already improved many lives but there are major downsides as a long-term weight reduction treatment. Most notably, they require daily or weekly injections, and they cause significant and unpleasant side effects in most patients (Weiss, Tracey, et al. "Real-world weight change, adherence, and discontinuation among patients with type 2 diabetes initiating glucagon-like peptide-1 receptor agonists in the UK." *BMJ Open Diabetes Research and Care* 10.1 (2022): e002517; Sikirica, Mirko V., et al. "Reasons for discontinuation of GLP1 receptor agonists: data from a real-world cross-sectional survey of physicians and their patients with type 2 diabetes." *Diabetes, metabolic syndrome and obesity: targets and therapy* (2017): 403-412). They are also difficult to manufacture in amounts adequate to meet global demand, leading to an expensive product with a limited potential patient population (Abramson et al., 2019). For these reasons, one-year adherence rates for incretin mimetics are below 50%. Weight rebounds immediately on treatment cessation (Caro, Rebecca, David Samsel, and Paul Savel. "Is there sustained weight loss after discontinuation of GLP-1 agonist for obesity treatment?" *Evidence-Based Practice* 26.5 (2023): 7-8). Incretin mimetics also cause significant loss of lean muscle, raising concerns about the health consequences of chronic therapy. For all these reasons there remains tremendous need for low-cost and orally delivered anti-obesity medications with minimal side effects.

A product with these characteristics will be a profound contribution to human health.

BRIEF SUMMARY

The present disclosure provides a recombinant leptin receptor agonist comprising an amino acid substitution at a position selected from the group consisting of Q4, K5, V6, T10, I17, V18, N22, S25, T27, S32, D40, L49, L51, K53, M54, T66, S67, S70, R71, 174, S77, N78, L83, H88, H97, T106, A116, T121, V124, A125, Q130, S132, and Q139, wherein the positions are determined by alignment with SEQ ID NO: 63. In some embodiments, the recombinant leptin receptor agonist provided herewith comprises an amino acid substitution at a position selected from the group consisting of Q4, V6, 117, V18, N22, D40, L49, T66, L83, H88, and Q139. In some embodiments, the recombinant leptin receptor agonist provided herewith comprises an amino acid substitution at a position selected from the group consisting of K5, T10, S25, T27, S32, L51, K53, M54, S67, S70, R71, 174, S77, N78, H97, T106, A116, T121, V124, A125, Q130, and S132.

In some embodiments of the present disclosure, the recombinant leptin receptor agonist provided herewith comprises an amino acid substitution selected from the group consisting of Q4E, K5Q, V6I, T10L, I17V, V18I, N22D, S25P, T27V, S32P, D40E, L49I, L51Y, K53D, M54A, T66S, S67L, S70E, R71P, I74Q, S77A, N78L, L83I, H88R, H97P, T106D, A116E, T121V, V124T, A125T, Q130K, S132F, and Q139E. In some embodiments, the recombinant leptin receptor agonist provided herewith comprises an amino acid substitution selected from the group consisting of Q4E, V6I, I17V, V18I, N22D, D40E, L49I, T66S, L83I, H88R, and Q139E. In some embodiments, the recombinant leptin receptor agonist provided herewith comprises an amino acid substitution selected from the group consisting of K5Q, T10L, S25P, T27V, S32P, L51Y, K53D, M54A, S67L, S70E, R71P, I74Q, S77A, N78L, H97P, T106D, A116E, T121V, V124T, A125T, Q130K, and S132F.

In some embodiments, the recombinant leptin receptor agonist provided herewith comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 amino acid substitutions at the recited positions. In some embodiments, the recombinant leptin receptor agonist provided herewith comprises amino acid substitutions at all of the recited positions. In some embodiments, the recombinant leptin receptor agonist provided herewith comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 of the recited amino acid substitutions. In some embodiments, the recombinant leptin receptor agonist provided herewith comprises all of the recited amino acid substitutions.

In some embodiments of the present disclosure, the recombinant leptin receptor agonist provided herewith comprises an amino acid sequence having at least about 80%, 81%, 82%, 83%, 84% 85%, 86%, 87%, 88%, 89%, 90%, 91%, 92%, 93%, 94%, 95%, 96%, 97%, 98%, or 99% sequence identity with an amino acid sequence selected from Table 4. In some embodiments, the recombinant leptin receptor agonist provided herewith comprises an amino acid sequence selected from Table 4. In some embodiments, the recombinant leptin receptor agonist provided herewith comprises an amino acid sequence having at least about 80%, 81%, 82%, 83%, 84% 85%, 86%, 87%, 88%, 89%, 90%, 91%, 92%, 93%, 94%, 95%, 96%, 97%, 98%, or 99% sequence identity with a sequence selected from the group consisting of SEQ ID NO: 22, 52, 53, 54, 55, 56, 57, 58, 59, 60, 61, 62, 63, and 64. In some embodiments, the recombinant leptin receptor agonist provided herewith comprises an amino acid sequence selected from the group consisting of SEQ ID NO: 22, 52, 53, 54, 55, 56, 57, 58, 59, 60, 61, 62, 63, and 64.

In some embodiments of the present disclosure, the recombinant leptin receptor agonist provided herewith does not comprise a substitution at an activity-reducing position selected from the group consisting of D9, L13, T16, R20, K33, Q34, K35, V36, T37, Q75, D85, L86, S117, Y119, and S120. In some embodiments, the recombinant leptin receptor agonist provided herewith comprises fewer than 15, 14, 13, 12, 11, 10, 9, 8, 7, 6, 5, 4, 3, 2, or 1 substitutions at an activity-reducing position selected from the group consisting of D9, L13, T16, R20, K33, Q34, K35, V36, T37, Q75, D85, L86, S117, Y119, and S120. In some embodiments, the recombinant leptin receptor agonist provided herewith does not comprise any substitutions at positions selected from the group consisting of D9, L13, T16, R20, K33, Q34, K35, V36, T37, Q75, D85, L86, S117, Y119, and S120.

In some embodiments of the present disclosure, the recombinant leptin receptor agonist provided herewith is comprised within a chimeric protein, wherein said chimeric protein comprising a protein fusion partner. In some embodiments, the protein fusion partner is N-terminally translationally fused to the recombinant leptin receptor agonist. In some embodiments, the protein fusion partner is C-terminally translationally fused to the recombinant leptin receptor agonist. In some embodiments, the protein fusion partner is a protein purification tag or solubility enhancer. In some embodiments, the protein purification tag is selected from the group consisting of a maltose binding protein (MBP), a histidine tag, a green fluorescent protein (GFP), a glutathione S-transferase (GST), a FLAG tag, a Strep tag comprising the amino acid peptide sequence of SEQ ID NO: 91 (WSHPQFEK), and a HA tag. In further embodiments, the protein purification tag is MBP. In some embodiments, the protein fusion partner and the recombinant leptin receptor agonist is connected via a peptide linker. In some embodiments, the peptide linker is a glycine-rich linker, a proline-rich linker, a serine-rich linker, or a protease-cleavable linker. In some embodiments, the peptide linker is a G4S linker.

In some embodiments of the present disclosure, the recombinant leptin receptor agonist provided herewith induces higher weight loss when administered to an overweight animal compared to an unmodified, wild-type, or non-recombinant leptin.

In some embodiments of the present disclosure, the recombinant leptin receptor agonist provided herewith results in a lower food intake by an overweight animal receiving the recombinant leptin receptor agonist compared to an unmodified, wild-type, or non-recombinant leptin. In some embodiments, the animal is selected from the group consisting of a cat, dog, horse, mouse, rat, rabbit, guinea pig, and pig. In some embodiments, the animal is a primate. In further embodiments, the animal is a human.

In some embodiments of the present disclosure, the recombinant leptin receptor agonist provided herewith exhibits reduced dimerization or aggregation when expressed in a recombinant host compared to an unmodified or wild-type leptin expressed in the same recombinant host.

In some embodiments of the present disclosure, the recombinant leptin receptor agonist provided herewith expresses at higher levels in a recombinant host compared to an unmodified or wild-type leptin expressed in the same recombinant host under similar conditions.

In some embodiments of the present disclosure, the recombinant leptin receptor agonist provided herewith expresses at higher levels in *E. coli* and/or *Spirulina*.

In some embodiments of the present disclosure, the recombinant leptin receptor agonist provided herewith exhibits stronger binding (higher KD or higher Ka) to the human leptin receptor compared to an unmodified, wild-type, or non-recombinant leptin.

In some embodiments of the present disclosure, the recombinant leptin receptor agonist provided herewith exhibits higher thermostability compared to an unmodified, wild-type, or non-recombinant leptin.

In some embodiments of the present disclosure, the recombinant leptin receptor agonist provided herewith exhibits higher bioactivity after exposure to a temperature of at least about 50 Celsius, at least about 70 Celsius, or at least about 90 Celsius. In some embodiments, the recombinant leptin receptor agonist exhibits higher bioactivity after exposure to a temperature between about 50 Celsius and about 90 Celsius.

In some embodiments of the present disclosure, the recombinant leptin receptor agonist is expressed and/or comprised within a biological cell. In some embodiments, the biological cell is a eukaryotic cell or prokaryotic cell. In some embodiments, the biological cell is a prokaryotic cell. In some embodiments, the biological cell is a eukaryotic cell. In some embodiments, the biological cell is prokaryotic cell, which is a bacterial cell or a blue-green algal cell. In some embodiments, the biological cell is an *Escherichia coli* cell. In some embodiments, the biological cell is a Cyanobacterium. In some embodiments, the Cyanobacterium is *Arthrospira platensis*. In some embodiments, the biological cell is a eukaryotic cell selected from the group consisting of a filamentous fungi cell, a yeast cell, an algal cell, and a plant cell. In some embodiments, the yeast cell is *Saccharomyces*

*cerevisiae* or *Pichia pastoris*. In some embodiments, the algal cell is *Chlorella*. In some embodiments, the algal cell is *Chlorella vulgaris*.

In some embodiments of the present disclosure, the biological cell is genetically engineered to express the recombinant leptin receptor agonist. In some embodiments, the biological cell is desiccated, dried, lyophilized, and/or non-living.

In some embodiments of the present disclosure, the recombinant leptin receptor agonist is comprised within a composition that does not include any added permeability enhancer excipient and/or absorption enhancer excipient.

In some embodiments of the present disclosure, the recombinant leptin receptor agonist is comprised within a composition comprising a protease inhibitor and/or proteinase inhibitor. In some embodiments, the protease inhibitor is soybean trypsin inhibitor.

In some embodiments of the present disclosure, the recombinant leptin receptor agonist is comprised within a composition comprising a second active composition selected from the group consisting of amylin, cholecystokinin (CCK), a GLP-1 agonist, glucagon, gastric inhibitory polypeptide (GIP), luminal CCK-releasing factor (LCRF), *Akkermansia muciniphila* protein P9, and a CG-1 inhibitor.

The present disclosure provides methods comprising orally administering a therapeutically effective dose of the recombinant leptin receptor agonist provided herewith, to an individual in need thereof. In some embodiments of the methods provided herewith, the recombinant leptin receptor agonist acts locally in the individual's gastrointestinal tissues. In some embodiments of the methods provided herewith, the recombinant leptin receptor agonist is systemically bioavailable in the individual's blood in an amount less than 0.05% of the administered dose. In some embodiments of the methods provided herewith, the individual is an overweight individual. In some embodiments of the methods provided herewith, the individual is an obese individual. In some embodiments of the methods provided herewith, administration of the recombinant leptin receptor agonist results in weight loss. In some embodiments of the methods provided herewith, administration of the recombinant leptin receptor agonist results in systemic glucose reduction.

The present disclosure provides methods further comprising administering a second composition before, during, or after delivering the recombinant leptin receptor agonist, wherein the second composition is selected from the group consisting of amylin, cholecystokinin (CCK), a GLP-1 agonist, glucagon, gastric inhibitory polypeptide (GIP), luminal CCK-releasing factor (LCRF), *Akkermansia muciniphila* protein P9, and a CG-1 inhibitor. In some embodiments of the methods provided herewith, the recombinant leptin receptor agonist is orally delivered after the individual ceases administration of the GLP-1 agonist. In some embodiments of the methods provided herewith, the recombinant leptin receptor agonist is orally delivered after the individual finishes dieting. In some embodiments of the methods provided herewith, the recombinant leptin receptor agonist is orally delivered after the individual undergoes bariatric surgery.

The present disclosure provides compositions comprising, consisting essentially of, or consisting of a therapeutically effective dose of a leptin receptor agonist for weight loss and/or weight maintenance when orally administered to an individual in need thereof, wherein after administration the leptin receptor agonist acts locally in the individual's gastrointestinal tissues, and wherein the leptin receptor agonist is not systemically bioavailable. In some embodiments, the present disclosure provides such compositions wherein after oral administration the leptin receptor agonist is systemically bioavailable in the blood of the individual in an amount less than 0.05% of the administered dose. In some embodiments, the leptin receptor agonists of the present disclosure are small molecules, proteins, or peptides.

In some embodiments of the present disclosure, the compositions provided herein comprise, consist essentially of, or consist of a drug delivery vehicle comprising a nanoparticle, nanoemulsion, nanostructure, nanocarrier, nanogel, nanocapsule, nanomaterial, nanovesicle, and combinations thereof. In some embodiments, the compositions comprise a drug delivery vehicle comprising a polyacrylamide, polyacrylate, chitosan, micelle, polymersome, dendrimer, liposome, polylactic acid (PLA), polyglutamic acid (PGA), poly(lactic-glycolic acid) (PLGA), virus, bacteriophage, bacteria-derived lipid vesicle, RNA nanoparticle, RNA vesicle, and combinations thereof.

In some embodiments of the present disclosure, the compositions provided herein comprise, consist essentially of, or consist of a drug delivery vehicle comprising eukaryotic cells, parts of eukaryotic organisms, eukaryotic organisms, or prokaryotic cells. In some embodiments, the prokaryotic cells of the present disclosure are bacterial cells or blue-green algal cells. In some embodiments, the bacterial cells of the present disclosure are *Escherichia coli* cells. In some embodiments, the blue-green alga is a Cyanobacterium. In some embodiments, Cyanobacterium comprises *Arthrospira platensis*. In some embodiments, the blue-green algal cells are *Arthrospira platensis* cells.

In some embodiments of the present disclosure, the compositions provided herein comprise, consist essentially of, or consist of eukaryotic cells selected from the group consisting of filamentous fungi cells, yeast cells, algal cells, and plant cells. In some embodiments, the yeast is *Saccharomyces cerevisiae* or *Pichia pastoris*. In some embodiments, the algal cell is *Chlorella*. In some embodiments, the algal cell is *Chlorella vulgaris*.

In some embodiments of the present disclosure, the compositions provided herein comprise, consist essentially of, or consist of a drug delivery vehicle comprising cells that have been genetically engineered to express a leptin receptor agonist.

In some embodiments of the present disclosure, the compositions provided herein comprise, consist essentially of, or consist of genetically engineered cells prepared by spray-drying, vacuum belt drying, refractive window drying, drum drying, tray drying, fluidized bed drying, or lyophilization before administration.

In some embodiments of the present disclosure, the genetically engineered cells used in the compositions disclosed herein undergo a simple lysis and tangential-flow filtration step prior to administration in order to separate the leptin receptor agonist from cell membranes.

In some embodiments of the present disclosure, the compositions comprise, consist essentially of, or consist of genetically engineered cells in the composition that are dead cells.

In some embodiments of the present disclosure, a portion of or all of the genetically engineered cells in the compositions provided herein are further genetically engineered to express a protease inhibitor and/or a proteinase inhibitor.

In some embodiments of the present disclosure, the leptin receptor agonists used in the compositions provided herein are leptin proteins or therapeutically active fragments thereof. In some embodiments, the leptin proteins or therapeutically active fragments thereof used in the compositions disclosed herein are wild-type leptins, modified wild-type leptins, mutant versions of wild-type leptins, or combinations thereof. In some embodiments, the modified wild-type leptins or mutant versions of wild-type leptins used in the compositions provided herein have increased stability compared to the wild-type leptins. In some embodiments, the modified wild-type leptins or mutant versions of the wild-type leptins used in the compositions provided herein have improved packing energies and/or binding energies compared to the corresponding wild-type leptins. In some embodiments, the modified wild-type leptins or mutant versions of wild-type leptins used in the compositions provided herein have increased binding to receptors in gastrointestinal tissues when compared to the corresponding wild-type leptins. In some embodiments, the modified wild-type leptins used in the compositions provided herein are engineered variants of leptins selected from the group consisting of the amino acid sequences listed in Table 2 and Table 4, and sequences with about 80%, or about 85%, or about 90%, or about 95%, or about 96%, or about 97%, or about 98%, or about 99%, or 100% sequence similarity to the amino acid sequences listed in Table 2 and Table 4.

In some embodiments of the present disclosure, the compositions do not further include an added or additional permeability enhancer and/or absorption enhancer isolated from their native sources or made recombinantly or synthetically prior to being added to the oral composition.

In some embodiments of the present disclosure, the compositions further comprise a protease inhibitor and/or proteinase inhibitor. In some embodiments, the protease inhibitors utilized in the compositions provided herein are soybean trypsin inhibitors.

In some embodiments of the present disclosure, the compositions are administered to individuals who are overweight and/or obese.

In some embodiments, the compositions of the present disclosure are administered to humans or animals. In some embodiments of the present disclosure the compositions are administered to cats, dogs, horses, mice, rats, rabbits, guinea pigs, or pigs.

In some embodiments of the present disclosure, the leptin receptor agonists in the compositions are protected from degradation during gastric transit. In some embodiments, the leptin receptor agonists of the presently disclosed compositions are protected from degradation during gastric transit using physical devices, robotic pills, microneedle pills or capsules, blended excipients, tablet coatings, enteric capsules, co-delivery with soluble leptin receptors, and combinations thereof. In some embodiments, the leptin receptor agonists of the presently disclosed compositions are protected from degradation during gastric transit by utilizing *Spirulina*-expressed leptins.

In some embodiments as disclosed herein, the leptin receptor agonists in the compositions are provided in doses insufficient to induce weight loss if they were injected into the individual, wherein the individual is obese and the obesity is not caused by a leptin deficiency.

The present disclosure provides methods comprising, consisting essentially of, or consisting of orally administering a therapeutically effective dose of a leptin receptor agonist for weight loss and/or weight maintenance to an individual in need thereof, wherein after administration the leptin receptor agonist acts locally in the individual's gastrointestinal tissues, and wherein the leptin receptor agonist is not systemically bioavailable. In some embodiments, after oral administration using the methods provided herein, the leptin receptor agonist is systemically bioavailable in the blood of the individual in an amount less than 0.05% of the administered dose.

In some embodiments, the compositions administered according to the methods disclosed herein comprise leptin receptor agonists that are administered as small molecules, proteins, or peptides.

In some embodiments, the compositions administered according to the methods disclosed herein comprise a drug delivery vehicle comprising a nanoparticle, nanoemulsion, nanostructure, nanocarrier, nanogel, nanocapsule, nanomaterial, nanovesicle, and combinations thereof. In some embodiments, the compositions administered by the methods provided herein comprise a drug delivery vehicle comprising a polyacrylamide, polyacrylate, chitosan, micelle, polymersome, dendrimer, liposome, polylactic acid (PLA), polyglutamic acid (PGA), poly(lactic-glycolic acid) (PLGA), virus, bacteriophage, bacteria-derived lipid vesicle, RNA nanoparticle, RNA vesicle, and combinations thereof.

In some embodiments as provided herein, the compositions administered by the disclosed methods comprise, consist essentially of, or consist of a drug delivery vehicle comprising eukaryotic cells, parts of eukaryotic organisms, eukaryotic organisms, or prokaryotic cells. In some embodiments, the prokaryotic cells in the compositions administered according to the methods disclosed herein are bacterial cells. In some embodiments, the bacterial cells in the compositions administered according to the methods disclosed herein are *Escherichia coli* cells.

In some embodiments, the eukaryotic cells in the compositions administered according to the methods disclosed herein are from the group consisting of filamentous fungi cells, yeast cells, algal cells, and plant cells. In some embodiments, the yeast cells in the compositions administered according to the methods disclosed herein are cells of *Saccharomyces cerevisiae* or *Pichia pastoris*. In some embodiments, the algae in the compositions administered according to the methods disclosed herein are Cyanobacterium. In some embodiments, the Cyanobacterium is *Spirulina*.

In some embodiments of the present disclosure, the methods provided herein utilize compositions wherein the drug delivery vehicles comprise cells that have been genetically engineered to express a leptin receptor agonist. In some embodiments, the methods provided herein utilize compositions comprising genetically engineered cells that are prepared by spray-drying before administration. In some embodiments, the methods provided herein utilize compositions comprising genetically engineered cells that have undergone a simple lysis and tangential-flow filtration step to separate the leptin receptor agonist from cell membranes. In some embodiments, the methods provided herein utilize compositions comprising genetically engineered cells in the compositions that are dead cells.

In some embodiments of the present disclosure, the methods provided herein utilize compositions comprising, consisting essentially of, or consisting of genetically engineered cells wherein all or a portion of the cells have been further genetically engineered to express a protease inhibitor and/or a proteinase inhibitor. In some embodiments, the methods provided herein utilize compositions comprising leptin receptor agonists that are leptin proteins or therapeutically active fragments thereof. In some embodiments, the methods provided herein utilize compositions comprising leptin proteins or therapeutically active fragments thereof that are wild-type leptins, modified wild-type leptins, mutant versions of wild-type leptins, or combinations thereof. In some embodiments, the methods provided herein utilize compositions wherein the modified wild-type leptins or mutant versions of wild-type leptins have increased stability compared to the wild-type leptin. In some embodiments, the methods provided herein utilize compositions wherein the modified wild-type leptins or mutant versions of a wild-type leptins have improved packing energies and/or binding energies compared to the corresponding wild-type leptins. In some embodiments, the methods provided herein utilize compositions comprising modified wild-type leptins or mutant versions of a wild-type leptins that have increased binding to receptors in gastrointestinal tissues when compared to the corresponding wild-type leptins. In some embodiments, the methods provided herein utilize compositions comprising modified wild-type leptins that are engineered variants of leptins selected from the group consisting of the amino acid sequences listed in Table 2 and Table 4, and sequences with about 80%, or about 85%, or about 90%, or about 95%, or about 96%, or about 97%, or about 98%, or about 99%, or 100% sequence similarity to the amino acid sequences listed in Table 2 and Table 4.

In some embodiments of the present disclosure, the methods utilize compositions that do not further include any added permeability enhancers and/or absorption enhancers isolated from their native sources or made recombinantly or synthetically prior to being added to the oral compositions.

In some embodiments, the methods provided herein utilize compositions further comprising one or more protease inhibitors and/or proteinase inhibitors. In some embodiments, the methods disclosed herein utilize compositions further comprising one or more soybean trypsin inhibitors.

In some embodiments of the present disclosure, the individuals administered the compositions according to the methods of the present disclosure are overweight and/or obese.

In some embodiments of the present disclosure, the individuals being administered the compositions according to the methods disclosed herein are humans or animals. In some embodiments, the methods disclosed herein involve administering the compositions disclosed herein to cats, dogs, horses, mice, rats, rabbits, guinea pigs, and pigs.

In some embodiments of the present disclosure, the methods disclosed herein utilize compositions comprising leptin receptor agonists that are protected from degradation during gastric transit. In some embodiments of the present disclosure, the methods disclosed herein utilize compositions comprising leptin receptor agonists protected from degradation by physical devices, robotic pills, microneedle pills or capsules, blended excipients, tablet coatings, enteric capsules, co-delivery with soluble leptin receptor, and combinations thereof.

In some embodiments of the present disclosure, the methods disclosed herein administer the leptin receptor agonists in a dose insufficient to induce weight loss if they were injected into individuals, wherein the individuals are obese and the obesity is not caused by a leptin deficiency.

In some embodiments of the present disclosure, the compositions comprise, consist essentially of, or consist of a therapeutically effective amount of leptin for weight loss and/or weight maintenance when orally administered to a person or animal in need thereof, wherein the orally delivered leptin is at a dose insufficient to induce weight loss if it were injected into the individual. In some embodiments, the methods disclosed herein comprise orally administering a therapeutically effective amount of leptin for weight loss and/or weight maintenance to a person or animal in need thereof, wherein the orally administered leptin is at a dose insufficient to induce weight loss if it were injected into the individual.

In some embodiments of the present disclosure, the compositions comprise, consist essentially of, or consist of a therapeutically effective amount of an engineered variant of leptin for weight loss and/or weight maintenance when parenterally delivered to a person or animal in need thereof, wherein the engineered variant of leptin has increased stability compared to wild-type leptin. In some embodiments, the methods disclosed herein comprise, consist essentially of, or consist of parenterally administering a therapeutically effective amount of an engineered variant of leptin for weight loss and/or weight maintenance delivered to a person or animal in need thereof, wherein the engineered variant of leptin has increased stability compared to wild-type leptin.

In some embodiments provided herein, the compositions comprise, consist essentially of, or consist of a therapeutically effective amount of an engineered variant of leptin for systemic glucose reduction when orally or parenterally delivered to a person or animal in need. In some embodiments, the methods disclosed herein comprise, consist essentially of, or consist of orally or parenterally delivering a composition comprising a therapeutically effective amount of an engineered variant of leptin for systemic glucose reduction to a person or animal in need.

In some embodiments, the compositions comprise, consist essentially of, or consist of an effective amount of an orally delivered leptin composition to induce weight loss in an individual who is overweight or obese, wherein the leptin is protected from degradation during gastric transit. In some embodiments, the methods disclosed herein comprise, consist essentially of, or consist of orally delivering an effective amount of a leptin composition to induce weight loss in an individual who is overweight or obese, wherein the leptin is protected from degradation during gastric transit.

In some embodiments, the methods disclosed herein comprise, consist essentially of, or consist of orally delivering an effective amount of a leptin composition to induce weight loss in an individual who is overweight or obese, wherein the leptin is protected from degradation during gastric transit, and wherein the methods further comprise administering a second composition before, during, or after delivering the orally delivered leptin, wherein the second composition is selected from the group consisting of amylin, cholecystokinin (CCK), a GLP-1 agonist, glucagon, gastric inhibitory polypeptide (GIP), luminal CCK-releasing factor (LCRF), *Akkermansia muciniphila* protein P9, and a CG-1 inhibitor. In some embodiments, the second such compositions delivered according to the methods disclosed herein are delivered orally or parenterally. In some embodiments, the leptins are orally delivered according to the present disclosure after the individuals cease administration of a GLP-1 agonist. In some embodiments, the leptins are orally delivered after the individuals finish dieting. In some embodiments, the leptins are orally delivered after the individuals undergo bariatric surgery.

In some embodiments, the methods disclosed herein comprise, consist essentially of, or consist of orally delivering an effective amount of a leptin composition to induce weight loss in an individual who is overweight or obese, wherein the leptin is protected from degradation during gastric transit, wherein the composition comprises cells genetically engineered to express the leptin. In some embodiments, the leptin that is delivered is expressed intracellularly in the genetically engineered cells. In some embodiments, the genetically engineered cells are prepared by spray-drying before being orally delivered to the individual. In some embodiments, the genetically engineered cells undergo a simple lysis and tangential-flow filtration step to separate the leptin from cell membranes prior to being orally delivered to the individual. In some embodiments, the genetically engineered cells in the oral composition delivered to the individual are dead cells. In some embodiments, the genetically engineered cells are further genetically engineered to express a protease inhibitor and/or a proteinase inhibitor prior to oral delivery to an individual. In some embodiments, the genetically engineered cells used in the methods of the present disclosure are bacteria cells. In some embodiments, the genetically engineered bacterial cells used in the methods of the present disclosure are Cyanobacteria cells. In some embodiments, the genetically engineered Cyanobacteria cells are *Spirulina* cells.

In some embodiments, the recombinant leptins utilized in the methods of the present disclosure have increased binding energy to receptors in GI tissues as compared to non-recombinant, control leptins following oral administration to an individual.

In some embodiments, the recombinant leptins utilized in the methods of the present disclosure are not systemically available following the oral administration to the individual.

In some embodiments, the methods of the present disclosure treat obesity in an individual by orally administering the recombinant leptins of the present disclosure to an individual in need thereof.

In some embodiments, the individual being administered the recombinant leptins according to the present disclosure has a greater weight loss over a set time period as compared to an individual administered a non-recombinant, control leptin.

In some embodiments, the administration of the recombinant leptins according to the present disclosure result in no evidence of malaise in the individual as compared to an individual not receiving the recombinant leptin.

In some embodiments, the individual being administered the compositions according to the present disclosure is a lean individual or an obese individual.

In some embodiments, the present disclosure provides recombinant *Spirulina* cells comprising an exogenous sequence encoding leptin.

In some embodiments, the present disclosure provides recombinant *Spirulina* cells wherein the exogenous sequence encoding the leptin is genomically integrated into the *Spirulina* cell genome. In some embodiments, such genomic integration is within a neutral genomic region. In some embodiments, the integration is accomplished without using markers to produce the recombinant *Spirulina* cells of the present disclosure. In some embodiments, the neutral genomic region of the recombinant *Spirulina* cells of the present disclosure is kanamycin aminoglycoside acetyltransferase.

In some embodiments of the present disclosure, the leptins expressed by the recombinant *Spirulina* cells of the present disclosure are mammalian leptins. In some embodiments, the mammalian leptins expressed by the recombinant *Spirulina* cells of the present disclosure are non-human leptins. In some embodiments, the leptins expressed by the recombinant *Spirulina* cells of the present disclosure are human leptins. In some embodiments, the human leptins expressed by the recombinant *Spirulina* cells of the present disclosure are wildtype human leptins. In some embodiments, the wildtype human leptins expressed by the recombinant *Spirulina* cells have a valine-to-methionine polymorphism at position 94. In some embodiments, the human leptins expressed by the recombinant *Spirulina* cells of the present disclosure are leptin mimetics.

In some embodiments of the present disclosure, the mimetic leptins expressed by the recombinant *Spirulina* cells comprise a sequence selected from the group consisting of the leptin sequences listed in Table 2 and Table 4, and sequences with about 80%, or about 85%, or about 90%, or about 95%, or about 96%, or about 97%, or about 98%, or about 99%, or 100% sequence similarity to the amino acid sequences listed in Table 2 and Table 4.

In some embodiments of the present disclosure, the recombinant *Spirulina* cells utilized in the compositions and methods disclosure herein are one more *Spirulina* species selected from the group consisting of: *A. amethystine, A. ardissonei, A. argentina, A. balkrishnanii, A. baryana, A. boryana, A. braunii, A. breviarticulata, A. brevis, A. curta, A. desikacharyiensis, A. funiformis, A. fusiformis, A. ghannae, A. gigantean, A. gomontiana, A. gomontiana* var. *crassa, A. indica, A. jenneri* var. *platensis, A. jenneri* Stizenberger, *A. jenneri* f. *purpurea, A. joshii, A. khannae, A. laxa, A. laxissima, A. laxissima, A. leopoliensis, A. major, A. margaritae, A. massartii, A. massartii* var. *indica, A. maxima, A. meneghiniana, A. miniata* var. *constricta, A. miniata, A. miniata* f. *acutissima, A. neapolitana, A. nordstedtii, A. oceanica, A. okensis, A. pellucida, A. platensis, A. platensis* var. non-*constricta, A. platensis* f. granulate, *A. platensis* f. minor, *A. platensis* var. *tenuis, A. santannae, A. setchellii, A. skujae, A. spirulinoides* f. *tenuis, A. spirulinoides, A. subsalsa, A. subtilissima, A. tenuis, A. tenuissima*, and *A. versicolor*. In some embodiments, the recombinant *Spirulina* cells utilized in the compositions and methods disclosure herein are *A. platensis* cells.

In some embodiments, the present disclosure provides populations of any one or more of the different recombinant *Spirulina* cells as disclosed herein. In some embodiments, the populations of recombinant *Spirulina* cells provided by the present disclosure are formulated for oral administration. In some embodiments, the populations of recombinant *Spirulina* cells provided by the present disclosure comprise at least about $1\times10^5$ cells, or at least about $1\times10^6$, or at least about $1\times10^7$ cells, or at least about $1\times10^8$, or at least about $1\times10^9$ cells. In some embodiments, the populations of recombinant *Spirulina* cells provided by the present disclosure further comprise an excipient.

In some embodiments, the present disclosure provides food supplement compositions comprising one or more of the recombinant *Spirulina* cells or populations of the recombinant *Spirulina* cells as provided herein.

In some embodiments, the present disclosure provides nutraceutical compositions comprising, consisting essentially of, or consisting of one or more of the recombinant *Spirulina* cells or the population of the recombinant *Spirulina* cells as provided herein.

In some embodiments, the present disclosure provides vectors comprising a nucleic acid sequence encoding for leptin, wherein the sequence comprises at least 80% identity, or at least 85% identity, or at least 90% identity, or at least 95% identity, or at least 96% identity, or at least 97% identity, or at least 98% identity, or at least 99% identity, or 100% identity to any one of the nucleic acid sequences selected from the group consisting of the leptin sequences listed in Table 2 and Table 4.

In some embodiments the present disclosure provides vectors comprising a nucleic acid sequence encoding for a leptin with an amino acid sequence which comprises at least 80% identity, or at least 85% identity, or at least 90% identity, or at least 95% identity, or at least 96% identity, or at least 97% identity, or at least 98% identity, or at least 99% identity, or 100% identity to any one of the amino acid sequences selected from the group consisting of the amino acid sequences listed in Table 2 and Table 4.

In some embodiments, the present disclosure provides vectors encoding protein pp 2054 produced by *Spirulina* strain SP2334.

In some embodiments, the vectors of the present disclosure further comprise a native *Spirulina* promoter. In some embodiments, such vectors comprise the native *Spirulina* promoter pCPC600.

In some embodiments, the vectors of the present disclosure comprise sequences encoding for leptin that is flanked by a pair of homology arms. In some embodiments, the homology arms of such vectors comprise a sequence homologous to a neutral site in the *Spirulina* genome. In some embodiments, the neutral site the vectors of the present disclosure further comprise a portion of a kanamycin aminoglycoside acetyltransferase gene.

In some embodiments, the present disclosure provides kits comprising, consisting essentially of, or consisting of the recombinant *Spirulina* cells disclosed herein, populations of the recombinant *Spirulina* cells disclosed herein, the food supplements disclosed herein, the nutraceuticals disclosed herein, and/or the vectors disclosed herein. In some embodiments, such kits further comprise instructions for use thereof.

In some embodiments, the present disclosure provides methods of making recombinant *Spirulina* cells comprising introducing into a wild type *Spirulina* cell one or more of the vectors as disclosed herein, thereby generating a recombinant *Spirulina* cell. In some embodiments, such methods further comprise culturing the recombinant *Spirulina* cells of the present disclosure thereby generating populations of recombinant *Spirulina* cells. In some embodiments, the culturing comprises antibiotic selection. In some embodiments, the antibiotic used for selection is kanamycin.

In some embodiments, the methods of the present disclosure comprise drying the recombinant *Spirulina* cells disclosed herein.

In some embodiments, the present disclosure provides methods of sustaining weight in a subject, the methods comprising administering the recombinant *Spirulina* disclosed herein to a subject in need thereof, wherein the recombinant *Spirulina* comprises an exogenous leptin sequence, thereby sustaining the weight in the subject in need. In some embodiments, the subject's weight is a normal weight as determined by body mass index. In some embodiments, the weight of the subject is overweight as determined by body mass index.

In some embodiments, the present disclosure provides methods of treatment, comprising, consisting essentially of, or consisting of administering recombinant *Spirulina* to a subject having a body mass index beyond a normal weight, wherein the recombinant *Spirulina* comprises an exogenous leptin sequence, and wherein the administration is continued until the body mass index returns to normal. In some embodiments, such exogenous sequences encoding the leptin used in the methods as disclosed herein are genomically integrated into the *Spirulina* cell genome. In some embodiments, such genomic integration used in the methods as disclosed herein is within a neutral genomic region. In some embodiments, such neutral genomic regions used in such methods as disclosed herein are kanamycin aminoglycoside acetyltransferase. In some embodiments, the leptins utilized in the compositions and methods of the present disclosure are mammalian leptins. In some embodiments, such mammalian leptins are non-human leptins. In some embodiments, such mammalian leptins used in the methods as disclosed herein are human leptins. In some embodiments, such human leptins used in the methods as disclosed herein are wildtype leptins.

The present disclosure provides leptin-based obesity products with promising in vivo data for weight loss and/or weight maintenance. No evidence has been found of any malaise or other indications that the resultant weight loss is driven by hidden pathologies. The leptin containing biologics provided herein show no evidence or theoretical support for safety and/or toxicity issues. In some embodiments, the leptin compositions and methods of the present disclosure have a unique safety profile as non-absorbed oral biologics.

Additional embodiments of the compositions and methods of the present disclosure as comprehended by those skilled in the art after reading the present disclosure are also encompassed by the disclosure herein.

BRIEF DESCRIPTION OF THE DRAWINGS

FIG. 6A provides an exemplary leptin construct. The construct, SEQ ID NO: 1, comprises: an N terminal MBP (maltose binding protein) acting as solubilization agent; a G4S linker (G4SKG4S-SEQ ID NO: 88 and/or G4S-SEQ ID NO: 90) between MBP and leptin which serves as a trypsin-cleavable sequence for potential duodenal site-specific release of leptin; human leptin with a valine-to-methionine variant at position 94; the *Arthrospira platensis* native pCPC600 promoter and 6×His tag (SEQ ID NO: 89). FIG. 6B provides a corresponding annotated DNA sequence.

FIG. 7E is a graphic of an exemplary vector, SEQ ID NO: 2, encoding any of the de novo leptin mimetics of the disclosure, including a G4S linker (SEQ ID NO: 88) and a 6×His tag (SEQ ID NO: 89). FIG. 7F provides the sequence alignment result of Gen1 leptin (SP2334; pp 2054; SEQ ID NO: 63) and Gen 2 leptin (SP3967; PP5867; SEQ ID NO: 17=SEQ ID NO: 56).

FIG. 11C provides IC50 values of wild-type and Gen2 leptin at various temperatures (4° C., 25° C., 50° C., 70° C., and 90° C.).

DETAILED DESCRIPTION OF THE DISCLOSURE

Figure 1A:
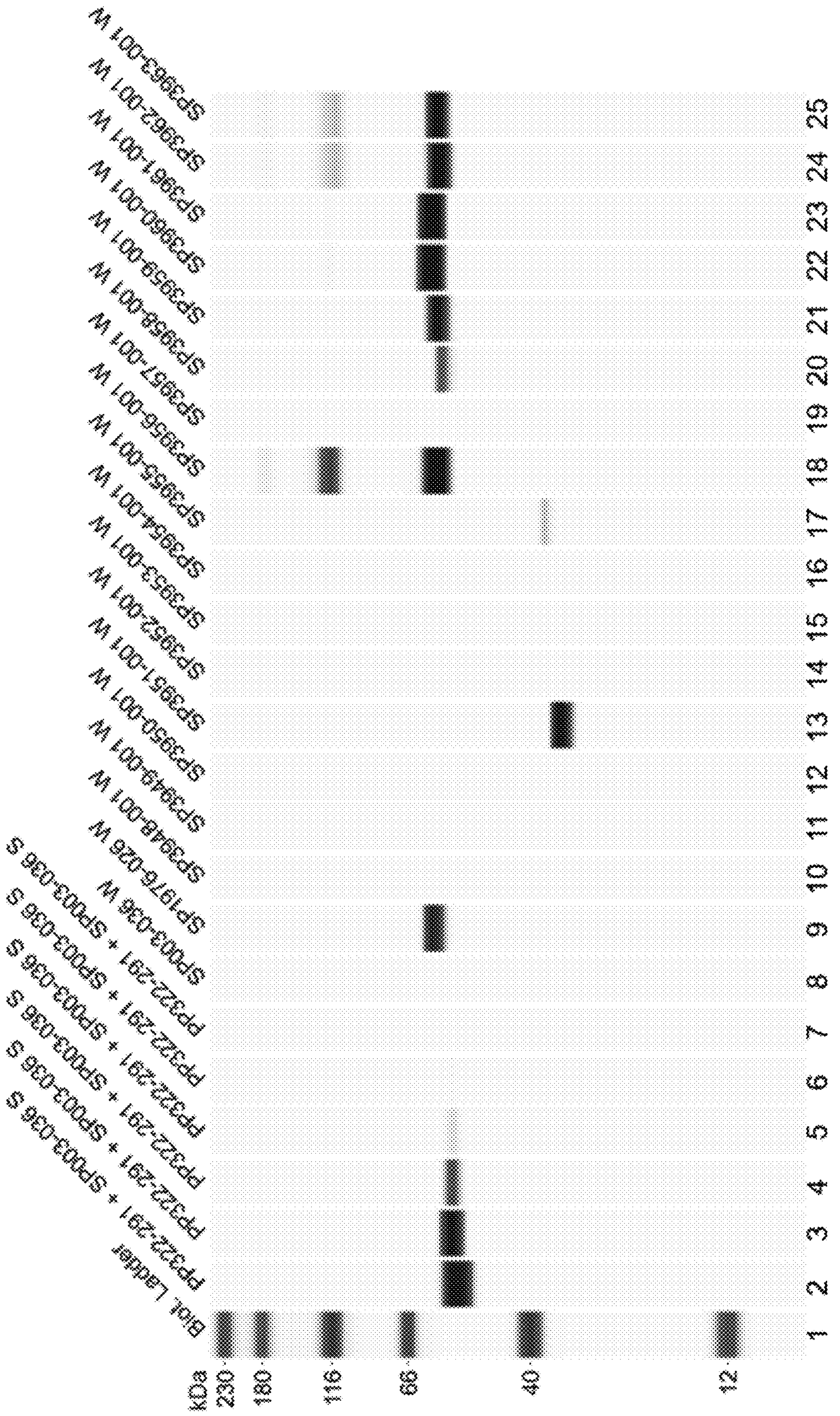
FIG. 1A shows a western blot analysis comparing *Spirulina*-expressed leptin mimetics.

The present disclosure provides orally delivered biologics expressed and delivered within a biomanufacturing host or administered via any other suitable delivery system. In some embodiments, the delivery system utilizes a bioengineered host such as *Escherichia coli* (*E. coli*) or *Spirulina*. In some embodiments, the product format is a small tablet, capsule, or pill taken daily. In some embodiments, the small tablet, capsule, or pill is taken with meals once, twice, or three times daily.

In some embodiments, the oral biologics of the present disclosure are massively scalable with potentially low to ultra-low cost of goods, thereby making these biologics more accessible and affordable to the general population.

The oral biologics of the present disclosure have multiple product uses including but not limited to monotherapy and/or combo treatments for weight loss induction and/or weight maintenance.

The present disclosure provides orally delivered biologics that act locally upon receptors in the gastrointestinal tissues. In some embodiments, the active moiety is a recombinant protein. In some embodiments, the recombinant protein is not absorbed into systemic circulation.

The present disclosure demonstrates that wild-type (WT) human leptin expresses well in *Spirulina* and, in in vitro experiments, signals like commercially acquired recombinant leptin. Surprisingly, the present disclosure also demonstrates that despite the lack of absorption-enhancing excipients, orally delivered, *Spirulina*-expressed leptin nevertheless induces weight loss in lean mice. The latter finding in Diet Induced Obese (DIO) mice mirrors prior human clinical trial results with a similarly sized recombinant therapeutic protein that was expressed and orally delivered within *Spirulina* at very high doses (9,000 mg of VHH-*Spirulina* biomass per day for 28 days) and was likewise not detectible in the blood serum (Jester et al., June 2022, Development of *Spirulina* for the manufacture and oral delivery of protein therapeutics, *Nature Biotechnology, Vol.* 40:956-964; Internet publication: Mar. 22, 2022). It is also surprising that the present disclosure demonstrates that orally delivered, *Spirulina*-expressed leptin also induces weight loss in diet-induced obese (DIO) mice—a surprising result unprecedented in the field. The products of the present disclosure were delivered without absorption-enhancing excipients or gastric-transit enhancing agents and levels of recombinant leptin were undetectable or virtually undetectable in the blood serum. The results present herein indicate that the dominant paradigm in the field—that leptin induces weight loss only via engagement with receptors in the hypothalamus—is incomplete and needs to be augmented with a role for local signaling by leptin in the gastrointestinal (GI) tract. It is compelling that (by comparison of the presently disclosed data to published data) the orally delivered leptin of the present disclosure is significantly more effective at causing weight loss in the DIO mouse model than is systemically delivered leptin. Prior to the present disclosure, leptin monotherapy had not been shown to induce significant weight loss in DIO rodents.

Beyond this fundamental advance, the present disclosure offers other advancements over the pre-existing state of the art in the field. For example, wild-type (WT) leptin is highly sensitive to gastrointestinal proteases. While the data provided herein show that this can be overcome by simply orally delivering a large bolus of WT leptin, smaller doses and/or less frequent dosing would be preferable. Consequently, as disclosed in detail herein, we further developed a set of novel proteolytically stable leptin mimetics that retain normal signaling.

Unless stated otherwise, all technical and scientific terms used herein have the same meaning as commonly understood by those of ordinary skill in the art to which the disclosure belongs. While the following terms are believed to be well understood by one of ordinary skill in the art, the following definitions are set forth to facilitate explanation of the presently disclosed subject matter. Although any methods and materials similar or equivalent to those described herein can be used in the practice or testing of the present disclosure, preferred methods and materials are described. The following terms are defined below. These definitions are for illustrative purposes and are not intended to limit the common meaning in the art of the defined terms.

I. Definitions

The term “a” or “an” refers to one or more of that entity, i.e., can refer to a plural referent. As such, the terms “a” or “an”, “one or more” and “at least one” are used interchangeably herein. In addition, reference to “an element” by the indefinite article “a” or “an” does not exclude the possibility that more than one of the elements is present, unless the context clearly requires that there is one and only one of the elements.

As used in this specification, the term “and/or” is used in this disclosure to mean either “and” or “or” unless indicated otherwise.

Throughout this specification, unless the context requires otherwise, the words “comprise”, or variations such as “comprises” or “comprising”, will be understood to imply the inclusion of a stated element or integer or group of elements or integers but not the exclusion of any other element or integer or group of elements or integers.

As used herein, the terms “having,” “has,” “contain,” “including,” “includes,” “include,” and “have” have the same open-ended meaning as “comprising,” “comprises,” and “comprise” provided above.

By “consisting of” is meant including, and limited to, whatever follows the phrase “consisting of.” Thus, the phrase “consisting of” indicates that the listed elements are required or mandatory, and that no other elements may be present.

By “consisting essentially of” is meant including any elements listed after the phrase and limited to other elements that do not interfere with or contribute to the activity or action specified in the disclosure for the listed elements. Thus, the phrase “consisting essentially of” indicates that the listed elements are required or mandatory, but that other elements are optional and may or may not be present depending upon whether or not they affect the activity or action of the listed elements.

The present description uses numerical ranges to quantify certain parameters relating to the disclosure. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting “greater than 10" (with no upper bounds) and a claim reciting "less than 100" (with no lower bounds) and provides literal support for the end points.

The present description uses specific numerical values to quantify certain parameters relating to the disclosure, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. These broad, intermediate, and narrow numerical ranges should be applied not only to the specific values but should also be applied to differences between these specific values.

As used in this application, the terms "about" and "approximately" are used as equivalents. Any numerals used in this application with or without about/approximately are meant to cover any normal fluctuations appreciated by one of ordinary skill in the relevant art. The term "approximately" or "about" refers to a range of values that fall within 10% of the stated reference value unless otherwise stated or otherwise evident from the context (except where such number would exceed 100% of a possible value).

As used herein, a "formulation" refers to a mixture or a structure such as a capsule, tablet, pill, or an emulsion, prepared according to a specific procedure (called a "formula").

As used herein, a "composition" refers to the nature of something's ingredients or constituents; the way in which a whole or mixture is made up. In some contexts herein, the terms "formulation" and "composition" are used interchangeably where they both refer to a mixture.

As used herein, "homogeneous" refers to a substance that is identical or nearly identical wherever it is sampled. A composition is considered homogeneous if it has uniform composition and properties throughout.

As used herein, "treatment", "treat", or "treating" refer to methods for obtaining beneficial or desired results for a patient, including clinical results. For purposes of the present disclosure, beneficial or desired clinical results include, but are not limited to, one or more of the following: alleviating one or more symptoms resulting from the disease, condition, disorder, and/or symptom; reducing the severity of the disease, condition, disorder, and/or symptom; stabilizing the disease, condition, disorder, and/or symptom (e.g., preventing or delaying its worsening); preventing or delaying the spread of the disease (e.g., metastasis), condition, disorder, and/or symptom; preventing or delaying the recurrence of the disease, condition, disorder, and/or symptom; delaying or slowing the progression of the disease, condition, disorder, and/or symptom; ameliorating the state of the disease, condition, disorder, and/or symptom; providing response (partial or total) to the disease, condition, disorder, and/or symptom; reducing the dose of one or more other drugs required to treat the disease, condition, disorder, and/or symptom; delaying the progression of the disease, condition, disorder, and/or symptom; improving the quality of life, and/or prolonging survival time. The compositions and methods of the present disclosure contemplate any one or more of these treatment aspects.

As used herein, a "pharmaceutically effective amount" refers to an amount sufficient to ameliorate or prevent a symptom or a sign of a medical disorder. Pharmaceutically effective amount also refers to an amount sufficient to allow or facilitate diagnosis. The effective amount for a particular patient may vary depending on factors such as the disease to be treated, the general health of the patient, the route of method, the dose of administration, and the severity of side effects. The pharmaceutically effective amount may be the maximum dose or administration regimen that avoids significant side effects or toxic effects. The effect will result in an improvement of the diagnostic measure or parameter by at least 5%, such as at least 10%, further such as at least 20%, further such as at least 30%, further such as at least 40%, further such as at least 50%, further such as at least 60%, further such as at least 70%, further such as at least 80%, and even further such as at least 90%, wherein 100% is defined as the diagnostic parameter displayed by a normal subject.

The term "pharmaceutically acceptable" refers to those compounds, materials, compositions and/or dosage forms which are suitable for being in contact with the tissues of human beings and animals without excessive toxicity, irritation, allergic response, or other problems or complications, and are commensurate with a reasonable benefit/risk ratio. For example, a pharmaceutically acceptable substance may be incorporated into a pharmaceutical composition administered to a patient without causing any significant undesirable biological effects or interacting in a deleterious manner with any of the other components of the composition in which it is contained. The pharmaceutically acceptable carrier or excipient preferably meets the requisite toxicological and manufacturing test standards and/or is included in the Inactive Ingredient Guide provided by U.S. Food & Drug Administration (FDA). FDA's Food Additives Status List, formerly called Appendix A of the Investigations Operations Manual (IOM), organizes additives found in many parts of 21 CFR into one alphabetized list. Additives included are those specified in the regulations promulgated under the FD&C Act, under Sections 401 (Food Standards), and 409 (Food Additives). The GRAS Substances (SCOGS) database allows access to opinions and conclusions from 115 SCOGS reports published between 1972-1980 on the safety of over 370 Generally Recognized As Safe (GRAS) food substances.

The term "pharmaceutically acceptable carrier" as used herein includes any and all solvents, dispersion media, coating agents, surfactants, antioxidants, preservatives (e.g., antibacterial agents or antifungal agents), isotonic agents, absorption delaying agents, salts, preservatives, drugs, drug stabilizers, binders, excipients, disintegrants, lubricants, sweeteners, flavoring agents, dyes, and the like, and combinations thereof, as known to those skilled in the art (see, e.g., *Remington's Pharmaceutical Sciences,* $18^{th}$ edition, Mack Printing Company, 1990, 1289-1329; and *Remington: The Science & Practice of Pharmacy,* $23^{rd}$ Edition, Editor: Adeboye Adejare, Academic Press, Oct. 30, 2020). The use of any conventional carrier in therapeutic or pharmaceutical compositions is contemplated herein unless it is incompatible with the active ingredient(s) of the present disclosure.

As used herein, the term "systemically bioavailable" refers to a drug or other substance that is either systemically administered (e.g., by injection, intravenous administration, sublingually, etc.) or taken by mouth that is meaningfully absorbed into the blood serum (i.e., bloodstream) and used by the body. In some instances, depending upon the context, "systemically bioavailable" as used herein refers to a drug or other substance that is available in the bloodstream to a meaningful extent or in a therapeutically effective amount. In other instances, depending on the context, "systemically bioavailable" refers to a drug or other substance that is present in the blood in amounts greater than or equal to 0.05% of an administered oral dose (i.e., ≥0.05%). Systemic bioavailability may be less than complete as a result of one of four main situations: denaturing or proteolytic degradation in the stomach or intestine, incomplete absorption due to very slow and/or incomplete dissolution of the drug in the gastrointestinal tract, incomplete absorption due to poor permeability of the drug through the intestinal epithelia, and biotransformation of the drug during its first passage through the liver.

As used herein, "non-systemic oral bioavailability" and "not systemically available" refer to a drug or other substance that is the fractional extent of the drug dosage or dosage of the other substance that reaches its therapeutic site of action but is not systemically bioavailable to a meaningful extent or in a therapeutically effective amount, for example due to limited tissue penetrance. In many cases, most of the orally administered drug or other substance is excreted or proteolytically degraded or otherwise metabolized before reaching systemic blood circulation. In other instances, depending on the context, "non-systemic oral bioavailability" or "not systemically available" refer to a drug or other substance that is present in blood in amounts less than 0.05% of the administered dose (i.e., <0.05%).

As used herein, the terms "local action", "acts locally", "acting locally", "local acting", and "locally acting" are all synonymous and refer to drug products or other substances that reach their site of action without entering systemic circulation.

As used herein, "active ingredient" refers to any component that provides pharmacological activity or other direct effect in the diagnosis, amelioration, cure, mitigation, treatment, or prevention of disease, or to affect the structure or any function of the body of man or animals.

As used herein, "pharmaceutically active ingredient" or API refer to the active ingredient(s) contained in medicines.

As used herein, a "nutraceutical" refers to non-pharmaceutical nutrients and supplements that are consumed for a health benefit, often in a concentrated form. Examples of nutraceuticals include but are not limited to vitamins, minerals, herbs, and extracts.

As used herein, a "protein mimetic" or "mimetic" refer to a molecule such as a peptide, a modified peptide, a protein fragment, or any other molecule that biologically mimics the action or activity of some other protein.

As used herein, the terms "protease inhibitor" and "proteinase inhibitor" are used synonymously and interchangeably to refer to a molecule or chemical compound that interferes with the ability of certain enzymes to break down proteins.

As used herein, the terms "penetration enhancer," "absorption enhancer," and "permeability enhancer" are used synonymously and interchangeably to refer to a molecule or chemical compound that interacts with constituents of the skin's outermost and rate limiting layer stratum corneum and increase its permeability or interacts with the constituents of the GI tract's mucus membrane and epithelial cell barriers to increase their permeability. One long-standing approach for improving transdermal drug delivery uses penetration enhancers (also called sorption promoters or accelerants) which penetrate into skin to reversibly decrease the barrier resistance. Similar approaches exist for achieving transepithelial drug delivery through the GI tract's mucus membrane and epithelial cell barriers.

The term "carrier" refers to a substance that serves as a vehicle for improving the efficiency of delivery and the effectiveness of a pharmaceutical composition.

The term "binder" refers to a substance or compound that promotes, provides, or improves cohesion, i.e., a substance that causes the components of a mixture to cohere to form a solid item that possesses integrity.

The term "excipient" refers to a pharmacologically inactive substance that is formulated in combination with a pharmacologically active ingredient of a pharmaceutical composition and is inclusive of, but not limited to, disintegrants, lubricants, flavorings, bulking agents, binders, fillers, diluents, preservatives, antioxidants, and adjuvants, synergists and products used for facilitating drug absorption or solubility or for other pharmacokinetic considerations. See, also, The Handbook of Pharmaceutical Excipients, 4$^{th}$ edition, ed. by Rowe et al., American Pharmaceuticals Association (2003); *Remington: The Science & Practice of Pharmacy,* 23$^{rd}$ Edition, Editor: Adeboye Adejare, Academic Press, Oct. 30, 2020).

As used herein, "disease" refers to a pathological process having a characteristic set of signs and symptoms. It may affect the whole body or any of its parts, and its etiology, pathology, and prognosis may be known or unknown.

As used herein, the current convention is that "lean" refers to an individual with a Body Mass Index (BMI)<25; "overweight" refers to an individual with a BMI≥25 and <30; and "obese" refers to an individual with a BMI≥30.

As used herein, "receptor agonist" refers to a drug or substance that binds to a receptor inside a cell or on its surface and causes the same action as the substance that normally binds to the receptor. Receptor agonists can be native or natural, synthetic, recombinant, or any combination thereof.

As used herein, "symptom" refers to any morbid phenomenon or departure from the normal in structure, function, or sensation experienced by a patient and indicative of disease.

As used herein, "disorder" refers to an abnormality, alteration, or derangement of function leading to a morbid physical or mental state.

As used herein, a "medical condition" refers to its use as a broad term that includes all diseases, lesions, and disorders. The Diagnostic and Statistical Manual of Mental Disorders (DSM) uses the term "general medical condition" to refer to all diseases, illnesses, and injuries except for mental disorder. In some contexts, the term medical condition is also a synonym for medical state, which describes an individual patient's current state from a medical standpoint.

The term "administered in combination with" or "co-administration" as used herein refers to the simultaneous or separate sequential administration in any manner of a solid or liquid oral pharmaceutical dosage form containing the drug-carrier complex disclosed herein and one or more other active agents known to be useful in the treatment of nervous system and/or mental diseases, conditions, disorders, and/or symptoms. Sequential administration must be sufficiently close in time such that the co-administered elements overlap in or on the patient's body. The term "other one or more active agent" as used herein includes any compound or therapeutic agent known or proven to exhibit advantageous properties when administered to a patient in need of treatment.

As used herein, the term "appropriate period of time" or "suitable period of time" refers to the period necessary to achieve a desired effect or result. For example, a mixture may be blended until a potency distribution is reached that is within an acceptable qualitative range for a given application or use of the blended mixture.

As used herein, the term "dose" or "unit dose" or "unit dosage" refers to a physically discrete unit that contains a predetermined quantity of active ingredient calculated to produce a desired therapeutic effect. The unit dose or unit dosage may be in the form of a tablet, capsule, sachet, liquid dispensing device, etc. referred to herein as a "unit dosage form."

As used herein, the term "at least a portion" or "fragment" of a nucleic acid or polypeptide means a portion having the minimal size characteristics of such sequences, or any larger fragment of the full-length molecule, up to and including the full-length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full-length polypeptide. The length of the portion to be used will depend on the application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids. In some embodiments, a fragment of a polypeptide or polynucleotide comprises at least about 10%, 20%, 30%, 40%, 50%, 60%, 70%, 80%, 90%, 95%, 96%, 97%, 98%, or 99% of the entire length of the reference polypeptide or polynucleotide. In some embodiments, a polypeptide or polynucleotide fragment may contain 5, 10, 15, 20, 25, 30, 35, 40, 45, 50, 60, 70, 80, 90, 100, 200, 300, 400, 500, 600, 700, 800, 900, 1000, 2000 or more nucleotides or amino acids.

As used herein, the term "codon optimization" implies that the codon usage of a DNA or RNA is adapted to that of a cell or organism of interest to improve the transcription rate of said recombinant nucleic acid in the cell or organism of interest. The skilled person knows a target nucleic acid can be modified at one position due to the codon degeneracy, whereas this modification will still lead to the same amino acid sequence at that position after translation, which is achieved by codon optimization to take into consideration the species-specific codon usage of a target cell or organism.

As used herein, the term "exogenous" refers to a substance coming from some source other than its native source. For example, the terms "exogenous protein," or "exogenous gene" refer to a protein or gene from a non-native source, and that has been artificially supplied to a biological system. As used herein, the term "exogenous" is used interchangeably with the term "heterologous," and refers to a substance coming from some source other than its native source.

The terms "genetically engineered host cell," "recombinant host cell," and "recombinant strain" are used interchangeably herein and refer to host cells that have been genetically engineered by the methods of the present disclosure. Thus, the terms include a host cell (e.g., bacteria, yeast cell, fungal cell, CHO, human cell, etc.) that has been genetically altered, modified, or engineered, such that it exhibits an altered, modified, or different genotype and/or phenotype (e.g., when the genetic modification affects coding nucleic acid sequences), as compared to the naturally-occurring host cell from which it was derived. It is understood that the terms refer not only to the recombinant host cell in question, but also to the progeny or potential progeny of such a host cell.

As used herein, the term "heterologous" refers to a substance coming from some source or location other than its native source or location. In some embodiments, the term "heterologous nucleic acid" refers to a nucleic acid sequence that is not naturally found in the organism. For example, the term "heterologous promoter" may refer to a promoter that has been taken from one source organism and utilized in another organism, in which the promoter is not naturally found. However, the term "heterologous promoter" may also refer to a promoter that is from within the same source organism, but has merely been moved to a novel location, in which said promoter is not normally located.

Heterologous gene sequences can be introduced into a target cell by using an "expression vector," which can be a eukaryotic expression vector, for example a bacterial expression vector. Methods used to construct vectors are well known to a person skilled in the art and described in various publications. Techniques for constructing suitable vectors, including a description of the functional components such as promoters, enhancers, termination and polyadenylation signals, selection markers, origins of replication, and splicing signals, are reviewed and available in the prior art. Vectors may include but are not limited to plasmid vectors, phagemids, cosmids, artificial/mini-chromosomes (e.g., ACE), or viral vectors such as baculovirus, retrovirus, adenovirus, adeno-associated virus, herpes simplex virus, retroviruses, bacteriophages. The eukaryotic expression vectors will typically contain also prokaryotic sequences that facilitate the propagation of the vector in bacteria such as an origin of replication and antibiotic resistance and/or tolerance genes for selection in bacteria. A variety of eukaryotic expression vectors, containing a cloning site into which a polynucleotide can be operatively linked, are well known in the art and some are commercially available from companies such as Agilent Technologies Santa Clara, Calif.; Invitrogen, Carlsbad, Calif.; Promega, Madison, Wis., or Takara Bio Inc., Japan. In some embodiments, the expression vector comprises at least one nucleic acid sequence which is a regulatory sequence necessary for transcription and translation of nucleotide sequences that encode for a peptide/polypeptide/protein of interest. In some embodiments, the expression vector comprises at least one nucleic acid sequence which is a regulatory sequence necessary for transcription and translation of nucleotide sequences that encode for a peptide/polypeptide/protein of interest.

As used herein, the term "naturally occurring" as applied to a nucleic acid, a polypeptide, a cell, or an organism, refers to a nucleic acid, polypeptide, cell, or organism that is found in nature. The term "naturally occurring" may refer to a gene or sequence derived from a naturally occurring source. Thus, for the purposes of this disclosure, a "non-naturally occurring" sequence is a sequence that has been synthesized, mutated, engineered, edited, or otherwise modified to have a different sequence from known natural sequences. In some embodiments, the modification may be at the protein level (e.g., amino acid substitutions). In some embodiments, the modification may be at the DNA level (e.g., nucleotide substitutions).

As used herein, the term "nucleotide change" or "nucleotide modification" refers to, e.g., nucleotide substitution, deletion, and/or insertion, as is well understood in the art. For example, such nucleotide changes/modifications include mutations containing alterations that produce silent substitutions, additions, or deletions, but do not alter the properties or activities of the encoded protein or how the proteins are made. As another example, such nucleotide changes/modifications include mutations containing alterations that produce replacement substitutions, additions, or deletions, that alter the properties or activities of the encoded protein or how the proteins are made.

As used herein, the term "protein modification" refers to, e.g., amino acid substitution, amino acid modification, deletion, and/or insertion, as is well understood in the art.

As used herein, the term "operably linked" refers to the association of nucleic acid sequences on a single nucleic acid fragment so that the function of one is regulated by the other. For example, a promoter is operably linked with a coding sequence when it can regulate the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

The terms "polynucleotide," "nucleic acid," and "nucleotide sequence," used interchangeably herein, refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. This term includes, but is not limited to, single-, double-, or multi-stranded DNA or RNA, genomic DNA, cDNA, DNA-RNA hybrids, or a polymer comprising purine and pyrimidine bases or other natural, chemically, or biochemically modified, non-natural, or derivatized nucleotide bases. It also includes modified nucleic acids such as methylated and/or capped nucleic acids, nucleic acids containing modified bases, backbone modifications, and the like. "Oligonucleotide" refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" "nucleic acid," and "nucleotide sequence" should be understood to include, as applicable to the embodiments being described, single-stranded (such as sense or antisense) and double-stranded polynucleotides.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. As used herein, an amino acid coding for a protein means the protein comprises that amino acid sequence.

As used herein, the phrases "recombinant construct," "expression construct," "chimeric construct," "construct," and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from various sources, or regulatory sequences and coding sequences derived from the same source but arranged in a manner different than that found in nature. Such construct may be used by itself or may be used in conjunction with a vector. If a vector is used, then the choice of vector is dependent upon the method that will be used to transform host cells as is well known to those skilled in the art. For example, a plasmid vector can be used. The skilled artisan is aware of the genetic elements that must be present on the vector to successfully transform, select and propagate host cells comprising any of the isolated nucleic acid fragments of the disclosure. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, which replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, which is not autonomously replicating. As used herein, the term "expression" refers to the production of a functional end-product e.g., an mRNA or a protein (precursor or mature), an mRNA or a protein (precursor or mature).

As used herein the term "targeted" refers to the expectation that one item or molecule will interact with another item or molecule with a degree of specificity, to exclude non-targeted items or molecules. For example, a first polynucleotide that is targeted to a second polynucleotide, according to the present disclosure has been designed to hybridize with the second polynucleotide in a sequence specific manner (e.g., via Watson-Crick base pairing). In some embodiments, the selected region of hybridization is designed to render the hybridization unique to the one, or more targeted regions. A second polynucleotide can cease to be a target of a first targeting polynucleotide if its targeting sequence (region of hybridization) is mutated or is otherwise removed/separated from the second polynucleotide. Furthermore, "targeted" can be interchangeably used with "site-specific" or "site-directed," which refers to an action of molecular biology which uses information on the sequence of a genomic region of interest to be modified, and which further relies on information of the mechanism of action of molecular tools, e.g., nucleases, including CRISPR nucleases and variants thereof, TALENs, ZFNs, meganucleases or recombinases, DNA-modifying enzymes, including base modifying enzymes like cytidine deaminase enzymes, histone modifying enzymes and the like, DNA-binding proteins, cr/tracr RNAs, guide RNAs and the like.

As used herein the term "sequence identity" refers to the extent to which two optimally aligned polynucleotides or polypeptide sequences are invariant throughout a window of alignment of residues, e.g. nucleotides or amino acids. An "identity fraction" for aligned segments of a test sequence and a reference sequence is the number of identical residues which are shared by the two aligned sequences divided by the total number of residues in the reference sequence segment, i.e. the entire reference sequence or a smaller defined part of the reference sequence. Percent "sequence identity" is the identity fraction times 100. Comparison of sequences to determine percent identity can be accomplished by a number of well-known methods, including for example by using mathematical algorithms, such as, for example, those in the BLAST suite of sequence analysis programs. Unless noted otherwise, the term "sequence identity" in the claims refers to sequence identity as calculated by MUSCLE (ebi.ac.uk/Tools/msa/muscle/) using default parameters.

"Complementary" refers to the capacity for pairing, through base stacking and specific hydrogen bonding, between two sequences comprising naturally or non-naturally occurring bases or analogs thereof. For example, if a base at one position of a nucleic acid is capable of hydrogen bonding with a base at the corresponding position of a target, then the bases are considered to be complementary to each other at that position. Nucleic acids can comprise universal bases, or inert abasic spacers that provide no positive or negative contribution to hydrogen bonding. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and Santa Lucia, Nucl. Acids Research, 2005; 33 (19): 6258-6267.

As referred to herein, a "complementary nucleic acid sequence" is a nucleic acid sequence comprising a sequence of nucleotides that enables it to non-covalently bind to another nucleic acid in a sequence-specific, antiparallel, manner (i.e., a nucleic acid specifically binds to a complementary nucleic acid) under the appropriate in vitro and/or in vivo conditions of temperature and solution ionic strength.

Methods of sequence alignment for comparison and determination of percent sequence identity and percent complementarity are well known in the art. Optimal alignment of sequences for comparison can be conducted, e.g., by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, WI), by manual alignment and visual inspection (see, e.g., Brent et al., (2003) Current Protocols in Molecular Biology), by use of algorithms know in the art including the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information. Some alignment programs are MacVector (Oxford Molecular Ltd, Oxford, U.K.), AlignPlus (Cognex, Natick, Massachusetts) and AlignX (Vector NTI, Invitrogen, Carlsbad, CA). Another alignment program is Sequencher (Gene Codes, Ann Arbor, Michigan), using default parameters, and MUSCLE (Multiple Sequence Comparison by Log-Expection; a computer software licensed as public domain).

Herein, the term "hybridize" refers to pairing between complementary nucleotide bases (e.g., adenine (A) forms a base pair with thymine (T) in a DNA molecule and with uracil (U) in an RNA molecule, and guanine (G) forms a base pair with cytosine (C) in both DNA and RNA molecules) to form a double-stranded nucleic acid molecule. (See, e.g., Wahl and Berger (1987) Methods Enzymol. 152:399; Kimmel, (1987) Methods Enzymol. 152:507). In addition, it is also known in the art that for hybridization between two RNA molecules (e.g., dsRNA), guanine (G) base pairs with uracil (U). For example, G/U base-pairing is partially responsible for the degeneracy (i.e., redundancy) of the genetic code in the context of tRNA anti-codon base-pairing with codons in mRNA. In the context of this disclosure, a guanine (G) of a protein-binding segment (dsRNA duplex) of a guide RNA molecule is considered complementary to an uracil (U), and vice versa. As such, when a G/U base-pair can be made at a given nucleotide position a protein-binding segment (dsRNA duplex) of a guide RNA molecule, the position is not considered to be non-complementary, but is instead considered to be complementary. It is understood in the art that the sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide can comprise at least about 70%, at least about 80%, at least about 90%, at least about 95%, at least about 99%, or 100% sequence complementarity to a target region within the target nucleic acid sequence to which they are targeted.

The term "modified" refers to a substance or compound (e.g., a cell, a polynucleotide sequence, and/or a polypeptide sequence) that has been altered or changed as compared to the corresponding unmodified substance or compound.

As used herein, the terms "stability" or "stable" with respect to a drug or nutraceutical refers to the item's ability to retain its chemical, physical, microbiological, and/or biopharmaceutical properties within specified limits throughout its production process and shelf-life (for example without limitation, thermostability or stability when exposed to light or moisture) and after administration it also refers to an item's resistance to degradation, structural modification or metabolism in vivo (for example without limitation, degradation by proteolysis or denaturing in bodily tissues or fluids).

As used herein, the term "isolated" refers to a material that is free to varying degrees from components which normally accompany it as found in its native state.

As used herein, the term "phenotype" refers to the observable characters of an individual cell, cell culture, organism (e.g., a bacterium), or group of organisms which results from the interaction between that individual's genetic makeup (i.e., genotype) and the environment.

The terms "transgene" or "transgenic" as used herein refer to at least one nucleic acid sequence that is taken from the genome of one organism, or produced synthetically, and which is then introduced into a host cell or organism or tissue of interest and which is subsequently integrated into the host's genome by means of "stable" transformation or transfection approaches. In contrast, the term "transient" transformation or transfection or introduction refers to a way of introducing molecular tools including at least one nucleic acid (DNA, RNA, single-stranded or double-stranded or a mixture thereof) and/or at least one amino acid sequence, optionally comprising suitable chemical or biological agents, to achieve a transfer into at least one compartment of interest of a cell, including, but not restricted to, the cytoplasm, an organelle, including the nucleus, a mitochondrion, a vacuole, a chloroplast, or into a membrane, resulting in transcription and/or translation and/or association and/or activity of the at least one molecule introduced without achieving a stable integration or incorporation and thus inheritance of the respective at least one molecule introduced into the genome of a cell. The terms "transgene-free" refers to a condition that transgene is not present or found in the genome of a host cell or tissue or organism of interest.

"Competent" refers to the ability of a cell to take up extracellular nucleotides from the surrounding environment. A cell may be "naturally competent" or "artificially competent." Naturally competent cells are able to take up nucleotides from their surrounding environment under natural conditions. Artificially competent cells are made passively permeable to extracellular nucleotides by exposing the cell to conditions that do not normally occur naturally including incubation in a solution of divalent cations, heat shock, electroporation, and ultrasound.

The terms "wild-type," "wild type," "wildtype," "WT," and "naturally occurring" are all used interchangeably to refer to an organism, gene, or gene product that has the characteristics of that organism, gene, or gene product (e.g., a polypeptide) when isolated from a naturally occurring source. A wild-type organism, gene, or gene product is that which is most frequently observed in a population and is thus arbitrarily designed the "normal" or "wild-type" form.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); Cell and Tissue Culture: Laboratory Procedures in Biotechnology (Doyle & Griffiths, John Wiley & Sons 1998); Molecular Cloning: A Laboratory Manual (Fourth Edition) Volumes 1, 2 and 3 (M. Green and J. Sambrook, Col Spring Harbor Laboratory Press, 2012); Lab Ref: A Handbook of Recipes, Reagents, and other Reference Tools for Use at the Bench (First Edition) (J. Roskams and L. Rodgers, Cold Spring Laboratory Press, 2002), the disclosures of which are incorporated herein by reference.

By "corresponds to" or "corresponding to" is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein.

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

As used herein, "obtained from" means that a sample such as, for example, a nucleic acid extract or polypeptide extract is isolated from, or derived from, a particular source.

As used herein, "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present disclosure are biologically active, that is they continue to possess the desired biological activity of the native protein, that is, modulating or regulatory activity as described herein. Such variants may result from, for example, genetic polymorphism or from human manipulation. Biologically active variants of a native protein of the disclosure will have at least about 40%, 50%, 60%, 70%, generally at least about 75%, 80%, 85%, preferably about 90% to 95% or more, and more preferably about 98% or more sequence identity to the amino acid sequence for the native protein as determined by sequence alignment programs described elsewhere herein using default parameters. A biologically active variant of a protein of the disclosure may differ from that protein by as few as 1-15 amino acid residues, as few as 1-10, such as 6-10, as few as 5, as few as 4, 3, 2, or even 1 amino acid residue.

The proteins of the disclosure may be altered in various ways including amino acid substitutions, deletions, truncations, and insertions. Methods for such manipulations are known in the art. For example, amino acid sequence variants of the proteins can be prepared by mutations in the DNA. Methods for mutagenesis and nucleotide sequence alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be preferable.

Individual substitutions deletions or additions that alter, add, or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another, Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine I, Lysine (K), Histidine (H); Acidic: Aspartic acid (D), Glutamic acid (E), Asparagine (N), Glutamine (Q). See also Creighton, 1984. In addition, individual substitutions, deletions, or additions which alter, add, or delete a single amino acid or a small percentage of amino acids in an encoded sequence are also "conservatively modified variations."

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a non-translated RNA, in the sense or antisense direction. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. The expression of the nucleotide sequence in the expression cassette may be under the control of a constitutive promoter or of an inducible promoter which initiates transcription only when the host cell is exposed to some external stimulus. In the case of a multicellular organism, the promoter can also be specific to a particular tissue or organ or stage of development.

As used herein, the term "vector", "plasmid", or "construct" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746).

Also, "vector" is defined to include, inter alia, any plasmid, cosmid, phage or Agrobacterium binary vector in double or single stranded linear or circular form which may or may not be self-transmissible or mobilizable, and which can transform prokaryotic or eukaryotic host either by integration into the cellular genome or exist extrachromosomally (e.g., autonomous replicating plasmid with an origin of replication).

Specifically included are shuttle vectors by which is meant a DNA vehicle capable, naturally or by design, of replication in two different host organisms, which may be selected from actinomycetes and related species, bacteria and eukaryotic (e.g., mammalian, yeast, or fungal cells).

Preferably the nucleic acid in the vector is under the control of, and operably linked to, an appropriate promoter or other regulatory elements for transcription in a host cell such as a microbial, e.g., bacterial cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance and/or tolerance, hygromycin resistance and/or tolerance or ampicillin resistance and/or tolerance.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest, or synthesizing from known or predicted sequence information, and may include sequences designed to have desired parameters.

As used herein, the term "endogenous" or "endogenous gene," refers to the naturally occurring gene, in the location in which it is naturally found within the host cell genome. "Endogenous gene" is synonymous with "native gene" as used herein. An endogenous gene as described herein can include alleles of naturally occurring genes that have been mutated according to any of the methods of the present disclosure.

As used herein, the term "genotype" refers to the genetic makeup of an individual cell, cell culture, tissue, organism, or group of organisms.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present disclosure relates to QTLs, i.e., genomic regions that may comprise one or more genes or regulatory sequences, it is in some instances more accurate to refer to "haplotype" (i.e., an allele of a chromosomal segment) instead of "allele", however, in those instances, the term "allele" should be understood to comprise the term "haplotype". Alleles are considered identical when they express a similar phenotype. Differences in sequence are possible but not important if they do not influence phenotype.

As used herein, the term "locus" (plural: "loci") refers to any site that has been defined genetically. A locus may be a gene, or part of a gene, or a DNA sequence that has some regulatory role, and may be occupied by different sequences.

As used herein, the term "molecular marker" or "genetic marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Mapping of molecular markers in the vicinity of an allele is a procedure which can be performed quite easily by the average person skilled in molecular-biological techniques which techniques are for instance described in Lefebvre and Chevre, 1995; Lorez and Wenzel, 2007, Srivastava and Narula, 2004, Meksem and Kahl, 2005, Phillips and Vasil, 2001. General information concerning AFLP technology can be found in Vos et al. (1995, AFLP: a new technique for DNA fingerprinting, Nucleic Acids Res. 1995 Nov. 11; 23 (21): 4407-4414).

As used herein, the term "hemizygous" refers to a cell, tissue, or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the term "heterozygote" refers to a diploid or polyploid individual cell or organism having different alleles (forms of a given gene) present at least at one locus.

As used herein, the term "heterozygous" refers to the presence of different alleles (forms of a given gene) at a particular gene locus.

As used herein, the term "homozygote" refers to an individual cell or organism having the same alleles at one or more loci.

As used herein, the term "homozygous" refers to the presence of identical alleles at one or more loci in homologous chromosomal segments.

As used herein, the term "homologous" or "homolog" is known in the art and refers to related sequences that share a common ancestor or family member and are determined based on the degree of sequence identity. The terms "homology", "homologous", "substantially similar" and "corresponding substantially" are used interchangeably herein. Homologs usually control, mediate, or influence the same or similar biochemical pathways, yet homologs may give rise to differing phenotypes. It is therefore understood, as those skilled in the art will appreciate, that the disclosure encompasses more than the specific exemplary sequences. These terms describe the relationship between a gene found in one species, subspecies, variety, cultivar, or strain and the corresponding or equivalent gene in another species, subspecies, variety, cultivar or strain. For purposes of this disclosure homologous sequences are compared.

The term "homolog" is sometimes used to apply to the relationship between genes separated by the event of speciation (see "ortholog") or to the relationship between genes separated by the event of genetic duplication (see "paralog").

The term "homeolog" refers to a homoeologous gene or chromosome, resulting from polyploidy or chromosomal duplication events. This contrasts with the more common 'homolog', which is defined immediately above.

The term "ortholog" refers to genes in different species that evolved from a common ancestral gene by speciation. Normally, orthologs retain the same function during evolution. Identification of orthologs is critical for reliable prediction of gene function in newly sequenced genomes.

The term "paralog" refers to genes related by duplication within a genome. While orthologs generally retain the same function in the course of evolution, paralogs can evolve new functions, even if these are related to the original one.

"Homologous sequences" or "homologs" or "orthologs" are thought, believed, or known to be functionally related. A functional relationship may be indicated in any one of several ways, including, but not limited to: (a) degree of sequence identity and/or (b) the same or similar biological function. Preferably, both (a) and (b) are indicated. The degree of sequence identity may vary, but In some embodiments, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in *Current Protocols in Molecular Biology* (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Michigan), AlignX, and Vector NTI (Invitrogen, Carlsbad, CA).

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T and G/C content) of primer. A pair of bi-directional primers consists of one forward and one reverse primer as commonly used in the art of DNA amplification such as in PCR amplification.

A probe comprises an identifiable, isolated nucleic acid that recognizes a target nucleic acid sequence. A probe includes a nucleic acid that is attached to an addressable location, a detectable label or other reporter molecule and that hybridizes to a target sequence. Typical labels include radioactive isotopes, enzyme substrates, co-factors, ligands, chemiluminescent or fluorescent agents, haptens, and enzymes. Methods for labelling and guidance in the choice of labels appropriate for various purposes are discussed, for example, in Sambrook et al. (ed.), *Molecular Cloning: A Laboratory Manual,* 2nd ed., vol. 1-3, Cold Spring Harbor Laboratory Press, Cold Spring Harbor, NY, 1989 and Ausubel et al. *Short Protocols in Molecular Biology,* 4th ed., John Wiley & Sons, Inc., 1999.

Methods for preparing and using nucleic acid probes and primers are described, for example, in Sambrook et al. (ed.), *Molecular Cloning: A Laboratory Manual,* 2nd ed., vol. 1-3, Cold Spring Harbor Laboratory Press, Cold Spring Harbor, NY, 1989; Ausubel et al. *Short Protocols in Molecular Biology,* 4th ed., John Wiley & Sons, Inc., 1999; and Innis et al. *PCR Protocols, A Guide to Methods and Applications*, Academic Press, Inc., San Diego, CA, 1990. Amplification primer pairs can be derived from a known sequence, for example, by using computer programs intended for that purpose such as PRIMER (Version 0.5, 1991, Whitehead Institute for Biomedical Research, Cambridge, MA). One of ordinary skills in the art will appreciate that the specificity of a particular probe or primer increases with its length. Thus, in order to obtain greater specificity, probes and primers can be selected that comprise at least 20, 25, 30, 35, 40, 45, 50 or more consecutive nucleotides of a target nucleotide sequences.

For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (2001) Molecular Cloning: A Laboratory Manual (3rd ed., Cold Spring Harbor Laboratory Press, Plainview, New York). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially mismatched primers, and the like.

The present disclosure provides isolated nucleic acid sequences comprising a native leptin sequence, a modified native leptin sequence, a leptin mimetic sequence, homologs of such sequences, orthologs of such sequences, paralogs of such sequences, and fragments and variations thereof as disclosed herein. In some embodiments, the present disclosure provides isolated polynucleotides encoding a native leptin protein, a modified native leptin sequence, or a leptin mimetic sequence produced by the nucleic acid sequences disclosed herein, comprising a nucleic acid sequence that shares at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to the sequences identified and presented herein.

Methods of alignment of sequences for comparison are well known in the art. Various programs and alignment algorithms are described in: Smith and Waterman (*Adv. Appl. Math.,* 2:482, 1981); Needleman and Wunsch (*J. Mol. Biol.,* 48:443, 1970); Pearson and Lipman (*Proc. Natl. Acad. Sci.,* 85:2444, 1988); Higgins and Sharp (*Gene,* 73:23744, 1988); Higgins and Sharp (*CABIOS,* 5:15153, 1989); Corpet et al. (*Nuc. Acids Res.,* 16:1088190, 1988); Huang et al. (*Comp. Appls Biosci.,* 8:15565, 1992); and Pearson et al. (*Meth. Mol. Biol.,* 24:30731, 1994). Altschul et al. (*Nature Genet.,* 6:11929, 1994) presents a detailed consideration of sequence alignment methods and homology calculations.

The present disclosure also provides a chimeric gene comprising the isolated nucleic acid sequence of any one of the polynucleotides described above operably linked to suitable regulatory sequences.

II. Leptin

Physiology of Leptin.

The peptide hormone leptin regulates food intake, body mass, and reproductive function and plays a role in fetal growth, proinflammatory immune responses, angiogenesis, and lipolysis (Obradovic, et al., May 2021, *Leptin and Obesity: Role and Clinical Implication, Frontiers in Endocrinology*, Volume 12, Article 585887, 14 pages). Leptin was one of the first identified satiety-inducing hormones. It is constitutively synthesized by adipose tissue to maintain whole-body energy homeostasis, and episodically secreted by gastric epithelial cells as an acute response to food intake. Natural leptin is secreted by the stomach in response to food intake as a complex with a soluble form of the leptin receptor. It is speculated that this complex protects leptin from gastric degradation.

Leptin is a bioactive adipokine and was classically described as a signal to inform the brain about the state of the body's adipose reserves. Leptin has been well studied in the context of the hypothalamic melanocortin circuits, whereby leptin inhibits orexigenic Agouti-Related Protein (AgRP) neurons and activates anorexigenic POMC neurons. AgRP is a powerful orexigenic peptide that increases food intake when ubiquitously overexpressed or when administered centrally. While the physiology of leptin made this ligand an attractive (albeit putative) anti-obesity target, previous clinical assessments of peripheral leptin receptor agonists resulted in only modestly decreased body weight and adiposity outside of individuals with lipodystrophy (a disease of leptin deficiency).

Despite the general body of evidence otherwise, we hypothesized that orally-delivered *Spirulina*-expressed leptin and leptin derivatives could possibly be a promising avenue for weight reduction and metabolic normalization in obese individuals.

A survey of the relevant literature for publications of clinical trials and animal (mice, rats, dogs) studies with leptin was conducted. The number of publications per primary mode of leptin administration/delivery disclosed in these as follows: (1) publications is intraperitoneally/intraperitoneal injection: 21 hits; (2) intravenous (IV) injection: 5 hits; (3) subcutaneous: 150 hits; (4) intrathecally: 1 hit; (5) intranasally: 2 hits; (6) intracerebroventricularly (ICV): 6 hits; (7) intrahippocampally: 1 hit; (8) via 3rd or 4th ventricle infusion: 2 hits; (9) intraduodenal infusions: 1 hit; (10) intrajejunal administration: 1 hit, and (11) orally: 4 hits. None of the oral delivery hits involved DIO models or obese or overweight humans; none were long-term chronic dosing to assess weight loss.

Currently available injectable leptin formulations have a short half-life in circulation and currently available oral leptin formulations are poorly absorbable and susceptible to mechanical and enzymatic degradation in the gastrointestinal tract.

The percent weight loss from leptin injections in obese humans is substantially less than the weight loss seen with incretin mimetics (Wadden, Thomas A., et al. "Tirzepatide after intensive lifestyle intervention in adults with overweight or obesity: the SURMOUNT-3 phase 3 trial." *Nature Medicine* 29.11 (2023): 2909-2918), the current top-of-the-line treatment for obesity. However, incretins have downsides as a long-term weight reduction treatment: they require daily or weekly subcutaneous injections; often lead to significant and unpleasant side effects that lead to treatment discontinuation (Weiss, Tracey, et al. "Real-world weight change, adherence, and discontinuation among patients with type 2 diabetes initiating glucagon-like peptide-1 receptor agonists in the UK." *wBMJ Open Diabetes Research and Care* 10.1 (2022): e002517; Sikirica, Mirko V., et al. "Reasons for discontinuation of GLP1 receptor agonists: data from a real-world cross-sectional survey of physicians and their patients with type 2 diabetes." *Diabetes, metabolic syndrome and obesity: targets and therapy* (2017): 403-412); incretin mimetic-mediated weight loss reverses upon treatment cessation (Caro, Rebecca, David Samsel, and Paul Savel. "Is there sustained weight loss after discontinuation of GLP-1 agonist for obesity treatment?" Evidence-Based Practice 26.5 (2023): 7-8); and incretin mimetics are difficult to manufacture, leading to an expensive product with a limited potential patient population (Abramson, Alex, et al. "Quantifying the value of orally delivered biologic therapies: a cost-effectiveness analysis of oral semaglutide." *Journal of pharmaceutical sciences* 108.9 (2019): 3138-3145). We hypothesized that these downsides presented an opportunity for a low-cost and orally delivered anti-obesity medication with minimal side effects, such as the orally delivered *Spirulina*-expressed leptin and leptin derivatives as provided herein.

Although systemically circulating leptin is known to control food intake in lean animals via receptors located in the central nervous system, obese individuals are resistant to circulating leptin. It is believed that individuals with leptin deficiencies start off being lean but get fat due to the absence of sufficient leptin levels. It is not clear whether the loss of circulating leptin and/or a loss of GI leptin is playing a role in this situation. Circulating leptin signals via receptors located in the central nervous system, but there are also leptin receptors located on the luminal surface of intestinal epithelial cells and on vagal afferent nerves that innervate the GI mucosa. Remarkably, prior to the present disclosure, the biological effects of leptin signaling via GI localized receptors in obese individuals has never been explored. It is generally believed that leptin secreted by the stomach engages receptors on intestine epithelial cells which results in leptin transcytosis across the GI epithelial and then entry into systemic circulation. This results in a transient surge in circulating leptin levels after a meal. It assumed that the satiety effects of both gut-derived and adipose-tissue derived leptin are mediated via the interactions of circulating leptin with its receptors in the brain. It assumed that the satiety effects of both gut-derived and adipose-tissue derived leptin are mediated via the interactions of circulating leptin with its receptors in the brain.

Myalept® (metreleptin) is an FDA-approved, orphan drug leptin analogue for injection used as an adjunct to diet as replacement therapy to treat the complications of leptin deficiency in patients with congenital or acquired generalized lipodystrophy (FDA Label for Myalept®, Reference ID: 3534419, Approval 2014). Lipodystrophy is a group of rare syndromes that cause a person to lose fat from some parts of the body, which gaining it in others, including on organs like the liver. A person can be born with lipodystrophy or develop it later in life. In either case, the resulting inability to maintain fat tissue beneath the skin can have severe, life-threatening consequences over time (Yale Medicine Fact Sheet, accessed online: Apr. 28, 2024).

Past Attempts at Oral Administration of Leptin

Despite the loss of attention and research funding, a trickle of leptin research continues. In one notable line of research, it was demonstrated that leptin administered to mice through a jejunal canula (bypassing gastric digestion) can reduce glucose production, a measure of glucose tolerance suggesting a potentially useful application in the field of diabetes. However, driven by the dominant theory that leptin's bioactivity requires modulation of the central nervous system, most research focused on developing new methods for achieving meaningful serum concentrations with orally delivered leptin. Oramed Pharma Inc. disclosed a preliminary Phase 1 efficacy trial involving administering a single 3 mg dose of leptin delivered orally to seven non-obese, fasting, Type 1 diabetic patients via a gastric transit capsule. This leptin composition was formulated for oral administration with excipients intended to aid in gastric transit and permeabilize the gastrointestinal lining and facilitate systemic absorption. The stated objective of this study was to demonstrate improvement in systemic glucagon and glucose levels and thereby help control and reduce obesity rates in humans. More specifically, the oral formulation designated ORMD-0701, included leptin, a species-specific protease inhibitor (i.e., a soybean trypsin inhibitor), and an absorption enhancer. The study found "ORMD-0701 had a transient glucose-lowering effect" and "no significant changes in blood leptin levels." See, e.g., Oramed Press Release, Dec. 23, 2020, Oramed Reports Positive First in Human Data from Oral Leptin Study (web.archive.org/web/20221005045311/and oramed.com/oramed-reports-positive-first-in-human-data-from-oral-leptin-study/); Kidron et al., 2021, Glucose- and Glucagon-Lowering Effect of a Single Oral Leptin Dose in Type I Diabetes Patients, Abstract: 121-LB, American Diabetes Association, 81st Scientific Sessions (virtual); and Jonathan Alicea, Jun. 29, 2021, Oral Leptin Formulation Offers Short-Term Benefit for Type 1 Diabetes Patients, HCPLive. Thus, while partial success in improving glucose sensitivity was claimed in the press release, sufficient data to draw firm conclusions are not available. No additional published information was identified that disclosed any follow-on studies or clinical trials with ORMD-0701. With these rare exceptions, leptin research has remained in the doldrums.

Bendayan & Cammissotto (2016, J. Endocrinology and Diabetes 3 (3): 1049) disclose a leptin-based formulation for the control of food intake and management of body weight in ob/ob mice, which lack a functional leptin gene. The first oral vehicle included leptin, the proteinase inhibitor aprotinin, and bicarbonate pH 9. The second vehicle included the components of the first vehicle plus sodium deoxycholate, which enhances duodenal absorption. For a long time the ob/ob mice were used as a model for obesity in humans, but later studies determined it was not a good model for obesity but rather it is merely a good model for acute lipodystrophy in humans, which is the orphan indication for the recombinant leptin Myalept™ approved for injection as discussed supra. Thus, Myalept™ is helpful for people who lack endogenous leptin. In genotypical normal obese humans and animals (i.e., those with a functional leptin receptor), though, leptin has been shown to have little effect on weight control or maintenance.

Bendayan & Cammissotto (2016, J. Endocrinology and Diabetes 3 (3): 1050) studied the control of food intake in 8-10 kg dogs (i.e., beagles) orally fed leptin compositions. The first pill included sodium bicarbonate and a trypsin inhibitor, while a second pill given 15 minutes after the first pill included sodium bicarbonate, sodium deoxycholate (a pharmaceutical penetration enhancer), aprotinin (proteinase inhibitor), and a human leptin.

None of the experiments disclosed by Bendayan & Cammissotto were done using obese animals. Clearly their work is based on the concept that the orally delivered leptin must enter systemic circulation to be effective, and it is generally understood that systemic leptin is not effective in obese animals. They included deoxycholate in all of their administration regimens as a pharmaceutical permeation enhancer and also administered fairly high doses of protease inhibitors.

Past Attempts at Delivering Leptin Intranasally.

A small number of reported studies have been done using intranasal delivery of leptin in DIO mice. Some of these studies purported to report at least some weight loss in the treated mice.

For example, Berger et al. (Intranasal leptin relieves sleep-disordered breathing in mice with diet-induced obesity, 2019, Am J Respir Crit Care Med, Issue 6:773-783) concluded that "chronic intranasal leptin decreased food intake and body weight" (see, e.g., Abstract). Schulz et al. (Intranasal leptin reduces appetite and induces weight loss in rats with diet-induced obesity (DIO), 2012, Endocrinology, 153 (1): 143-153) reported that intranasal leptin reduced appetite and induced weight loss in DIO rats to the same extent as in lean rats. Hebebrand et al. (The role of leptin in rodent and human sleep: a transdiagnostic approach with a particular locus on anorexia nervosa, Apr. 7, 2023 (online), Neuroscience and Biobehavioral Reviews, 149:105164) provide a review of literature focused on the interactions of anorexia nervosa (AN), sleep, and leptin. Among their conclusions they "speculate that human recombinant leptin may be useful for the treatment of treatment-resistant sleep-wake disorders, which are associated with (relative) hypoleptinemia." M. Ip and B. Mokhlesi (Activating leptin receptors in the central nervous system using intranasal leptin, 2019, American Journal of Respiratory and Critical Care Medicine, Vol. 199, No. 6, pages 689-690) review the implications of a finding that intranasal leptin can alleviate hypoventilation and upper-airway obstruction in an obese mice model. They concluded "the translation to humans cannot be taken on a mere leap of faith" and that "further research is needed to identify the patient population that will be most responsive to this therapeutic modality.

Prior Compositions Including Leptin and Derivatives of *Spirulina*

International Application Publication Number WO 2020/187772 (September 2020) discloses oral pharmaceutical compositions containing meat-derived polypeptides or potato-derived proteinase inhibitors and gastrointestinal peptide hormones used for "weight management and preventing or reducing the incidence of obesity." In some of the compositions the gastrointestinal peptide hormone can be leptin. The publication also discloses that such compositions can further include a protein substrate derived "from micro or macroalgae, such as *Spirulina*." The publication does not disclose using dead or living *Spirulina* cells per se.

Published US Patent Application Number 2007/0037776 (February 2007) discloses compositions for enhanced delivery across epithelium, wherein the compositions contain an active agent and a polysaccharide or non-polysaccharide polymer. A long list of possible "agents" that could be used in the compositions includes leptin. In some instances, the active agent can be administered "by oral delivery." The polysaccharide or non-polysaccharide polymers "allow for enhanced delivery of active agents across epithelial barriers." An extensive list of disorders that allegedly can be treated by these compositions includes "obesity." In some instances, the polysaccharide can be "Calcium spirulan (CA-SP, isolated . . . from *Spirulina platensis*) and derivatives and analogs thereof." Reference to "Calcium spirulan" is in the definition of "polysaccharide" at [0138]. No evidence is presented that CA-SP is "capable of altering, e.g., increasing or decreasing the permeability of intercellular junctions between epithelial tissue." Nor does the publication disclose using dead or living *Spirulina* cells per se. Thus, this publication is merely an invitation to try one of an extremely large number of possible alternative agents and different administration methods using the polymer compositions disclosed therein.

The Prior Art Teaches Away From Using Leptin as a Therapeutic

As disclosed herein, we have developed novel protein therapeutics for oral delivery using our unique *Spirulina*-based biomanufacturing and delivery system (Jester et al., June 2022, Development of *Spirulina* for the manufacture and oral delivery of protein therapeutics, *Nature Biotechnology*, Vol. 40:956-964; Internet publication: Mar. 22, 2022). As noted elsewhere herein, manufacturing cost and manufacturing scalability are major issues for all putative biologic therapies, and this is particularly important for highly prevalent disorders like being overweight and/or obese. This is true even for products like incretin mimetics, which are polypeptides injected in very small quantities; the issue is even more pronounced for proteins delivered orally. This is because proteins are more costly to manufacture than peptides, and oral delivery requires far larger volumes over time than parenteral delivery. In the case of the GLP-1 analogue semaglutide, for example, the oral formulation requires 280-fold more active pharmaceutical ingredient than parenteral delivery (Abramson et al., September 2019, Quantifying the value of orally delivered biologic therapies: a cost-effectiveness analysis of oral semaglutide, J Pharm Sci, 108 (9): 3138-3145). In contrast, the *Spirulina*-based platform utilized in the present disclosure lowers the cost of orally delivered protein therapeutics by 100-fold or more compared to conventional, sterile-fermentation-based systems like *E. coli* and yeast (Jester et al., June 2022, supra).

The prior state of the art taught against the compositions and methods of making and using the compositions for at least several key reasons. First, the dominant theories about leptin's biological function were developed in the context of parenteral delivery and focus on the molecule's interaction with the central nervous system, especially the hypothalamus. The dominance of this reigning paradigm meant that oral delivery experiments focused on achieving meaningful serum concentrations through, for example, co-formulation with excipients, such as permeability enhancers and/or absorption enhancers, overlooking the possibility of a gut-brain axis by which systemic effects on overweight and obesity can be mediated by leptin signaling within gastrointestinal tissues (Thomas S. Kuhn, December 1996, The structure of scientific revolutions University of Chicago Press, 3rd edition, 212 pages).

Second, research in the 1990s revealed that leptin functions differently in normal weight individuals compared to the overweight and obese. These results are recapitulated in DIO rodent models. After the biopharmaceutical industry largely abandoned the leptin field in the early 2000s, funding for leptin experiments of any sort became harder to come by. The relatively few experiments that continued with leptin instead focused on experiments directed at markers of glucose homeostasis for diabetes management: the latter in vivo experiments are significantly faster and cheaper to run.

Third, prior to the *Spirulina*-based system used in the present disclosure, there were no Good Manufacturing Practice (GMP) platforms with the scalability and cost-effectiveness required to profitably supply a mass-market application like oral leptin for weight loss. Researchers in the field have emphasized the lack of available clinical materials as an explanation for why leptin biology remains underexplored. In a recent survey the authors explained (emphasis added): "Perhaps the most likely explanation for the limited progress toward understanding leptin biology in human obesity is the unavailability of leptin for human clinical investigations. Three companies developed leptin analogs for potential use in obesity, and the failure of studies of these analogs to produce sufficient clinical benefit caused these efforts to be terminated. Along the way, internal studies and analyses that might have been done were never published, and requests from investigators for the hormone were typically denied. Rights to the best-studied analog, metreleptin, were passed to progressively smaller companies. Today, the sole use of leptin is for treatment of exceptionally rare cases of total leptin deficiency as well as rare lipodystrophies, where reversal of hypoleptinemia has beneficial metabolic effects" (Flier and Ahima, January 2024, Leptin physiology and pathophysiology: knowns and unknowns 30 years after its discovery, J Clin Invest. 2024; 134 (1): e174595). This issue is greatly exacerbated in the oral delivery context, because orally delivered protein therapeutics must be GMP-manufactured at colossal scale due to the need for daily or multiple-times-a-day dosing (as compared with parenterally delivered protein therapeutics, which can be administered as infrequently and every three months) (Jester et al., 2022, supra). This barrier is less profound with respect to acute diseases like diabetes where the underlying health economics—driven by the more severe, short-term health consequences of the underlying disease—are more likely to support higher prices for treatments, perhaps even high enough for oral biologics on a conventional manufacturing platform. By contrast, inducing weight loss among the overweight and obese is very important for human flourishing and long-term health, but it lacks the immediate societal value of averting the high rates of mortality and morbidity associated with diabetes. The lack of commercially viable path to market for oral protein therapeutics for weight loss may therefore explain why comparatively few researchers were funded to investigate oral leptin therapy.

Fourth, methodological considerations discourage investigation of therapeutic proteins active in the small bowel. Larger volumes of recombinant protein must be manufactured for each study than for comparable parenteral studies. Leptin is highly unstable under gastric conditions, so to ensure duodenal or jejunal delivery of purified leptin, cannulation procedures are required in mice. These are not only costly for researchers, but they are also cumbersome and incompatible with long-term studies with DIO rodents of the sort necessary to investigate oral leptin's bioactivity in the small bowel.

Leptin Derivatives

Fully wild-type leptin is challenging to express as a soluble, monodisperse protein. We have generated a series of *Spirulina* strains that express variations of human leptin as well as human leptin mimetics generated using machine learning techniques. The design incorporates solubility enhancers connected to the leptin and leptin derivative molecules with a protease-cleavable linker as well as a polyhistidine tag for affinity purification. Expression in *Spirulina* is driven by the pCPC600 promoter, a native *Spirulina* promoter. The molecule is expressed from a genomically integrated transgene at a neutral site (Jester et al., 2022, supra). The unmodified human leptin sequence ("wild type" leptin) contains the valine-to-methionine polymorphism at position 94 (Courbage, Sophie, et al. "Implication of heterozygous variants in genes of the leptin-melanocortin pathway in severe obesity." *The Journal of Clinical Endocrinology & Metabolism* 106.10 (2021): 2991-3006.) expressed starting at position 22 to eliminate amino acids 1-21, which comprise a secretion tag (Zhang, Yiying, et al. "Positional cloning of the mouse obese gene and its human homologue." *Nature* 372.6505 (1994): 425-432.). The de novo sequence ("derivative" leptins) designs were expressed using an identical framework. Derivative leptins were generated using a combination of Rosetta (Rohl, Carol A., et al. "Protein structure prediction using Rosetta." Methods in enzymology. Vol. 383. *Academic Press,* 2004. 66-93.) and ProteinMPNN (Dauparas, Justas, et al. "Robust deep learning-based protein sequence design using ProteinMPNN." Science 378.6615 (2022): 49-56.). Confirmation of leptin receptor binding was via both leptin receptor ELISA as well as a eukaryotic cell culture system in which engagement of the leptin receptor and activation of a downstream signal transduction pathway is monitored by transcriptional activation of a reporter gene encoding luciferase. In vivo activity was confirmed via oral delivery of leptin or leptin derivatives into mice whose weights and food intake were measured. In one experiment the mice were lean and in other experiments the mice were obese due to consumption of a high fat diet. Orally administered *Spirulina*-expressed leptin significantly reduced food intake and cause reduction in body weight compared to mice administered either buffer or wild-type *Spirulina*. These effects were maintained for at least 3 weeks of once-daily dosing.

The leptin utilized in the experiments provided herein is not "wild-type" leptin but rather it is a fusion protein of maltose binding protein (MBP) joined at its c-terminus to the N-terminus of leptin. MBP, in some manner that is not precisely known, increases the amount of the fusion protein that is expressed in *Spirulina*. While not wishing to be bound by any particular theory, it is probably acting as a solubility enhancer (aka chaperone). The amino acid linker that connects MBP to leptin contains a highly sensitive trypsin cleavage site, so that the MBP quickly becomes separated from leptin in the intestine.

The leptin proteins used in the experiments of the present disclosure also lack the N-terminal 21 amino acids of the wild-type protein. Those 21 amino acids are a "signal sequence" that directs the transport of wild type leptin to a cellular export pathway. Lastly, the leptin proteins utilized in the experiments disclosed herein are a natural polymorphism designated V94M (i.e., it differs from the most prevalent natural form of leptin by having a methionine at position 94 instead of a valine).

Human Leptin Mimetics Generated Using Artificial Intelligence/Machine Learning Techniques We generated a series of *Spirulina* strains that express human leptin mimetics generated using machine learning techniques.

In some embodiments, the Artificial Intelligence (AI)/Machine Learning (ML) methodologies utilized and disclosed herein include the following activities: ProteinMPNN for amino acid sequence design, and AlphaFold for structural predictions.

In some embodiments, the present disclosure provides (1) cell culture activity analysis and concentration analysis; (2) enzyme-linked immunosorbent assay (ELISA) binding protein concentration analysis; (3) automated western expression analysis; (4) trypsin and chymotrypsin resistance assays; and (5) using message-passing neural network (MPNN) for molecular property prediction and using Rosetta software for macromolecular modeling for Generation 2 (Gen 2) designs.

In summary, the basic Generation 1 (Gen 1) procedures include design, DNA sequence, amino acid sequence, results in vitro, and results in vivo.

In summary, the basic Gen 2 procedures include design, mutations from wildtype, DNA sequence, amino acid sequence, and results in vitro. More specifically, in some embodiments of the present disclosure, the MPNN and Rosetta methodologies for Gen 2 designs includes the following activities: (1) identifying the protein of interest (e.g., leptin); (2) finding and using available structural information for design processes (e.g., to determine amino acid residues to preserve and those allowed to vary); (3) defining the spatial parameters (shape) of the desired protein backbone for initial 3-Dimensional (3D) structures; (4) using AI/ML (e.g., ProteinMPNN) algorithm to generate new amino acid sequences predicted to give the desired protein shape (the "reverse folding problem"), wherein the algorithm has been trained using all available protein backbone features in existing structure databases; (5) use AlphaFold2 Protein Structure Database to down-select designed proteins based on the similarity of the predicted structures to the target structure; and (6) use Rosetta-based energy scores (e.g., packing and binding energies) to further down-select redesigned candidates (i.e., filter the designs on computational metrics from structure prediction and Rosetta-based energy scores).

This short list of candidates is then scored for bioactivity. For leptin this can be done via a cell-based assay that uses signaling from the leptin receptor to report an IC50. In some embodiments, we down-select based on an IC50 that is no more than 10-fold higher than the wild-type protein (i.e., 10-fold weaker receptor interaction). In some embodiments we select based on other features. For example, in some embodiments the resulting modified leptins exhibit improvements in stability.

In some embodiments, the Gen 2 methodologies as provided by the present disclosure can be used to create improved leptins, such as more stable and/or hyper stable leptin mimetics when compared to wildtype leptin or to the leptin precursor used to create the improved leptin.

In some embodiments, the Gen 2 methodologies as provided by the present disclosure can be used to create leptin mimetics suitable for any specific administration route, including but not limited to oral administration, topical administration, injected administration, etc.

In some embodiments, the Gen 2 methodologies provided by the present disclosure can be used to create leptin mimetics suitable for any specific disease, disorder, condition, etc., including but not limited to weight loss, maintenance of weight loss, maintenance of weight loss following treatment with a GLP-1 agonist (e.g., semaglutide), following diet-induced weight loss, following bariatric surgery, for glucose control, combined with a GLP-1 agonist (e.g., semaglutide), and/or as a pro-healing agent (e.g., for stomach ulcers), etc.

As one example of the leptin mimetic development series disclosed herein, we generated 65 leptin designs; down-selected to 12 based on AlphaFold2 and Rosetta scores, and then to a final set of 9 based on an IC50 within a factor of 3 of wild type.

In some embodiments, Gen 1 leptin created by basic Generation 1 (Gen 1) procedures as provided by the present disclosure comprises a 146 amino acid (AA) peptide (SP2334; pp 2054; SEQ ID NO: 63) starting at position 22 to 167 of human leptin protein to eliminate amino acids 1-21 (e.g., a secretion tag) with one AA substitution introduced at V94M, wherein the positions are determined by alignment with human wild type leptin protein sequence (GenBank ID: AAH69452). In some embodiments, Gen 1 leptin is a human leptin 22-167AA V94M, which is SEQ ID NO: 63 (SP2334; pp 2054).

In some embodiments, Gen 2 methodologies as provided by the present disclosure were used to create improved leptins. In some embodiments, the improved leptins are created by de novo designs based on Gen 1 leptin (SEQ ID NO: 63). In some embodiments, the improved leptins are Gen 2 leptin (SEQ ID NO: 56) and Gen 2 leptin mutants (including, but are not limited to SEQ ID NO: 22, 52-55, and 57-62). The consensus sequence among improved leptin peptide is SEQ ID NO: 64. In some embodiments, a recombinant leptin receptor agonist comprises the improved leptin, including but not limited to Gen 2 leptin (SEQ ID NO: 56) and its mutants.

Leptin Property-Enhancing Substitutions

Mutations imparting improved functionality to leptin receptor agonists identified through methods of the present disclosure are recited herein. In some embodiments, the present disclosure provides a recombinant leptin receptor agonist comprising an amino acid substitution at a position selected from the group consisting of Q4, K5, V6, T10, I17, V18, N22, S25, T27, S32, D40, L49, L51, K53, M54, T66, S67, S70, R71, 174, S77, N78, L83, H88, H97, T106, A116, T121, V124, A125, Q130, S132, and Q139, wherein the positions are determined by alignment with SEQ ID NO: 63.

In some embodiments, the recombinant leptin receptor agonist provided herewith comprises an amino acid substitution at a position selected from the group consisting of Q4, V6, I17, V18, N22, D40, L49, T66, L83, H88, and Q139. In some embodiments, the recombinant leptin receptor agonist provided herewith comprises an amino acid substitution at a position selected from the group consisting of K5, T10, S25, T27, S32, L51, K53, M54, S67, S70, R71, 174, S77, N78, H97, T106, A116, T121, V124, A125, Q130, and S132.

In some embodiments, the recombinant leptin receptor agonist provided herewith comprises an amino acid substitution selected from the group consisting of Q4E, K5Q, V6I, T10L, I17V, V18I, N22D, S25P, T27V, S32P, D40E, L49I, L51Y, K53D, M54A, T66S, S67L, S70E, R71P, I74Q, S77A, N78L, L83I, H88R, H97P, T106D, A116E, T121V, V124T, A125T, Q130K, S132F, and Q139E.

In some embodiments, the recombinant leptin receptor agonist provided herewith comprises an amino acid substitution selected from the group consisting of Q4E, V6I, I17V, V18I, N22D, D40E, L49I, T66S, L83I, H88R, and Q139E.

In some embodiments, the recombinant leptin receptor agonist provided herewith comprises an amino acid substitution selected from the group consisting of K5Q, T10L, S25P, T27V, S32P, L51Y, K53D, M54A, S67L, S70E, R71P, I74Q, S77A, N78L, H97P, T106D, A116E, T121V, V124T, A125T, Q130K, and S132F.

In some embodiments, the recombinant leptin receptor agonist provided herewith comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 amino acid substitutions at the recited positions. In some embodiments, the recombinant leptin receptor agonist provided herewith comprises amino acid substitutions at all of the recited positions. In some embodiments, the recombinant leptin receptor agonist provided herewith comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 of the recited amino acid substitutions.

In some embodiments, the recombinant leptin receptor agonist provided herewith comprises all of the recited amino acid substitutions.

In some embodiments of the present disclosure, the recombinant leptin receptor agonist provided herewith comprises an amino acid sequence having at least about 80%, 81%, 82%, 83%, 84% 85%, 86%, 87%, 88%, 89%, 90%, 91%, 92%, 93%, 94%, 95%, 96%, 97%, 98%, or 99% sequence identity with an amino acid sequence selected from Table 4.

In some embodiments, the recombinant leptin receptor agonist provided herewith comprises an amino acid sequence selected from Table 4. In some embodiments, the recombinant leptin receptor agonist provided herewith comprises an amino acid sequence having at least about 80%, 81%, 82%, 83%, 84% 85%, 86%, 87%, 88%, 89%, 90%, 91%, 92%, 93%, 94%, 95%, 96%, 97%, 98%, or 99% sequence identity with a sequence selected from the group consisting of SEQ ID NO: 22, 52, 53, 54, 55, 56, 57, 58, 59, 60, 61, 62, 63, and 64.

In some embodiments, the recombinant leptin receptor agonist provided herewith comprises an amino acid sequence selected from the group consisting of SEQ ID NO: 22, 52, 53, 54, 55, 56, 57, 58, 59, 60, 61, 62, 63, and 64.

Leptin Activity Reducing Substitutions

Techniques described herein, were also able to identify sequences critical for leptin functionality. These positions, and activity-reducing substitutions therein are described to provide further guidance to persons having skill in the art.

In some embodiments, the recombinant leptin receptor agonist provided herewith does not comprise a substitution at an activity-reducing position selected from the group consisting of D9, L13, T16, R20, K33, Q34, K35, V36, T37, Q75, D85, L86, S117, Y119, and S120, wherein the positions are determined by alignment with SEQ ID NO: 63.

In some embodiments, the recombinant leptin receptor agonist provided herewith comprises fewer than 15, 14, 13, 12, 11, 10, 9, 8, 7, 6, 5, 4, 3, 2, or 1 substitutions at an activity-reducing position selected from the group consisting of D9, L13, T16, R20, K33, Q34, K35, V36, T37, Q75, D85, L86, S117, Y119, and S120, wherein the positions are determined by alignment with SEQ ID NO: 63.

In some embodiments, the recombinant leptin receptor agonist provided herewith does not comprise any substitutions at positions selected from the group consisting of D9, L13, T16, R20, K33, Q34, K35, V36, T37, Q75, D85, L86, S117, Y119, and S120, wherein the positions are determined by alignment with SEQ ID NO: 63.

In some embodiments, the recombinant leptin receptor agonist provided herewith does not comprise an amino acid substitution selected from the group consisting of D9E, L13Q, T16N or T16K, R20N or R20K, K33D or K33E or K33N, Q34L or Q34K or Q34I, K35V, V36I, T37E, Q75E or Q75T, S117R or S117Q, Y119E or Y119K or Y119D, and S120E or S120K or S120D., wherein the positions are determined by alignment with SEQ ID NO: 63

Leptin Dosing. The optimal dose of the compositions and formulations of the present disclosure can be determined empirically for everyone using known methods and will depend upon a variety of factors, including, but not limited to: the genus and/or species of the organism; the degree of progression of the disease, disorder, or condition; age; body weight; body mass index (BMI); height; general health; gender; the diet of the individual; the time, route, and frequency of administration; pregnancy status; family health history; genes; adverse reactions; pending medical procedures such as radiation treatments, surgeries, heart conditions, etc.; and other medications the individual is taking. Optimal doses may be established using routine testing and procedures that are well known in the art. Scaling of dosing from mouse model data to humans is based on the intestine free fluid volume so as to keep the concentration of the drug (i.e., leptin) the same or similar in the intestine lumen. In some embodiments, the amount of the drug (i.e., leptin) administered to a human will be about 100 times (about 100×) that given to mice.

Dosing regimens can be 1 time daily (1×, quaque die, q.d., qd, QD), 2 times daily (2×, bis in die, b.i.d., bid, BID), or 3 times daily (3×, t.i.d., tid, TID). In some embodiments, dosing or administration can be before meals (ante cibum, a.c., ac, AC), during or with meals, after meals (post cibum, p.c., pc, PC), and/or at bedtime (hora somni, h.s., hs, HS).

In some embodiments, the dosing for humans can be up to 3 times daily (≤3×, ≤TID). In some embodiments, the dosing or administration for humans will be before meals (AC). In other embodiments, the dosing or administration for humans will be 3× daily before meals (TID AC).

The amount of the active ingredient (e.g., an API) in the final composition, formulation, or product of the present disclosure in dry weight/weight may be about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, about 5.0%, about 6.0%, about 7.0%, about 8.0%, about 9.0%, about 10.0%, about 11.0%, about 12.0%, about 13.0%, about 14.0%, about 15.0%, about 16.0%, about 17.0%, about 18.0%, about 19.0%, about 20.0%, about 21%, about 22%, about 23%, about 24%, or about 25%, or greater. In some embodiments, the amount of the active ingredient (e.g., an API) in the final composition or product of the present disclosure in dry weight/weight ranges from about 0.1% to about 5.0%; about 1.0% to about 5.0%, about 5.0% to about 10.0%, about 10.0% to about 20.0%, about 1.0% to about 20%, or about 0.1% to about 20.0%.

The amount of leptin protein in each dose for an average human as utilized in the compositions and administration methods of the present disclosure may be about 0.5 milligram (mg), about 1.0 mg, about 1.5 mg, about 2.0 mg, about 2.5 mg, about 3.0 mg, about 3.5 mg, about 4.0 mg, about 4.5 mg, about 5.0 mg, about 5.5 mg, about 6.0 mg, about 6.5 mg, about 7.0 mg, about 7.5 mg, about 8.0 mg, about 8.5 mg, about 9.0 mg, about 9.5 mg, about 10.0 mg, about 10.5 mg, about 11.0 mg, about 11.5 mg, about 12.0 mg, about 12.5 mg, about 13.0 mg, about 13.5 mg, about 14.0 mg, about 14.5 mg, about 15.0 mg, about 15.5 mg, about 16.0 mg, about 16.5 mg, about 17.0 mg, about 17.1 mg, about 17.2 mg, about 17.3 mg, about 17.4 mg, about 17.5 mg, about 17.6 mg, about 17.7 mg, about 17.8 mg, about 17.9 mg, about 18.0 mg, about 18.1 mg, about 18.2 mg, about 18.3 mg, about 18.4 mg, about 18.5 mg, about 18.6 mg, about 18.7 mg, about 18.8 mg, about 18.9 mg, about 19.0 mg, about 19.1 mg, about 19.2 mg, about 19.3 mg, about 19.4 mg, about 19.5 mg, about 19.6 mg, about 19.7 mg, about 19.8 mg, about 19.9 mg, about 20.0 mg, about 20.5 mg, about 21.0 mg, about 21.5 mg, about 22.0 mg, about 22.5 mg, about 23.0 mg, about 23.5 mg, about 24.0 mg, about 24.5 mg, about 25.0 mg, about 25.5 mg, about 26.0 mg, about 26.5 mg, about 27.0 mg, about 27.5 mg, about 28.0 mg, about 28.5 mg, about 29.0 mg, about 30.0 mg, about 30.5 mg, about 31.0 mg, about 31.5 mg, about 32.0 mg, about 32.5 mg, about 33.0 mg, about 33.5 mg, about 34.0 mg, or greater. In some embodiments, the amount of leptin protein in each dose for an average human as utilized in the compositions and administration methods of the present disclosure may be from about 17.5 mg to about 18.5 mg. In some embodiments, the amount of leptin protein in each dose for an average human as utilized in the compositions and administration methods of the present disclosure may be from about 18.0 mg TID AC to about 19.0 mg TID AC. In some embodiments, the dosing regimen for humans will be about 18.0 mg or about 19.0 mg TID AC.

The percentage of body weight lost in an individual being administered the compositions of the present disclosure at a dosing schedule of about 9.0 mg TID AC over about 10 to about 30 days as compared to the same or comparable individual receiving a placebo may be about 1.0%, about 2.0%, about 3.0%, about 4.0%, about 5.0%, about 6.0%, about 7.0%, about 8.0%, about 9.0%, about 10.0%, about 10.5%, about 11.0%, about 11.5%, about 12.0%, about 12.5%, about 13.0%, about 13.5%, about 14.0%, about 14.5%, about 15.0%, about 15.5%, about 16.0%, about 16.5%, about 17.0%, about 17.5%, about 18.0%, about 18.5%, about 19.0%, about 19.5%, about 20.0%, about 20.5%, about 21.0%, about 22.0%, about 23.0%, about 24.0%, about 25.0%, about 26.0%, about 27.0%, about 28.0%, about 29.0%, or about 30.0%, or greater. In some embodiments, administration of the leptin compositions of the present disclosure can result in about 10.0% to about 15.0%, or greater, reduction in weight. In some embodiments, administration of the leptin compositions of the present disclosure can result in about 12.5% to about 17.5%, or greater, reduction in weight. In some embodiments, administration of the leptin compositions of the present disclosure can result in about 15.0% to about 20.0%, or greater, reduction in weight.

The amount of body weight lost in an individual being administered the compositions of the present disclosure at a dosing schedule of about 18.0 mg TID AC over about 10 to about 30 days as compared to the same or comparable individual receiving a placebo may be about 1.0 pound (lb.), about 2.0 lbs., about 3.0 lbs., about 4.0 lbs., about 5.0 lbs., about 6.0 lbs., about 7.0 lbs., about 8.0 lbs., about 9.0 lbs., about 10.0 lbs., about 10.5 lbs., about 11.0 lbs., about 11.5 lbs., about 12.0 lbs., about 12.5 lbs., about 13.0 lbs., about 13.5 lbs., about 14.0 lbs., about 14.5 lbs., about 15.0 lbs., about 15.5 lbs., about 16.0 lbs., about 16.5 lbs., about 17.0 lbs., about 17.5 lbs., about 18.0 lbs., about 18.5 lbs., about 19.0 lbs., about 19.5 lbs., about 20.0 lbs., about 20.5 lbs., about 21.0 lbs., about 22.0 lbs., about 23.0 lbs., about 24.0 lbs., about 25.0 lbs., about 26.0 lbs., about 27.0 lbs., about 28.0 lbs., about 29.0 lbs., or about 30.0 lbs., or greater. In some embodiments, administration of the leptin compositions of the present disclosure can result in about 10 lbs. to about 15 lbs., or greater, reduction in weight. In some embodiments, administration of the leptin compositions of the present disclosure can result in about 12.5 lbs. to about 17.5 lbs., or greater, reduction in weight. In some embodiments, administration of the leptin compositions of the present disclosure can result in about 15.0 lbs. to about 20.0 lbs., greater, reduction in weight.

The percentage decrease in food consumption for an individual being administered the compositions of the present disclosure on an hourly, daily, weekly, monthly, or yearly time period as compared to the same or comparable individual receiving a placebo may be about 1.0%, about 2.0%, about 3.0%, about 4.0%, about 5.0%, about 6.0%, about 7.0%, about 8.0%, about 9.0%, about 10.0%, about 10.5%, about 11.0%, about 11.5%, about 12.0%, about 12.5%, about 13.0%, about 13.5%, about 14.0%, about 14.5%, about 15.0%, about 15.5%, about 16.0%, about 16.5%, about 17.0%, about 17.5%, about 18.0%, about 18.5%, about 19.0%, about 19.5%, about 20.0%, about 20.5%, about 21.0%, about 22.0%, about 23.0%, about 24.0%, about 25.0%, about 26.0%, about 27.0%, about 28.0%, about 29.0%, about 30.0%, about 35.0%, about 40.0%, about 45.0%, about 50.0%, about 55.0%, about 60.0%, about 65.0%, about 70.0%, about 75.0%, about 80.0%, about 85.0%, about 90.0%, about 95.0%, or about 100.0%, or greater. In some embodiments, administration of the leptin compositions of the present disclosure can result in about 10.0% to about 15.0%, or greater, decrease in food consumption. In some embodiments, administration of the leptin compositions of the present disclosure can result in about 15.0% to about 20.0%, or greater, decrease in food consumption. In some embodiments, administration of the leptin compositions of the present disclosure can result in about 20.0% to about 30.0%, or greater, decrease in food consumption. In some embodiments, administration of the leptin compositions of the present disclosure can result in about 30.0% to about 40.0%, or greater, decrease in food consumption. In some embodiments, administration of the leptin compositions of the present disclosure can result in about 40.0% to about 50.0%, or greater, decrease in food consumption.

The percentage decrease in fat mass for an individual being administered the compositions of the present disclosure on an hourly, daily, weekly, monthly, or yearly time period as compared to the same or comparable individual receiving a placebo may be about 1.0%, about 2.0%, about 3.0%, about 4.0%, about 5.0%, about 6.0%, about 7.0%, about 8.0%, about 9.0%, about 10.0%, about 10.5%, about 11.0%, about 11.5%, about 12.0%, about 12.5%, about 13.0%, about 13.5%, about 14.0%, about 14.5%, about 15.0%, about 15.5%, about 16.0%, about 16.5%, about 17.0%, about 17.5%, about 18.0%, about 18.5%, about 19.0%, about 19.5%, about 20.0%, about 20.5%, about 21.0%, about 22.0%, about 23.0%, about 24.0%, about 25.0%, about 26.0%, about 27.0%, about 28.0%, about 29.0%, about 30.0%, about 35.0%, about 40.0%, about 45.0%, about 50.0%, about 55.0%, about 60.0%, about 65.0%, about 70.0%, about 75.0%, about 80.0%, about 85.0%, about 90.0%, about 95.0%, or about 100.0%, or greater. In some embodiments, administration of the leptin compositions of the present disclosure can result in about 10.0% to about 15.0%, or greater, decrease in fat mass. In some embodiments, administration of the leptin compositions of the present disclosure can result in about 15.0% to about 20.0%, or greater, decrease in fat mass. In some embodiments, administration of the leptin compositions of the present disclosure can result in about 20.0% to about 30.0%, or greater, decrease in fat mass. In some embodiments, administration of the leptin compositions of the present disclosure can result in about 30.0% to about 40.0%, or greater, decrease in fat mass. In some embodiments, administration of the leptin compositions of the present disclosure can result in about 40.0% to about 50.0%, or greater, decrease in fat mass. In some embodiments, administration of the leptin compositions of the present disclosure can result in about 50.0% to about 60.0%, or greater, decrease in fat mass.

The percentage decrease in calorie intake for an individual being administered the compositions of the present disclosure on an hourly, daily, weekly, monthly, or yearly time period as compared to the same or comparable individual receiving a placebo may be about 1.0%, about 2.0%, about 3.0%, about 4.0%, about 5.0%, about 6.0%, about 7.0%, about 8.0%, about 9.0%, about 10.0%, about 10.5%, about 11.0%, about 11.5%, about 12.0%, about 12.5%, about 13.0%, about 13.5%, about 14.0%, about 14.5%, about 15.0%, about 15.5%, about 16.0%, about 16.5%, about 17.0%, about 17.5%, about 18.0%, about 18.5%, about 19.0%, about 19.5%, about 20.0%, about 20.5%, about 21.0%, about 22.0%, about 23.0%, about 24.0%, about 25.0%, about 26.0%, about 27.0%, about 28.0%, about 29.0%, about 30.0%, about 35.0%, about 40.0%, about 45.0%, about 50.0%, about 55.0%, about 60.0%, about 65.0%, about 70.0%, about 75.0%, about 80.0%, about 85.0%, about 90.0%, about 95.0%, or about 100.0%, or greater. In some embodiments, administration of the leptin compositions of the present disclosure can result in about 10.0% to about 15.0%, or greater, decrease in calorie intake. In some embodiments, administration of the leptin compositions of the present disclosure can result in about 15.0% to about 20.0%, or greater, decrease in calorie intake. In some embodiments, administration of the leptin compositions of the present disclosure can result in about 20.0% to about 30.0%, or greater, decrease in calorie intake.

The initial amount of the other excipients utilized in the methods and compositions of the present disclosure in dry weight/weight may be about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%.

In some embodiments, the initial amount of the other excipients utilized in the methods and compositions of the present disclosure in dry weight/weight ranges from about 0.1% to about 1%, about 0.1% to about 2%, about 0.1% to about 3%, about 0.1% to about 4%, about 0.1% to about 5%, about 0.1% to about 6%, 0.1% to about 7%, 0.1% to about 8%, 0.1% to about 9%, 0.1% to about 10%, about 0.1% to about 11%, about 0.1% to about 12%, about 0.1% to about 13%, about 0.1% to about 14%, about 0.1% to about 15%, about 0.1% to about 16%, 0.1% to about 17%, 0.1% to about 18%, 0.1% to about 19%, 0.1% to about 20%, about 0.1% to about 21%, about 0.1% to about 22%, about 0.1% to about 23%, about 0.1% to about 24%, or about 0.1% to about 25%. In some embodiments, the initial amount of other excipients utilized in the methods and compositions of the present disclosure is zero (i.e., no extra excipients).

Leptin Fusion Protein. In some embodiments of the present disclosure, the recombinant leptin receptor agonist provided herewith is comprised within a chimeric protein, wherein said chimeric protein comprising a protein fusion partner. In some embodiments, the protein fusion partner is N-terminally translationally fused to the recombinant leptin receptor agonist. In some embodiments, the protein fusion partner is C-terminally translationally fused to the recombinant leptin receptor agonist. In some embodiments, the protein fusion partner is a protein purification tag or solubility enhancer. In some embodiments, the protein purification tag is selected from the group consisting of a maltose binding protein (MBP), a histidine tag, a green fluorescent protein (GFP), a glutathione S-transferase (GST), a FLAG tag, a Strep tag comprising the amino acid peptide sequence of SEQ ID NO: 91 (WSHPQFEK), and a HA tag. In some embodiments, the protein purification tag is MBP. In some embodiments, the protein fusion partner and the recombinant leptin receptor agonist is connected via a peptide linker. In some embodiments, the peptide linker is a glycine-rich linker, a proline-rich linker, a serine-rich linker, or a protease-cleavable linker. In some embodiments, the peptide linker is a G4S linker.

Functionality of Leptin Receptor Agonist

The present disclosure provides a novel recombinant leptin receptor agonist, which exhibits a range of advantageous biochemical, pharmacological, and expression characteristics, as compared to its unmodified (e.g., lacking one or more of the beneficial substitutions recited herein), wild-type, or non-recombinant comparator/counterpart, or a control lacking one of the beneficial sequence substitutions identified in this disclosure. The recombinant leptin receptor agonist has been produced by amino acid substitution modifications as described in the methods herewith and demonstrates superior performance in both expression systems and biological assays, making it highly suitable for therapeutic or dietary supplement applications, including in the treatment of obesity and metabolic disorders.

(1) Improved degree of weight loss in overweight animals. In some embodiments of the present disclosure, the recombinant leptin receptor agonist provided herewith induces higher weight loss when administered to an overweight animal, as compared to an unmodified (e.g., lacking one or more of the beneficial substitutions recited herein), wild-type, or non-recombinant leptin. In some embodiments, the term higher weight loss refers to a reduction in body weight of at least about 1% to 100%, more specifically at least about 5%, 10%, 15%, 20%, 25%, 30%, 35%, 40%, 45%, 50%, 55%, 60%, 65%, 70%, 75%, 80%, 85%, 90%, 95%, or 100% higher than a control counterpart/comparator after at least 3 days or 4 days of treatment. In some embodiments, weight loss improvements are compared after 3, 4, 5, 6, 7, 8, 9, 10, 11, 12, 13, 14, 15, 16, 17, 18, 19, 20, 21, 22, 23, 24, 25, 26, 27, 28, 29, 30, or 31 days of treatment.

In some embodiments, the recombinant leptin receptor agonist induces a weight loss of at least about 1% in an animal. In some embodiments, the recombinant peptide agonist induces a weight loss of at least about 5% in an animal. In some embodiments, the recombinant leptin receptor agonist induces a weight loss of at least about 10%. Further embodiments include weight loss of at least about 15%, 20%, 25%, 30%, 35%, 40%, 45%, 50%, 55%, 60%, 65%, 70%, 75%, 80%, 85%, 90%, 95%, or 100% in an animal. In some embodiments, overweight animals are administered either the recombinant leptin receptor agonist or an unmodified (e.g., lacking one or more of the beneficial substitutions recited herein), wild-type, or non-recombinant leptin. In some embodiments, the recombinant leptin receptor agonist induces significantly higher weight loss, as compared to an unmodified (e.g., lacking one or more of the beneficial substitutions recited herein), wild-type, or non-recombinant leptin. In some embodiments, the recombinant leptin receptor agonist induces a weight loss (i.e., reduction in body weight) of at least about 1%, 5%, 10%, 20%, 30%, 40%, 50%, 60%, 70%, 80%, 90%, or 100% higher than an unmodified (e.g., lacking one or more of the beneficial substitutions recited herein), wild-type, or non-recombinant leptin.

(2) Notable reduction in food intake. In some embodiments of the present disclosure, the recombinant leptin receptor agonist provided herewith results in a lower food intake by an overweight animal receiving the recombinant leptin receptor agonist, as compared to an unmodified (e.g., lacking one or more of the beneficial substitutions recited herein), wild-type, or non-recombinant leptin. In some embodiments, the term lower food intake refers to a reduction in cumulative or daily food of at least about 1% to about 100%, more specifically at least about 5%, 10%, 15%, 20%, 25%, 30%, 35%, 40%, 45%, 50%, 55%, 60%, 65%, 70%, or 75% by a subject (e.g., an animal or human) over a defined period of time, relative to a control comparator after at least 2 days of treatment. The reduction can be measured in terms of weight (e.g., grams/day). In some embodiments, lower food intake is observed in subjects administered recombinant leptin receptor agonist as compared to those administered an unmodified (e.g., lacking one or more of the beneficial substitutions recited herein), wild-type, or non-recombinant leptin, under substantially similar conditions.

In some embodiments, the animal is selected from the group consisting of a cat, dog, horse, mouse, rat, rabbit, guinea pig, and pig. In some embodiments, the animal is a primate. In some embodiments, the animal is a human.

In some embodiments, the recombinant leptin receptor agonist results in a food intake reduction of at least about 1% in an animal. In some embodiments, the recombinant peptide agonist results in a food intake reduction of at least about 5% in an animal. In some embodiments, the recombinant leptin receptor agonist results in a food intake reduction of at least about 10%. Further embodiments include food intake reduction of at least about 15%, 20%, 25%, 30%, 35%, 40%, 45%, 50%, 55%, 60%, 65%, 70%, 75%, 80%, 85%, 90%, 95%, or 100% in an animal. In some embodiments, overweight animals are administered either the recombinant leptin receptor agonist or an unmodified (e.g., lacking one or more of the beneficial substitutions recited herein), wild-type, or non-recombinant leptin. In some embodiments, the recombinant leptin receptor agonist results in significantly lower food intake, as compared to an unmodified (e.g., lacking one or more of the beneficial substitutions recited herein), wild-type, or non-recombinant leptin. In some embodiments, the recombinant leptin receptor agonist results in a cumulative or daily food intake that is reduced by at least about 1%, 5%, 10%, 20%, 30%, 40%, 50%, 60%, 70%, 80%, 90%, or 100% in an animal, as compared to an unmodified (e.g., lacking one or more of the beneficial substitutions recited herein), wild-type, or non-recombinant leptin.

(3) Reduced aggregation or dimerization tendencies when expressed in a recombinant host. In some embodiments of the present disclosure, the recombinant leptin receptor agonist provided herewith exhibits reduced dimerization or aggregation when expressed in a recombinant host compared to an unmodified (e.g., lacking one or more of the beneficial substitutions recited herein) or wild-type leptin expressed in the same recombinant host. In some embodiments, the term reduced dimerization or aggregation refers to a decrease in the formation of non-covalent or covalent dimers (i.e., dimerization) or higher-order aggregates (i.e., aggregation) of the expressed agonist of at least about 1% to about 100%, more specifically at least about 5%, 10%, 15%, 20%, 25%, 30%, 35%, 40%, 45%, 50%, 55%, 60%, 65%, 70%, 75%, 80%, 85%, 90%, 95%, or 100% lower than a control comparator within 28 hours at 37° C.

In some embodiments, the recombinant leptin receptor agonist exhibits a reduction in its dimerization or aggregation at least about 1% when expressed in a recombinant host. In some embodiments, the recombinant peptide agonist exhibits a reduction in its dimerization or aggregation at least about 5% when expressed in a recombinant host. In some embodiments, the recombinant leptin receptor agonist exhibits a reduction in its dimerization or aggregation at least about 10% when expressed in a recombinant host. Further embodiments include reduced dimerization or aggregation of at least about 15%, 20%, 25%, 30%, 35%, 40%, 45%, 50%, 55%, 60%, 65%, 70%, 75%, 80%, 85%, 90%, 95%, or 100% when expressed in a recombinant host. In some embodiments, recombinant hosts are engineered to express either the recombinant peptide agonist or an unmodified (e.g., lacking one or more of the beneficial substitutions recited herein), wild-type, or non-recombinant leptin. In some embodiments, the recombinant leptin receptor agonist exhibits significantly reduced dimerization or aggregation, as compared to an unmodified (e.g., lacking one or more of the beneficial substitutions recited herein), wild-type, or non-recombinant leptin. In some embodiments, the recombinant leptin receptor agonist exhibits reduced dimerization or aggregation of at least about 1%, 5%, 10%, 20%, 30%, 40%, 50%, 60%, 70%, 80%, 90%, or 100%, relative to the unmodified (e.g., lacking one or more of the beneficial substitutions recited herein), wild-type, or non-recombinant leptin, which expresses no or minimal reduction in dimerization or aggregation.

(4) Higher expression, including notably enhanced expression in *Escherichia coli* or *Spirulina* systems under comparable conditions. In some embodiments, the recombinant leptin receptor agonist provided herewith are expressed at higher levels in *E. Coli* and/or *Spirulina*, as compared to an unmodified (e.g., lacking one or more of the beneficial substitutions recited herein), wild-type, or non-recombinant leptin. In some embodiments, the term higher expression level refers to an increase in peptide expression and/or accumulation of at least about 1% to about 100%, more specifically at least about 5%, 10%, 15%, 20%, 25%, 30%, 35%, 40%, 45%, 50%, 55%, 60%, 65%, 70%, 75%, 80%, 85%, 90%, 95%, or 100% by *E. coli* or *Spirulina* host cells engineered to express a nucleic acid encoding a recombinant leptin receptor agonist over expression of an unmodified (e.g., lacking one or more of the beneficial substitutions recited herein), wild-type, or non-recombinant leptin. In some embodiments, the recombinant leptin receptor agonist is expressed at a level that is at least about 1% higher in *E. Coli* and/or *Spirulina* relative to an unmodified (e.g., lacking one or more of the beneficial substitutions recited herein), non-recombinant control leptin expressed in *E. coli* or *Spirulina* host cells. The control leptin lacks one or more features of the improved leptin receptor agonist disclosed in the specification. In some embodiments, the recombinant leptin receptor agonist expresses at a level that is at least about 5% higher in *E. Coli* and/or *Spirulina*, as compared to a control leptin lacking one or more features of the improved leptin receptor agonist disclosed in the specification. In some embodiments, the recombinant leptin receptor agonist expresses at a level that is at least about 10% higher in *E. Coli* and/or *Spirulina*, as compared to a control leptin lacking one or more features of the improved leptin receptor agonist disclosed in the specification. Further embodiments include expression levels that are at least about 15%, 20%, 25%, 30%, 35%, 40%, 45%, 50%, 55%, 60%, 65%, 70%, 75%, 80%, 85%, 90%, 95%, or 100% higher in *E. Coli* and/or *Spirulina*, as compared to a control leptin lacking one or more features of the improved leptin receptor agonist disclosed in the specification.

(5) Stronger binding affinity to the human leptin receptor. In some embodiments, a lower equilibrium dissociation constant $K_D$ value indicates higher affinity of the recombinant leptin agonist for the human leptin receptor. In some embodiments, the recombinant leptin receptor agonist provided herewith exhibits stronger binding (lower $K_D$) to the human leptin receptor, as compared to an unmodified (e.g., lacking one or more of the beneficial substitutions recited herein), wild-type, or non-recombinant leptin. In some embodiments, the term stronger binding refers to in the enhanced affinity of the recombinant leptin receptor agonist binding to its target leptin receptor, characterized by a equilibrium dissociation constant ($K_D$), that is at least about 1% to about 100%, more specifically at least about 5%, 10%, 15%, 20%, 25%, 30%, 35%, 40%, 45%, 50%, 55%, 60%, 65%, 70%, 75%, 80%, 85%, 90%, 95%, or 100%, lower than the corresponding KD of an unmodified (e.g., lacking one or more of the beneficial substitutions recited herein), wild-type, or non-recombinant leptin to the same receptor. The equilibrium dissociation constant (Kd) can be determined using standard biophysical or biochemical techniques well known in the art.

In some embodiments, the recombinant leptin receptor agonist exhibits a binding affinity that is at least about 1% stronger than the unmodified (e.g., lacking one or more of the beneficial substitutions recited herein), wild-type or non-recombinant leptin, as indicated by a lower Kp. In some embodiments, the recombinant leptin receptor agonist exhibits a binding affinity that is at least about 5% stronger than the unmodified (e.g., lacking one or more of the beneficial substitutions recited herein), wild-type or non-recombinant leptin. In some embodiments, the recombinant leptin receptor agonist exhibits a binding affinity that is at least about 10% stronger than the unmodified (e.g., lacking one or more of the beneficial substitutions recited herein), wild-type or non-recombinant leptin. Further embodiments include binding affinities that are at least about 15%, 20%, 25%, 30%, 35%, 40%, 45%, 50%, 55%, 60%, 65%, 70%, 75%, 80%, 85%, 90%, 95%, or 100% stronger than the unmodified (e.g., lacking one or more of the beneficial substitutions recited herein), wild-type or non-recombinant leptin.

(6) Enhanced thermal resilience relative to an unmodified (e.g., lacking one or more of the beneficial substitutions recited herein), wild-type or non-recombinant leptin. In some embodiments, the recombinant leptin receptor agonist provided herewith exhibits higher thermostability compared to an unmodified (e.g., lacking one or more of the beneficial substitutions recited herein), wild-type, or non-recombinant leptin. In some embodiments, the term thermostability refers to the ability of a leptin receptor agonist to maintain its structural integrity and/or functional bioactivity at elevated temperatures. Thermostability is characterized by the receptor agonist's resistance to denaturation, aggregation, or loss of biological activity when exposed to heat. In some embodiments, a recombinant leptin receptor agonist retains at least about 1% to about 100% of its activity after being exposed to temperatures ranging from about 25° C. to about 100° C. In some embodiments, thermostability refers to the retention of at least about 5%, 10%, 15%, 20%, 25%, 30%, 35%, 40%, 45%, 50%, 55%, 60%, 65%, 70%, 75%, 80%, 85%, 90%, 95%, or 100% of the recombinant leptin receptor agonist's activity under specified thermal conditions. In some embodiments, the term higher thermostability refers to the ability of the peptide agonist to maintain its structural integrity and functional bioactivity at elevated temperatures, characterized by a retention of activity that is at least about 1% to about 100%, more specifically at least about 5%, 10%, 15%, 20%, 25%, 30%, 35%, 40%, 45%, 50%, 55%, 60%, 65%, 70%, 75%, 80%, 85%, 90%, 95%, or 100% higher than that of an unmodified (e.g., lacking one or more of the beneficial substitutions recited herein), wild-type, or non-recombinant leptin.

In some embodiments, the recombinant leptin receptor agonist exhibits a thermostability that is at least about 1% higher than the unmodified (e.g., lacking one or more of the beneficial substitutions recited herein), wild-type, or non-recombinant leptin. In some embodiments. In some embodiments, the recombinant leptin receptor agonist exhibits a thermostability that is at least about 5% higher than the unmodified (e.g., lacking one or more of the beneficial substitutions recited herein), wild-type, or non-recombinant leptin. In some embodiments, the recombinant leptin receptor agonist exhibits a thermostability that is at least about 10% higher than the unmodified (e.g., lacking one or more of the beneficial substitutions recited herein), wild-type, or non-recombinant leptin. In some embodiments. Further embodiments include thermostability levels that are at least about 15%, 20%, 25%, 30%, 35%, 40%, 45%, 50%, 55%, 60%, 65%, 70%, 75%, 80%, 85%, 90%, 95%, or 100% higher than the unmodified (e.g., lacking one or more of the beneficial substitutions recited herein), wild-type, or non-recombinant leptin.

(7) Higher structural integrity and functional bioactivity following exposure to elevated temperatures, including at least about 50° C. In some embodiments, the recombinant leptin receptor agonist provided herewith exhibits higher bioactivity after exposure to a temperature of at least about 50° C., at least about 70° C., or at least about 90° C. In some embodiments, the recombinant leptin receptor agonist exhibits higher bioactivity after exposure to a temperature between about 50° C. and about 90° C. In some embodiments, the term higher bioactivity after exposure to the specified temperatures refers to the ability of the recombinant leptin receptor agonist to retain a greater portion of its functional, biological activity of at least about 1% to about 100%, more specifically at least about 5%, 10%, 15%, 20%, 25%, 30%, 35%, 40%, 45%, 50%, 55%, 60%, 65%, 70%, 75%, 80%, 85%, 90%, 95%, or 100% after being subjected to the specified temperatures, as compared to an unmodified (e.g., lacking one or more of the beneficial substitutions recited herein), wild-type, or non-recombinant version of leptin under substantially similar conditions. In some embodiments, the recombinant leptin receptor agonist exhibits a bioactivity that is at least about 1% higher after exposure to a temperature of at least about 50° C. than the unmodified (e.g., lacking one or more of the beneficial substitutions recited herein), wild-type, or non-recombinant leptin. In some embodiments, the recombinant leptin receptor agonist exhibits a bioactivity that is at least about 5% higher after exposure to a temperature of at least about 50° C. than the unmodified (e.g., lacking one or more of the beneficial substitutions recited herein), wild-type, or non-recombinant leptin. In some embodiments, the recombinant leptin receptor agonist exhibits a bioactivity that is at least about 10% higher after exposure to a temperature of at least about 50° C. than the unmodified (e.g., lacking one or more of the beneficial substitutions recited herein), wild-type, or non-recombinant leptin. Further embodiments include bioactivity levels that are at least about 15%, 20%, 25%, 30%, 35%, 40%, 45%, 50%, 55%, 60%, 65%, 70%, 75%, 80%, 85%, 90%, 95%, or 100% higher after exposure to the specified temperatures than the unmodified (e.g., lacking one or more of the beneficial substitutions recited herein), wild-type, or non-recombinant leptin.

III. Drug Delivery Vehicles and Systems for Administering Leptin

Drug Delivery Systems. Drug delivery systems describe technologies that carry drugs into or throughout the body. They can also describe the way that drugs are 'packaged' to protect the drugs from degradation and thereby allowing them to travel wherever they need to go in the body to be therapeutically effective. Drug delivery systems are typically described in two broad categories: routes of delivery and delivery vehicles. See, e.g., National Institute of Biomedical Imaging and Bioengineering, Drug Delivery Systems, July 2022.

The present disclosure provides drug delivery vehicles and routes of drug delivery for delivering a therapeutically effective amount of a leptin receptor agonist for weight loss and/or maintenance when orally administered to an individual in need thereof. In some embodiments, the drug delivery systems of the present disclosure are administered so that the leptin compositions (i.e., delivery vehicle) act locally in the individual's gastrointestinal (GI) tract (i.e., route of delivery). In some embodiments of the delivery vehicles and systems of the present disclosure, the leptin compositions are not systemically bioavailable at a therapeutically effective amount for weight loss and/or maintenance.

Currently at least two sites of leptin action in the gut are known. One is the leptin receptors located at different places along the luminal surface of the intestine epithelium. This is below the mucus layer of the lumen but is still considered the GI lumen. Some of those receptors trigger cholecystokinin (CCK) release (another satiety hormone) and some modulate nutrient uptake. A second set of leptin receptors is on the vagal afferents that innervate the GI tract (stomach and intestine). Those afferents are located in the lamina propria which is on the non-luminal side of the GI epithelium. As used herein, these terms include these receptors as well as any other receptors in the lamina propria.

In some embodiments, the leptin delivery vehicles and systems of the present disclosure include but are not limited to living cells and organisms, dead cells and organisms, molecular compositions, chemical compositions, foods, beverages, physical devices such as mechanical force-responsive drug delivery systems, and/or electrically controlled drug release systems.

Non-Living Drug Delivery Systems. The present disclosure encompasses using any suitable non-living drug delivery system to administer the leptins of the present disclosure.

In some embodiments, the leptin can be delivered using any suitable nanoparticle, including a precision engineered nanoparticle, nanoemulsion, nanomaterial, nanostructure, nanogel, nanocapsule, nanovesicle, and/or any other suitable nanoscale drug carrier, and combinations thereof. In some embodiments, polymer-based nanocarriers that can be used as a drug delivery vehicle include but are not limited to polymeric liposomes, polymersomes, polymeric nanogels, polymeric nanocapsules, polymeric nanoparticles, dendrimers, and combinations thereof. In some embodiments, the drug delivery vehicle for the leptin can be any lipid-based nanocarrier including but not limited to nanoemulsions, phospholipid micelles, liposomes, solid lipid nanocarriers, nanostructured lipid carriers, and combinations thereof. In some embodiments, the drug delivery vehicle for the leptin can be a plant-derived nanovesicle. In some embodiments, the drug delivery vehicle for the leptin can be any suitable polyacrylamide, polyacrylate, chitosan, micelle, polymersome, dendrimer, liposome, polylactic acid (PLA), polyglutamic acid (PGA), poly(lactic-glycolic acid) (PLGA), virus, bacteriophage, bacteria-derived lipid vesicle, RNA nanoparticle, RNA vesicle, and combinations thereof. Where drug delivery uses synthetic polymeric nanoparticles, the leptin can be incorporated either during or after polymerization. Depending on the polymerization chemistry utilized, the leptin can be covalently bonded, encapsulated in a hydrophobic core, or conjugated electrostatically. See, e.g., Mitchell et al., 2020, Engineered precision nanoparticles for drug delivery, Nature Reviews Drug Discovery, 20:101-124; Afzal et al., 2022, Nanoparticles in drug delivery: from history to therapeutic applications, Nanomaterials (Basel), 12 (24): 4494; Han et al., 2018, Polymer-based nanomaterials and applications for vaccines and drugs, Polymers, 10 (1), 31; Haider et al., July 2022, Polymeric nanocarriers: a promising tool for early diagnosis and efficient treatment of colorectal cancer, Journal of Advanced Research, Vol. 39, pages 237-255; Oliver et al., 2021, Current approaches in lipid-based nanocarriers for oral drug delivery, Drug Deliv Transl Res, 11 (2): 471-497; Yu et al., 2020, Plant-derived nanovesicles: a novel form of nanomedicine, Front. Bioeng. Biotechnol., Vol. 8; and Patra et al., 2018, Nano based drug delivery systems: recent developments and future prospects, Journal of Nanobiotechnology, 16, Article No. 71.

In some embodiments, the leptin can be delivered using robotic pills. As used herein, the terms “robotic pill” or “robo-pill” each refer to a pill that can propel itself through mucus in the intestine to enable some injection-only drugs, such as insulin or certain antibiotics, to be delivered by mouth. Robotic pills respond to a physiological cue after ingestion, triggering the injection of medication payload into the walls of the gastrointestinal walls. See, e.g., National Institute of Biomedical Imaging and Bioengineering, Mar. 2, 2022, Robotic pill can orally deliver large doses of biologic drugs, Science Highlights.

In some embodiments, the leptin can be delivered using microneedle pills or capsules. As used herein, “microneedle pill” or “microneedle capsule” each refer to a pill or capsule that when swallowed passes through the stomach whole, then opens in the small intestine to reveal “microneedles” that attach to the intestine surface and deliver drugs to the bloodstream. See, e.g., Emily Matchar, Oct. 22, 2019, A “microneedle” pill you can swallow could replace insulin shots, Smithsonian Magazine, Innovation.

Living and Dead Microbes, Cells and Organisms. As used herein, the terms “synthetic living therapies”, “living drugs” or “living medicines” each refer to a type of a biologic that consists of a bioengineered living microbe, cell, or organism that is used to treat a disease, disorder, or condition. See, e.g., Wu et al., June 2022, Living cells for drug delivery, Engineered Regeneration, Vol. 3, Issue 2:131-148. In some embodiments, the cells are killed and/or lysed before delivery. Examples of microbe-based, cell-based, and organism-based therapeutics that can be used to deliver a leptin receptor agonist include but are not limited to bacteria, bacteriophages, bacteria-derived lipid vesicles, eukaryotic cells, yeast, viruses, plants, filamentous fungi, and algae. Such drugs usually take the form of a fully functional cell or a virus that has been genetically engineered or otherwise modified to possess therapeutic properties for a specific disease, disorder, or condition. See, e.g., G. Bickerton, Jan. 31, 2022, Cargo cells-safe, genetically engineered cells to precisely deliver therapeutics, BioTechniques; and A. Adams, Mar. 21, 2016, Can bioengineering transform cells into drug factories, Stanford Engineering.

In some embodiments, engineered bacteria can be used to deliver the leptin receptor agonists of the present disclosure. Many bacterial strains have been discovered as possible medication delivery systems. Examples of suitable bacteria include but are not limited to gram-positive pathogens like *Listeria monocytogenes* and *Clostridium novyi*-NT, as well as gram-negative species like *Salmonella typhimurium* and *E. coli*. See, e.g., J. Claesen and M. Fikschbach, Jul. 31, 2014, Synthetic microbes as drug delivery systems, American Chemical Society Synth. Biol. 4, 4, 358-364; Omer et al., Apr. 28, 2022 (online), Engineered bacteria-based living materials for biotherapeutic applications, Frontiers in Bioengineering and Biotechnology, 10:870675; Y. Zhou and Y. Han, September 2022, Engineered bacteria as drug delivery vehicles: principles and prospects, Engineering Microbiology, Vol. 2, Issue 3, 100034; Lynch et al., 2023, Engineered *Escherichia coli* for the in situ secretion of therapeutic nanobodies in the gut, Cell Host & Microbe, 31:634-649; and Faghihkhorasani et al., 2023, The potential use of bacteria and bacterial derivatives as drug delivery systems for viral infection, Virology Journal, 20, Article No. 222.

In some embodiments, engineered yeast can be used to deliver the leptin receptor agonists of the present disclosure. Yeast *Saccharomyces cerevisiae* is the best-studied and most widely used yeast species in industrial applications. However, other species, such as *Pichia pastoris, Hansenula polymorpha, Yarrowia lipolytica*, and *Kluyveromyces marxianus*, are also emerging as valuable tools in engineering biology. See, e.g., Jiang et al., 2023, Engineering biology of yeast for advanced biomanufacturing, Bioengineering, 10, 10. Sabu et al., 2019, Yeast-inspired drug delivery: biotechnology meets bioengineering and synthetic biology, Expert Opin Drug Deliv, 16 (1): 27-41; Tan et al., 2022, Yeast as carrier for drug delivery and vaccine construction, J Control Release, 346:358-379; Heavey et al., May 6, 2024, Targeted delivery of the probiotic *Saccharomyces boulardii* to the extracellular matrix enhances gut residence time and recovery in murine colitis, Nature Communications, 15, Article No. 3784; and P. Srinivasan and C. Smolke, 2020, Biosynthesis of medicinal tropane alkaloids in yeast, Nature, 585: 614-619.

In some embodiments, engineered plants and plant cells can be used to deliver the leptin receptor agonists of the present disclosure. See, e.g., D. Goldstein and J. Thomas, 2004, Biopharmaceuticals derived from genetically modified plants, QJM: An International Journal of Medicine, Vol. 97, Issue 11, 705-716; and Daniell et al., 2023, Plant cell-based drug delivery enhances affordability of biologics, Nature Biotechnology, 41, 1186-1187.

In some embodiments, engineered viruses can be used to deliver the leptin receptor agonists of the present disclosure. See, e.g., Shan et al., 2023, Rational design of virus-like particles for nanomedicine, Acc. Mater. Res., 4, 10, 814-826; Aljabali et al., Jul. 13, 2021 (online), The viral capsid as novel nanomaterials for drug deliver, Future Science, Vol. 7, No. 9; Sokullu et al., 2019, Plant/bacterial virus-based drug discovery, drug delivery, and therapeutics, Pharmaceuticals, 11 (5): 211; and Chung et al., 2020, Viral nanoparticles for drug delivery, imaging, immunotherapy, and theranostic applications, Adv Drug Deliv Rev., 156:214-235.

In some embodiments, engineered fungi, such as filamentous fungi, can be used to deliver the leptin receptor agonists of the present disclosure. See, e.g., Strong et al., August 2022, Filamentous fungi for future functional food and feed, Current Opinion in Biotechnology, Vol. 76, 102729; H. Wösten, October 2019, Filamentous fungi for the production of enzymes, chemicals and materials, Current Opinion in Biotechnology, Vol. 59:65-70; Nielsen et al., Jun. 4, 2021, Metabolic engineering of filamentous fungi, Metabolic Engineering: Concepts and Applications, Vo. 13b; and Wang et al., Apr. 8, 2020, Genetic engineering of filamentous fungi for efficient protein expression and secretin, Front. Bioeng. Biotechnol., Vol. 8.

In some embodiments, transient expression vector strategies, such as RNA nanoparticles or vesicles, can be used to induce the production of leptin receptor agonists of the present disclosure in gastrointestinal and mucosal tissues. See, e.g., Abramson, Alex, et al. "Oral mRNA delivery using capsule-mediated gastrointestinal tissue injections." *Matter* 5.3 (2022): 975-987; Ball, Rebecca L., Palak Bajaj, and Kathryn A. Whitehead. "Oral delivery of siRNA lipid nanoparticles: fate in the GI tract." *Scientific reports* 8.1 (2018): 2178; Van Hoecke, Lien, et al. "mRNA encoding a bispecific single domain antibody construct protects against influenza A virus infection in mice." *Molecular Therapy-Nucleic Acids* 20 (2020): 777-787.

Photosynthetic Microorganisms. In some embodiments, modified photosynthetic microorganisms are bioengineered to express or otherwise comprise leptin. Examples of photosynthetic microorganisms that can be so bioengineered include but are not limited to photosynthetic bacteria, green algae, and cyanobacteria. The photosynthetic microorganism can be, for example, a naturally photosynthetic microorganism, such as a Cyanobacterium, or an engineered photosynthetic microorganism, such as an artificially photosynthetic bacterium. Exemplary microorganisms that are either naturally photosynthetic or can be engineered to be photosynthetic include, but are not limited to, bacteria; fungi; archaea; protists; eukaryotes, such as a green alga; and animals such as plankton, planarian, and amoeba. Examples of naturally occurring photosynthetic microorganisms include, but are not limited to, *Spirulina* maximum, *Spirulina platensis, Dunaliella salina, Botrycoccus braunii, Chlorella vulgaris, Chlorella pyrenoidosa, Serenastrum capricomutum, Scenedesmus auadricauda, Porphyridium cruentum, Scenedesmus acutus, Dunaliella* sp., *Scenedesmus obliquus, Anabaenopsis, Aulosira, Cylindrospermum, Synechococcus* sp., *Synechocystis* sp., and/or *Tolypothrix.*

A modified Cyanobacteria of the present disclosure may be from any genera or species of Cyanobacteria that is genetically manipulable, i.e., permissible to the introduction and expression of exogenous genetic material. Examples of Cyanobacteria that can be engineered according to the methods of the present disclosure include, but are not limited to, the genus *Synechocystis, Synechococcus, Thermosynechococcus, Nostoc, Prochlorococcu, Microcystis, Anabaena, Spirulina*, and *Gloeobacter.*

Cyanobacteria, also known as blue-green algae, blue-green bacteria, or Cyanophyta, is a phylum of bacteria that obtain their energy through photosynthesis. Cyanobacteria can produce metabolites, such as carbohydrates, proteins, lipids and nucleic acids, from $CO_2$, water, inorganic salts and light. Any Cyanobacteria may be used according to the present disclosure.

Cyanobacteria include both unicellular and colonial species. Colonies may form filaments, sheets or even hollow balls. Some filamentous colonies show the ability to differentiate into several different cell types, such as vegetative cells, the normal, photosynthetic cells that are formed under favorable growing conditions; akinetes, the climate-resistant spores that may form when environmental conditions become harsh; and thick-walled heterocysts, which contain the enzyme nitrogenase, vital for nitrogen fixation.

Heterocysts may also form under the appropriate environmental conditions (e.g., anoxic) whenever nitrogen is necessary. Heterocyst-forming species are specialized for nitrogen fixation and are able to fix nitrogen gas, which cannot be used by plants, into ammonia ($NH_3$), nitrites ($NO_2^-$), or nitrates ($NO_3^-$), which can be absorbed by plants and converted to protein and nucleic acids.

Many Cyanobacteria also form motile filaments, called hormogonia, which travel away from the main biomass to bud and form new colonies elsewhere. The cells in a hormogonium are often thinner than in the vegetative state, and the cells on either end of the motile chain may be tapered. In order to break away from the parent colony, a hormogonium often must tear apart a weaker cell in a filament, called a necridium.

Each individual Cyanobacterial cell typically has a thick, gelatinous cell wall. Cyanobacteria differ from other gram-negative bacteria in that the quorum sensing molecules autoinducer-2 and acyl-homoserine lactones are absent. They lack flagella, but hormogonia and some unicellular species may move about by gliding along surfaces. In water columns, some Cyanobacteria float by forming gas vesicles, like in archaea.

Cyanobacteria have an elaborate and highly organized system of internal membranes that function in photosynthesis. Photosynthesis in Cyanobacteria generally uses water as an electron donor and produces oxygen as a by-product, though some Cyanobacteria may also use hydrogen sulfide, similar to other photosynthetic bacteria. Carbon dioxide is reduced to form carbohydrates via the Calvin cycle. In most forms, the photosynthetic machinery is embedded into folds of the cell membrane, called thylakoids. Due to their ability to fix nitrogen in aerobic conditions, Cyanobacteria are often found as symbionts with a number of other groups of organisms such as fungi (e.g., lichens), corals, pteridophytes (e.g., *Azolla*), and angiosperms (e.g., *Gunnera*), among others.

Cyanobacteria are the only group of organisms that are able to reduce nitrogen and carbon in aerobic conditions. The water-oxidizing photosynthesis is accomplished by coupling the activity of photosystems (PS) II and I (Z-scheme). In anaerobic conditions, Cyanobacteria are also able to use only PS I (i.e., cyclic photophosphorylation) with electron donors other than water (e.g., hydrogen sulfide, thiosulphate, or molecular hydrogen), similar to purple photosynthetic bacteria. Furthermore, Cyanobacteria share an archaeal property: the ability to reduce elemental sulfur by anaerobic respiration in the dark. The Cyanobacterial photosynthetic electron transport system shares the same compartment as the components of respiratory electron transport. Typically, the plasma membrane contains only components of the respiratory chain, while the thylakoid membrane hosts both respiratory and photosynthetic electron transport.

Phycobilisomes, attached to the thylakoid membrane, act as light harvesting antennae for the photosystems of Cyanobacteria. The phycobilisome components (phycobiliproteins) are responsible for the blue-green pigmentation of most Cyanobacteria. Color variations are mainly due to carotenoids and phycoerythrins, which may provide the cells with a red-brownish coloration. In some Cyanobacteria, the color of light influences the composition of phycobilisomes. In green light, the cells accumulate more phycoerythrin, whereas in red light they produce more phycocyanin. Thus, the bacteria appear green in red light and red in green light. This process is known as complementary chromatic adaptation and represents a way for the cells to maximize the use of available light for photosynthesis.

In some embodiments, the Cyanobacteria may be, e.g., a marine form of Cyanobacteria or a freshwater form of Cyanobacteria. Examples of marine forms of Cyanobacteria include, but are not limited to *Synechococcus* WH8102, *Synechococcus* RCC307, *Synechococcus* NKBG 15041c, and *Trichodesmium*. Examples of freshwater forms of Cyanobacteria include, but are not limited to, *S. elongatus* PCC 7942, *Synechocystis* PCC 6803, *Plectonema boryanum*, and *Anabaena* sp. Exogenous genetic material encoding the desired enzymes or polypeptides may be introduced either transiently, such as in certain self-replicating vectors, or stably, such as by integration (e.g., recombination) into the Cyanobacterium's native genome.

In other embodiments, a genetically modified Cyanobacteria of the present disclosure may be capable of growing in brackish or salt water. When using a freshwater form of Cyanobacteria, the overall net cost for production of triglycerides will depend on both the nutrients required to grow the culture and the price for freshwater. One can foresee freshwater being a limited resource in the future, and in that case it would be more cost effective to find an alternative to freshwater. Two such alternatives include: (1) the use of wastewater from treatment plants; and (2) the use of salt or brackish water.

Salt water in the oceans can range in salinity between 3.1% and 3.8%, the average being 3.5%, and this is mostly, but not entirely, made up of sodium chloride (NaCl) ions. Brackish water, on the other hand, has more salinity than freshwater, but not as much as seawater. Brackish water contains between 0.5% and 3% salinity, and thus includes a large range of salinity regimes and is therefore not precisely defined. Wastewater is any water that has undergone human influence. It consists of liquid waste released from domestic and commercial properties, industry, and/or agriculture and can encompass a wide range of possible contaminants at varying concentrations.

There is a broad distribution of cyanobacteria in the oceans, with *Synechococcus* filling just one niche. Specifically, *Synechococcus* sp. PCC 7002 (formerly known as *Agmenellum quadruplicatum* strain PR-6) grows in brackish water, is unicellular and has an optimal growing temperature of 38° C. While this strain is well suited to grow in conditions of high salt, it will grow slowly in freshwater. In some embodiments, the present disclosure contemplates the use of a Cyanobacteria *S. elongatus* PCC 7942, altered in a way that allows for growth in either wastewater or salt/brackish water. A *S. elongatus* PCC 7942 mutant resistant to sodium chloride stress has been described (Bagchi, S. N. et al., Photosynth Res. 2007, 92:87-101), and a genetically modified *S. elongatus* PCC 7942 tolerant of growth in salt water has been described (Waditee, R. et al., PNAS 2002, 99:4109-4114). According to the present disclosure, a salt water tolerant strain is capable of growing in water or media having a salinity in the range of 0.5% to 4.0% salinity, although it is not necessarily capable of growing in all salinities encompassed by this range. In some embodiments, a salt tolerant strain is capable of growth in water or media having a salinity in the range of 1.0% to 2.0% salinity. In some embodiments, a salt water tolerant strain is capable of growth in water or media having a salinity in the range of 2.0% to 3.0% salinity.

Examples of Cyanobacteria that may be utilized and/or genetically modified according to the methods described herein include, but are not limited to, Chroococcales Cyanobacteria from the genera *Aphanocapsa, Aphanothece, Chamaesiphon, Chroococcus, Chroogloeocystis, Coelosphaerium, Crocosphaera, Cyanobacterium, Cyanobium, Cyanodictyon, Cyanosarcina, Cyanothece, Dactylococcopsis, Gloecapsa, Gloeothece, Merismopedia, Microcystis, Radiocystis, Rhabdoderma, Snowella, Synychococcus, Synechocystis, Thermosenechococcus*, and *Woronichinia*; Nostacales Cyanobacteria from the genera *Anabaena, Anabaenopsis, Aphanizomenon, Aulosira, Calothrix, Coleodesmium, Cyanospira, Cylindrospermosis, Cylindrospermum, Fremyella, Gleotrichia, Microchaete, Nodularia, Nostoc, Rexia, Richelia, Scytonema, Sprirestis*, and *Toypothrix*; Oscillatoriales Cyanobacteria from the genera *Arthrospira, Geitlerinema, Halomicronema, Halospirulina, Katagnymene, Leptolyngbya, Limnothrix, Lyngbya, Microcoleus, Oscillatoria, Phormidium, Planktothricoides, Planktothrix, Plectonema, Pseudoanabaena/Limnothrix, Schizothrix, Spirulina, Symploca, Trichodesmium, Tychonema; Pleurocapsales* cyanobacterium from the genera *Chroococcidiopsis, Dermocarpa, Dermocarpella, Myxosarcina, Pleurocapsa, Stanieria, Xenococcus; Prochlorophytes* cyanobacterium from the genera *Prochloron, Prochlorococcus, Prochlorothrix*; and *Stigonematales* cyanobacterium from the genera *Capsosira, Chlorogeoepsis, Fischerella, Hapalosiphon, Mastigocladopsis, Nostochopsis, Stigonema, Symphyonema, Symphonemopsis, Umezakia*, and *Westiellopsis*. In some embodiments, the *Cyanobacterium* is from the genus *Synechococcus*, including, but not limited to *Synechococcus bigranulatus, Synechococcus elongatus, Synechococcus leopoliensis, Synechococcus lividus, Synechococcus nidulans*, and *Synechococcus* rubescens.

In some embodiments, the *Cyanobacterium* is *Anabaena* sp. strain PCC 7120, *Synechocystis* sp. strain PCC 6803, *Nostoc muscorum, Nostoc ellipsosporum*, or *Nostoc* sp. strain PCC 7120. In some embodiments, the *Cyanobacterium* is *S. elongatus* sp. strain PCC 7942.

Additional examples of Cyanobacteria that may be utilized in the methods provided herein include, but are not limited to, *Synechococcus* sp. strains WH7803, WH8102, WH8103 (typically genetically modified by conjugation), Baeocyte-forming *Chroococcidiopsis* spp. (typically modified by conjugation/electroporation), non-heterocyst-forming filamentous strains *Planktothrix* sp., *Plectonema boryanum* M101 (typically modified by electroporation), and Heterocyst-forming strains *Anabaena* sp. strains ATCC 29413 (typically modified by conjugation), *Tolypothrix* sp. strain PCC 7601 (typically modified by conjugation/electroporation) and *Nostoc punctiforme* strain ATCC 29133 (typically modified by conjugation/electroporation).

In some embodiments, the *Cyanobacterium* may be *S. elongatus* sp. strain PCC 7942 or *Synechococcus* sp. PCC 7002 (originally known as *Agmenellum quadruplicatum*).

In some embodiments, the genetically modified, photosynthetic microorganism, e.g., Cyanobacteria, of the present disclosure may be used to produce triglycerides and/or other carbon-based products from just sunlight, water, air, and minimal nutrients, using routine culture techniques of any reasonably desired scale. In some embodiments, the present disclosure contemplates using spontaneous mutants of photosynthetic microorganisms that demonstrate a growth advantage under a defined growth condition.

In some embodiments of the present disclosure, the recombinant leptin receptor agonist is expressed and/or comprised within a biological cell. In some embodiments, the biological cell is a eukaryotic cell or prokaryotic cell. In some embodiments, the biological cell is a prokaryotic cell.

In some embodiments, the biological cell is a eukaryotic cell. In some embodiments, the biological cell is a bacterial cell or a blue-green algal cell. In some embodiments, the biological cell is an *Escherichia coli* cell. In some embodiments, the biological cell is a *Cyanobacterium*. In some embodiments, the *Cyanobacterium* is *Arthrospira platensis*. In some embodiments, the biological cell is a eukaryotic cell selected from the group consisting of a filamentous fungi cell, a yeast cell, an algal cell, and a plant cell. In some embodiments, the yeast cell is *Saccharomyces cerevisiae* or *Pichia pastoris*. In some embodiments, the algal cell is *Chlorella vulgaris*.

In some embodiments of the present disclosure, the biological cell is genetically engineered to express the recombinant leptin receptor agonist. In some embodiments, the biological cell is desiccated, dried, lyophilized, and/or non-living.

IV. *Spirulina*

As used herein "*Spirulina*" is synonymous with "*Arthrospira*." The genus *Arthrospira* includes 57 species of which 22 are currently taxonomically accepted. Thus, reference to "*Spirulina*" or "*Arthrospira*" without further designation includes reference to any of the following species: *A. amethystine, A. ardissonei, A. argentina, A. balkrishnanii, A. baryana, A. boryana, A. braunii, A. breviarticulata, A. brevis, A. curta, A. desikacharyiensis, A. funiformis, A. fusiformis, A. ghannae, A. gigantean, A. gomontiana, A. gomontiana* var. *crassa, A. indica, A. jenneri* var. *platensis, A. jenneri* Stizenberger, *A. jenneri* f. *purpurea, A. joshii, A. khannae, A. laxa, A. laxissima, A. laxissima, A. leopoliensis, A. major, A. margaritae, A. massartii, A. massartii* var. *indica, A. maxima, A. meneghiniana, A. miniata* var. *constricta, A. miniata, A. miniata* f. *acutissima, A. neapolitana, A. nordstedtii, A. oceanica, A. okensis, A. pellucida, A. platensis, A. platensis* var. non-*constricta, A. platensis* f. granulate, *A. platensis* f. minor, *A. platensis* var. *tenuis, A. santannae, A. setchellii, A. skujae, A. spirulinoides* f. *tenuis, A. spirulinoides, A. subsalsa, A. subtilissima, A. tenuis, A. tenuissima*, and *A. versicolor.*

Targeted Mutations in *Spirulina.*

There are some publications reporting using *Spirulina* itself as a possible diet drug. See, e.g., Moradi et al., 2019, Effects of *Spirulina* supplementation on obesity: a systematic review and meta-analysis of randomized clinical trials, Complement Ther Med, 47:102211; Hernández-Lepe et al., 2019, Hypolipidemic effect of *Arthrospira* (*Spirulina*) maxima supplementation and a systematic physical exercise program in overweight and obese men: a double-blind, randomized, and crossover controlled trial, Marine Drugs, 17:270; and Masuda et al., 2019, Multiple micronutrient supplementation using *Spirulina platensis* during the first 1000 days is positively associated with development in children under five years: a follow up of a randomized trial in Zambia, Nutrients, 11:730.

Jester et al. (June 2022, supra) provide detailed scientific and experimental information about the development of *Spirulina* for the manufacture and oral delivery of protein therapeutics. For additional relevant scientific and experimental information for the use of *Spirulina* as a biomanufacturing platform see, for example, also, U.S. Pat. Nos. 8,835,137, 8,394,614, 8,394,621, 8,980,613, 9,523,096, 9,914,907, 10,131,870, 10,336,982, 10,415,012, 10,415,013, 10,563,168, 10,654,901, 10,760,045, 10,787,488, 11,174,294, and 11,279,912. See also, e.g., U.S. Published Patent Application Nos. US20210213124, US20210338751, and US20240002481.

As disclosed herein, we have generated novel leptins that in some embodiments are delivered into the gastrointestinal system by means of a *Spirulina*-based delivery system. These prokaryotes surprisingly protect the leptin protein cargo from the acidic environment in the stomach to deliver this bioactive payload to the upper small intestine. The disclosure provided herein demonstrates the ability of these administered leptins to inhibit food intake and decrease body weight in preclinical models in both acute and sub chronic settings.

According to the present disclosure, *Spirulina*-expressed leptin and leptin derivatives can be grown quickly and in large volumes, significantly undercutting the cost of incretin competitor molecules. *Spirulina* is also a GRAS organism widely used as a dietary supplement (Karkos et al., 2011). This makes it an attractive vehicle for direct-to-gut leptin delivery as *Spirulina*-expressed proteins do not require any further purification prior to ingestion, thus lowering the production cost and greatly increasing the ease of administration compared to injected incretins. Further, the weight loss induced by leptin is reported to be lean-body mass sparing (e.g., fat-specific). The typical result in published studies of leptin (humans and rodents) is that >95% of the weight loss from leptin is due to loss of fat. Overall, *Spirulina*-based delivery of leptin and leptin mimetics according to the present disclosure would circumvent many issues found with current anti-obesity medications.

The *Spirulina* expression platform allows for the production of a full length, bioactive leptin that is released in the GI tract where it interacts with GI located receptors. In vivo activity of *Spirulina* leptin was demonstrated by oral delivery of *Spirulina*-leptin or leptin derivatives into mice whose weights and food intake were measured. The mice were obese due to consumption of a high fat diet. Orally administered *Spirulina*-expressed leptin significantly reduced food intake and cause reduction in body weight of DIO mice compared to mice administered either buffer or wild-type *Spirulina*. These effects were maintained for at least 3 weeks of once daily dosing.

These experiments have led to our discovery of a satiety signal that is generated via a GI-local leptin pathway that is anatomically and functionally different from the well-known pathway triggered by systemically circulating leptin. Leptin administered orally via leptin-*Spirulina* was not detected in systemic circulation, confirming that its actions on food intake and weight loss are local to the GI tract. Furthermore, it is well established that obese animals are resistant to the satiety effect of circulating leptin. The ability of orally delivered *Spirulina*-leptin to induce profound weight loss in DIO mice as disclosed herein provides further evidence that its activity is mediated by a local GI pathway.

Methods of Production

We observed that leptin administered orally as a purified protein was inactive in suppressing food intake or causing weight loss. We have demonstrated in the present disclosure that delivery as a leptin-*Spirulina* complex allows for bioactivity in vivo. While not wishing to be bound to any particular theory, the positive results of the present disclosure may be due to bioencapsulation of the leptin protein inside the *Spirulina* cell, which protects it from degradation in the stomach. It is possible that other formulations which similarly protect leptin during gastric transit may also allow for leptin bioactivity in the GI tract and such alternative formulations are also encompassed by the present disclosure.

In some embodiments, the compositions of the present disclosure comprise dead cells (once they come out of the spray drier), containing expressed leptin (intracellularly). The cells are dead but visually intact under a microscope. In some embodiments, the spray drying can be done without trehalose.

Alternative Fractionation Step

A rough fractionation of the *Spirulina* cells expressing leptin may improve the dosage form. In summary, this fractionation is a simple lysis plus a tangential-flow filtration step that essentially just separates the soluble protein fraction from the cell membranes etc. This can be done using food processing equipment and processes or pharmaceutical grade equipment, but a food-grade process would not produce injection-grade purity. The primary purpose for such an additional step is to decrease the dosage size for a scenario where humans or animals are taking the oral compositions of the present disclosure, e.g., as pills, with each meal. The downsides of adding this additional step is that it can add expense and these increased costs might limit some patient access.

V. Protease Inhibitors and/or Proteinase Inhibitors

In some embodiments, the methods of administering the leptin compositions of the present disclosure include administering a protease inhibitor and/or a proteinase inhibitor before, during (i.e., simultaneously or nearly simultaneously), or after administration of the leptin compositions of the present disclosure.

Combination of a protease inhibitor or a proteinase inhibitor with a protease sensitive therapeutic or a proteinase sensitive therapeutic, respectively, may enhance the intact, active molecule local-regional or targeted cell or tissue concentration, peak concentration and/or duration of the therapeutic exposure, thereby increasing its therapeutic efficacy. As provided herein, in some embodiments the protease inhibitors and/or proteinase inhibitors protect the leptins of the present disclosure from cleavage. In some embodiments, the present disclosure provides protease inhibitors and/or proteinase inhibitors that facilitate leptin absorption. Protease inhibitors and/or proteinase inhibitors that can be used in the methods of the present disclosure include those that may be expressed as complete proteins or as peptide fragments corresponding to the active inhibitory site.

Examples of protease inhibitors and/or proteinase inhibitors that can be used in the methods of the present disclosure include are not limited to aprotinin, cathepsin inhibitor peptide sc-3130, *Neisseria* protease inhibitor, lymphocyte protease inhibitor, maspin, matrix metalloprotease inhibitors, macroglobulins, antithrombin, equistatin, Bowman-Birk inhibitor family, ovomucoid, ovoinhibitor-proteinase inhibitors from avian serum, dog submandibular inhibitors, inter-a-trypsin inhibitors from mammalian serum, chelonianin from turtle egg white, soybean trypsin inhibitor (Kunitz), secretory trypsin inhibitors (Kazal) ai-proteinase inhibitor, *Streptomyces* subtilisin inhibitor, plasminostreptin, plasmin inhibitor, factor Xa inhibitor, coelenterate protease inhibitors, protease inhibitor anticoagulants, ixolaris, human Serpins (SerpinA1(alpha 1-antitrypsin), SerpinA2, SerpinA3, SerpinA4, SerpinA5, SerpinA6, SerpinA7, SerpinA8, SerpinA9, SerpinA10, SerpinA11, SerpinA12, SerpinA13, SerpinB1, SerpinB2, SerpinB3, SerpinB4, SerpinB5, SerpinB6, SerpinB7, SerpinB8, SerpinC1 (antithrombin), SerpinD1, SerpinE1, SerpinE2, SerpinF1, SerpinF2, SerpinG1, SerpinNI1, SerpinNI2), cowpea trypsin inhibitor, onion trypsin inhibitor, alpha 1-antitrypsin, *Ascaris* trypsin and pepsin inhibitors, lipocalins, CI inhibitor, plasminogen-activator inhibitor, collagenase inhibitor, Acp62F from *Drosophila*, bombina trypsin inhibitor, bombyx subtilisin inhibitor, von Willebrand factor, leukocyte secretory protease inhibitor, $H_2$ receptor antagonists, such as cimetidine, famotidine, nizatidine and ranitidine; and proton pump inhibitors, such as omeprazole, lansoprazole, dexlansoprazole, esomeprazole, rabeprazole and ilaprazole. For a list of these and other protease inhibitors that can be used in the methods of the present disclosure see, e.g., Laskowski and Kato, 1980, Annual Review of Biochemistry, 49:593-626; U.S. Pat. Nos. 10,583,177; 10,857,233; and 11,660,327.

In some embodiments of the present disclosure, the recombinant leptin receptor agonist is comprised within a composition comprising a protease inhibitor and/or proteinase inhibitor. In some embodiments, the protease inhibitor is soybean trypsin inhibitor.

VI. Penetration Enhancers

As discussed supra, penetration enhancers are also known as permeability enhancers and/or absorption enhancers. In some embodiments, the methods of administering the leptin compositions of the present disclosure include administering a penetration enhancer before, during (i.e., simultaneously or nearly simultaneously), or after administration of the leptin compositions of the present disclosure. In some embodiments, the leptin compositions of the present disclosure may further comprise, consist essentially of, or consist of a penetration enhancer.

Combination of a penetration enhancer with a leptin therapeutic of the present disclosure may enhance the intact, active molecule local-regional or targeted cell or tissue concentration, peak concentration and/or duration of the therapeutic exposure, thereby increasing its therapeutic efficacy.

Numerous compounds have been evaluated for penetration enhancing activity, including sulphoxides (such as dimethylsulphoxide, DMSO), Azones (e.g., laurocapram), pyrrolidones (for example 2-pyrrolidone, 2P), alcohols and alkanols (ethanol, or decanol), glycols (for example propylene glycol, PG, a common excipient in topically applied dosage forms), surfactants (also common in dosage forms) and terpenes.

Penetration enhancers have been applied to improve the absorption of poorly permeable, hydrophilic drugs or macromolecules. Permeation enhancers that have been used successfully for oral drug development include but are not limited to medium-chain fatty acids like caprylic acid or caprate, or its amino acid ester like salcaprozate sodium (SNAC). These permeation/penetration enhancers have a surfactant-like activity where they perturb the intestinal epithelium, promoting transcellular or paracellular absorption.

Many different compounds have been explored as potential penetration enhancers to facilitate transdermal drug delivery. These include but are not limited to dimethylsulphoxide, azones (such as laurocapram), pyrrolidones (for example, 2-pyrrolidone), alcohols (ethanol and decanol), glycols (for example propylene glycol), surfactants, urea, various hydrocarbons and terpenes. In some embodiments of the present disclosure, the recombinant leptin receptor agonist is comprised within a composition that does not include any added permeability enhancer excipient and/or absorption enhancer excipient.

In some embodiments of the present disclosure, the recombinant leptin receptor agonist is comprised within a composition that does not include any added permeability enhancer excipient and/or absorption enhancer excipient.

VII. GLP-1 Agonists

Glucagon-like peptide-1 (GLP-1) agonists (also known as GLP-1 receptor agonists, incretin mimetics, or GLP-1 analogs) are a class of medications that mainly help manage blood sugar (glucose) levels in people with Type 2 diabetes mellitus and, in some cases, can also help treat obesity.

GLP-1 agonists are most often injectable medications (i.e., injected as a liquid medication with a needle and syringe). The shots are typically given in the fatty tissue just under the skin (i.e., subcutaneous injection) of the belly, outer thighs, upper buttocks, and/or backs of the arms.

Examples of GLP-1 agonists include but are not limited to following generic names (with their brand names in parenthesis afterwards): exenatide (twice daily, exenatide BID) (Byetta®), exenatide extended-release (once weekly, exenatide QW) (Bydureon®), lixisenatide (once daily) (Adlyxin®), liraglutide (once daily) (Victoza®), albiglutide, dulaglutide (Trulicity®), semaglutide injection (once weekly subcutaneously) (Ozempic®), and semaglutide tablets (Rybelsus®), tirzepatide (once weekly) (Zepbound®, Mounjaro®), and albiglutide (once weekly) (Eperzan®, Tanzeum®). The GLP-1 agonists above are all modified peptide drugs, but small-molecule agonists are also in development, including GSBR-1290, danuglipron, and lotiglipron.

Sides effects of GLP-1 agonists can include nausea, vomiting, constipation, and diarrhea. Less common sides effects include pancreatitis (an inflammation of the pancreas that causes abdominal pain), gastroparesis (movement of food out of the stomach is slowed or stopped), and bowel obstruction (keeps food from passing through the intestines).

Undesirable loss of muscle mass, including but not limited to lean muscle loss, can also be a major side effect of GLP-1 agonists. For example, in one clinical study involving Ozempic® the weight loss breakdown was, on average, 8.36 kg of fat and 5.26 kg of lean body mass (Wilding et al., 2021, Once-weekly semaglutide in adults with overweight or obesity, N Engl J Med, 384:989-1001 and the Supplementary Appendix, Table S5).

In some embodiments of the present disclosure, the recombinant leptin receptor agonist is comprised within a composition comprising a second active composition selected from the group consisting of amylin, cholecystokinin (CCK), a GLP-1 agonist, glucagon, gastric inhibitory polypeptide (GIP), luminal CCK-releasing factor (LCRF), *Akkermansia muciniphila* protein P9, and a CG-1 inhibitor.

VIII. Pharmaceutical and Non-Pharmaceutical Compositions and Their Administration Administration of the compositions of the present disclosure can be via any method which delivers a compound of this disclosure systemically and/or locally, including oral routes, sublingual routes, transdermal routes, etc. In accordance with this formulation, the compound of the present disclosure may be in a solid, semi-solid, or liquid form. Thus, the compositions of the present disclosure can be administered by any of the following administration methods where necessary and/or appropriate: orally, sublingually, parenteral administration (e.g., intravenous (IV), intramuscular, subcutaneous (SQ or Sub-Q) injections, or intramedullary), transdermal, via inhalation, topically, via suppository, sublingual administration, and buccal administration.

A pharmaceutical composition can be in the form of an orally acceptable dosage form including, but not limited to, capsules, tablets, buccal forms, troches, lozenges, and oral liquids in the form of emulsions, aqueous suspensions, dispersions, or solutions.

A pharmaceutical composition can be in the form of a hard or soft gelatin capsule. Capsules may contain mixtures of a compound of the present disclosure with inert fillers and/or diluents such as the pharmaceutically acceptable starches (e.g., corn, potato, or tapioca starch), sugars, artificial sweetening agents, powdered celluloses, such as crystalline and microcrystalline celluloses, flours, gelatins, gums, etc. For oral administration in a capsule form, useful diluents include lactose and dried corn starch.

If desired, certain sweetening and/or flavoring and/or coloring agents may be added. In some embodiments, the initial amount of flavoring and/or flavoring oil utilized in the methods and compositions of the present disclosure is zero (i.e., no flavoring or flavoring oil is added).

In some embodiments, the tablet can comprise a unit dosage of a compound of the present disclosure together with an inert diluent or carrier such as a sugar or sugar alcohol, for example lactose, sucrose, sorbitol, or mannitol. In the case of tablets for oral use, carriers which are commonly used include lactose and corn starch. Lubricating agents, such as magnesium stearate, can also be added. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g., swellable crosslinked polymers such as crosslinked carboxymethylcellulose), lubricating agents (e.g., stearates), preservatives (e.g., parabens), antioxidants (e.g., BHT), buffering agents (for example phosphate or citrate buffers), and effervescent agents such as citrate/bicarbonate mixtures.

The tablet can be a coated tablet. The coating can be a protective film coating (e.g., a wax or varnish) or a coating designed to control the release of the active agent, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

When aqueous suspensions and/or emulsions are administered orally, the compound of the present disclosure may be suspended or dissolved in an oily phase is combined with emulsifying and/or suspending agents.

A pharmaceutical composition can be in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present disclosure as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

The pharmaceutical compositions for use in the methods of the present disclosure can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value.

Among the surfactants for use in the compositions of the disclosure are polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides.

The present disclosure also provides packaging and kits comprising pharmaceutical compositions for use in the methods of the present disclosure. The kit can comprise one or more containers selected from the group consisting of a bottle, a vial, an ampoule, a blister pack, and a syringe. The kit can further include one or more of instructions for use in treating and/or preventing a disease, condition, or disorder of the present disclosure, one or more syringes, one or more applicators, or a sterile solution suitable for reconstituting a pharmaceutical composition of the present disclosure.

The following references, provide detailed, background information on methods of preparing pharmaceutical compositions, methods of formulating pharmaceutical compositions, and methods of their administration: U.S. Pat. Nos. 8,278,277; 8,776,802; 9,789,104; 10,463,736; 9,034,376; 10,052,286; 10,292,966; 11,878,025; 9,072,663; 9,408,835; 9,457,086; 9,918,982; 9,274,109; 9,480,661; 10,500,282; 10,226,423; 11,541,021; 11,975,104; 11,957,691; 11,877,999; 11,865,372; 11,826,325; 11,813,314; 11,773,394; 11,701,402; 11,654,183; and 11,654,114. Some of the detailed description in this section are derived from one or more of these references.

In some embodiments, the compositions, including pharmaceutical compositions, disclosed herein may be prepared by any suitable method including but not limited to spray-drying, exposure to hot air, refractive window belt drying, drying in an oven, tray drying, vacuum drying, vacuum belt drying, continuous vacuum belt drying, conveyor belt with vacuum suction, evaporation, fluidized bed drying, lyophilization, and combinations thereof. The following references provide detailed, background information on methods of preparing compositions: U.S. Pat. Nos. 6,470,597; 8,586,094; 9,427,604; 10,512,654; 10,639,283; 10,973,759; 11,191,726; 11,197,843; 11,433,027; 11,660,272; 11,752,105; 11,964,002; 11,801,222; and 11,938,133. See also, e.g., Kozanoglu et al., (2012), Influence of particle size on vacuum-fluidized bed drying, Drying Technology, 30 (2), 138-145; Haron et al., (2017), Recent advances in fluidized bed drying, IOP Conf. Mater. Sci. Eng. 243, 012038; Majumder et al., (2022), A comprehensive review of fluidized bed drying: sustainable design approaches, hydrodynamic and thermodynamic performance characteristics, and product quality, Sustainable Energy Technologies and Assessments, Vol. 53, Part C; Lakat et al., (2021), Lyophilization and homogenization of biological samples improves reproducibility and reduces standard deviation in molecular biology techniques, Amino Acids, 53 (6): 917-928; P. Manohar and N. Ramesh, (2019), Improved lyophilization conditions for long-term storage of bacteriophages, Sci Rep 9, 15242; Kasper et al., (2013), Recent advances and further challenges in lyophilization, European Journal of Pharmaceutics and Biopharmaceutics, Vol. 85, Issue 2:162-169; Sinha, et al., (2022),. Manipulation of spray-drying conditions, Pharmaceutics, 14 (7): 1432; F. Gaspar, (2014), Spray drying in the pharmaceutical industry, European Pharmaceutical Review, Issue 5; and Pinto et al., (2021) Progress in spray-drying of protein pharmaceuticals: literature analysis of trends in formulation and process attributes, Drying Technology, 39 (11): 1415-1446.

In some embodiments, the compositions, including pharmaceutical compositions, disclosed herein may also comprise other conventional pharmaceutically acceptable ingredients, commonly referred to as carriers, excipients, or adjuvants. Excipients or adjuvants include, but are not limited to: disintegrants, binders, lubricants, glidants, stabilizers, fillers, diluents, colorants, sweeteners, flavoring agents, and preservatives. For example, useful additives include materials such as agents for retarding dissolution (e.g., paraffin), resorption accelerators (e.g., quaternary ammonium compounds), surface active agents (e.g., cetyl alcohol, glycerol monostearate, and sodium lauryl sulfate), adsorptive carriers (e.g., kaolin and bentonite), preservatives, sweeteners, coloring agents, flavoring agents (e.g., chocolate mint, citric acid, menthol, glycine or orange powder), stabilizers (e.g., acid or citric sodium citrate), binders (e.g., hydroxypropylmethylcellulose), and mixtures thereof. Those of ordinary skill in the art may, by conventional experimentation, select one or more of the above carriers based on the desired properties of the dosage form without undue burden. The amount of each carrier used is within the conventional range in the art.

In some embodiments, the compositions of the present disclosure may be a powdered extract which may optionally be combined with one or more inactive, neutral compounds/ingredients which can be pharmaceutically acceptable excipients or carriers, including, but not limited to, binders, antioxidants, adjuvants, synergists and/or preservatives.

Some embodiments of the present disclosure are directed to dosage forms that are formulated as solid articles suitable for sublingual or oral administration, such as troches, lozenges, pills, oral dissolving strips, caps, pouches, or boluses. These solid dosage forms may comprise additional excipients. Both hard and chewable lozenges and troches are within the scope of the present disclosure. In some embodiments, the oral dosage forms are formulated as capsules in which the compositions of the present disclosure are encapsulated in soft or hard gelatin capsules.

Some embodiments of the present disclosure are directed to dosage forms that are formulated as topical formulations, including but not limited to creams, ointments, and gel, using formulation methods as are known in the art. In one embodiment, the topical formulation is a transdermal patch, using formulation methods and technologies as are known in the art.

Some embodiments of the present disclosure are directed to dosage forms that are formulated as solid articles suitable for administration as vaginal ovules or rectal suppositories, using formulation methods as are known in the art.

Some embodiments of the present disclosure are directed to dosage forms that are formulated as liquids, including but not limited to emulsions, liposomes, dispersions, oils, and tinctures, and beverages using formulation methods as are known in the art. A dispersible or liquid format is probably required for pediatric medical delivery.

Some embodiments of the present disclosure are directed to dosage forms that are formulated as beverages and edibles, wherein the compositions are incorporated into food, treat, and drink products. In some embodiments, the food and treat compositions may further comprise, consist essentially of, or consist of a bacteria-derived, plant-derived, or animal-derived part or product that inherently contains or that obtains via processing one or more protease inhibitors, proteinase inhibitors, permeation enhancers, penetration enhancers, and/or absorption enhancers. For example, protease inhibitors are widely distributed through nature and are found in plants, animals, and microorganisms. Protease inhibitors have been found in a great variety of plants, including most legumes and cereals and certain fruits (e.g., apples, bananas, pineapples, and raisins). It has been estimated that between 5% to 10% of the soluble proteins in barley, wheat, and rye grains are protease inhibitors. Robert A. Burns, February 1987, Protease inhibitors in processed plant foods, Journal of Food Protection, Vol. 50, No. 2, pages 161-166.

Five protease inhibitors isolated from peanut seeds were believed to be Bowman-Birk type inhibitors judging from their low molecular weights and high cysteine contents. Norioka et al., April 1982, Purification and characterization of protease inhibitors from peanuts (*Arachis hypogaea*), J Biochem, 91 (4): 1427-1434. Thus, foods formulated with peanut solids in order to make them especially tasty to mice may contain protease inhibitors from the peanuts.

Some embodiments of the present disclosure are directed to dosage forms that are formulated as smokeable or vaporizable formulations.

In some embodiments, the compositions of the present disclosure are formulated to include fully ingestible delivery mechanisms with gut absorption, wherein such formulations assist in bypassing or reducing first-pass metabolism by the hepatic system. Examples of such formulations include but are not limited to beverages, gummies, chewables, etc.

In some embodiments, the dosage forms of the present disclosure can be formulated, as appropriate, to include disintegrants, including but not limited to starch, cellulose derivatives and alginates, crosslinked sodium carboxymethyl cellulose (corscarmellose sodium) (e.g., AC-DI-SOL from FMC), hydroxypropylmethyl cellulose (HPMC), crosslinked polyvinylpyrrolidone (crospovidone), clay, cellulose, gum, crosslinked polymers (e.g., crospolyvinylpyrrolidone or crospovidone, such as POLYPLASDONE XL from ISP (International Specialty Products, Wayne, N.J.)), croscarmellose calcium, soybean polysaccharide, and/or guar gum.

The dosage forms of the present disclosure can be formulated, as appropriate, to include glidants, including but not limited to silicon dioxide, colloidal anhydrous silicon, and other silica compounds, and/or lubricants including stearic acid and salts thereof, such as magnesium stearate.

The compositions of the present disclosure can be delivered using any suitable delivery vehicle, including but not limited to robotic pills, microneedle pills, living drugs, plant-based expression systems, adding blended excipients, applying tablet coatings, using enteric capsules, and co-delivery with soluble leptin receptor. In some embodiments, the viral and non-viral vectored nucleic acids can be delivered to induce expression of the protein therapeutics of the present disclosure in host gut tissues.

In some embodiments, the oral protein therapeutics of the present disclosure can be delivered via plant-based expression systems known to those skilled in the art. Examples of such plant-based expression systems include but are not limited to those using *Spirulina*, rice, duckweed, and tobacco. In some embodiments, the plant cells of such systems are alive and in other embodiments they are dead cells. For a review of such plant-based drug delivery systems see, e.g., Eidenberger et al., Mar. 21, 2023, Plant-based biopharmaceutical engineering, Nature Reviews Bioengineering, 1:426-439.

In some embodiments, sweeteners that can be used for formulating dosage forms of the present disclosure include but are not limited to sucralose, neotame, modified steviol glycosides, neohesperidin dihydrochalcone, aspartame, acesulfame potassium, advantame, sucrose, fructose, maltitol, xylitol, sorbitol, gelatin, sodium saccharin, mannitol, and stevioside.

In some embodiments, the dosage forms of the present disclosure may optionally be formulated to further comprise one or several antioxidants. Antioxidants can increase the chemical stability of the active ingredients. Examples of pharmaceutically acceptable antioxidants include but are not limited to: (1) water-soluble antioxidants, such as ascorbic acid, cysteine hydrochloride, sodium bisulfate, sodium metabisulfite and sodium sulfite; (2) oil-soluble antioxidants, such as ascorbyl palmitate, butylated hydroxyanisole (BHA), butylated hydroxytoluene (BHT), lecithin, propyl gallate and a-tocopherol; and (3) metal chelating agents, such as citric acid, ethylenediamine tetraacetic acid (EDTA), sorbitol, tartaric acid and phosphoric acid. Additional examples of oxidants that could be used according to the present disclosure include but are not limited to a-tocopherol acetate, acetone sodium bisulfite, acetylcysteine, cysteine, tocopherol natural, tocopherol synthetic, dithiothreitol, monothioglycerol, nordihydroguaiaretic acid, propyl gallate, quercetin, sodium formaldehyde sulfoxylate, sodium metabisulfite, sodium sulfite, sodium thiosulfate, thiourea and/or tocopherols.

In some embodiments, the dosage forms of the present disclosure may optionally be formulated to further comprise one or several adjuvants or synergists. If adjuvants or synergists are used, non-limiting examples of those that can be used include citric acid, EDTA (ethylenediaminetetraacetate) and salts, hydroxyquinoline sulfate, phosphoric acid, and/or tartaric acid.

In some embodiments, the dosage forms of the present disclosure may optionally further comprise one or several preservatives. If preservatives are used, non-limiting examples of those that can be used include benzalkonium chloride, benzethonium chloride, benzoic acid and salts, benzyl alcohol, boric acid and salts, cetylpyridinium chloride, cetyltrimethyl ammonium bromide, chlorobutanol, chlorocresol, chorhexidine gluconate or chlorhexidine acetate, cresol, ethanol, imidazolidinyl urea, metacresol, methylparaben, nitromersol, o-phenyl phenol, parabens, phenol, phenylmercuric acetate/nitrate, propylparaben, sodium benzoate, sodium nitrate, potassium sorbate, sorbic acids and salts, o-phenylethyl alcohol, and/or thimerosal.

Examples of pharmaceutically acceptable surfactants for use in the present disclosure include but are not limited to polyvinylpyrrolidone, polyethylene glycol surfactants, oleic acid, and/or lecithin.

Examples of pharmaceutically acceptable lubricants and pharmaceutically acceptable glidants include, but are not limited to: silica gel, magnesium trisilicate, starch, talc, tricalcium phosphate, magnesium stearate, aluminum stearate, calcium stearate, magnesium carbonate, magnesium oxide, polyethylene glycol, powdered cellulose, and/or microcrystalline cellulose.

Examples of pharmaceutically acceptable fillers and pharmaceutically acceptable diluents include, but are not limited to: powdered sugar, compressible sugar, glucose binding agents, dextrin, dextrose, lactose, mannitol, maltitol, xylitol, microcrystalline cellulose, powdered cellulose, sorbitol, sucrose, and/or talc.

The amount of each composition or formulation of the present disclosure that may be combined with the carrier materials to produce a single dosage form will vary depending upon the individual treated and the mode of administration. Individual characteristics to be considered for proper dosage include but are not limited to weight, height, body mass index, age, health status, existing conditions, etc. In some embodiments, when the composition or formulation comprises another active agent in addition to the active ingredient, the unit dosage forms as described herein will contain a certain amount of each agent of the combination that is typically administered when the agent is administered alone.

In some embodiments, the drug-carrier complex disclosed herein is administered to a patient in need thereof in the form of a pharmaceutical composition. In some embodiments, the drug-carrier complex disclosed herein is present in a pharmaceutically effective amount.

The present disclosure provides methods comprising orally administering a therapeutically effective dose of the recombinant leptin receptor agonist provided herewith, to an individual in need thereof. In some embodiments of the methods provided herewith, the recombinant leptin receptor agonist acts locally in the individual's gastrointestinal tissues. In some embodiments of the methods provided herewith, the recombinant leptin receptor agonist is systemically bioavailable in the individual's blood in an amount less than 0.05% of the administered dose. In some embodiments of the methods provided herewith, the individual is an overweight individual. In some embodiments of the methods provided herewith, the individual is an obese individual. In some embodiments of the methods provided herewith, administration of the recombinant leptin receptor agonist results in weight loss. In some embodiments of the methods provided herewith, administration of the recombinant leptin receptor agonist results in systemic glucose reduction.

The present disclosure provides methods further comprising administering a second composition before, during, or after delivering the recombinant leptin receptor agonist, wherein the second composition is selected from the group consisting of amylin, cholecystokinin (CCK), a GLP-1 agonist, glucagon, gastric inhibitory polypeptide (GIP), luminal CCK-releasing factor (LCRF), *Akkermansia muciniphila* protein P9, and a CG-1 inhibitor. In some embodiments of the methods provided herewith, the recombinant leptin receptor agonist is orally delivered after the individual ceases administration of the GLP-1 agonist. In some embodiments of the methods provided herewith, the recombinant leptin receptor agonist is orally delivered after the individual finishes dieting. In some embodiments of the methods provided herewith, the recombinant leptin receptor agonist is orally delivered after the individual undergoes bariatric surgery.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

IX. Botanicals, Foods, and Dietary Supplements

As used herein in its broadest sense, "natural products" refer to a generic term for plants, animals, minerals, microorganisms, and their metabolites found in nature. See, e.g., K. Ahn, 2017, The worldwide trend of using botanical drugs and strategies for developing global drugs, BMB Report, 50 (3): 111-1116.

As used herein, "botanical" refers to a plant or plant part valued for its medicinal or therapeutic properties, flavor, and/or scent. Herbs are a subset of botanicals. Products made from botanicals that are used to maintain or improve health are sometimes called herbal products, botanical products, or phytomedicines. See, e.g., National Institutes of Health, Office of Dietary Supplements, Dec. 11, 2020 (updated), Botanical Dietary Supplements Background Information, Fact Sheet for Consumers.

As used herein "food" refers to (1) articles used for food or drink for man or other animals, (2) chewing gum, and (3) articles used for components of any such article. Section 201(f) of the Federal Food, Drug, and Cosmetic Act (FD&C Act) (21 U.S.C. 321(f)).

As used herein, "food additive" refers to any substance added to food that affects its characteristics (e.g., taste, color, shelf life, texture), unless it is Generally Recognized as Safe (GRAS), a prior-sanctioned substance, or exempted by regulation. Section 201 (s), FD&C Act.

As used herein, "GRAS" is a designation by the FDA that a substance added to food is considered safe by experts, and thus is exempt from the usual food additive tolerance requirements under the FD&C Act. In general, a substance is GRAS if qualified experts agree it's safe to use under the conditions intended (1) based on a history of safe use in food prior to 1958 (e.g., vinegar, salt) or (2) scientific evidence published in the public domain (like peer-reviewed studies) that supports its safety. On Aug. 17, 2016, FDA issued a final rule (The GRAS final rule; 81 FR 54960) that formalized a notification procedure and established regulations in Subpart E of part 170. The regulations state that any person may notify FDA of a conclusion that a substance is GRAS under the conditions of its intended use. The regulations further explain that any person may notify FDA of a view that a substance is not subject to the premarket approval requirements of section 409 of the FD&C Act based on that person's conclusion that the substance is GRAS under the conditions of its intended use. Subpart E of part 170 further describes how to notify FDA through the submission of a GRAS notice and explains what FDA will do with a GRAS notice. See, e.g., FDA, October 2016 (current as of Jan. 4, 2018), About the GRAS Notification Program. These procedures establish how someone can seek what is generally known as a 'No Questions GRAS Letter' from the FDA, which is also known as a GRAS Determination.

The FDA regulates botanical foods under the same framework it uses for other types of foods, dietary supplements, and drugs, depending on the product's intended use and labeling. If a botanical product is consumed as food (e.g., teas, spices, juices), the FDA treats it like any other conventional food. If a botanical is intended to treat, prevent, or cure disease, it is regulated as a drug, even if it's natural. If marketed as a dietary supplement, botanical products fall under the Dietary Supplement Health and Education Act (DSHEA) of 1994. See, e.g., S. Bass and D. McEnroe, Apr. 23, 2025, Dietary Supplement Health or Structure/Function Claims, Sidley Austin LLP.

As used herein, "drug" refers to a substance intended for use in the diagnosis, cure, mitigation, treatment, or prevention of disease. In general, the term "drug" includes therapeutic biological products. See, e.g., U.S. Food & Drug Administration, Nov. 14, 2017, Drugs-FDA Glossary of Terms.

As used herein, "botanical drug product" refers to a product containing vegetable materials, such as plant materials, algae, or macroscopic fungi, that is intended for use in the diagnosis, cure, mitigation, treatment, or prevention of disease in humans. As a result of the Biologics Price Competition and Innovation Act (BPCIA) passed in 2010, the definition of "biological product" expanded to include "proteins." FDA further defined the term "protein" so that it includes any peptide product that has an amino acid sequence greater than 40 amino acids. See, e.g., S. W. Koblitz, 2023, The Active Ingredient Stands Alone, FDA Law Blog, Hyman Phelps & McNamara.

To date, four botanical products have fulfilled the Botanical Guidance definition of a botanical drug product. The botanical drug products have been approved for marketing as prescription drugs under both the New Drug Application (NDA) and Biologics License Application (BLA) pathways. The approved NDAs include Veregen® (sinecatechins), Mytesi™ (crofelemer), and Filsuvez® (birch triterpenes). The BLA licensed product is NexoBrid® (anacaulase-bcdb). There are some botanical drugs, including cascara, psyllium, and senna, that are included in the over-the-counter (OTC) drug review. For a botanical drug substance to be included in an OTC monograph, there must be published data establishing a general recognition of safety and effectiveness, including the results of adequate and well-controlled clinical studies. See, e.g., FDA, Jan. 7, 2025, What is a Botanical Drug.

As used herein, "dietary supplement" refers to a product intended for ingestion that, among other requirements, contains a "dietary ingredient" intended to supplement the diet. The term "dietary ingredient" includes vitamins and minerals; herbs and other botanicals; amino acids; "dietary substances" that are part of the food supply, such as enzymes and live microbials (commonly referred to as "probiotics"); and concentrates, metabolites, constituents, extracts, or combinations of any dietary ingredient from the preceding categories. See, e.g., FDA, Feb. 21, 2024, Questions and Answers on Dietary Supplements.

As used herein "botanical dietary supplements" (aka herbals or herbal dietary supplements) are products made from plants, plant parts, or plant extracts. They are meant to be consumed and contain one or more ingredients meant to supplement the diet. See, e.g., National Toxicology Program, U.S. Department of Health and Human Services, Apr. 23, 2025 (updated), Botanical Dietary Supplements, Research Overview.

The FDA regulates dietary supplements under a different set of rules than those for conventional foods and drug products. Among the claims that can be used on food and dietary supplement labels are three categories of claims that are defined by statute and/or FDA regulations: health claims, nutrient content claims, and structure/function claims.

Structure/function claims (e.g., "supports immune health") are allowed, but they must be truthful and not misleading; and they must include the following disclaimer: "This statement has not been evaluated by the Food and Drug Administration. This product is not intended to diagnose, treat, cure, or prevent any disease."

Supplements must be labeled as a "dietary supplement" and include: (1) a 'Supplement Facts' panel; (2) the name and quantity of each ingredient; (3) serving size and suggested use; and (4) any other ingredients (e.g., fillers or binders).

As discussed supra, the common food algae *Spirulina* is a GRAS organism widely used as both a food and as a dietary supplement.

As used herein, "enteric" refers to anything relating to, occurring in, or affecting the intestines or gastrointestinal tract. In some embodiments, "enteric" refers to oral delivery systems designed to release active agents in the intestinal tract after bypassing the stomach. An "enteric capsule" or "enteric-coated capsule" refers to a capsule formulation that resists degradation in the acidic gastric environment and dissolves in the pH environment of the stomach until they reach the next stage of digestion and then dissolve in the less acidic or slightly alkaline intestine to be absorbed.

As used herein, "non-enteric" refers to anything that are not associated with or related to the intestines or gastrointestinal tract. In some embodiments, "non-enteric" refers to oral formulations that do not have an enteric coating. A "non-enteric capsule" refers to a standard immediate-release capsule that releases its contents in the stomach shortly after ingestion, as opposed to an enteric capsule being delayed until reaching the intestines.

As used herein, "BMI" or Body Mass Index refers to a numerical value calculated as an individual's weight in kilograms divided by the square of their height in meters ($kg/m^2$). BMI is a widely used parameter to categorize body weight status, with thresholds established for underweight, normal weight, overweight, and obesity in clinical and regulatory contexts.

The present disclosure provides that spray-dried biomass of SP3967 (400 mg) was formulated into size 0 hypromellose capsules (non-enteric). Non-obese human volunteers designated "X" and "Y" self-administered one (Y) or two (X) capsules of the product daily (q.d.) each morning for 7 days. Daily weights were gathered at the same time each morning by internet-connected home scales (WiFi- or Bluetooth-connected).

Volunteer Y's weight declined from 175.2 pounds at day 0 to 171.8 pounds at day 7 (−3.4 pounds; −1.94%), and was associated with an improvement in serum high-density lipoprotein (HDL) from a stable baseline below 31 mg/dL to 50 mg/dL and a decrease in serum triglycerides from a stable baseline measurement of 268 mg/dL to 225 mg/dL.

Volunteer X's weight declined from 175.2 pounds at day 0 to 169.0 pounds at day 7 (6.2 pounds; −3.5%) and was associated with a significant decrease in body fat from a stable baseline of 20.6% to 19.4% and no significant change in lean mass (in each case, as measured by dual-energy x-ray absorptiometry).

The present disclosure provides *Spirulina* strains expressing a variant of the human hormone protein, leptin, such as the recombinant leptin receptor agonists of the present disclosure, wherein the resultant strains and compositions comprising, consisting essentially of, or consisting of the strains are designated and used as foods or dietary supplements.

In some embodiments, the foods or dietary supplements of the present disclosure are in the form of a spray-dried biomass of a *Spirulina* strain that has been modified to express a variant of leptin, such as one or more of the recombinant leptin receptor agonists provided by the present disclosure. In some embodiments, the dietary supplements comprise, consist essentially of, or consist of spray-dried biomass of SP3967 (400 mg) formulated into size 0 hypromellose capsules (non-enteric).

In some embodiments, the present disclosure provides recombinant leptin receptor agonists and compositions comprising the recombinant leptin receptor agonists as dietary supplements and methods of their use as dietary supplements. In such embodiments, the dietary supplements comprising the recombinant leptin receptor agonists are not indicated for treating and/or preventing a disease.

In some embodiments, the present disclosure provides packages, kits, and systems comprising, consisting essentially of, or consisting of foods or dietary supplements along with labeling instructions for how to use them as foods or dietary supplements.

In some embodiments, the foods or dietary supplements comprising the recombinant leptin receptor agonists disclosed herein are used in methods for inducing and/or maintaining weight loss in individuals with a BMI >25.

In some embodiments, the foods or dietary supplements comprising the recombinant leptin receptor agonists disclosed herein are used in methods for modifying HDL, tryglicerides, fat/lean mass ratios, or other structures or functions of the body in individuals with a BMI >25.

In some embodiments, the packages, kits, and systems of the present disclosure comprise, consist essentially of, or consist of the foods or dietary supplements along with labeling instructions disclosing the dosages of the foods or dietary supplements that can be used for inducing and/or maintaining weight loss or modifying other structures or functions of the body in individuals with a BMI >25.

In some embodiments, the packages, kits, and systems of the present disclosure comprise, consist essentially of, or consist of spray-dried biomass of SP3967 (400 mg) formulated into size 0 hypromellose capsules (non-enteric) along with labeling instructions to administer one (1) or two (2) capsules daily. In some embodiments, the labeling instructions include taking the dietary supplement in the morning.

X. Translatable DIO Mouse Model

The present disclosure utilizes the diet-induced obesity (DIO) mouse model as a preclinical system for evaluating the efficacy of anti-obesity agents, including recombinant leptin receptor agonists. The DIO model is established by subjecting wild-type mice to a high-fat or energy-dense diet over a sustained period, leading to the development of obesity. The present disclosure teaches that the DIO mouse model is translatable to human obesity, owing to conserved regulatory pathways that govern energy balance, food intake, and body weight homeostasis across mammalian species. This translational relevance is supported by publications, such as *Nature Reviews Drug Discovery* (Müller et al., 2022, vol. 21, pp. 201-223), which shows a consistent correlation between body weight loss observed in DIO mice and in human subjects treated with various anti-obesity agents. This reference notes differences in mouse model response magnitudes, while replicating overall effect. This makes the DIO mouse a good model due to the larger dynamic range and more immediate impact on weight loss in rodents relative to humans.

In some embodiments, the DIO model reliably predicts the relative performance of anti-obesity interventions in humans. In some embodiments, the use of DIO mice allows for the evaluation of dose-response relationships and durability of weight loss effects in a biologically relevant setting.

In some embodiments, the experimental data described herein, including the observed effects of recombinant leptin receptor agonists on body weight reduction and food intake in DIO mice, are considered predictive of clinical relevance in humans, and support the therapeutic potential of the disclosed compositions for treating obesity and related metabolic disorders.

EXAMPLES

Example 1: Leptin Expression in *Escherichia coli*

Gen 1 leptins were produced and evaluated in *E. coli* primarily to validate bioactivity of 58 various designs before proceeding with *Spirulina* strain construction. Various iterations of the designs included using or more of the following elements: different mouse and human leptin variants; removing the signal peptide; producing various MBP (maltose binding protein) fusions at the N- and C-termini; producing different concatemers (dimers, trimers, tetramers) using flexible or rigid linkers; scaffold multimerization (dimers, trimers); various cysteine replacements, including mutations to abrogate disulfide bonds as well as C167S and C167V replacements; and various truncations (e.g., leptin 22-115).

These *E. coli* models were also used to assess the trypsin sensitivity of the peptide linkers to be used to connect MBP to leptin. And similarly the trypsin sensitivity of the linkers used in the designs were used to create tandem leptin fusion proteins. In one test, the purified leptins used as a comparison to leptin-*Spirulina* was made in *E coli.*

Based on the tests of leptin production in *E. coli* using these designs, another 42 Gen 1 leptin designs were produced and evaluated in *Spirulina*, some of which are discussed in the following examples and some of which were used as the basis for designing the Gen 2 leptins.

Example 2: Initial Expression and Testing of Bioactive Human Leptin in Recombinant *Spirulina*

Expression of Bioactive Human Leptin in *Spirulina*. Recombinant (i.e., transformed) *Spirulina*-expressed MBP-leptin were generated according to the procedures provided by Jester et al. (2022, supra). Expression of bioactive human leptin in the recombinant *Spirulina* (0.3% of dry biomass) was confirmed, leptin was successfully purified from the recombinant *Spirulina*, and the bioactivity of the purified human leptin from *Spirulina* was confirmed ($EC_{50}$=0.5 nM; data not provided). Tests demonstrated that increased pH causes rapid release of the expressed biologics (i.e., leptin) from the recombinant *Spirulina* biomass with the cargo being fully released at pH >5. This result was confirmed by bioactivity and Western Blot analyses of the recovered cargo in resuspension buffer at 30 minutes.

Pharmacokinetic (PK) Studies. In vitro PK experiments demonstrated protection of the recombinantly expressed MBP-leptin in gastric conditions and its release in intestine conditions.

Purified leptin and recombinant *Spirulina*-expressed MBP-leptin were assessed for digestibility via a widely used pepsin resistance test. Two replicates of each sample were exposed to no pepsin (i.e., gastric digestion control with no pepsin) and simulated gastric fluid consisting of 50 mM citrate-phosphate pH 3.0, 94 mM NaCl, 13 mM KCl, 1 mg/ml pepsin at 37° C. Digests were sampled after 0, 30, 60, and 120 minutes of gastric digestion. SDS-PAGE analysis definitively demonstrated that *Spirulina*-leptin is superior to the purified leptin regarding pepsin resistance. No leptin was detected for the purified leptin samples at any of the sampling times. The results clearly showed that the *Spirulina* biomass protected the intracellular leptin from pepsin digestion at pH=3.0 over the entire testing period (data not shown).

Study Using Standard DIO Protocol. This experiment followed standard DIO protocol. See, e.g., Fructuoso et al., 2019, Protocol for measuring compulsive-like feeding behavior in mice, Bio-protocol, 9 (14): e3308; and Bagnol et al., April 2012, Diet-induced models of obesity (DIO) in rodents, Current Protocols in Neuroscience, Vol. 59, Issue 1, pages 9.38.1-9.38.13.

In summary, animals were housed individually and maintained on a 45% high fat diet until they reached weight stability, at which point the experiment was initiated. Animals continued to be fed ad libitum with the 45% high fat diet and were dosed once daily at lights out with either control wild-type *Spirulina* (WT *Spirulina*) or *Spirulina*-expressed MBP-leptin (*Spirulina*-leptin). Leptin was expressed in *Spirulina* and the animals were dosed with whole, dry *Spirulina* biomass containing intracellular leptin which constituted 0.3% of the *Spirulina* biomass. Two different doses of leptin were delivered per day; either 0.03 mg or 0.18 mg. Controls were dosed with an equivalent amount of WT *Spirulina*. The lower dose was administered by gavage, and the larger dose was administered as an edible treat.

Food intake and weight loss was measured in the same experiment. Food intake was continuously measured using BioDAQ cages. Weights were measured once daily. Controls gained minimal amounts of weight in the ensuing 14 days. Animals dosed with leptin lost weight, as demonstrated in FIGS. 6C-6G.

Example 3: Leptin Expression in *Spirulina* a) Western Blot Analysis

An automated Western expression analysis was performed to determine relative expression of exemplary leptin mimetics in *Spirulina.*

Recombinant protein expression in *Spirulina* was measured by capillary electrophoresis immunoassay (CEIA) using a Jess system (ProteinSimple), which was run as recommended by the manufacturer. In brief, dried biomass samples were diluted to a concentration of 0.2 mg ml-1 using water and a 5× master mix prepared from an EZ Standard Pack 1, in either reducing or nonreducing format (Bio-Techne). Purified protein controls used to generate standard curves were typically loaded at a range of concentrations from 0.5 to 20 μg ml-1. A 12-230-kDa Jess/Wes Separation Module (ProteinSimple) was used and 3 μl of each sample was loaded for 9 s. A mouse anti-His-tag antibody (GenScript) was diluted 1:100 and used as the primary detection antibody. An anti-mouse horseradish peroxidase (HRP)-conjugated secondary antibody (ProteinSimple) was primarily used for chemiluminescent detection; fluorescently labeled anti-mouse antibodies (ProteinSimple) for infrared or near infrared fluorescence detection were used for some experiments. Data analysis was performed using the Protein Simple Compass software.

TABLE 1

Exemplary leptin mimetics.

| SEQ ID NO | Construct | Modification | Sequence |
|---|---|---|---|
| 3 | PP322-291 + SP003-036 S | N/A (Negative Control) | N/A |
| 4 | SP003-036 W | N/A (Negative Control) | N/A |
| 5 | SP1976-026 W | N/A (Negative control; irrelevant protein) | N/A |
| 6 | PP3956-001 W 8DHA-ABC-001 | mouse leptin based Rosetta structural optimization | VPIQKVIDDTKTLIKTILTRINDISYTQSVSA KQRVTGLDFIPGLHPILSLSKMLQTLAFYQ QVLLSLPSQLVLQIANDLENLRDLLILLAQ SKNCQLPDTSNLKKPESLDDILRNSLYSIEV VALSRLQIVLQDILQQLDHDPDC |
| 7 | SP3957-001 W 8DHA-ABC-002 | mouse leptin based Rosetta structural optimization | VPIQKVFDDTKTLIKTILTRINDISYTQSVS AKQRVTGLDFIPGLHPILSLSKMLQTLAFY QQVLLSLPSQLVLQIANDLENLRDLLHLLA FSKNCSLPDTSNLQKPESLDEVLRNSLYSIE VVALSRLQISLQDILQQLDVDPEC |
| 8 | SP3958-001 W 8DHA-ABC-003 | mouse leptin based Rosetta structural optimization | VPIQKVQDDTKTLIKVILTRINTLQYTQEVS SKLIVFGLDFIPGLEPILSLSKMLQTLAVYQ QVLLSLPSEDVLQIAADLENLRLLLHLLAQ SKNCQLPDTSNLKKPESLDEILRNSLYSIEV VALSRLQGSLLIILQQLDHDPDC |
| 9 | SP3959-001 W 8DHA-ABC-004 | mouse leptin based deep-learning sequence redesign structural optimization | MPIEEVRKNTKTLIKTIITKIDTIPYVQDVSP EITVTGLDFIPGDKPITSLSEAVLTLTRYRQ VLLSLPDPETQQIALDLDNLIELFRELAASK GCTLPDPSNLATPPELAEVLKDSEFAVYVT ALTKLKKNLENILKELEKDLAC |
| 10 | SP3960-001 W 8DHA-ABC-005 | mouse leptin based deep-learning sequence redesign structural optimization | RPLEQVRRDLKTLIKTIITKIDTIPYVQDVN PDITVTGLDFIPGNRPITSLSEAKKTLTKYV QVLESLDDPETQEIALDLKNVIELIDELAKS RGCTLPDTSTLEKDPRLEEVKKDSEFAITT TALRNLKINLEIILKELERDPAC |
| 11 | SP3961-001 W 8DHA-ABC-006 | mouse leptin based deep-learning sequence redesign structural optimization | VPIEKVREDLKTLIKTIIKKIDTIPEVQDVSP EITVTGLDFIPGNEPINSLSEAVLTLTRYRQ VLESLDDPETQQIALDLQNLIELLKELAKE KGCTLPDPSNLKKPEELEKVLEDAEFAVR VTALTNLKKNLENILKVLETDPAC |
| 12 | SP3962-001 W 7Z3Q-ABC-001 | human leptin based Rosetta structural optimization | VPIQKVQDDTKTLIKTIITRINDISHTQSVSS KVKVTGLDFIPGRHPILTLSKMDQTLAVY QQILTSMPDPNVIQIANDLENLRDLLHVLA FSKSCPLPWASGLETLDSLRKVLEASLYST EVVALSRLQGVLQDMLKQLDLSPGC |
| 13 | SP3963-001 W 7Z3Q-ABC-002 | human leptin based Rosetta structural optimization | VPIQKVQDDTKTLIKTIITRINDISHTQSVSS KVKVTGLDFIPGRHPILTLSKMDQTLAVY QQILESMPDPNVIQIANDLENLRDLLHVLA FSKSCPLPWASGLETLDSLRKVLEASLYST EVVALSRLQGVLQDMLKQLDLSPGC |
| 14 | SP3964-001 W 7Z3Q-ABC-003 | human leptin based Rosetta structural optimization | VPIQKVFDDTKTLIKTIITRINTIEHTQSVSS KIKVTGLDFIPGLQPILTLSKMDQTLAVYQ QILLSMPVPLVIQIAADLENLRLLLHLLAKS KNCPLPWASGLEDEDMLRRVLEASLYSTE VVTLLRLQGVLLQMLEQLDLSPGC |
| 15 | SP3965-001 W 7Z3Q-ABC-004 | human leptin based deep-learning sequence redesign structural optimization | VPLEKIREDTKTLIRTIITRIDQIPYVADVSP KQKVTGLDFIPGTKDKYTYSDFAATLAKY REILSATDDPELQQIALDLDNLIDLIRELAK SKGCPLPEATGLPDPEKLKEALKESGYSVE VETARKLKAFLEKALEELEKDPGC |
| 16 | SP3966-001 W 7Z3Q-ABC-005 | human leptin based deep-learning sequence redesign structural optimization | VPEEQIRNDLKTLTKTIITRIDQIPAVKEVSP KQKVTGLEIIPGTKDKYTFTDMSATLAVY REIFSMLDEPEVQQIALDLDNLIDLIKELAK TKGCPLPEAKGVADKAKIEELIKESGYSVY VTTATNLKAVLEKFIKELEKDPGC |

TABLE 1-continued

| Exemplary leptin mimetics. | | | |
|---|---|---|---|
| SEQ ID NO | Construct | Modification | Sequence |
| 17 | SP3967-001 W 7Z3Q-ABC-006 | human leptin based deep-learning sequence redesign structural optimization | VPVEQIRKDLETLIRTVITRIDTIPYVKEVSP KQKVTGLEFIPGTKEKITYTDADETLAIYQ EILSLLPEPELQQIALDLDNIRDLIRELAAT KNCPLPRASGLPDREKLLEAIKESGYSVAV TTATKLKEFLEKLIEELKKDPGC |

FIG. 1A provides a reproduction of the blot depicting the relative expression for each mimetic as compared to control.

b) ELISA Analysis

ELISA analysis was additionally conducted to quantify leptin protein concentration. In brief, *Spirulina* were modified to express WT human leptin, resulting in the strain SP2334. An extract from batch 012 of SP2334 was compared to an extract from a negative control strain (SP1976-026) expressing an irrelevant protein and an identical leptin protein purified from *E. coli* as a control (PP2054-012), see FIG. 1B. The extract from Sp2334-012 was less potent than purified leptin protein, because less than 1% of the protein in the extract is leptin.

High-binding, 96-well plates (Greiner Bio-one) were coated with antigen by the addition of 92 μl of 1 μg/ml recombinant protein (hLeptin receptor 6H/Fc) in carbonate-bicarbonate buffer (Sigma) to each well and incubation overnight at 4° C. Plates were washed three times with 300 μl of PBS supplemented with 0.05% Tween-20 (PBS-T). Washed plates were blocked with 184 μl of PBS-T supplemented with 5% nonfat dry milk (PBS-TB) for 2 h at room temperature. Blocking solution was discarded, and 150 μl of leptin-expressing *Spirulina* sample was added to each well. Samples were prepared by dilution of purified protein or *Spirulina* extracts with PBS-TB, and samples in a dilution series were serially diluted with PBS-TB. Samples were incubated at room temperature for 1 h to allow binding of leptin to receptor. After incubation, plates were washed three times with 300 μl of PBS-TB. Wash was discarded. Then 92 μl of anti-MBP HRP antibody was diluted in carbonate-bicarbonate buffer to a concentration of 35 ng/mL and added to each well. The plates were incubated at room temperature for 1 h. Plates were developed using the 1-Step Ultra TMB-ELISA Substrate Solution (Thermo Scientific) following the manufacturer's recommendations. Peroxidase activity was quenched after 5-10 min with 75 μl of 1 M HCl. Absorbance at 450 nm (A450) was measured on a Tecan plate reader. All samples were tested in duplicate. Data analysis was performed using Prism (GraphPad Software).

Figure 1B:
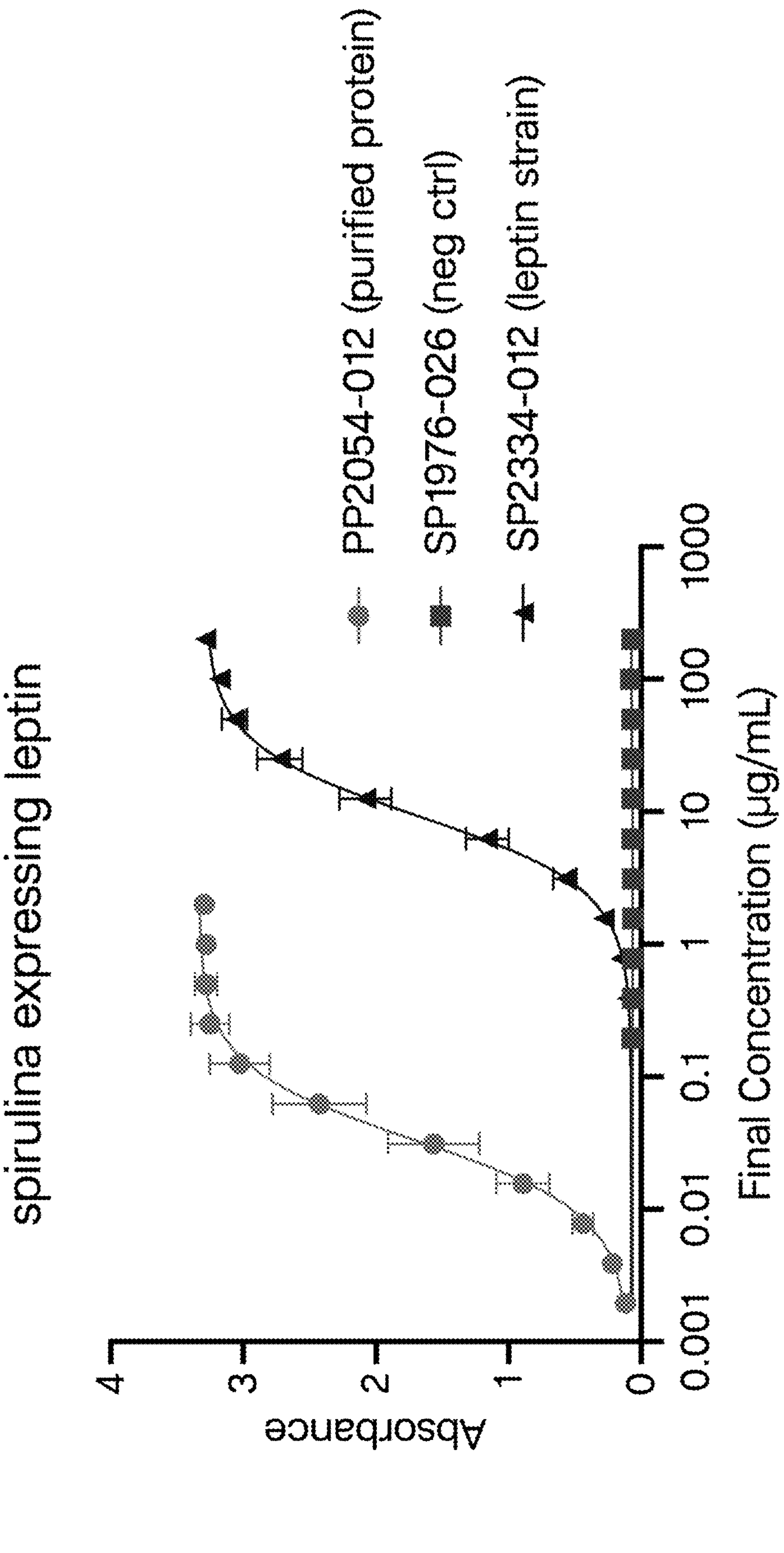
FIG. 1B shows results of an ELISA assay comparing *Spirulina*-expressed leptin, SP2334-012, to purified control leptin, PP2054-012, and to the negative control, SP1976-026. The "–012" and "-026" suffixes indicate the batch number. Every time a new culture is started from a frozen stock, it gets its own batch number designation.

Results show that as compared to negative and purified protein control, the *Spirulina*-expressed leptin exhibited a surprisingly increased protein concentration, as demonstrated in FIG. 1B.

Example 4: Evaluation of Leptin Mimetic Functionality

A bioluminescence assay was completed to determine functionality of leptin purified from *Spirulina* (PP2054-012) as compared to control purified leptin. In brief, 293T cells expressing luciferase activated by leptin receptor engagement were exposed to control and *Spirulina*-expressed purified leptin (PP2054-012).

Leptin reporter 293T cells were seeded in poly-L-lysine (Sigma-Aldrich, Cat #P4707) coated black 96 well plates (Corning, Cat #3904) at 30,000 cells/well in 100 μl of DMEM (Gibco, Cat #11965118) with 10% FBS and penicillin/streptomycin (100 U/ml, Thermo scientific, Cat #15140122). The cells were incubated for 24 hr at 37° C. in a humidified incubator with 5% $CO_2$. *Spirulina* lysates expressing leptin were made at 10 mg/ml of biomass in 1×PBS with 1× Halt protease inhibitor cocktail (Thermo scientific, Cat #87786). *Spirulina* cells were lysed using a bead beater 3 times for 30 sec with 5 min incubation on ice between each bead beating cycle. Soluble protein fraction was collected by spinning down the lysates for 15 min at 15,000 RCF at 4° C. Control *Spirulina* lysate was filtered through a 0.2 μm filter, diluted 20-fold in media and used as diluent matrix. *Spirulina* extracts expressing leptin and purified leptin (R&D, Cat #398-LP-01M) were then serially diluted in the matrix. 50 μL of media was removed from each of the 293T seeded wells. 50 μL of *Spirulina* extract or purified leptin dilutions were then added to the wells. Plates were then incubated at 37° C. in a humidified incubator with 5% $CO_2$ for 21 hr. At the end of the incubation period, 70 μL of media was removed from the treated wells. 30 μL of 2× Bright glow luciferase reagent (Promega, Cat #E2620) was added to the treated wells. Plate was incubated in dark for 2 min to ensure complete cell lysis and luciferase signal was read using a Tecan plate reader.

Figure 2:
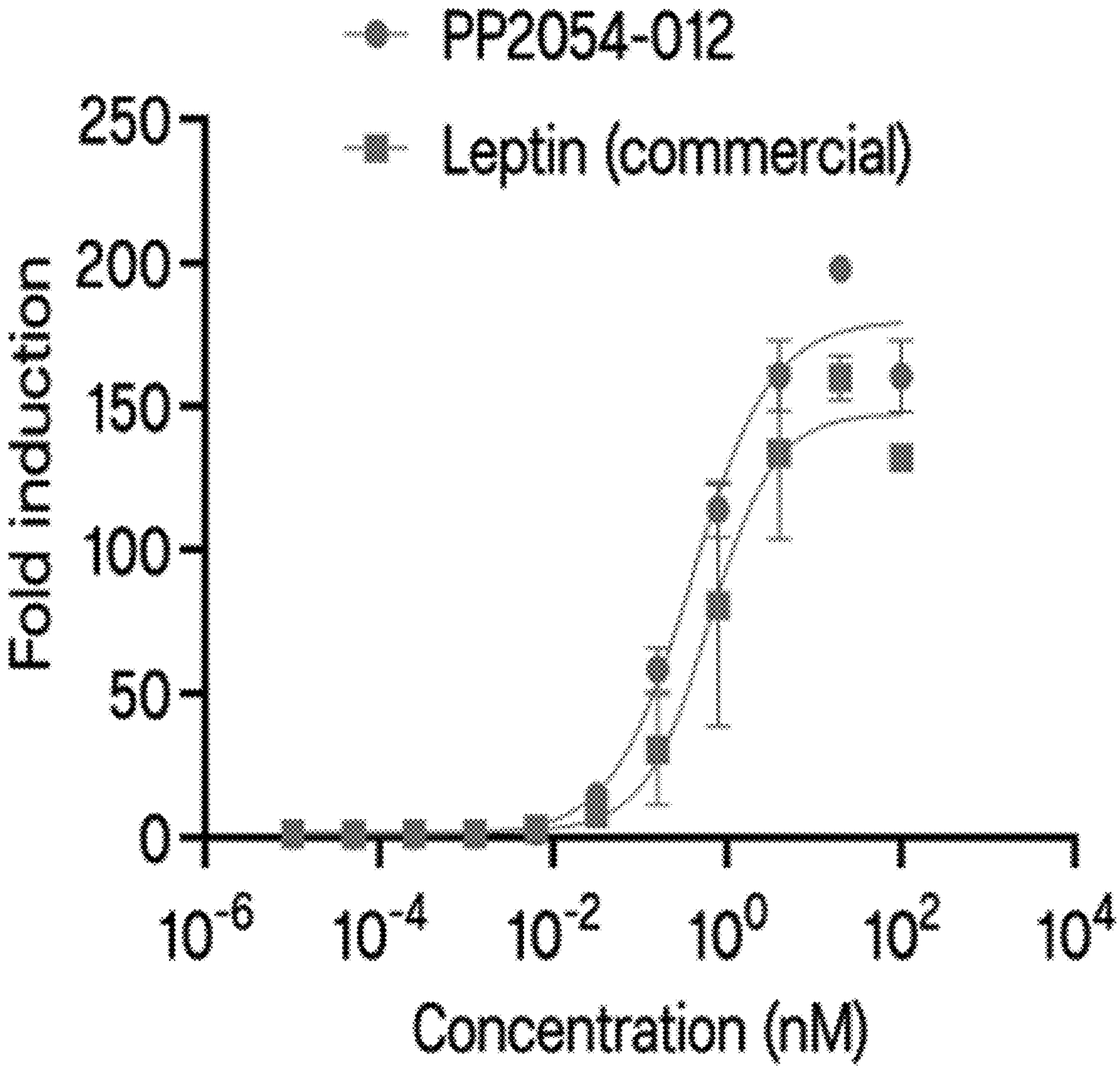
FIG. 2 shows results of a bioluminescence analysis comparing *Spirulina*-expressed leptin to commercially available purified control leptin.

Results at FIG. 2 show that, as compared to control, the *Spirulina*-expressed leptin demonstrated comparable activity thereby establishing that the *Spirulina* expression does not negatively impact its functionality.

Example 5: Leptin Protease Sensitivity Assessment

Poly-histidine tagged proteins of interest were expressed in *E. coli* and purified using standard nickel affinity purification. Once purified, proteins were diluted to a concentration of 200 μg/mL in protease digest buffer (20 mM Bis-Tris, 150 nM NaCl, 3 mM CaCl2, pH 6.0). 10 μL of the resuspended protein was mixed with 10 μL of protease (trypsin or chymotrypsin). The sample was incubated at 37 C with shaking at 600 RPM in a Thermomixer for 1 hr. 20 μL of 2 mM PMSF resuspended in PBS was added to the sample to stop the protease digest reaction. Sample was then analyzed by a bioluminescence binding assay as described above.

Figure 3A:
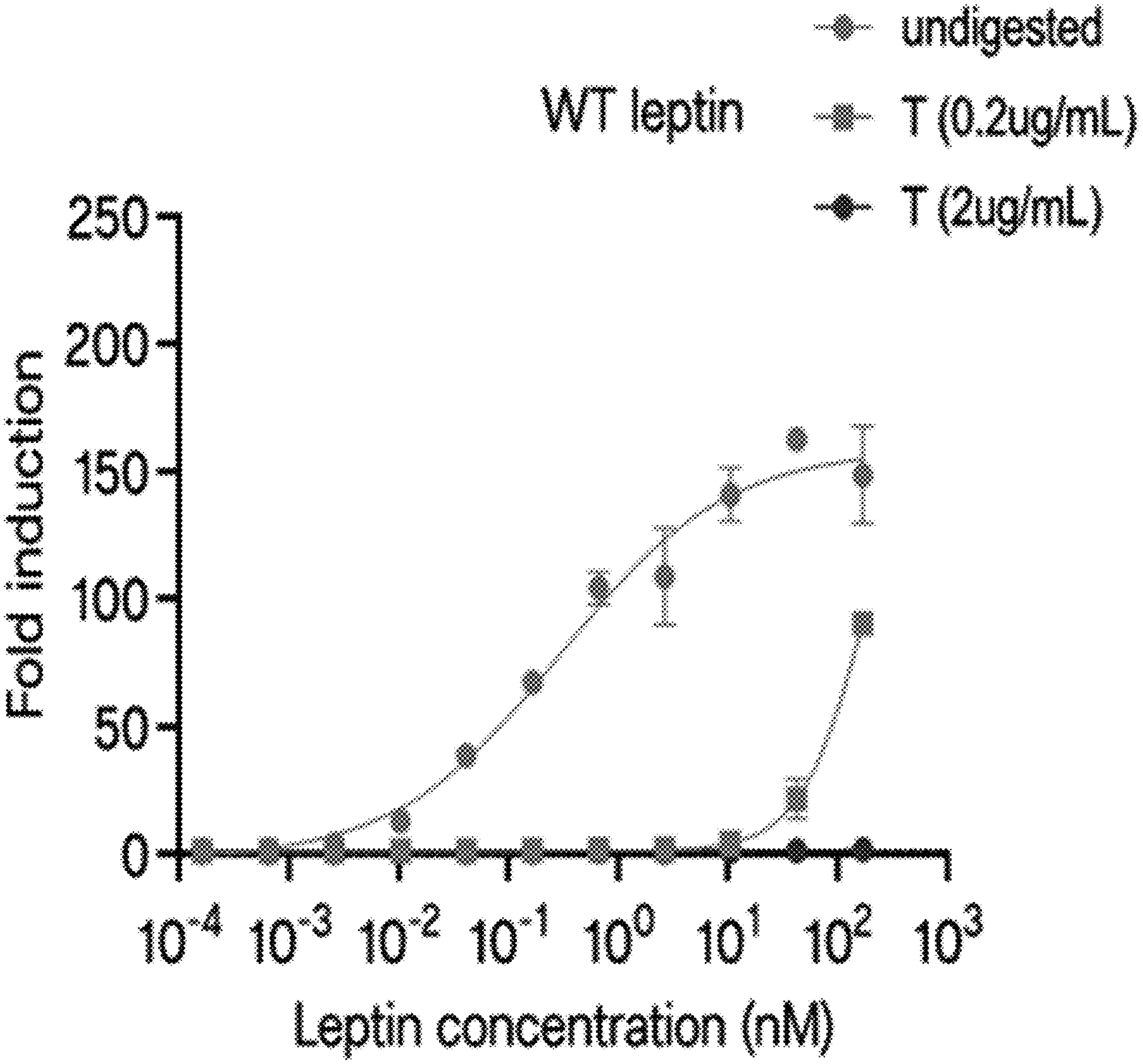
FIGS. 3A-3B show results of a bioluminescence analysis comparing trypsin resistance of *Spirulina*-expressed leptin (FIG. 3B), which is de novo mimetic (7Z3Q-ABC-006, 56% consensus), to *Spirulina*-expressed WT leptin (FIG. 3A) at concentrations of 0.2 μg/mL or 2 μg/mL.
Figure 3B:
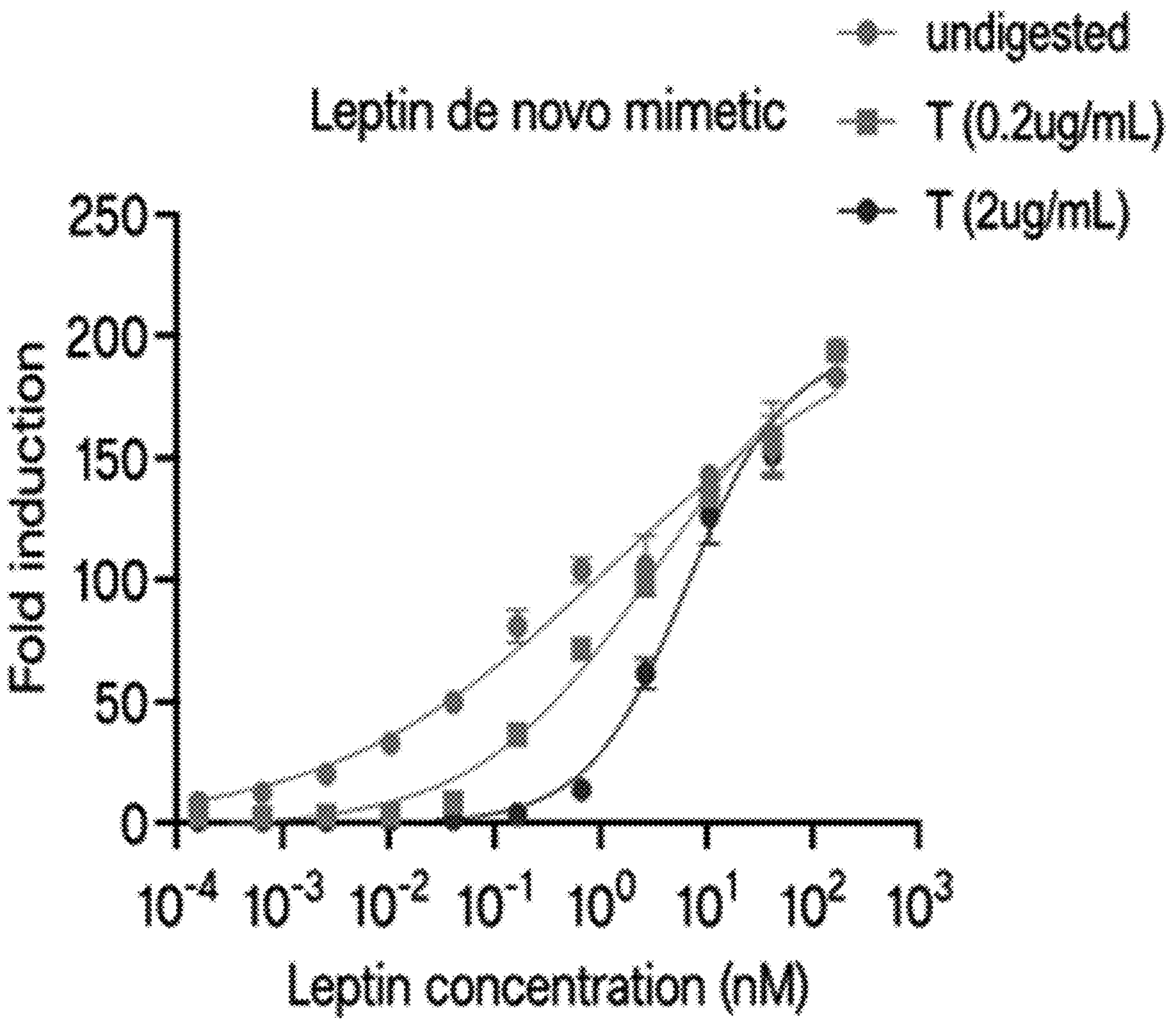

FIG. 3 results show that, as compared to WT leptin control, the exemplary mimetic leptin exhibited increased resistance to trypsin digestion in a dose dependent fashion.

Example 6: Leptin Protein Design

Message passing neural network (MPNN), such as AlphaFold2, ColabFold, ProteinMPNN, and Rosetta, were utilized to design Leptin mutants.

Figure 4:
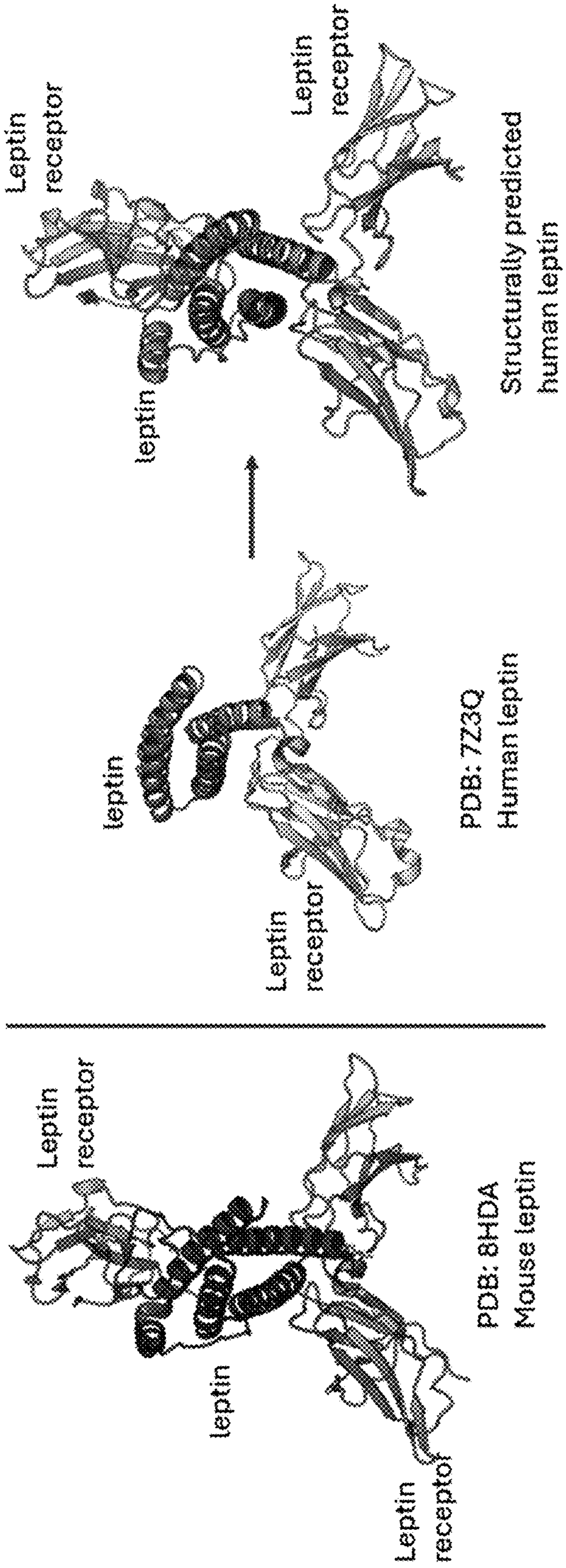
FIG. 4 shows crystal structures for mouse leptin (left) and human leptin (right).

De novo designs were based on either the 8DHA crystal structure (rcsb.org/structure/8DHA) of mouse leptin bound to receptor or the 7Z3Q crystal structure (rcsb.org/structure/7Z3Q) of human leptin bound to receptor. Sequences were designed using either ProteinMPNN or Rosetta. AlphaFold was used to predict the designed structures. Finally, the designs were filtered on computational metrics from structure prediction and Rosetta-based energy scores In brief, available structural information on the leptin protein was ascertained to determine amino acid residues to preserve and those available for design. Preliminary 3D structures were obtained from the program for both mouse and human leptin, see FIG. 4. Afterwards, ProteinMPNN was employed for sequence design and AlphaFold was subsequently used to identify predicted design structures. Finally, designs were filtered on computational metrics from structure prediction and Rosetta-based energy scores.

Figure 5A:
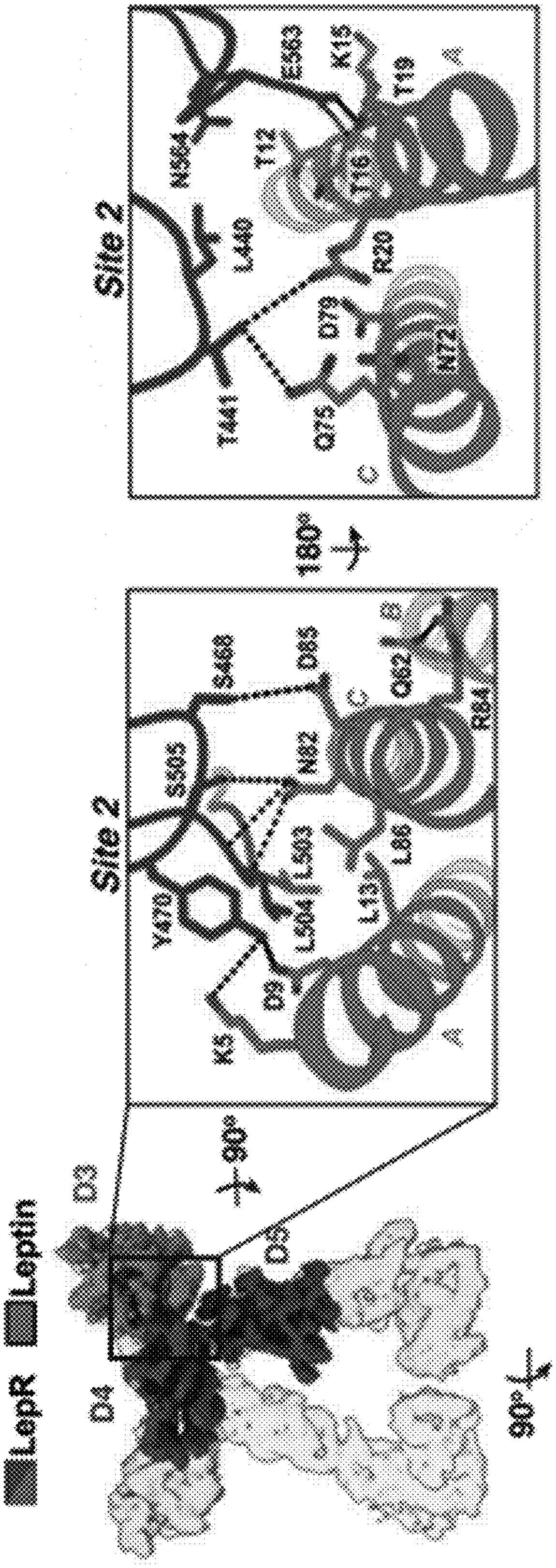
FIG. 5A is a graphic depicting fixed positions available for design within Site 2.
Figure 5B:
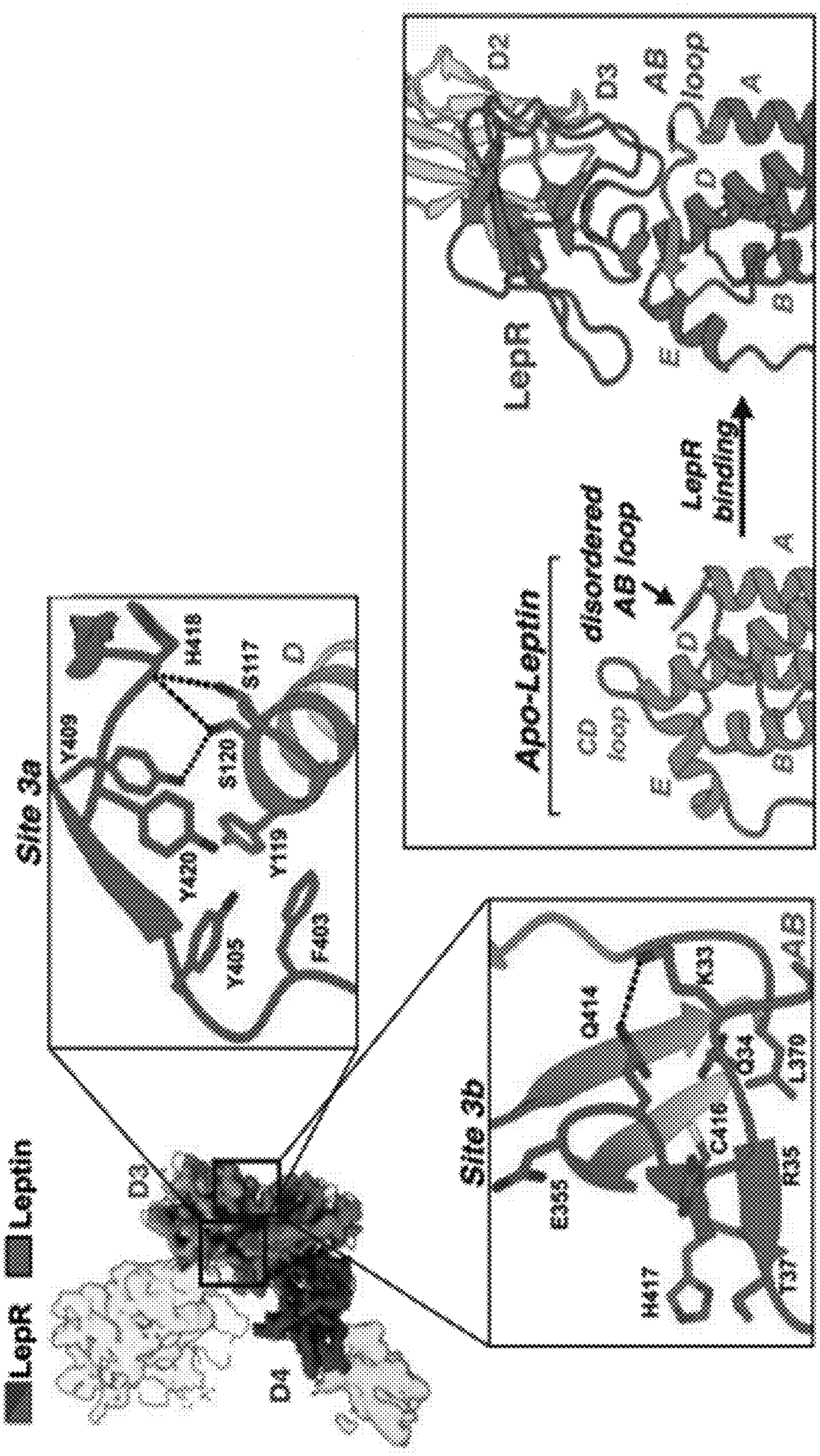
FIG. 5B is a graphic showing fixed positions available for design within Site 3. (Saxton, R. A., Caveney, N. A., Moya-Garzon, M. D. et al. Structural insights into the mechanism of leptin receptor activation. Nat Commun 14, 1797 (2023)).

FIG. 5A depicts fixed positions available for design within site 2. FIG. 5B shows fixed positions available for design within site 3. Specifically, within 8DHA (Leptin-bound leptin receptor complex-focused interaction), the fixed positions are: 5, 9, 12, 16, 19, 20, 23, 24, 25, 27, 28, 29, 30, 31, 32, 33, 34, 35, 36, 37, 38, 39, 40, 41, 42, 43, 44, 45, 46, 47, 48, 49, 50, 70, 71, 75, 78, 79, 81, 82, 85, 117, 119, 120, and 122. Within the 7Z3Q (human leptin: LepR-CRH2 complex), the fixed positions are: 9, 13, 16, 20, 33, 34, 35, 36, 37, 75, 85, 86, 117, 119, and 120.

Example 7: Exemplary Constructs

Human leptin 22-167AA V94M Mutant

Construct designs incorporate solubility enhancers connected to the leptin and leptin derivative molecules with a protease-cleavable linker as well as a polyhistidine tag for affinity purification. Expression in *Spirulina* is driven by the pCPC600 promoter, a native *Spirulina* promoter. The molecule is expressed from a genomically integrated transgene at a neutral site (Jester et al., 2022). The unmodified human leptin sequence ("wild type" leptin) contains the valine-to-methionine polymorphism at position 94 (Courbage et al., 2021) expressed starting at position 22 to eliminate amino acids 1-21, which comprise a secretion tag (Zhang et al., 1994).

FIG. 6A provides an exemplary leptin construct. The construct comprises: an N terminal MBP (maltose binding protein) acting as solubilization agent; a G4S linker between MBP and leptin which serves as a trypsin-cleavable sequence for potential duodenal site-specific release of leptin; human leptin with a valine-to-methionine variant at position 94; and the *Arthrospira platensis* native pCPC600 promoter.

TABLE 2

Human leptin 22-167AA V94M Mutant DNA and Amino Acid Sequences.

| ID | SEQ ID NO | Amino Acid |
|---|---|---|
| MBP | 65 | MKIEEGKLVIWINGDKGYNGLAEVGKKFEKDTGIKVTVEHPDKLE EKFPQVAATGDGPDIIFWAHDRFGGYAQSGLLAEITPDKAFQDKL YPFTWDAVRYNGKLIAYPIAVEALSLIYNKDLLPNPPKTWEEIPAL DKELKAKGKSALMFNLQEPYFTWPLIAADGGYAFKYENGKYDIK DVGVDNAGAKAGLTFLVDLIKNKHMNADTDYSIAEAAFNKGETA MTINGPWAWSNIDTSKVNYGVTVLPTFKGQPSKPFVGVLSAGINA ASPNKELAKEFLENYLLTDEGLEAVNKDKPLGAVALKSYEEELAK DPRIAATMENAQKGEIMPNIPQMSAFWYAVRTAVINAASGRQTVD EALKDAQT |
| G4S linker | 66 | SGGGGGSKGGGGSA |
| V94M Mutant Leptin | 67 | GGVPIQKVQDDTKTLIKTIVTRINDISHTQSVSSKQKVTGLDFIPGL HPILTLSKMDQTLAVYQQILTSMPSRNMIQISNDLENLRDLLHVLA FSKSCHLPWASGLETLDSLGGVLEASGYSTEVVALSRLQGSLQDM LWQLDLSPGCSS |

In vitro Results for Human Leptin 22-167AA V94M Mutant

Confirmation of leptin receptor binding was completed via both leptin receptor ELISA as well as a eukaryotic cell culture system in which engagement of the leptin receptor and activation of a downstream signal transduction pathway was monitored by transcriptional activation of a reporter gene encoding luciferase.

Table 3 provides results of in vitro assays evaluating expression, binding, and protease resistance for the human leptin V94M Mutant. The study methodologies for each assay are described above.

TABLE 3

In vitro results of human leptin V94M Mutant Expression, Binding, and Protease Resistance.

| | | | Expression | | Binding | Protease resistance, % | |
|---|---|---|---|---|---|---|---|
| | | | | Jess % | $IC_{50}$ protein | untreated | |
| Sample ID | Protein Product | Description | Active, % DW ELISA | Soluble DW | luciferase assay | trypsin 0.2 μg/mL | chymotrypsin 10 μg/mL |
| SP2334 | PP2054 | MBP-(G4S)-human leptin V94M-6His | 0.2-0.3 | 0.3-0.5 | 0.4 | 0.09 | 0 |

Weight Loss Study for Human Leptin 22-167AA V94M Mutant

A study was completed demonstrating efficacy of the human leptin in promoting weight loss in mice. The V94M natural polymorphism of human leptin was used in these experiments.

Figure 6C:
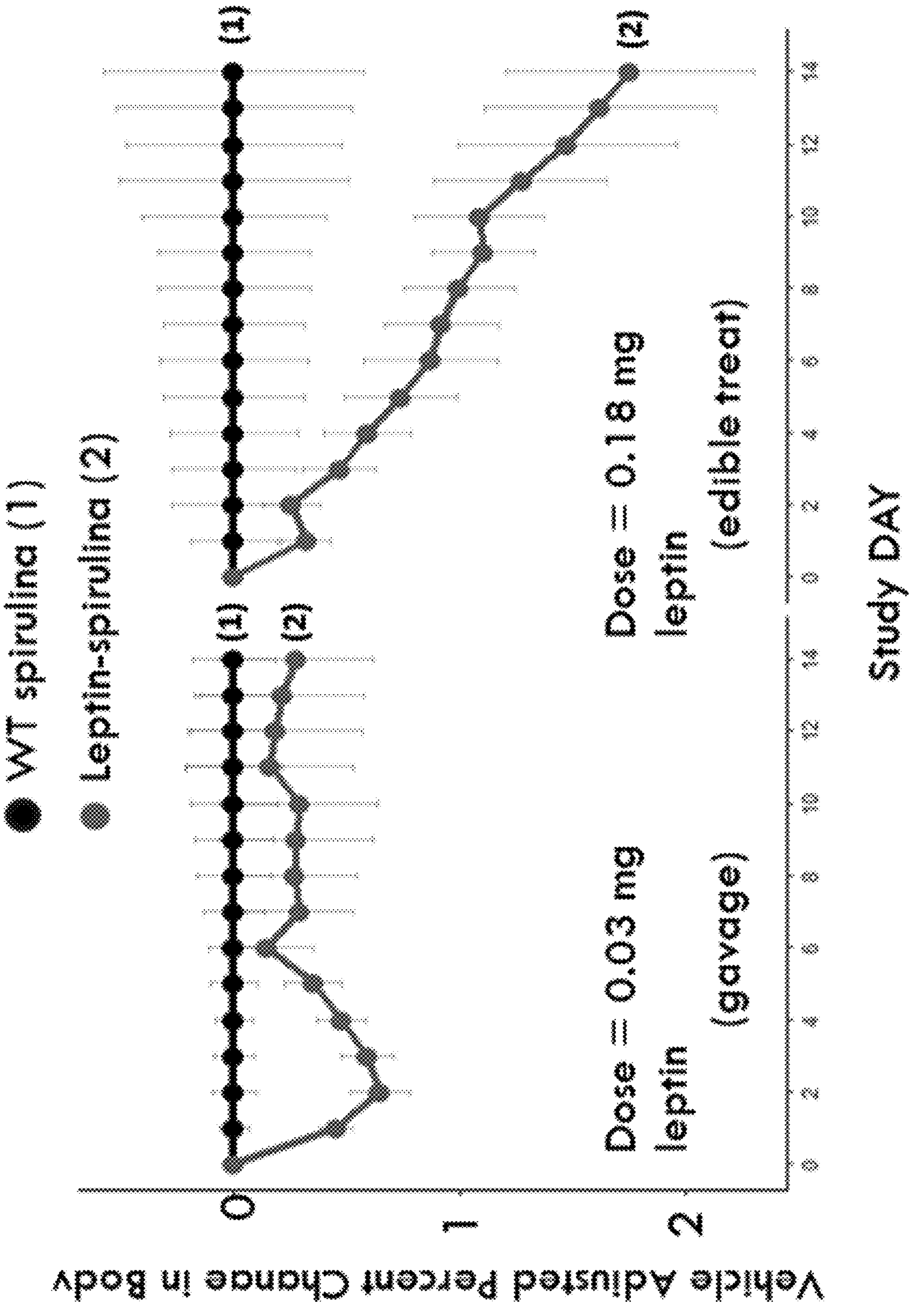
FIG. 6C provides results of an in vivo chronic dosage study of *Spirulina* strain UTEX "SP3" (WT *Spirulina*, control) and SP2334 (Leptin-*Spirulina*) in diet-induced obese (DIO) mice.
Figure 6D:
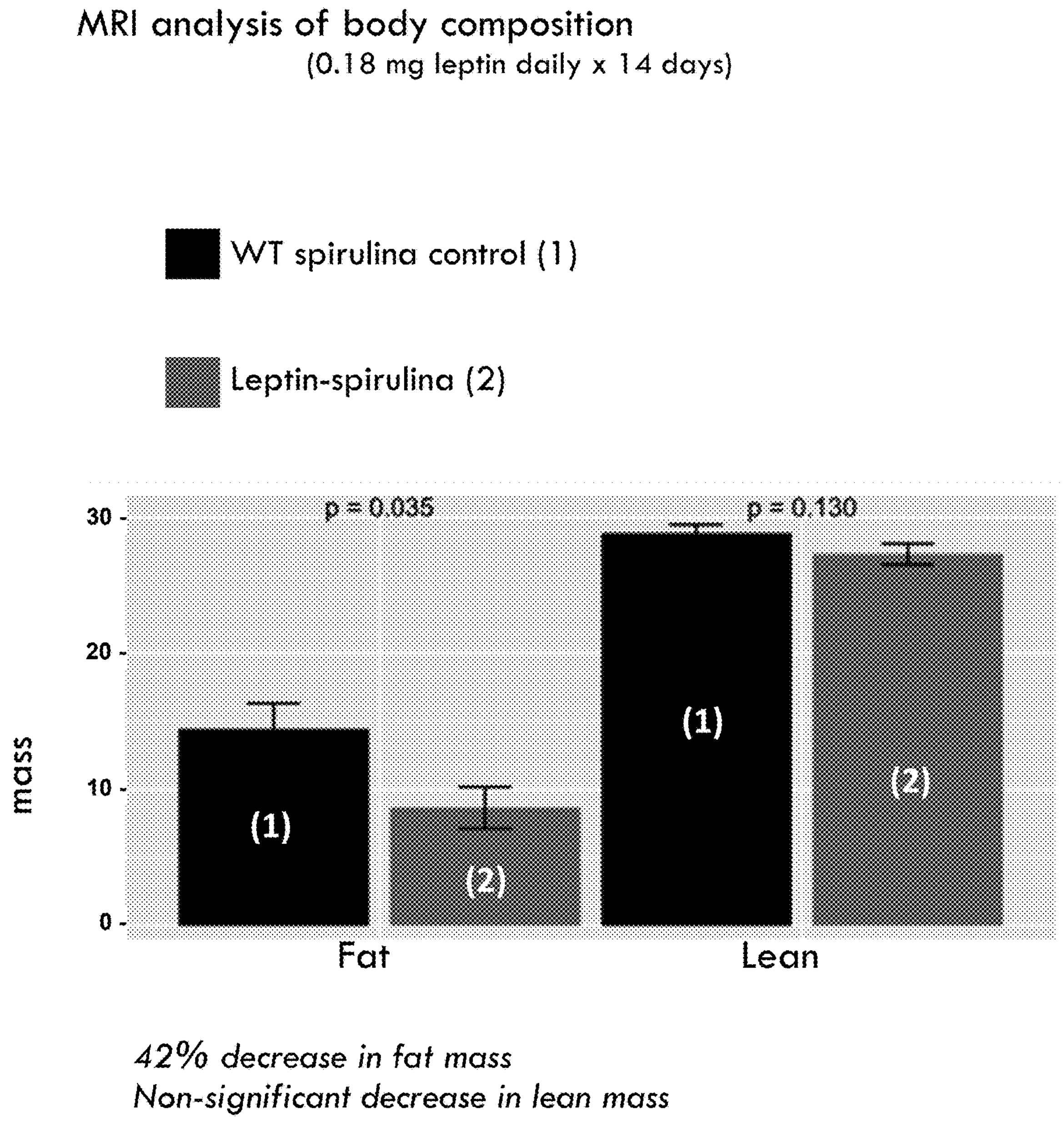
FIG. 6D provides the Magnetic Resonance Imaging (MRI) analysis of mice dosed with 0.18 mg of leptin daily for 14 days with wild-type (WT) *Spirulina* (control) versus with leptin-*Spirulina*.
Figure 6E:
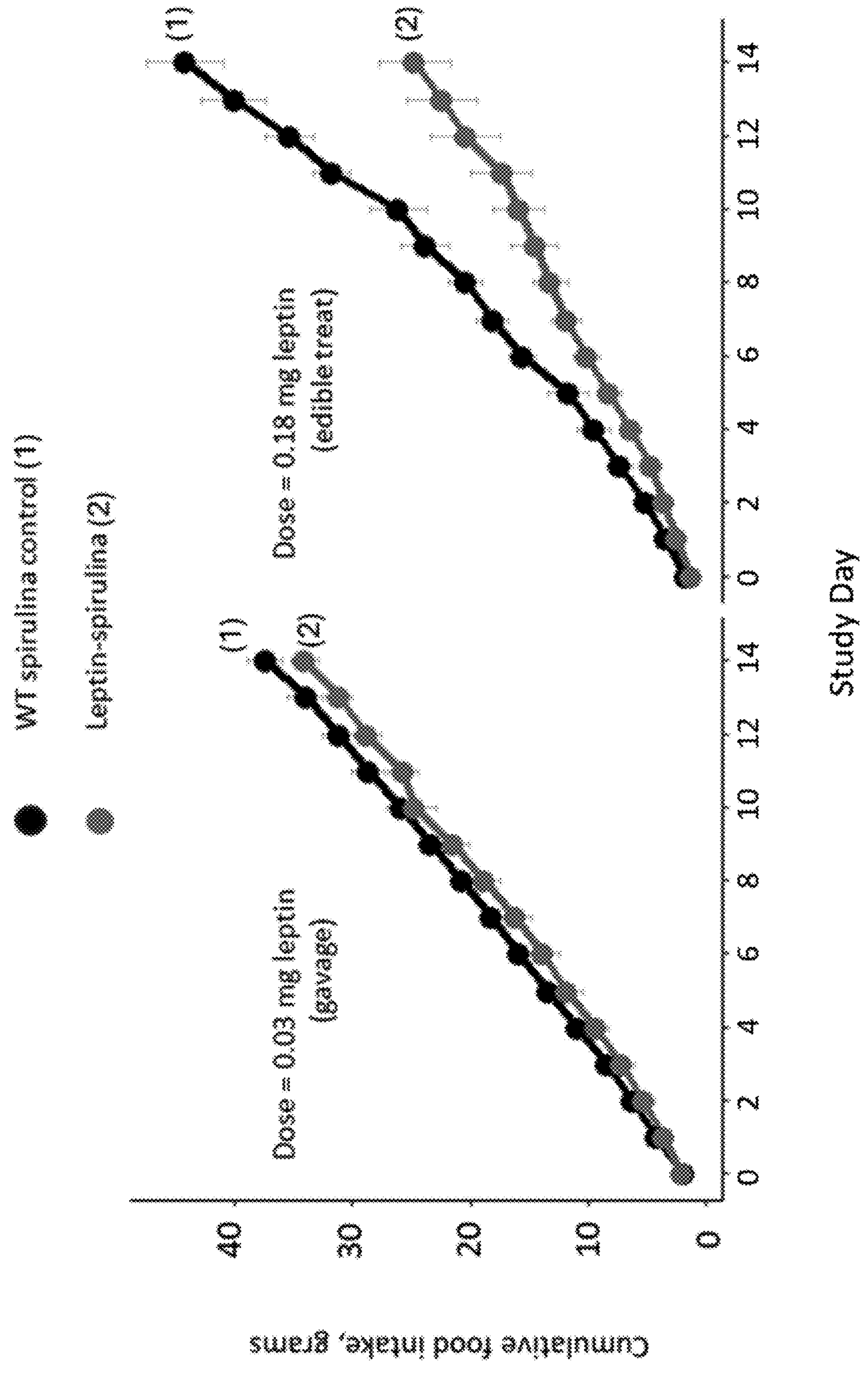
FIG. 6E provides the cumulative food intake (in grams) of mice administered an 0.03 mg dose of WT *Spirulina* or leptin-*Spirulina* via gavage and of mice administered an 0.18 mg dose of WT *Spirulina* or leptin-*Spirulina* as an edible treat.
Figure 6F:
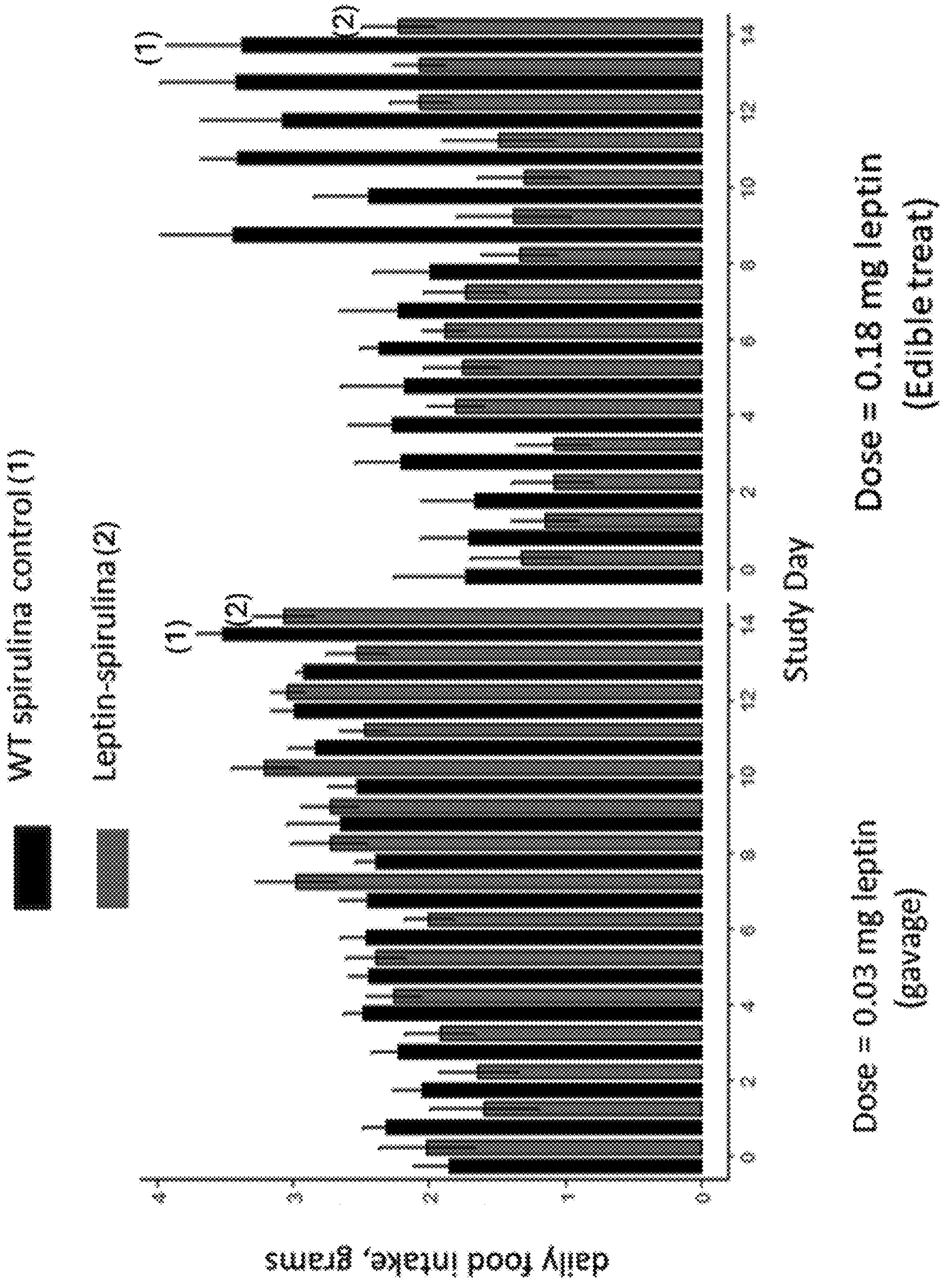
FIG. 6F provides the daily food intake (in grams) of mice administered an 0.03 mg dose of WT *Spirulina* or leptin-*Spirulina* via gavage and of mice administered an 0.18 mg dose of WT *Spirulina* or leptin-*Spirulina* as an edible treat.
Figure 6G:
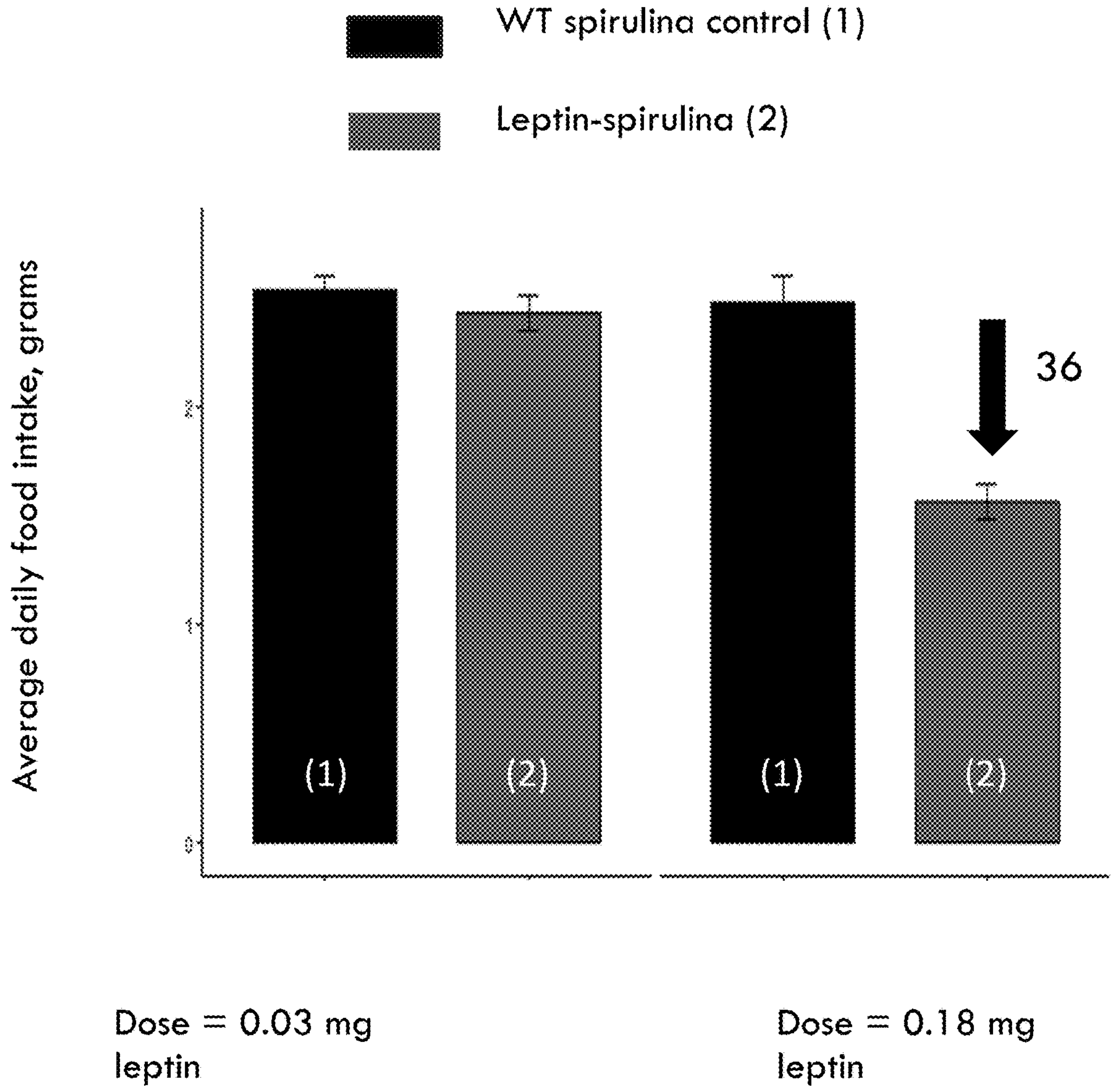
FIG. 6G provides the average daily food intake (in grams) of mice administered an 0.03 mg dose of WT *Spirulina* or leptin-*Spirulina* via gavage and of mice administered an 0.18 mg dose of WT *Spirulina* or leptin-*Spirulina* as an edible treat.

Obese DIO mice (40-45 grams, 8 mice per cohort) were dosed once daily at lights out with an oral gavage of WT *Spirulina* control (10 mg) or *Spirulina* (10 mg) containing 30 micrograms of leptin, or an edible treat of either wild-type *Spirulina* (UTEX/SP3) (60 mg) or *Spirulina* (60 mg) expressing human leptin (180 micrograms) (SP2334). Treats were formulated with peanut solids and glucose for palatability and total treat weight for both the leptin and placebo groups was 0.21 grams per day and were identical except for the presence or absence of leptin protein. Body weight was measured once daily, and food intake was continuously measured using mice housed in BioDaq cages. Shown in FIG. 6C is placebo-adjusted change in body weight for each study day. Shown in FIG. 6D is a body composition analysis by MRI, wherein the fat mice administered leptin-*Spirulina* demonstrated a 42% decrease in fat mass when compared to fat mice administered WT *Spirulina* (control). Shown in FIG. 6E is cumulative food intake (in grams) among the four treatments. Shown in FIG. 6F is daily food intake (in grams) among the four treatments. Shown in FIG. 6G is percent change in average daily food intake (in grams), wherein the mice fed 0.18 mg leptin in a leptin-*Spirulina* edible treat demonstrated a 36% reduction in average daily food intake (in grams) when compared to mice fed WT *Spirulina* (control).

Results show a dose-dependent effect of oral leptin on body weight, food intake and body composition. DIO mice dosed with 180 micrograms of leptin lost on average approximately 18% of body weight in 14 days compared to the wild-type *Spirulina* (placebo) control ($p<0.05$). This was due to a 42% decrease in fat body mass, and there was Average daily food intake of mice fed *Spirulina* leptin was reduced by 36% compared to mice fed wild-type *Spirulina* (~30% reduction; $p<0.05$). Orally administered *Spirulina*-expressed leptin significantly reduced food intake and caused reduction in body weight of both lean and DIO mice compared to mice administered either buffer or wild-type *Spirulina.*

To verify the results described above, further experiment was conducted by dosing obese DIO mice (8 mice per cohort) once daily 30 minutes before lights out with 60 mg of leptin-expressing *Spirulina* biomass (generation 1 leptin) or control biomass (wild type *Spirulina*) in the form of an edible treat for 21 days. C57Bl/6J mice fed DIO (45% fat) diet. Cut-off weight for enrollment in the study was ≥45 g. Acclimatization proceeded for 5 days in an 80° F./40% humidity, 4 am/4 pm day/night cycle room. Mice were single housed in Biodaq cages. Treats were administered 30 minutes prior to lights out (4 pm). EchoMRI and terminal blood draw were performed at 21 days. Treats were formulated with peanut solids and glucose for palatability and total treat weight for both the leptin and control groups was 0.21 grams per day and were identical except for the presence or absence of leptin protein. Body weight was measured once daily, and food intake was continuously measured using mice housed in BioDaq cages. Food intake was monitored by measured by BioDAQ Food intake monitoring system (Research Diets INC.). Intake is measured with a hopper attached to the metabolic cage that measures the weight of food removed from the hopper in real time. This approach provides information about meal size, duration, and number of feeding bouts in real time.

Figure 6H:
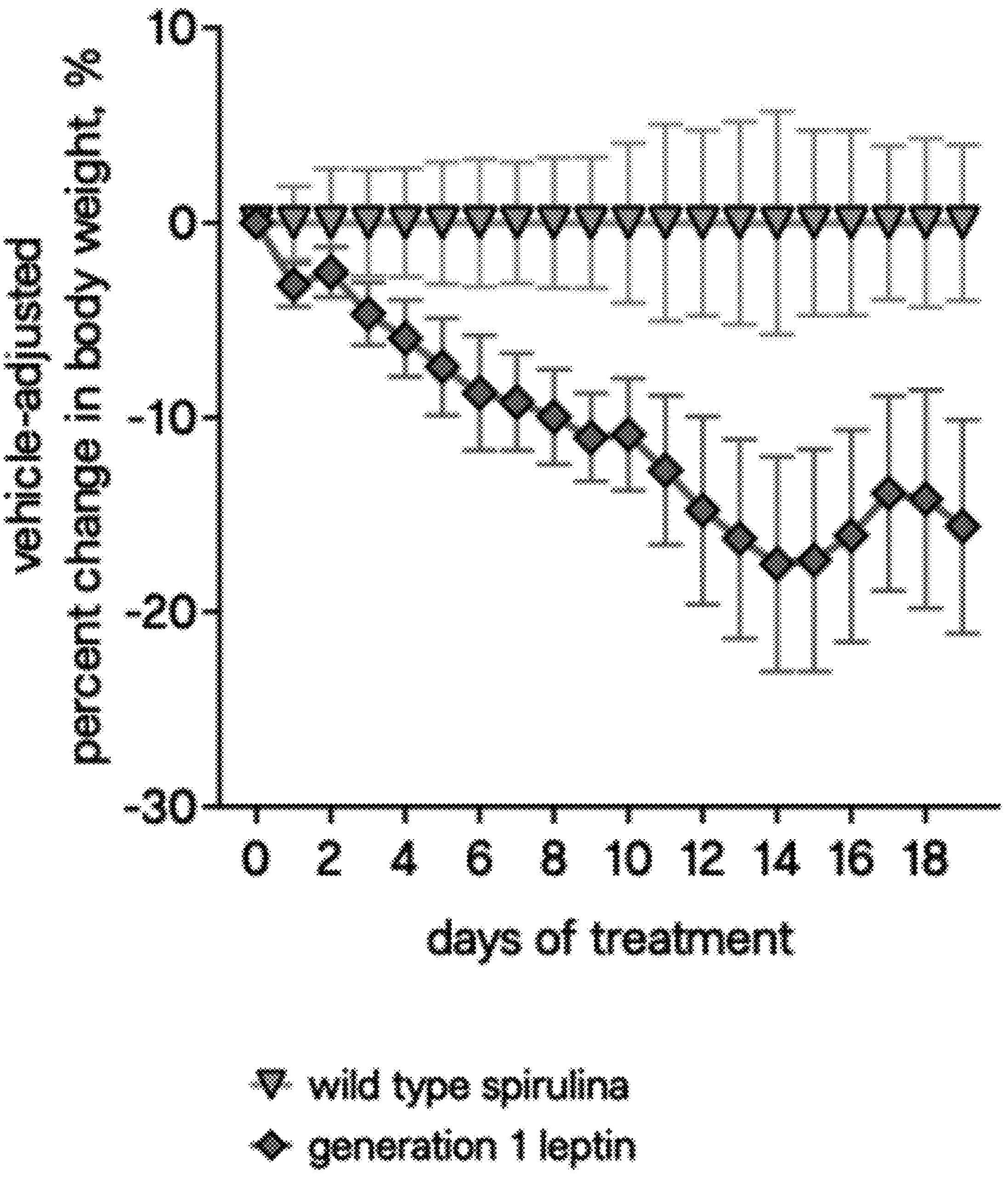
FIG. 6H provides vehicle-adjusted percent change in body weight over 21 days of treatment when WT *Spirulina* (control) and *Spirulina* expressing generation 1 leptin (SP2334) were delivered to diet-induced obese (DIO) mice.
Figure 6I:
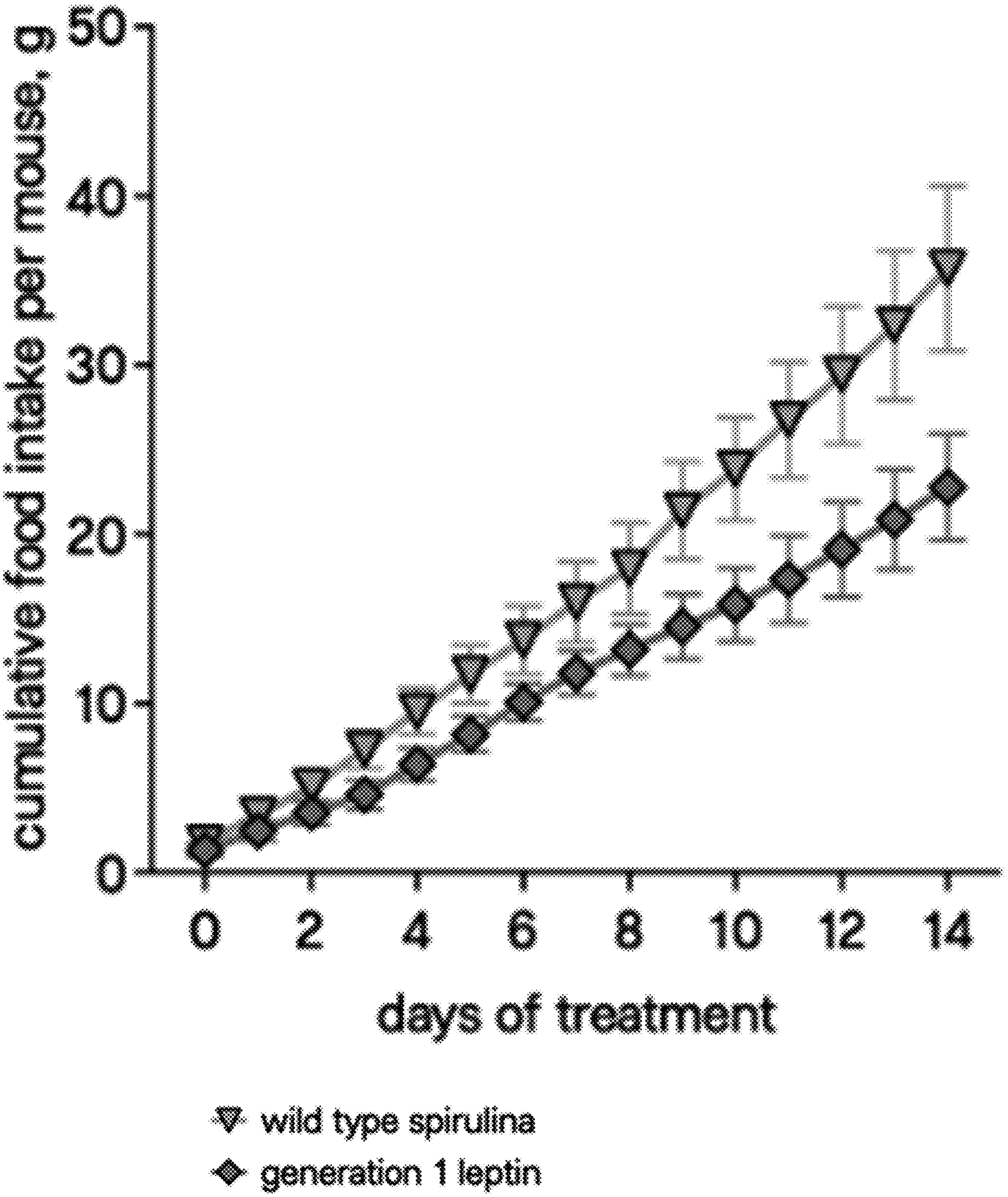
FIG. 6I provides cumulative food intake per mouse in grams over 14 days of treatment when WT *Spirulina* (control) and *Spirulina* expressing generation 1 leptin (SP2334) were delivered to diet-induced obese (DIO) mice.
Figure 6J:
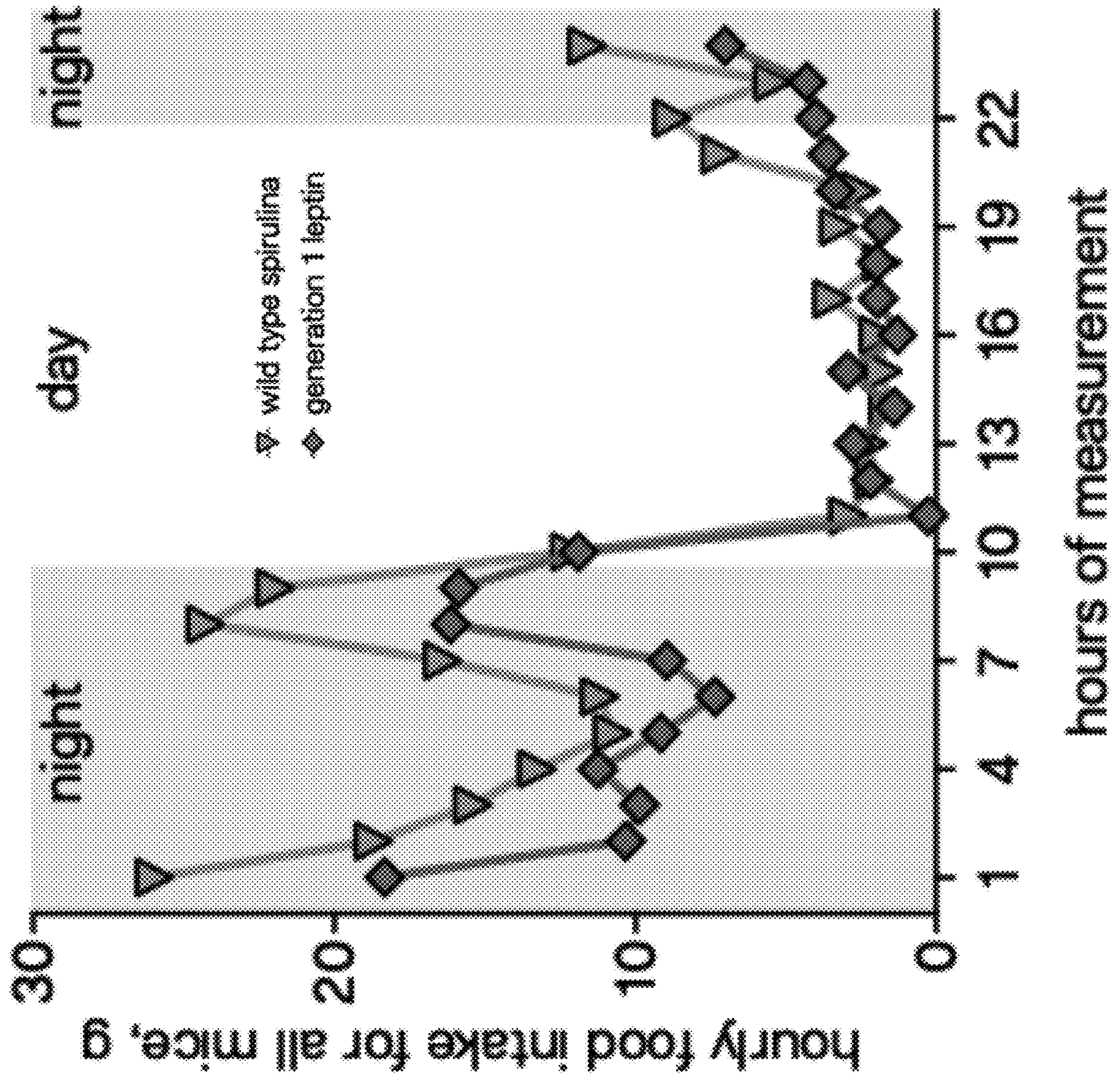
FIG. 6J provides hourly food intake over the course of 24 hours for all treatment subjects; WT *Spirulina* (control) and *Spirulina* expressing generation 1 leptin (SP2334), each of which were delivered to diet-induced obese (DIO) mice. Treatment bolus delivered at the beginning of the feeding night cycle.
Figure 6K:
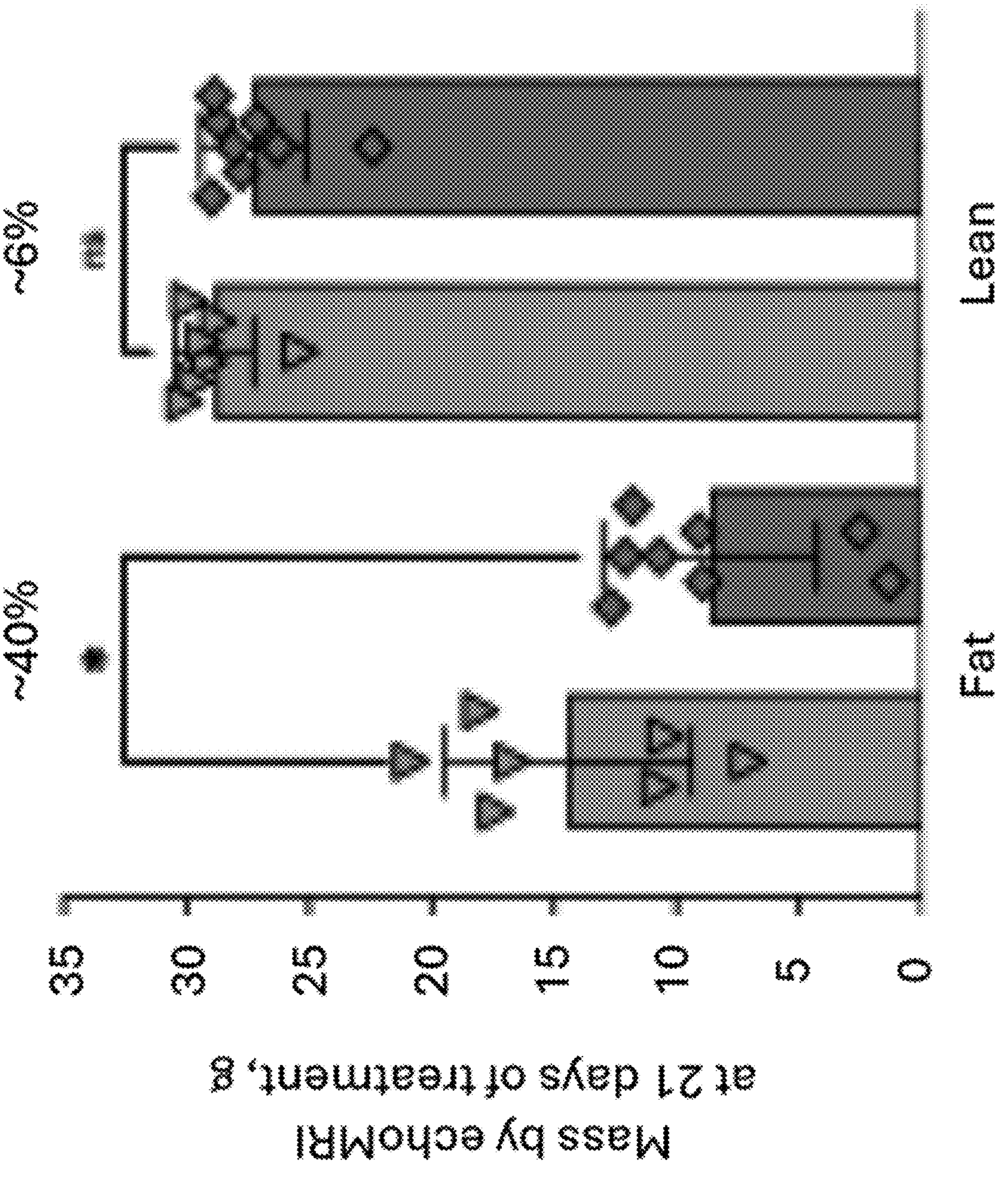
FIG. 6K provides body mass difference between control (WT *Spirulina*) and test group (*Spirulina* expressing generation 1 leptin (SP2334)) in fat and lean tissue as measured by echo MRI.

FIG. 6H shows vehicle-adjusted percent change in body weight over 21 days of treatment, which provides treatment results of one additional week (from 15 to 21 days) compared to FIG. 6C. In FIG. 6I, a cumulative food intake pattern is presented per mouse in grams over 14 days of treatment, which is almost identical to FIG. 6E. Further, FIG. 6J displays hourly food intake over the course of 24 hours for all treatment subjects. Treatment bolus delivered at the beginning of the feeding night cycle. FIG. 6K provides a body mass difference between control and treatment groups in fat and lean tissue as measured by echo MRI at 21 days of treatment, wherein the fat mice administered generation 1 leptin demonstrated about 40% decrease in fat mass when compared to fat mice administered WT *Spirulina* (control), which is compatible with FIG. 6D.

Figure 6L:
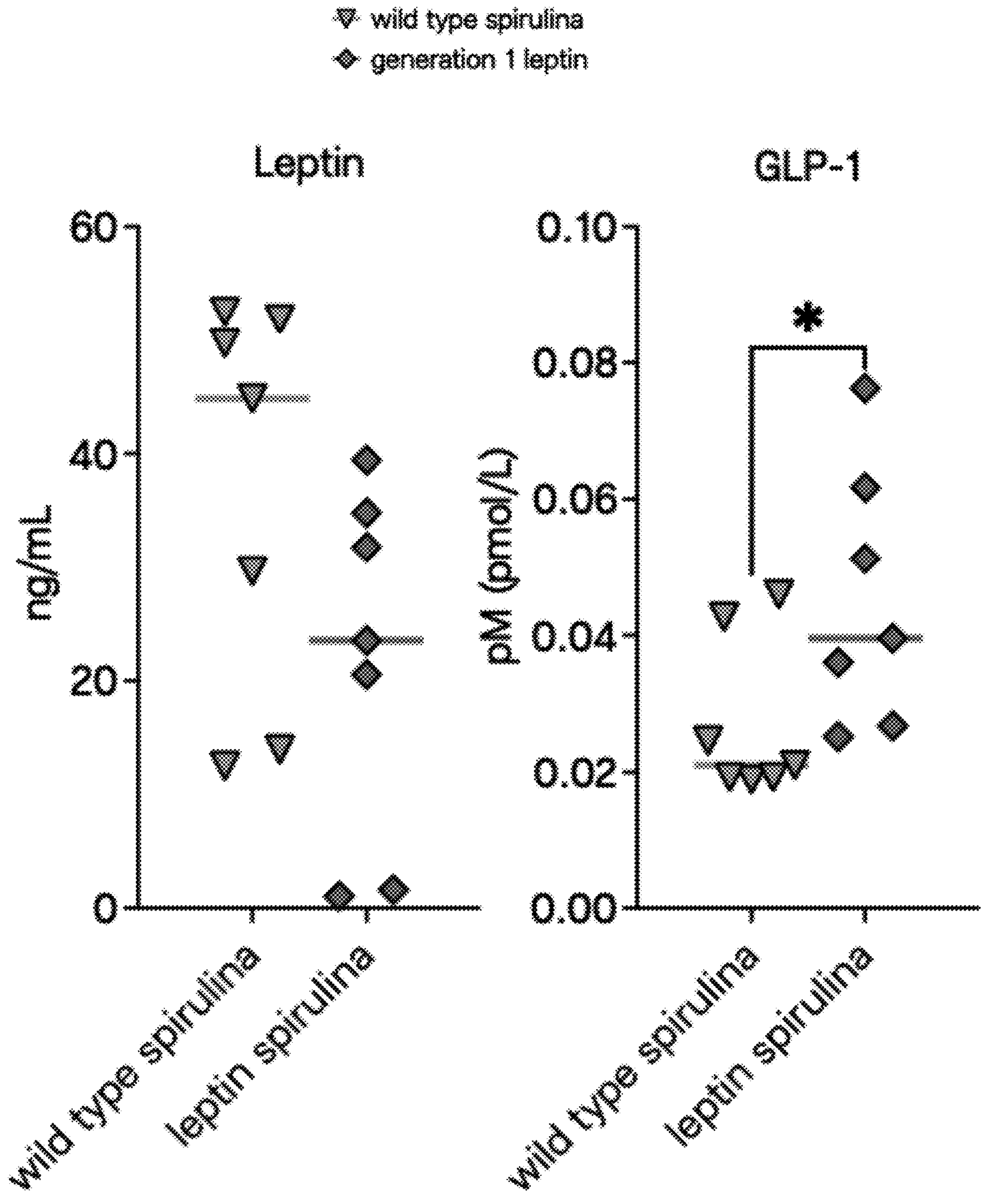
FIG. 6L provides terminal blood draw serum analysis for endogenous leptin and endogenous GLP-1.

To assess the effect of Leptin *Spirulina* treatment on metabolic hormone and cytokine levels in mouse serum, the MSD U-PLEX Metabolic Hormone Combo 1 (Mouse) kit was used which quantifies ten analytes including Leptin and GLP-1. A biotinylated capture antibody specific to each analyte was coupled to a unique linker, and the linker-coupled antibodies were combined to prepare the coating solution. Each well of a 96-well MSD plate was coated with 50 μL of this solution and incubated at room temperature for 1 hour, followed by three washes with MSD wash buffer. Mouse serum samples were diluted 2-fold using metabolic assay working solution supplemented with 1× HALT protease inhibitor, Aprotinin at 1,000 KIU/mL, and Diprotin A at 0.1 mM. A calibrator standard solution was prepared by combining kit-provided calibrators and serially diluted 4-fold in the same working solution. Fifty microliters of each diluted serum sample and calibrator were plated in duplicate and incubated for 2 hours at room temperature on a shaker. After washing the plate three times, 150 μL of Sulfo-tagged detection antibody mixture was added to each well, followed by a 1-hour incubation at room temperature. Plates were then washed again, and 150 μL of MSD Gold Read Buffer was added to each well before immediate reading on an MSD Reader. Shown in FIG. 6L is a result of terminal blood draw serum analysis for endogenous leptin and endogenous GLP-1 when wild type *Spirulina* (WT *Spirulina*) and *Spirulina* expressing Gen 1 leptin (Gen1 leptin *Spirulina*) were treated, respectively. Here, endogenous leptin levels from DIO mice fed with Gen1 leptin *Spirulina* decrease in serum, which is an expected outcome of weight loss. An increase in GLP1 levels is likely due to the therapeutic leptin signaling.

b) De novo leptin Mimetics

Figure 7A:
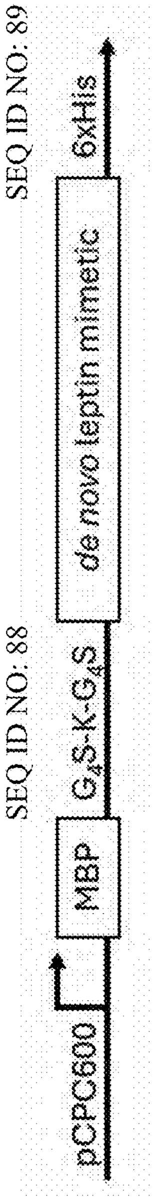
FIG. 7A is a schematic of an exemplary vector encoding a de novo leptin mimetic, including a G4S linker (SEQ ID NO: 88) and a 6×His tag (SEQ ID NO: 89).

The de novo sequence ("derivative" leptins) designs were expressed using an identical framework as described above. Derivative leptins were generated using a combination of Rosetta (Rohl et al., 2004, supra) and ProteinMPNN (Dauparas et al., 2022, supra), FIG. 7A.

Figure 7B:
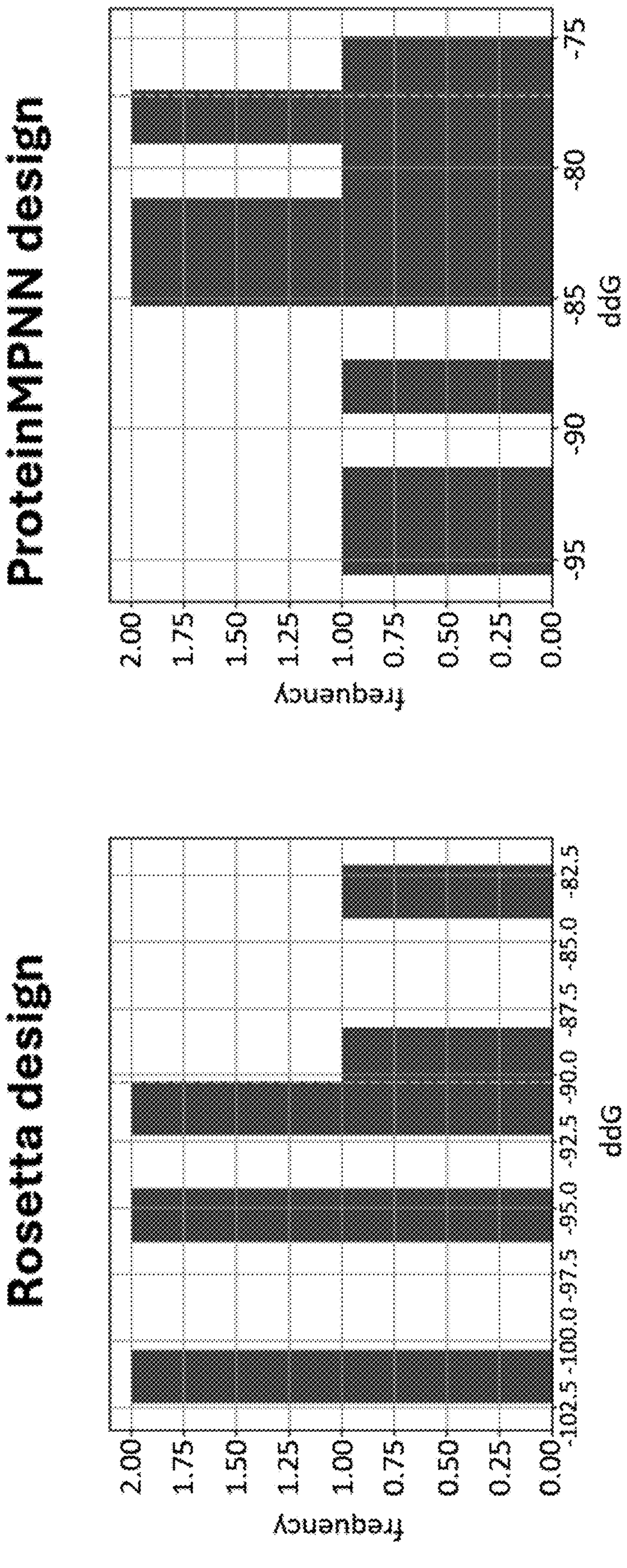
FIG. 7B shows exemplary design metrics for Rosetta (left) and ProteinMPNN (right) based on human leptin.

In brief, the exemplary de novo leptin mimetics were selected for having increased binding energy when in complex with leptin receptors (ddG) as compared to control, dotted line in FIG. 7B.

Various designs were selected according to methodologies described in Example 1 and are provided below in Table 4 and annotated at FIG. 7C. Protein sequences with the 7Z3Q prefix are redesigns of human leptin, and sequences with the 8DHA prefix are redesigns of murine leptin. FIG. 7D provides structural renditions of the leptin proteins of the 7Z3Q_001 (left) and 7Z3Q_004 (right) clones with mutations noted in red. An exemplary vector backbone is depicted in FIG. 7D.

Table 4 provides exemplary de novo leptin mimetics. The leptin mimetics presented in Table 4 do not include the fusion sequences; (i) an MBP (maltose binding protein) sequence (SEQ ID NO: 65) fused to N terminal of the leptin mimetics and (ii) a G4S linker (SEQ ID NO: 66) between MBP and leptin. Accordingly, the 'parent' leptin designs presented in Table 4 have the same sequence as those in Table 1. As the MBP and G4S linker are not included in the amino acid sequence in Table 4, the leptin mimetics sequences (SEQ ID NOs: 22 and 52-56) in Table 4 are identical to SEQ ID NO: 12-17 in Table 1, and (SEQ ID NOs: 57-62) in Table 4 are identical to SEQ ID NO: 6-11 in Table 4.

Figure 7C:
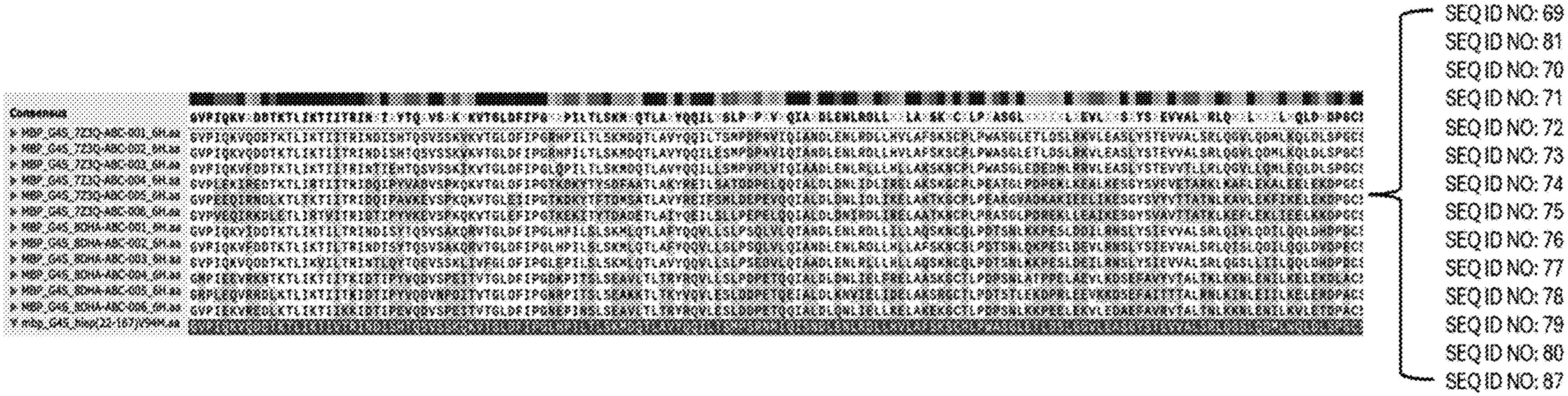
FIG. 7C is a graphic listing exemplary de novo leptin mimetics and their consensus sequence. SEQ ID NO: 69 is a consensus sequence of SEQ ID NOs: 70-81
Figure 7D:
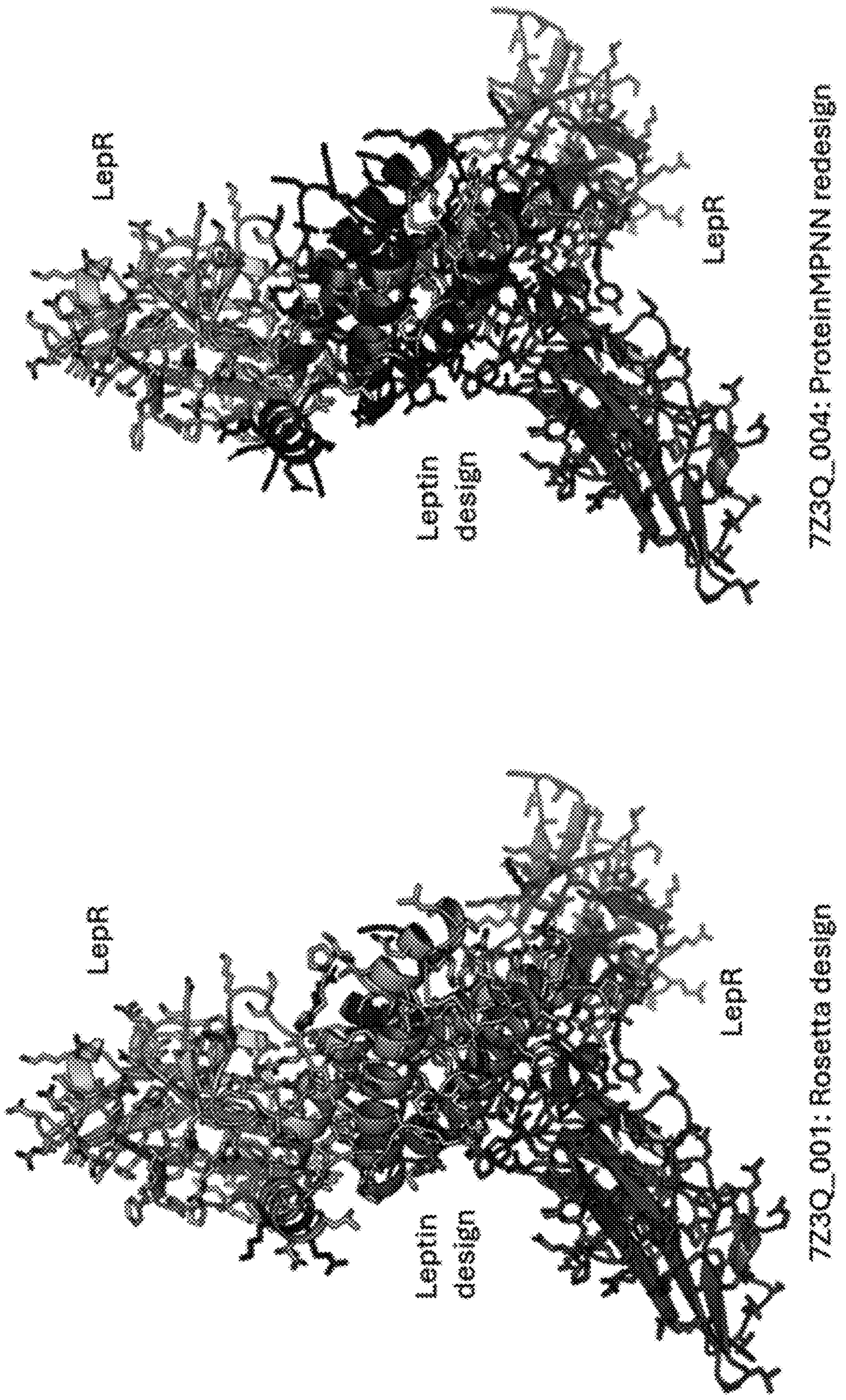
FIG. 7D is a graphic of the leptin protein with mutations provided in red for the 7Z3Q_001 (left) and 7Z3Q_004 (right) clones.

As presented in FIG. 7C, SEQ ID NO:81 has G at 5'end of SEQ ID NO:22. SEQ ID NOs: 70-80 have G at 5'end of SEQ ID NOs: 52-62, respectively. SEQ ID NO:87 has G at 5' end of SEQ ID NO:63.

TABLE 4

Exemplary de novo leptin mimetics

| ID | SEQ ID NO | Amino Acid |
|---|---|---|
| MBP_G4S_7Z3Q-ABC-001_6H.AA | 22 | VPIQKVQDDTKTLIKTIITRINDISHTQSVSSKVKVTGLDFIPGRHPILTLSKMDQTLAVYQQILTSMPDPNVIQIANDLENLRDLLHVLAFSKSCPLPWASGLETLDSLRKVLEASLYSTEVVALSRLQGVLQDMLKQLDLSPGC |
| MBP_G4S_7Z3Q-ABC-002_6H.AA | 52 | VPIQKVQDDTKTLIKTIITRINDISHTQSVSSKVKVTGLDFIPGRHPILTLSKMDQTLAVYQQILESMPDPNVIQIANDLENLRDLLHVLAFSKSCPLPWASGLETLDSLRKVLEASLYSTEVVALSRLQGVLQDMLKQLDLSPGC |
| MBP_G4S_7Z3Q-ABC-003_6H.AA | 53 | VPIQKVFDDTKTLIKTIITRINTIEHTQSVSSKIKVTGLDFIPGLQPILTLSKMDQTLAVYQQILLSMPVPLVIQIAADLENLRLLLHLLAKSKNCPLPWASGLEDEDMLRRVLEASLYSTEVVTLLRLQGVLLQMLEQLDLSPGC |
| MBP_G4S_7Z3Q-ABC-004_6H.AA | 54 | VPLEKIREDTKTLIRTIITRIDQIPYVADVSPKQKVTGLDFIPGTKDKYTYSDFAATLAKYREILSATDDPELQQIALDLDNLIDLIRELAKSKGCPLPEATGLPDPEKLKEALKESGYSVEVETARKLKAFLEKALEELEKDPGC |
| MBP_G4S_7Z3Q-ABC-005_6H.AA | 55 | VPEEQIRNDLKTLTKTIITRIDQIPAVKEVSPKQKVTGLEIIPGTKDKYTFTDMSATLAVYREIFSMLDEPEVQQIALDLDNLIDLIKELAKTKGCPLPEAKGVADKAKIEELIKESGYSVYVTTATNLKAVLEKFIKELEKDPGC |
| MBP_G4S_7Z3Q-ABC-006_6H.AA | 56 | VPVEQIRKDLETLIRTVITRIDTIPYVKEVSPKQKVTGLEFIPGTKEKITYTDADETLAIYQEILSLLPEPELQQIALDLDNIRDLIRELAATKNCPLPRASGLPDREKLLEAIKESGYSVAVTTATKLKEFLEKLIEELKKDPGC |
| MBP_G4S_8DHA-ABC-001_6H.AA | 57 | VPIQKVIDDTKTLIKTILTRINDISYTQSVSAKQRVTGLDFIPGLHPILSLSKMLQTLAFYQQVLLSLPSQLVLQIANDLENLRDLLILLAQSKNCQLPDTSNLKKPESLDDILRNSLYSIEVVALSRLQIVLQDILQQLDHDPDC |
| MBP_G4S_8DHA-ABC-002_6H.AA | 58 | VPIQKVFDDTKTLIKTILTRINDISYTQSVSAKQRVTGLDFIPGLHPILSLSKMLQTLAFYQQVLLSLPSQLVLQIANDLENLRDLLHLLAFSKNCSLPDTSNLQKPESLDEVLRNSLYSIEVVALSRLQISLQDILQQLDVDPEC |
| MBP_G4S_8DHA-ABC-003_6H.AA | 59 | VPIQKVQDDTKTLIKVILTRINTLQYTQEVSSKLIVFGLDFIPGLEPILSLSKMLQTLAVYQQVLLSLPSEDVLQIAADLENLRLLLHLLAQSKNCQLPDTSNLKKPESLDEILRNSLYSIEVVALSRLQGSLLIILQQLDHDPDC |
| MBP_G4S_8DHA-ABC-004_6H.AA | 60 | MPIEEVRKNTKTLIKTIITKIDTIPYVQDVSPEITVTGLDFIPGDKPITSLSEAVLTLTRYRQVLLSLPDPETQQIALDLDNLIELFRELAASKGCTLPDPSNLATPPELAEVLKDSEFAVYVTALTKLKKNLENILKELEKDLAC |
| MBP_G4S_8DHA-ABC-005_6H.AA | 61 | RPLEQVRRDLKTLIKTIITKIDTIPYVQDVNPDITVTGLDFIPGNRPITSLSEAKKTLTKYVQVLESLDDPETQEIALDLKNVIELIDELAKSRGCTLPDTSTLEKDPRLEEVKKDSEFAITTTALRNLKINLEIILKELERDPAC |
| MBP_G4S_8DHA-ABC-006_6H.AA | 62 | VPIEKVREDLKTLIKTIIKKIDTIPEVQDVSPEITVTGLDFIPGNEPINSLSEAVLTLTRYRQVLESLDDPETQQIALDLQNLIELLKELAKEKGCTLPDPSNLKKPEELEKVLEDAEFAVRVTALTNLKKNLENILKVLETDPAC |

TABLE 4-continued

| Exemplary de novo leptin mimetics | | |
|---|---|---|
| ID | SEQ ID NO | Amino Acid |
| Mbp_G4S_hlep<br>(22-167)V94M.AA<br>(Gen 1 Control) | 63 | VPIQKVQDDTKTLIKTIVTRINDISHTQSVSSKQKVTGLDF<br>IPGLHPILTLSKMDQTLAVYQQILTSMPSRNMIQISNDLEN<br>LRDLLHVLAFSKSCHLPWASGLETLDSLGGVLEASGYST<br>EVVALSRLQGSLQDMLWQLDLSPGC |
| Consensus<br>(50%+) | 64; 69 | GVPIQKVXDDTKTLIKTIITRINXIXYTQXVSXKXKVTGL<br>DFIPGXXPILTLSKMXQTLAXYQQILXSLPXPXVXQIAXD<br>LENLRDLLXXLAXSKXCXLPXASGLXXXXXLXEVLXXS<br>XYSXEVVALXRLQXXLXXXLXQLDXDPGC |
| MBP_G4S_7Z3Q-<br>ABC-<br>001_6H.AA with<br>G at 5' end | 81 | GVPIQKVQDDTKTLIKTIITRINDISHTQSVSSKVKVTGLD<br>FIPGRHPILTLSKMDQTLAVYQQILESMPDPNVIQIANDLE<br>NLRDLLHVLAFSKSCPLPWASGLETLDSLRKVLEASLYS<br>TEVVALSRLQGVLQDMLKQLDLSPGC |
| MBP_G4S_7Z3Q-<br>ABC-<br>002_6H.AA with<br>G at 5' end | 70 | GVPIQKVFDDTKTLIKTIITRINTIEHTQSVSSKIKVTGLDFI<br>PGLQPILTLSKMDQTLAVYQQILLSMPVPLVIQIAADLEN<br>LRLLLHLLAKSKNCPLPWASGLEDEDMLRRVLEASLYST<br>EVVTLLRLQGVLLQMLEQLDLSPGC |
| MBP_G4S_7Z3Q-<br>ABC-<br>003_6H.AA with<br>G at 5' end | 71 | GVPLEKIREDTKTLIRTIITRIDQIPYVADVSPKQKVTGLD<br>FIPGTKDKYTYSDFAATLAKYREILSATDDPELQQIALDL<br>DNLIDLIRELAKSKGCPLPEATGLPDPEKLKEALKESGYS<br>VEVETARKLKAFLEKALEELEKDPGC |
| MBP_G4S_7Z3Q-<br>ABC-<br>004_6H.AA with<br>G at 5' end | 72 | GVPEEQIRNDLKTLTKTIITRIDQIPAVKEVSPKQKVTGLE<br>IIPGTKDKYTFTDMSATLAVYREIFSMLDEPEVQQIALDL<br>DNLIDLIKELAKTKGCPLPEAKGVADKAKIEELIKESGYS<br>VYVTTATNLKAVLEKFIKELEKDPGC |
| MBP_G4S_7Z3Q-<br>ABC-<br>005_6H.AA with<br>G at 5' end | 73 | GVPVEQIRKDLETLIRTVITRIDTIPYVKEVSPKQKVTGLE<br>FIPGTKEKITYTDADETLAIYQEILSLLPEPELQQIALDLDN<br>IRDLIRELAATKNCPLPRASGLPDREKLLEAIKESGYSVA<br>VTTATKLKEFLEKLIEELKKDPGC |
| MBP_G4S_7Z3Q-<br>ABC-<br>006_6H.AA with<br>G at 5' end | 74 | GVPIQKVIDDTKTLIKTILTRINDISYTQSVSAKQRVTGLD<br>FIPGLHPILSLSKMLQTLAFYQQVLLSLPSQLVLQIANDLE<br>NLRDLLILLAQSKNCQLPDTSNLKKPESLDDILRNSLYSIE<br>VVALSRLQIVLQDILQQLDHDPDC |
| MBP_G4S_8DHA-<br>ABC-<br>001_6H.AA with<br>G at 5' end | 75 | GVPIQKVFDDTKTLIKTILTRINDISYTQSVSAKQRVTGLD<br>FIPGLHPILSLSKMLQTLAFYQQVLLSLPSQLVLQIANDLE<br>NLRDLLHLLAFSKNCSLPDTSNLQKPESLDEVLRNSLYSI<br>EVVALSRLQISLQDILQQLDVDPEC |
| MBP_G4S_8DHA-<br>ABC-<br>002_6H.AA with<br>G at 5' end | 76 | GVPIQKVQDDTKTLIKVILTRINTLQYTQEVSSKLIVFGLD<br>FIPGLEPILSLSKMLQTLAVYQQVLLSLPSEDVLQIAADLE<br>NLRLLLHLLAQSKNCQLPDTSNLKKPESLDEILRNSLYSIE<br>VVALSRLQGSLLIILQQLDHDPDC |
| MBP_G4S_8DHA-<br>ABC-<br>003_6H.AA with<br>G at 5' end | 77 | GMPIEEVRKNTKTLIKTIITKIDTIPYVQDVSPEITVTGLDF<br>IPGDKPITSLSEAVLTLTRYRQVLLSLPDPETQQIALDLDN<br>LIELFRELAASKGCTLPDPSNLATPPELAEVLKDSEFAVY<br>VTALTKLKKNLENILKELEKDLAC |
| MBP_G4S_8DHA-<br>ABC-<br>004_6H.AA with<br>G at 5' end | 78 | GRPLEQVRRDLKTLIKTIITKIDTIPYVQDVNPDITVTGLD<br>FIPGNRPITSLSEAKKTLTKYVQVLESLDDPETQEIALDLK<br>NVIELIDELAKSRGCTLPDTSTLEKDPRLEEVKKDSEFAIT<br>TTALRNLKINLEIILKELERDPAC |
| MBP_G4S_8DHA-<br>ABC-<br>005_6H.AA with<br>G at 5' end | 79 | GVPIEKVREDLKTLIKTIIKKIDTIPEVQDVSPEITVTGLDFI<br>PGNEPINSLSEAVLTLTRYRQVLESLDDPETQQIALDLQN<br>LIELLKELAKEKGCTLPDPSNLKKPEELEKVLEDAEFAVR<br>VTALTNLKKNLENILKVLETDPAC |
| MBP_G4S_8DHA-<br>ABC-<br>006_6H.AA with<br>G at 5' end | 80 | GVPIQKVQDDTKTLIKTIVTRINDISHTQSVSSKQKVTGL<br>DFIPGLHPILTLSKMDQTLAVYQQILTSMPSRNMIQISNDL<br>ENLRDLLHVLAFSKSCHLPWASGLETLDSLGGVLEASGY<br>STEVVALSRLQGSLQDMLWQLDLSPGC |
| Mbp_G4S_hlep<br>(22-167) V94M.AA<br>with G at 5' end | 87 | GVPIQKVQDDTKTLIKTIVTRINDISHTQSVSSKQKVTGL<br>DFIPGLHPILTLSKMDQTLAVYQQILTSMPSRNMIQISNDL<br>ENLRDLLHVLAFSKSCHLPWASGLETLDSLGGVLEASGY<br>STEVVALSRLQGSLQDMLWQLDLSPGC |

The above noted de novo mimetics were utilized to complete in vitro assays evaluating expression, binding, and protease resistance.

Table 5 below provides the complete vector sequences for all constructs that were utilized during in vitro assays.

TABLE 5

| Vector sequences | |
|---|---|
| SEQ ID NO | Construct |
| 37 | Left homologous arm |
| 38 | Right homologous arm |
| 39 | WT (help(22-167)V94M) leptin |
| 40 | 8DHA-ABC-001 |
| 41 | 8DHA-ABC-002 |
| 42 | 8DHA-ABC-003 |
| 43 | 8DHA-ABC-004 |

TABLE 5-continued

| Vector sequences | |
|---|---|
| SEQ ID NO | Construct |
| 44 | 8DHA-ABC-005 |
| 45 | 8DHA-ABC-006 |
| 46 | 7Z3Q-ABC-001 |
| 47 | 7Z3Q-ABC-002 |
| 48 | 7Z3Q-ABC-003 |
| 49 | 7Z3Q-ABC-004 |
| 50 | 7Z3Q-ABC-005 |
| 51 | 7Z3Q-ABC-006 |

The vectors of Table 5 were utilized in Western blot (CEIA using a Jess system) and ELISA assays according to the methods of Example 1.

Table 6 below provides results of the in vitro assays. Note: SP #=strain designation; PP #=protein designation.

TABLE 6

Results of in vitro assays of the exemplary de novo leptin mimetics.

| SP # | PP # | Name | % SDW Jess | % ELISA active per DW | CBA $IC_{50}$ | ELISA $IC_{50}$ | trypsin 0.2 µg/mL % untreated | chymotrypsin 10 µg/mL % untreated |
|---|---|---|---|---|---|---|---|---|
| SP2334 | PP2054 | mbp_G4S_hlep(22-167)V94M (SEQ ID NO: 63) | 0.2-0.3 | 0.2-0.3 | 0.22 | 0.4 | 0 | 0.09 |
| SP3956 | PP5856 | MBP_G4S_8DHA-ABC-001_6H (SEQ ID NO: 57) | 1.51 | 0.89 | 0.9 | 0.3 | 0.62 | 5.03 |
| SP3957 | PP5857 | MBP_G4S_8DHA-ABC-002_6H (SEQ ID NO: 58) | | | 1.92 | 0.4 | | |
| SP3958 | PP5858 | MBP_G4S_8DHA-ABC-003_6H (SEQ ID NO: 59) | | | 14.98 | 2.7 | | |
| SP3959 | PP5859 | MBP_G4S_8DHA-ABC-004_6H (SEQ ID NO: 60) | | | 0.25 | 0.8 | | |
| SP3960 | PP5860 | MBP_G4S_8DHA-ABC-005_6H (SEQ ID NO: 61) | | | 18.66 | 8.1 | | |
| SP3961 | PP5861 | MBP_G4S_8DHA-ABC-006_6H (SEQ ID NO: 62) | | | 12.97 | 64.7 | | |
| SP3962 | PP5862 | MBP_G4S_7Z3Q-ABC-001_6H (SEQ ID NO: 22) | | | 4.41 | 0.4 | | |
| SP3963 | PP5863 | MBP_G4S_7Z3Q-ABC-002_6H (SEQ ID NO: 52) | 2.17 | 1.28 | 0.47 | 0.4 | 13.64 | 1.26 |
| SP3964 | PP5864 | MBP_G4S_7Z3Q-ABC-003_6H (SEQ ID NO: 53) | 2.67 | 3.50 | 0.51 | 0.3 | 3.91 | 3.01 |
| SP3965 | PP5865 | MBP_G4S_7Z3Q-ABC-004_6H (SEQ ID NO: 54) | 2.58 | 2.25 | 0.85 | 0.4 | 9.62 | 5.21 |
| SP3966 | PP5866 | MBP_G4S_7Z3Q-ABC-005_6H (SEQ ID NO: 55) | 4.11 | 3.95 | 0.34 | 0.3 | 3.15 | 28.84 |
| SP3967 | PP5867 | MBP_G4S_7Z3Q-ABC-006_6H (SEQ ID NO: 56) | 4.51 | 2.53 | 0.28 | 0.5 | 9.81 | 43.48 |

As noted in Table 6 above, the de novo leptin mutants exhibited superior expression, binding, and resistance to protease digestion as compared to control. A global sequence alignment between Gen 1 leptin (SP2334; pp 2054) and Gen 2 leptin (SP3967; PP5867) constructs was performed using Needleman-Wunsch version 2.6.1 in SnapGene (Version 8.0.2) and substitution Matrix scoring using BLOSUM62. Gen2 Leptin sequence is provided as SEQ ID NO: 56 (same as SEQ ID NO: 17). The sequence alignments were conducted using the leptin sequences only (not including the MBP tag, linker sequences, and the 6×His affinity tags). The sequence alignment result is presented in FIG. 7F. There are about 43.84% identity and about 69.18% similarity between Gen 1 and Gen 2 leptin amino acid sequences.

Gen 1 leptin was used to generate Gen 2 leptin by de novo designs, as described above.

Example 8: Simultaneous and Sequential Leptin/GLP-1 Agonist Combo Treatments As presented in the Examples above, we have demonstrated the efficacy of chronically dosed SP2334 (leptin agonist, dosed orally) to reduce food intake and body weight in DIO mice, and to reduce total body fat mass without reducing lean body mass.

With that background, initial exploratory studies, described below are using mice fed a liquid containing wild-type *Spirulina* or *Spirulina* containing leptin, and are also administered subcutaneously an FDA-approved GLP-1 agonist. More specifically the purpose of this study is to test the therapeutic potential of SP3967 in a DIO model both as a monotherapy and in combination with a GLP-1 agonist to assess weight loss synergy or weight maintenance after weight loss. The experiment has indicated that such co-dosing has potential for possible weight loss synergy and/or for weight maintenance.

Subchronic Food Intake Study. Mice are singly housed in HM2 cages to monitor daily food intake and body weight for 28 days. Animals are randomly assigned (n=10/group) to receive an oral dose of vehicle, null *Spirulina* (negative control-10 mg, oral), SP3967 (10 mg, oral), and the GLP-1 agonist (0.2 mg/kg, s.c.) or (0.2 mg/kg, s.c.)+SP3967 (10 mg, oral). In this study, animals will be dosed daily (oral for SP3967, s.c. for the GLP-1 agonist) for a total of 28 days.

A second group of DIO mice are dosed with PBS (oral) for 42 days, the GLP-1 agonist (0.4 mg/kg, s.c.) for 42 days, or the GLP-1 agonist (0.4 mg/kg, s.c.) or for 21 days and then switched to SP3967 or WT *Spirulina* for a subsequent 21 days. All mice will be dosed 30 min prior to lights out to maximize the potential impact of compounds on food intake and body weight. Animals will be dosed daily (oral for SP3967, s.c. for the GLP-1 agonist) for 42 days total in the second study. At study conclusion, the body composition of the DIO mice (EchoMRI) will be measured to assess the amount of lean versus adipose mass after treatment with SP3967+/−the GLP-1 agonist.

To further assess the potential synergy of the leptin and GLP-1 pathways on body weight loss, we will administer daily for 21 days either oral control *Spirulina* or a range of oral SP3967 amounts, either alone or in combination with a GLP-1 agonist given subcutaneously. An FDA-approved, commercially available GLP-1 agonist is used throughout these experiments. In addition, on experimental days 22-35 mice will be administered either high or low amounts of SP3967 to evaluate maintenance of weight loss after cessation of the GLP-1 agonist.

DIO male C57/B16J mice will be sourced from Jackson Laboratories and further maintained on a 45% HFD or 60% HFD until a minimum weight of 40 grams is reached. Animals will be allowed to acclimate for at least seven days prior to beginning study. The model utilized in these experiments is considered standard for diet-induced obese rodents and has been widely adopted in both academic and pharmaceutical settings for assessing compounds to treat obesity. In this model, leptin dosed centrally (i.e.v.) or peripherally (s.c., i.p.) have modest acute effects on feeding and minimal durable effect on body mass in a sub chronic setting.

Blood sampling. Interim blood samples (conscious, tail vein) will be obtained as outlined in the study designs above. Blood will be collected for analysis in satellite animals (n=3) from both studies at 1, 7 and 24 hr post-dosing. Additionally, terminal blood from the animals may be collected from the subchronic study (n=70) at study termination for analysis as described below.

We may measure the potential systemic concentrations of SP3967 in circulation by means of a human-specific leptin ELISA assay in both satellite mice (AFI and subchronic study, n=6) and study mice (subchronic study, n=70). We may measure terminal levels of mouse leptin (MSD), insulin (MSD), GLP-1 (MSD), glucagon (MSD), CCK (ELISA), glucose (glucometer) and triglycerides (chemistry analyzer) at the study conclusion from animals in the 28-day subchronic food intake/body weight study (n=70). Data will be analyzed by t-test to establish differences between untreated DIO and DIO mice treated with SP3967+/−the GLP-1 agonist, then by one-way ANOVA with Dunnett's post-hoc comparison to test if groups treated with the GLP-1 agonist are different than SP3967 alone. Data will be presented as mean±SE and represented as individual data points using GraphPad Prism (La Jolla, CA).

Figure 8A:
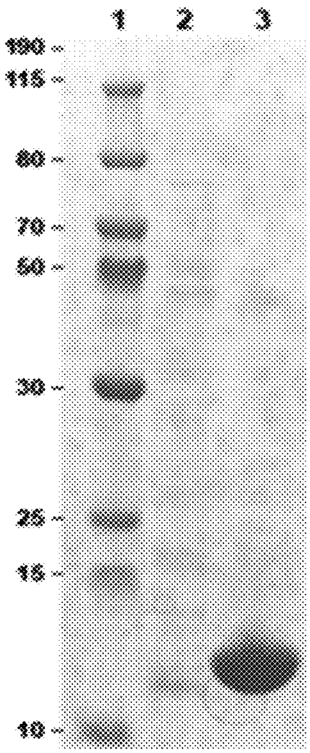
FIG. 8A provides SDS-PAGE analysis for soluble protein expression level of each Gen 1 and Gen 2 leptin.

Example 9: Improved Expression of Gen 2 Leptin while Preserving Binding Affinity The coding sequences for the leptin portions of Gen 1 Leptin (Wild Type Leptin) and Gen 2 Leptin were cloned into an *E. coli* expression vector. Plasmids transformed into *E. coli* protein expression strain BL21DE3. SDS-PAGE assessed the soluble protein expression level and recovery post-affinity purification under reducing conditions. FIG. 8A demonstrates the expression of Gen 1 and Gen 2 leptin, each of which is not fusion tagged.

Figure 8B:
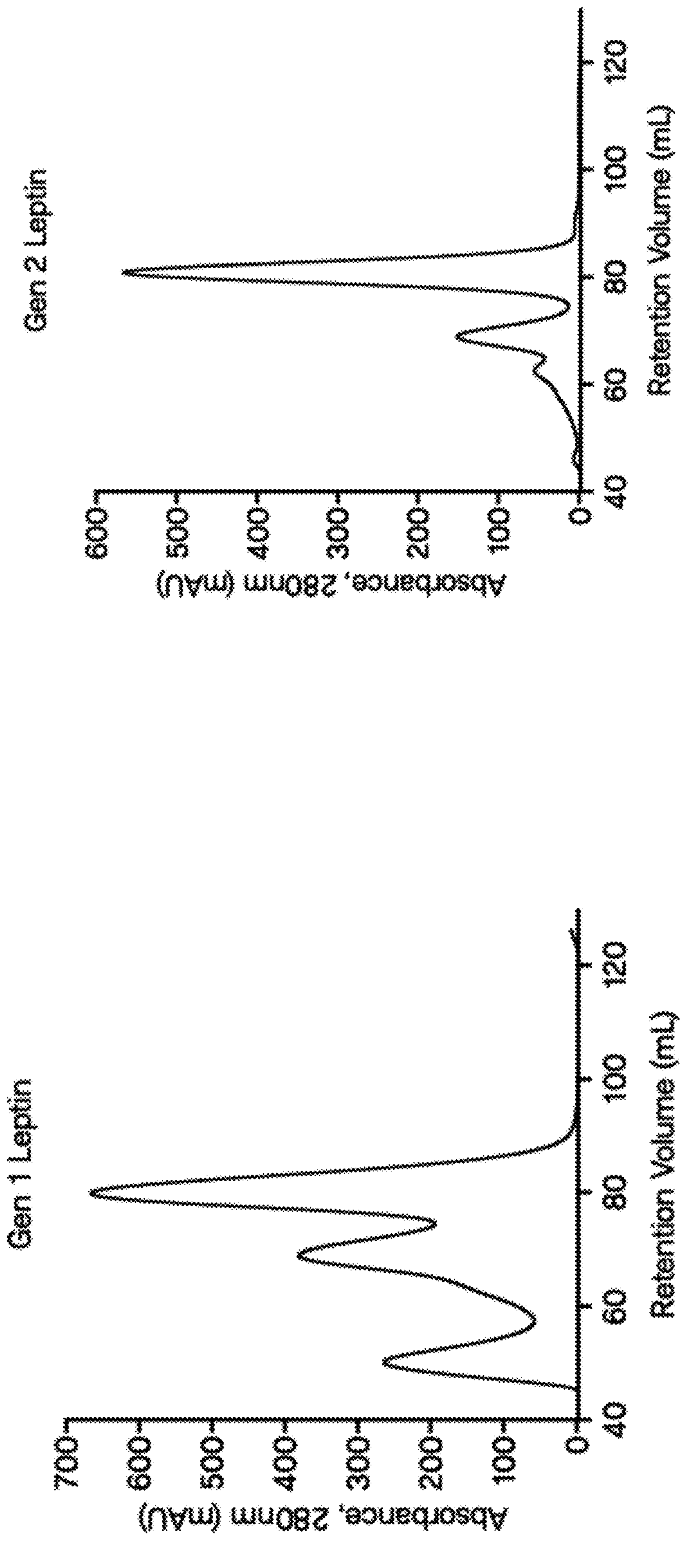
FIG. 8B provides protein folding analysis results by size exclusion chromatography between Gen 1 and Gen 2 leptins and FIG. 8C shows a bar graph of FIG. 8B.

The coding sequences for Gen 1 and Gen 2 Leptin were cloned into an *E. coli* expression vector. Plasmids transformed into *E. coli* protein expression strain BL21DE3. Soluble protein portions were assessed for proper folding using Size Exclusion Chromatography post-affinity purification. The monomeric, properly folded protein was separated from dimeric or higher-order forms of the protein. FIG. 8B displays protein folding analysis results by size exclusion chromatography.

Figure 8C:
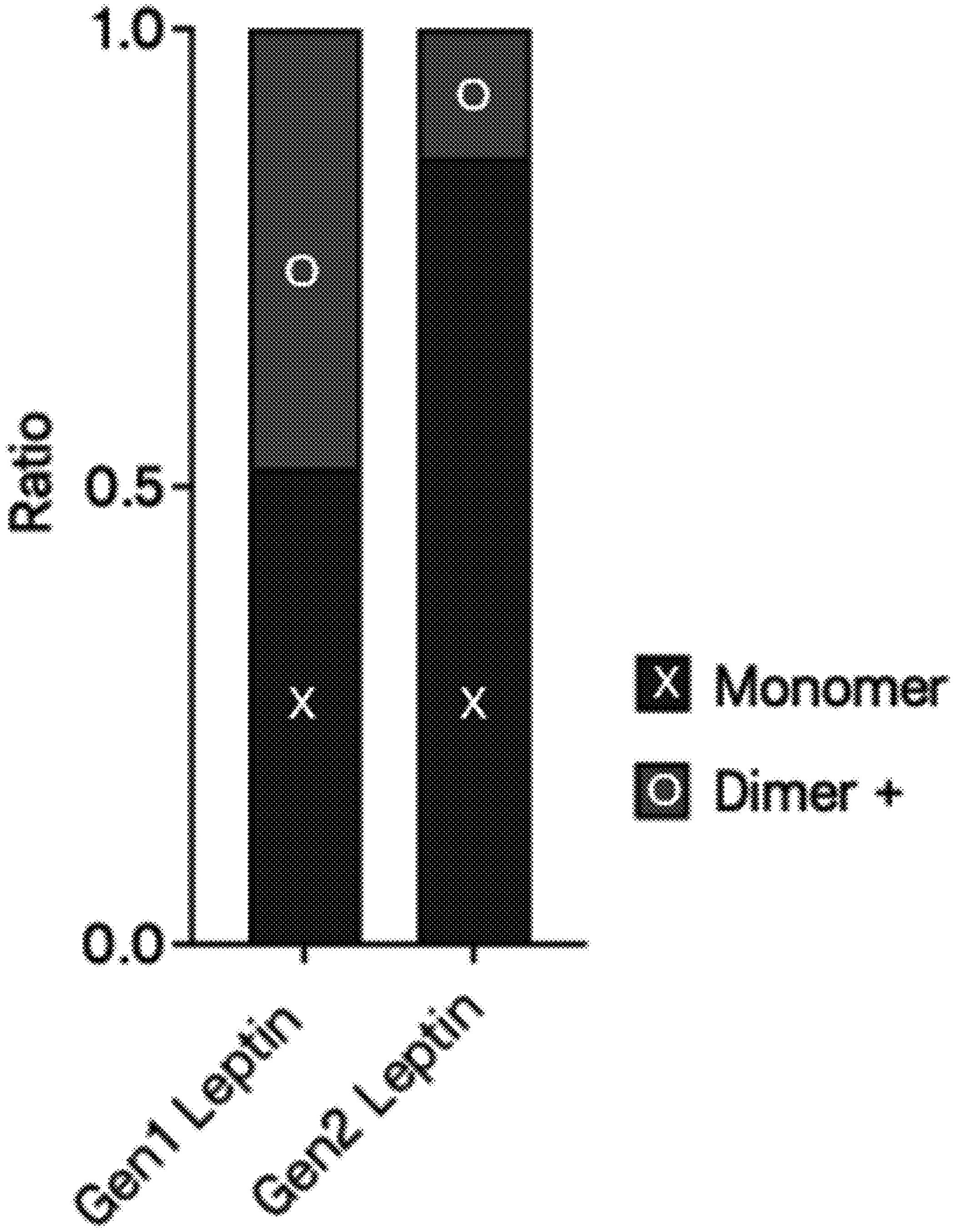

The proportion of properly folded protein and misfolded protein from the SEC chromatogram in FIG. 8B is presented in FIG. 8C as a bar graph format. These results indicate that Gen2 leptin has greater expressivity in *E. coli* and is less prone to dimerization and aggregation.

Figure 9A:
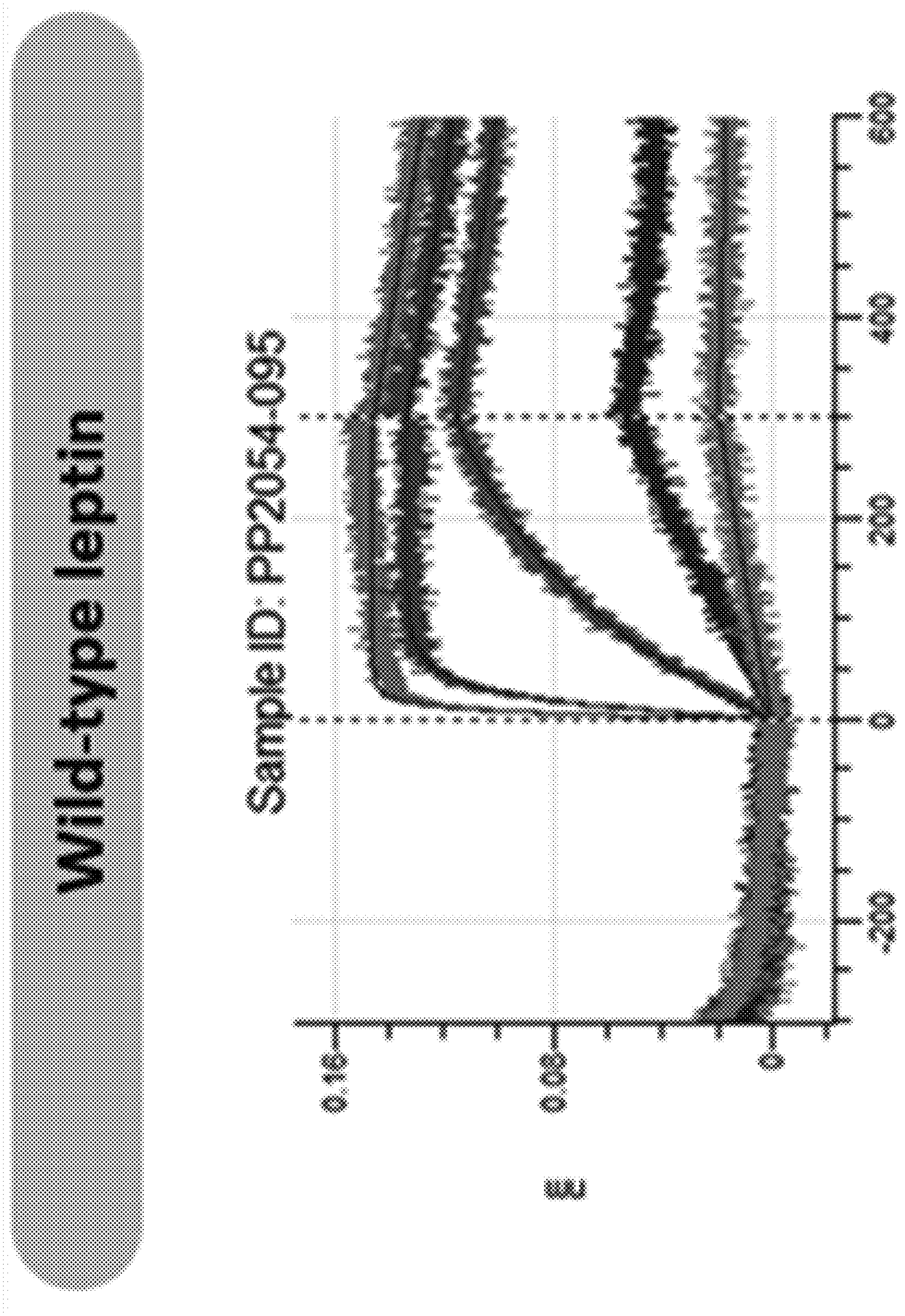
FIGS. 9A-9B provide binding affinity of wild-type leptin and Gen 2 leptin, and FIG. 9C provides a summary table of KD, Ka, and Kd is values of control (WT leptin) and test group (Gen 2 leptin).
Figure 9B:
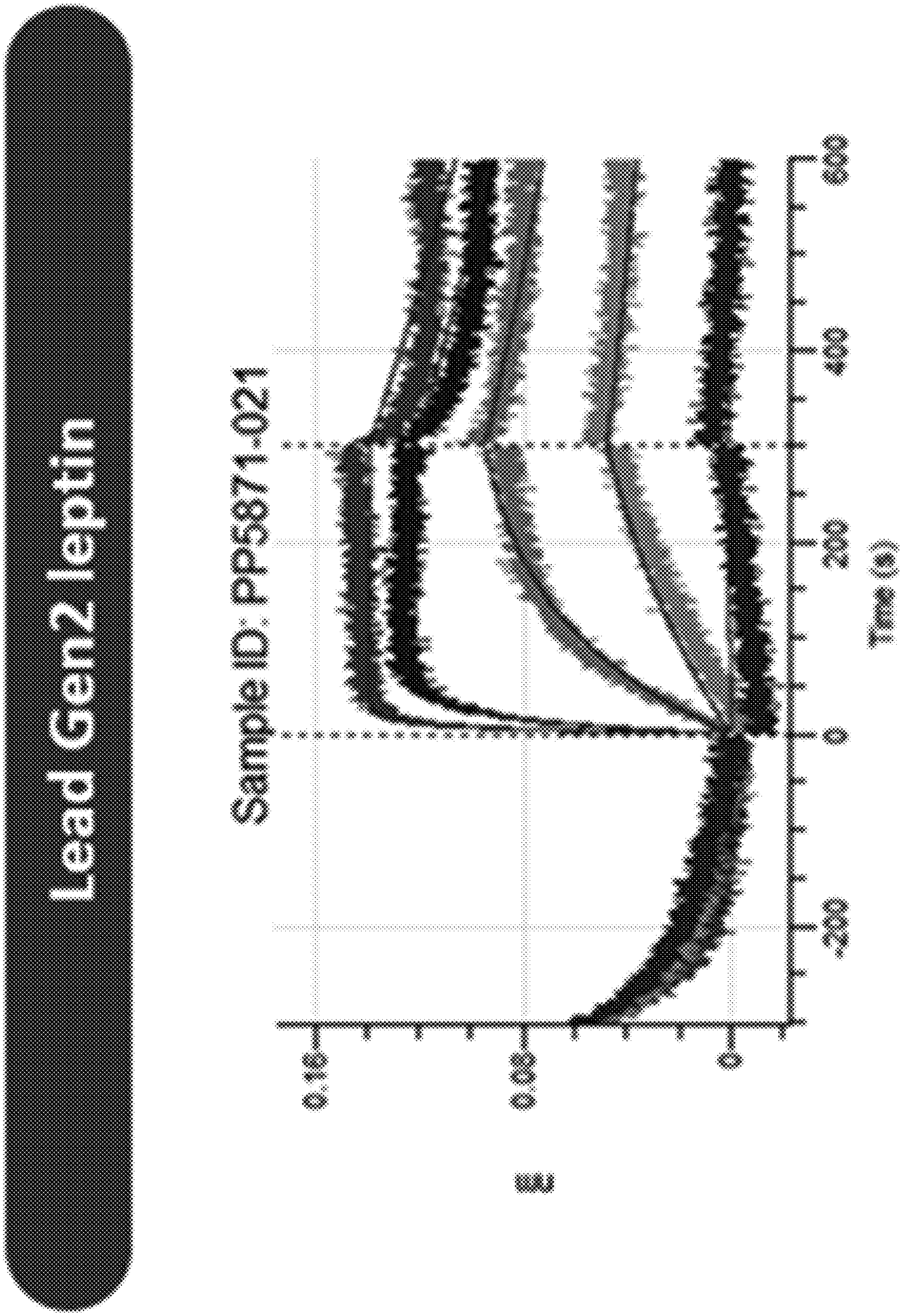

To understand the biding affinity of Gen 2 leptin to leptin receptor, Gen 1 and Gen 2 leptin binding kinetics to the dimeric human leptin receptor was measured using label-free Biolayer interferometry (BLI) based methods. The human FC-tagged dimeric leptin receptor was immobilized and captured on ProtA biosensors (Sartorius). The binding kinetics of Gen 1 and Gen 2 leptin were determined using a concentration series of the analytes ranging from 300 nM to 1.24 nM. *E. coli*-expressed, and SEC-purified wild-type leptin (Gen 1) and Gen 2 leptin proteins were used as analytes serially diluted three-fold from 300 nM. Rates of association and dissociation are used to generate apparent equilibrium kinetic binding (KD). FIGS. 9A-9C show that binding affinity of Gen 2 leptin to the leptin receptor is unaltered when compared to the wild type leptin (Gen 1).

Example 10: Thermal Stability of Gen 2 Leptin

Figures 10A, 10B:
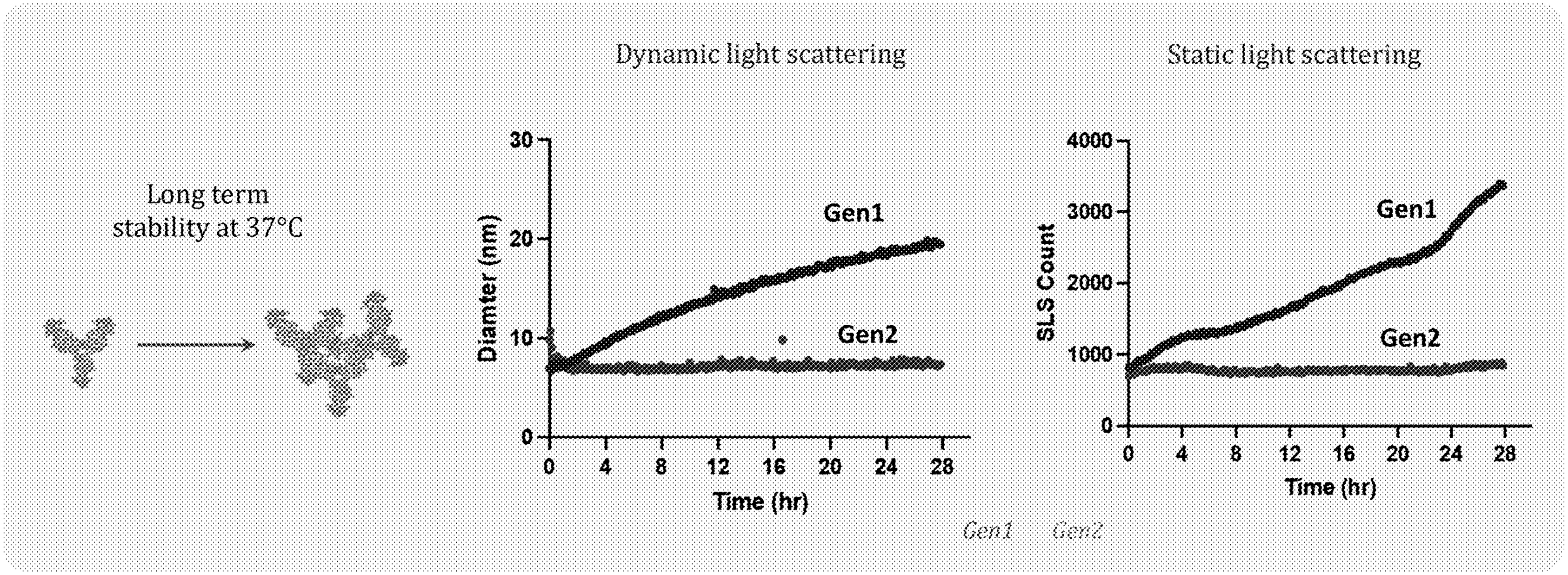
FIG. 10A provides a table presenting quantified expression by receptor binding ELISA and Western Blot analysis; activity ($IC_{50}$) by cell-based assay, and protease resistance by trypsin and chymotrypsin.
FIG. 10B provides dynamic and static light scattering results between Gen 1 and Gen 2 leptins to test long term stability at 37° C. for 28 hours.

The thermal stability of Gen 1 and Gen 2 leptin constructs was studied using the Uncle instrument from Unchained Labs. *E. coli*-expressed, and SEC-purified Gen 1 and Gen 2 proteins were diluted to 1 mg/mL in 1×PBS supplemented with 5% glycerol at pH 7.4. Thermal stability was measured using Uncle instrument (Unchained Labs). The protein samples were studied using Unchained Labs' uni cuvettes and the Uncle instrument at 37° C. for 28 hours. Protein aggregation was monitored using static light scattering (SLS), while polydispersity was assessed with dynamic light scattering (DLS). Protein aggregation was inferred from an increase in particle diameter using DLS or an increase in SLS count. As shown in FIGS. 10A and 10B, Gen 2 leptin has greater expressivity in *Spirulina* and is more stable than wild-type human leptin (Gen 1). Experiments described above using *E. coli* expressed Leptin were repeated using *Spirulina*-expressed Leptin. The results were similar, in that *Spirulina*-expressed and purified Gen2 leptin was similarly less prone to aggregation (data not shown).

Figure 11A:
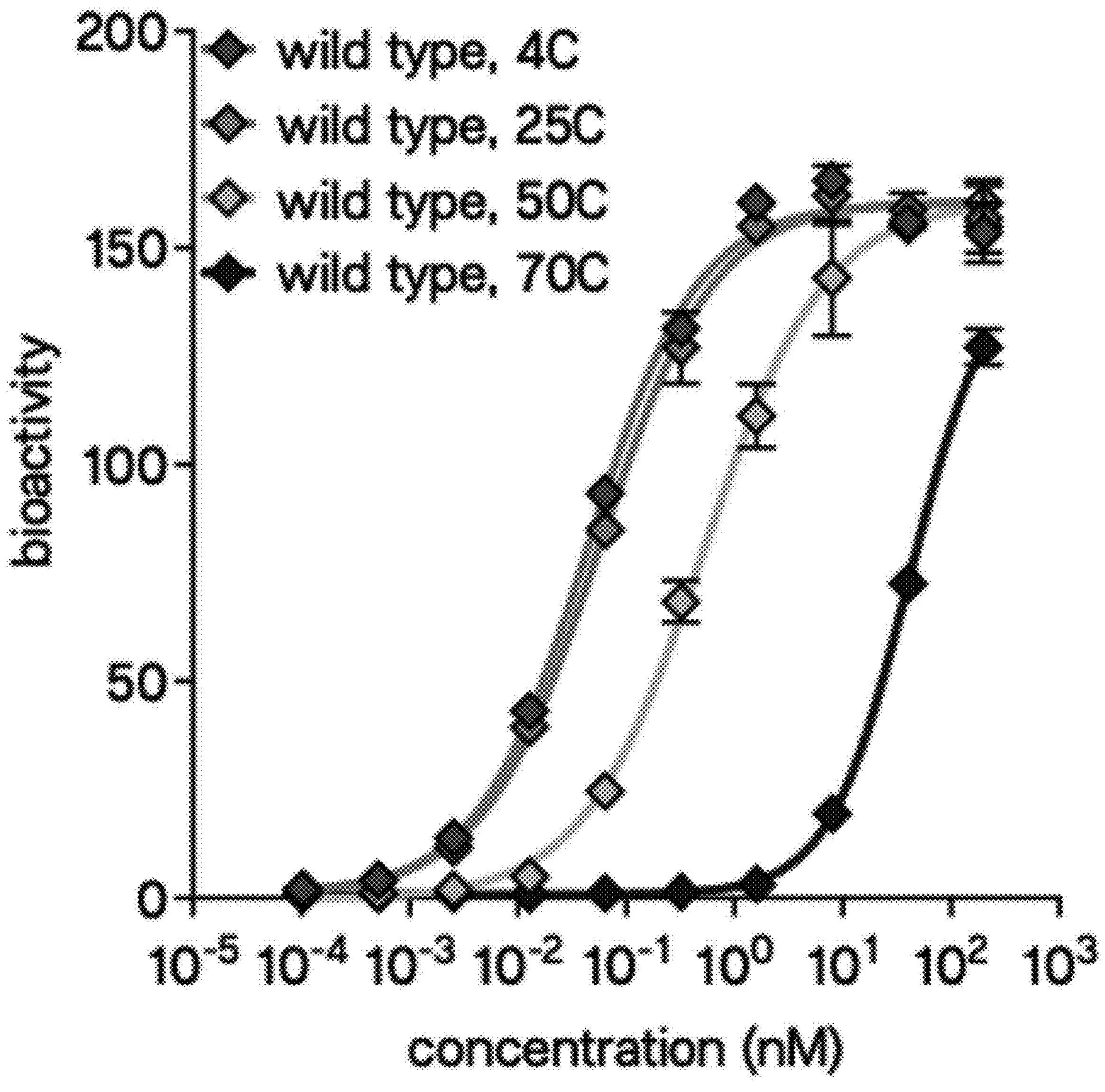
FIG. 11A provides the thermostability of heat-treated wild type leptin at various temperatures (4° C., 25° C., 50° C., 70° C., and 90° C.).
Figure 11B:
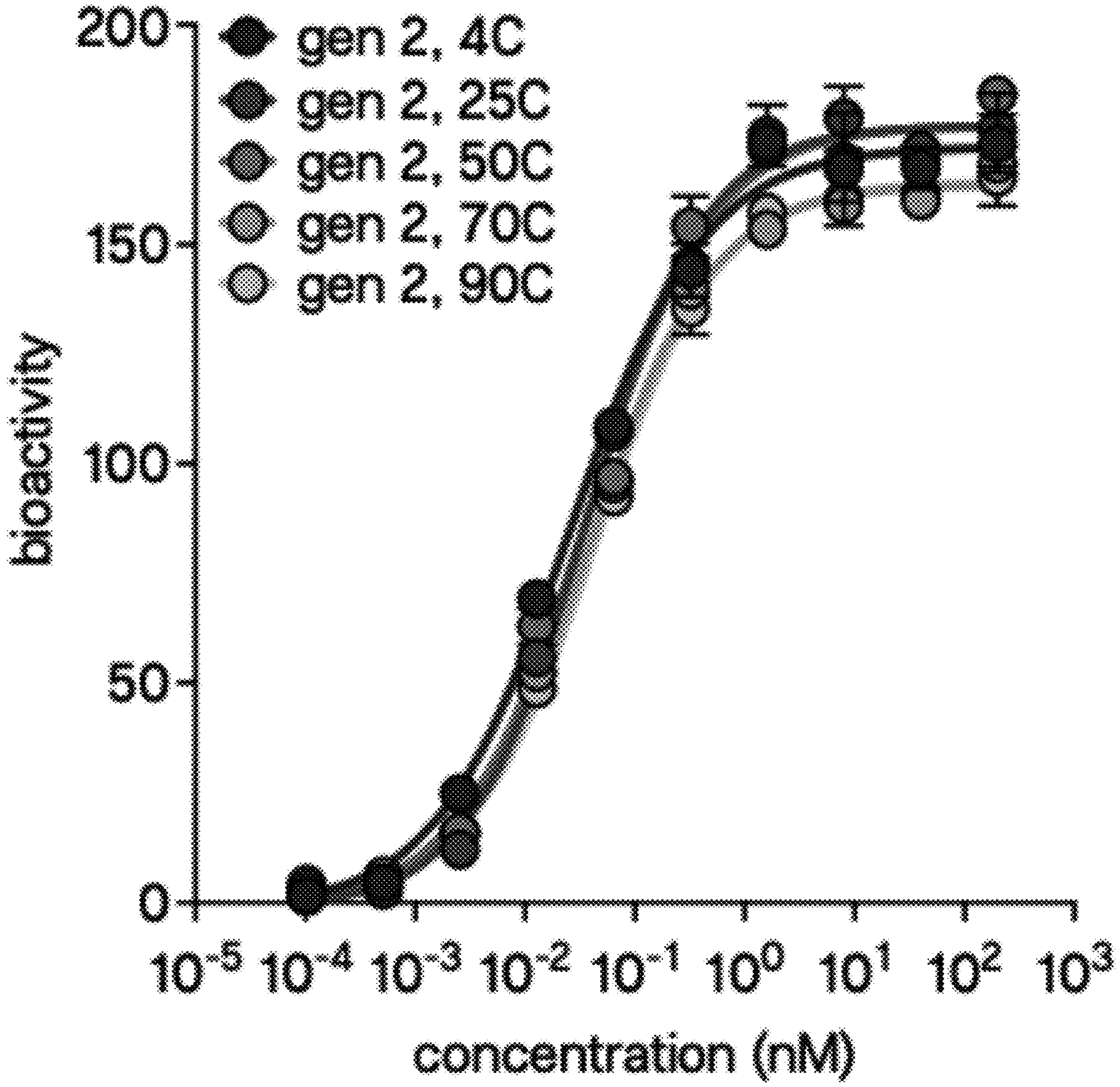
FIG. 11B provides the thermostability of heat-treated generation 2 (Gen 2) leptin at various temperatures (4° C., 25° C., 50° C., 70° C., and 90° C.).

To further compare the thermostability of Gen 2 leptin with wild type leptin (Gen 1), proteins purified from *E. coli* were diluted to 100 μg/mL in PBS and incubated at the indicated temperatures for 1 hr. Treated samples were serial diluted and assayed for their potency using leptin reporter cell line. Fold induction of luciferase signal over non-treated control cells was calculated and plotted. IC50 of each sample were calculated with Prism. As shown in FIGS. 11A-11C, Gen 2 leptin has remarkable thermostability, maintaining the ability to active the reporter line even after treatments of 90° C. Experiments described above using *E. coli* expressed Leptin were repeated using *Spirulina*-expressed Leptin. The results were similar, in that *Spirulina*-expressed and SEC-purified Gen 2 leptin exhibit similar bioactivity post incubation at various temperatures as protein generated using *E. coli* system (data not shown).

Example 11: Receptor Signaling and Signaling Specificity of Gen 2 Leptin

Figure 12A:
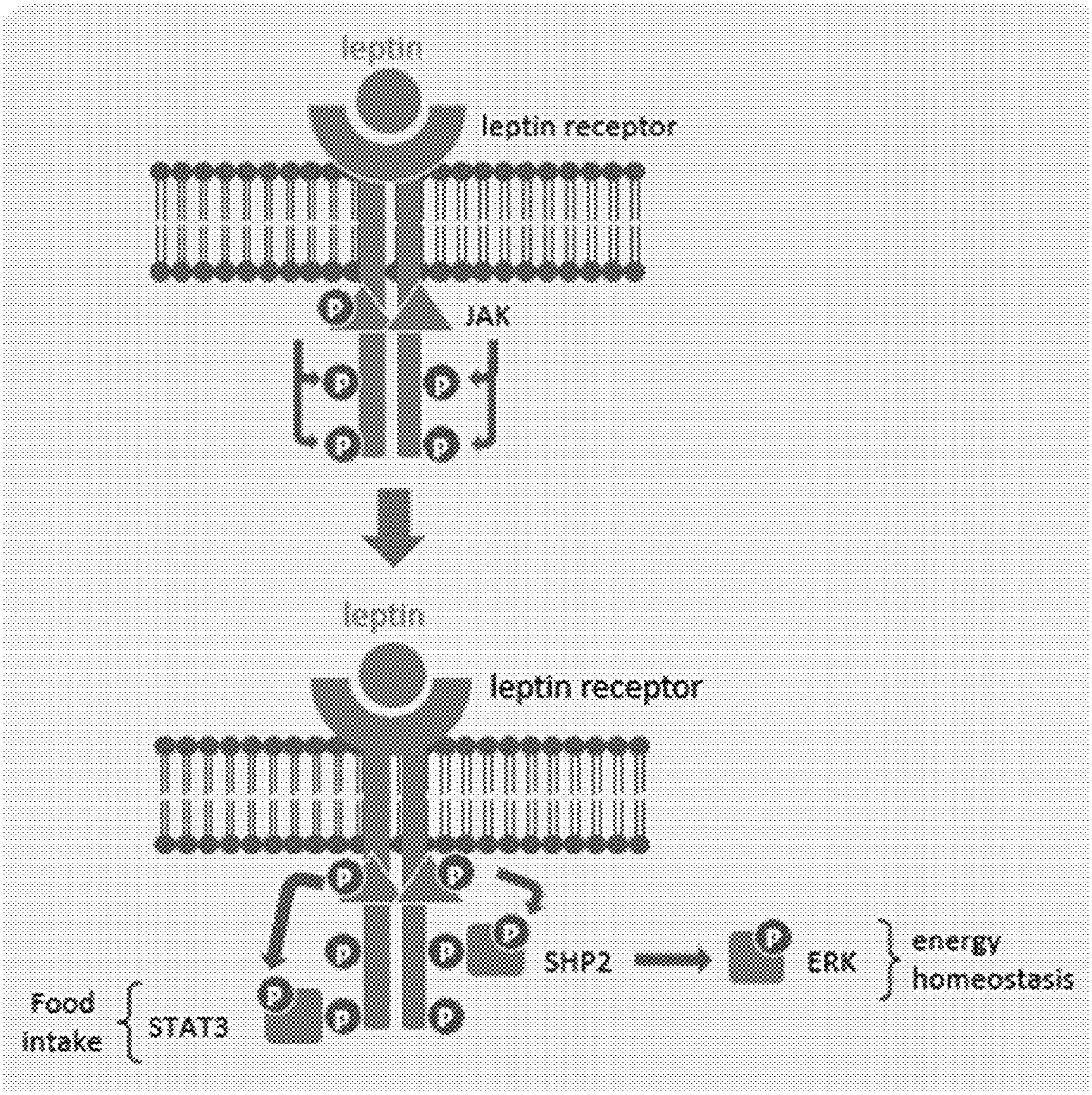
FIG. 12A provides a schematic of the signaling cascade upon leptin binding to receptor.
Figure 12B:
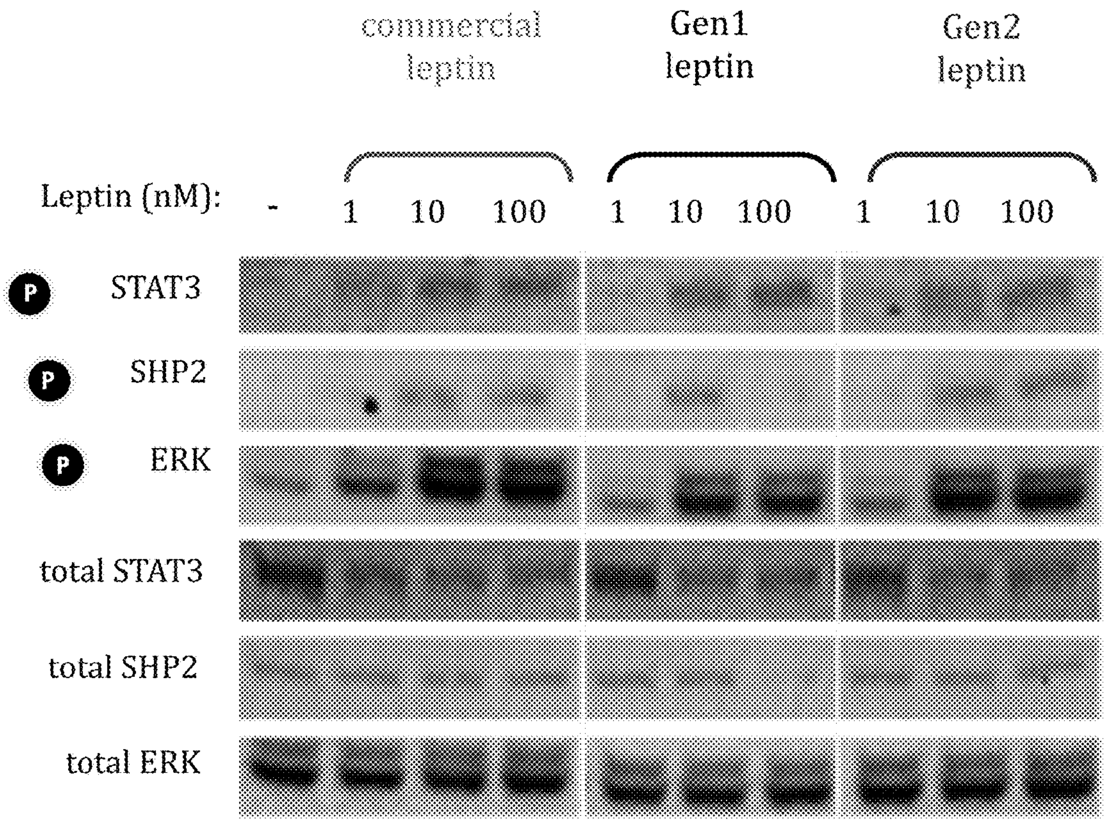
FIG. 12B provides phosphorylation levels of commercial leptin, Gen1 and Gen2 leptin using Western blot analyses.

To understand if Gen 2 leptin can initial normal receptor signaling, 1.2 million of 293T epithelial cells stably expressing human leptin receptor and SIE (STAT3 activated sis-inducible element)-Luciferase were seeded in 2 mL volume in each well on poly-L-lysine coated 6 well plate in DMEM culture medium with 10% fetal bovine serum and Pen-Strep. Cells were incubated at 37° C. for 24 hours. 1 mL of the medium were replaced with medium containing leptin. The final concentration of leptin is 0, 1, 10 and 100 nM. After incubation at 37° C. for 20 minutes, cells were washed with pre-chilled PBS and lysed with lysis buffer in the presence of protease and phosphatase inhibitor on ice for 5 minutes. Cells were then scraped from the plate and transferred into 1.5 mL Eppendorf tubes, followed by sonication. Cells lysate were centrifuged at 14000 g for 10 min at 4° C. Supernatant was collected and subject to Western blotting to assess phosphorylation of STAT3, SHP2 and ERK. FIG. 12A presents a schematic of the signaling cascade upon leptin binding to receptor. FIG. 12B shows the phosphorylation of commercial, Gen1 and Gen2 leptin. Gen2 leptin by Western blot. The results indicates that Gen 2 leptin initiates normal receptor signaling.

Figure 13A:
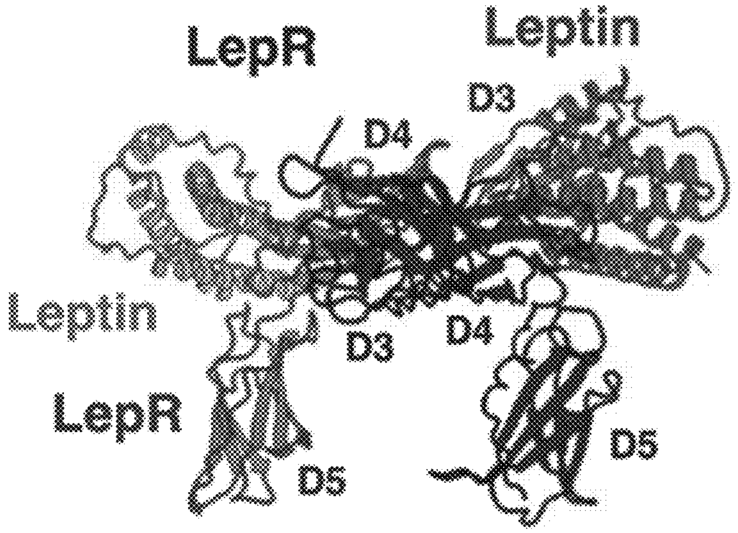
FIG. 13A provides a crystal structure for Leptin-LepR complex (PDB ID: 8DH9).
Figure 13B:
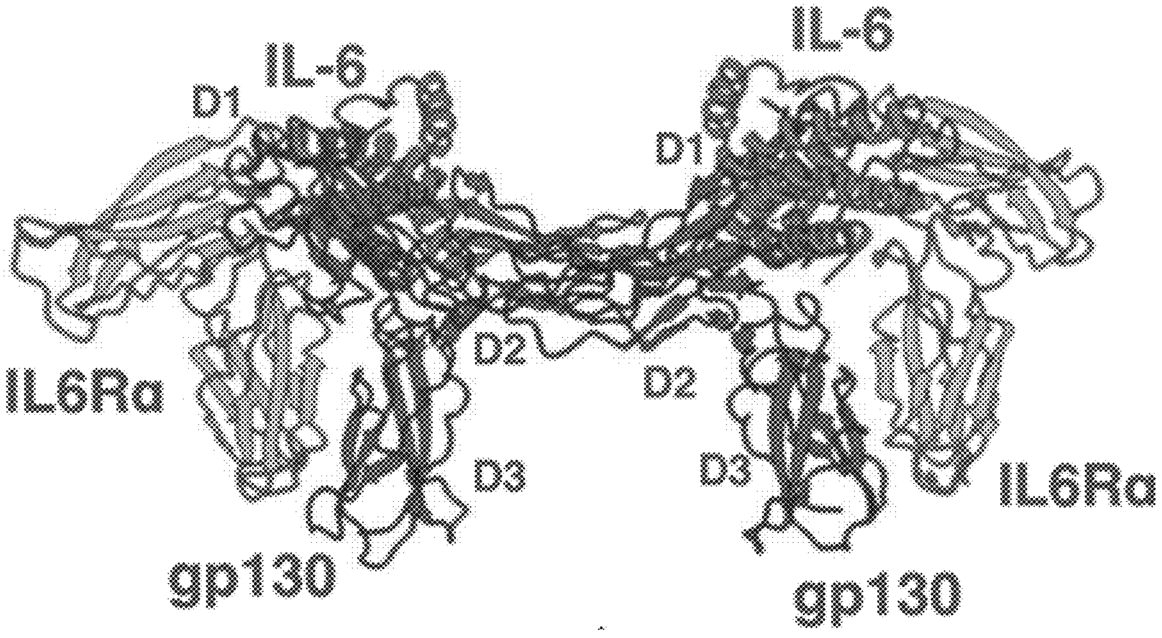
FIG. 13B provides a crystal structure for IL-6Rα-gp 130 complex (PDB ID: 1P9M).
Figure 13C:
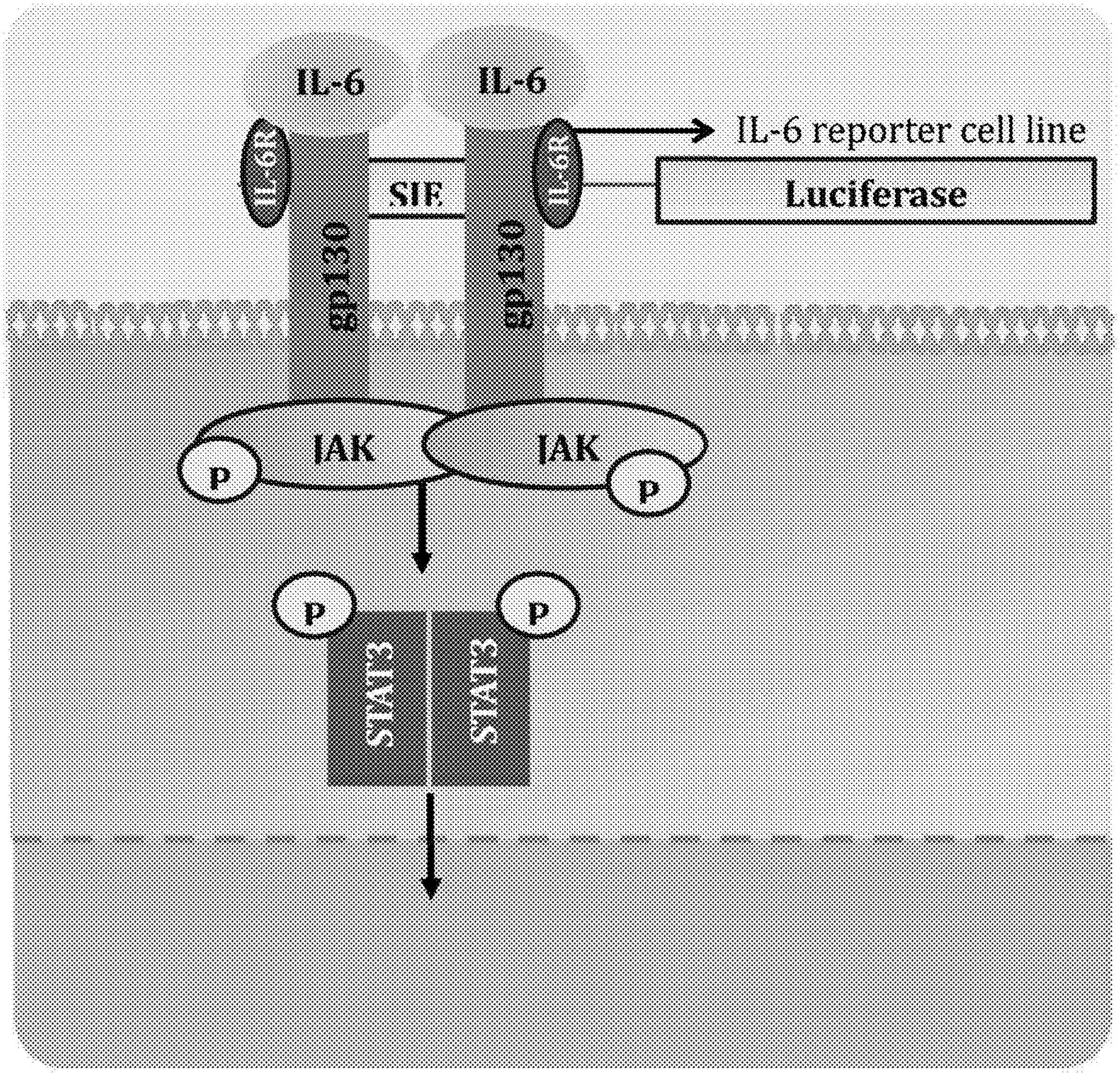
FIG. 13C provides a schematic of the IL-6 reporter cell line.
Figure 13D:
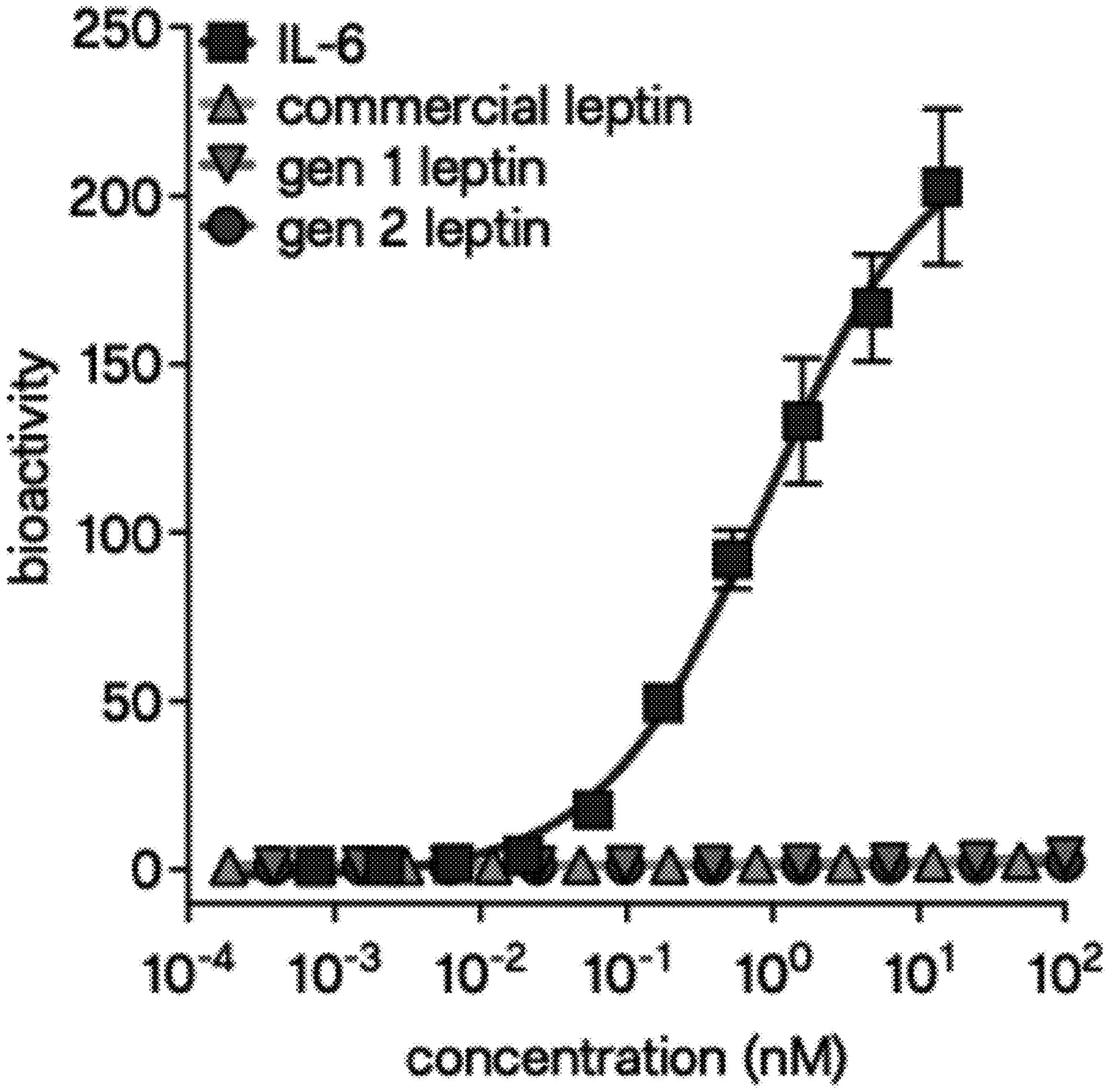
FIG. 13D provides bioactivity comparisons of IL-6, commercial leptin, Gen 1 leptin, and Gen 2 leptin.

Leptin is most closely related to IL6 family cytokines. Docking of leptin to the leptin receptor is structurally similar to the docking of IL6 to gp130 as demonstrated in FIGS. 13B-13C. Lack of IL-6 signaling by leptin and Gen 2 leptin was assessed using an IL-6 reporter cell line. To assess the specificity of Gen 2 leptin, 293T cells stably expressing luciferase driven by SIE were used. IL6 is included in the experiment since IL-6 also induce STAT3. Cells were seeded at 30000 cells per well in poly-L-lysine coated black 96 well plates and incubated at 37° C. for overnight. IL-6, Gen1 (wt) and Gen2 leptin were serial diluted and incubated with cells for 21 hr. Luciferase activity was measured. Fold induction of luciferase signal over non-treatment control cells was calculated and plotted with Prism. FIG. 13D shows bioactivity (IC50 values) of the various Gen2 leptins, indicating that mutations (N2K, S120A, and N82K/S120A) that decrease wild-type human leptin activity similarly affect the bioactivity of Gen2 leptin.

Example 12: Identification of Critical Residues for Bioactivity

Figures 14A, 14B:
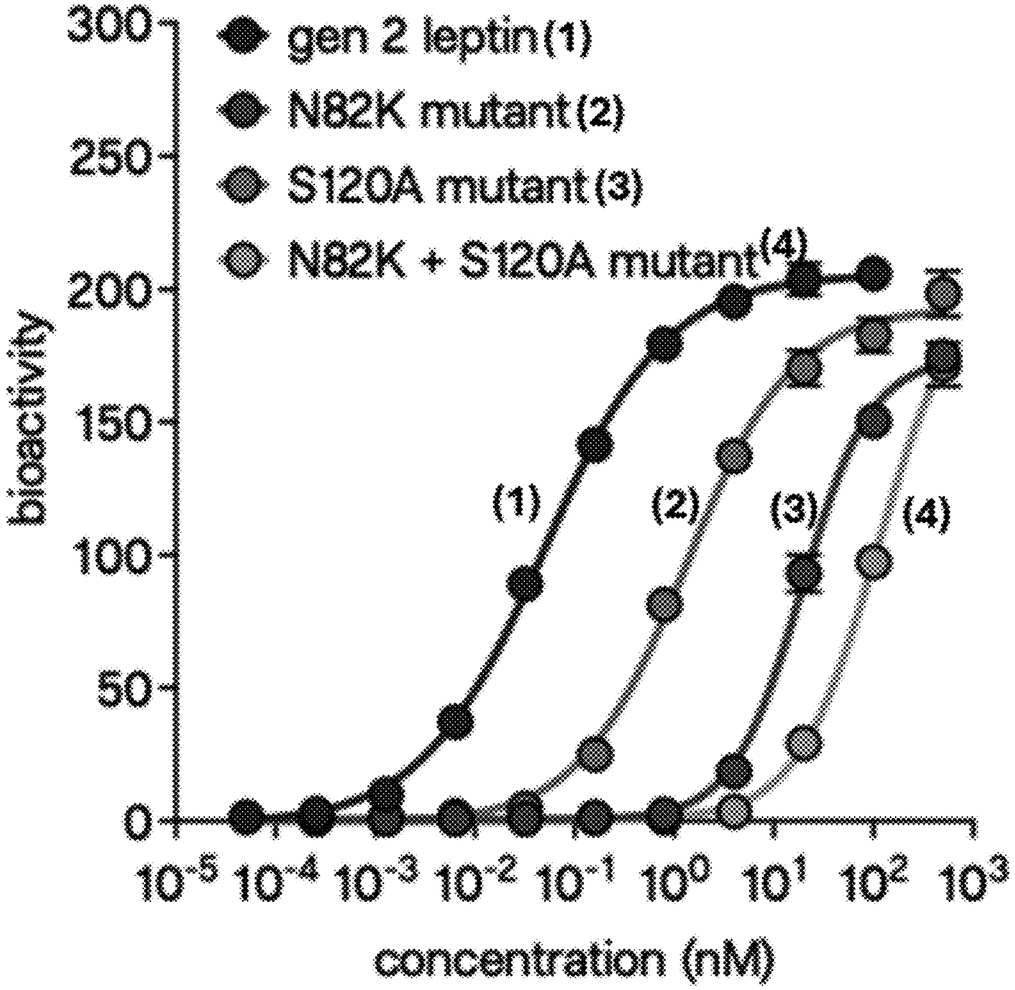
FIG. 14A provides bioactivity of various Gen2 leptin mutations; (1) N82K mutant (PP8709-001); (2) S120A mutant (PP8710-001); (3) N82K+S120A mutant (PP8711-001), when compared to Gen 2 leptin (PP5867-117).
FIG. 14B provides IC50 values of three Gen 2 leptin mutants along with control (Gen 2 leptin; PP5867-117).

To compare the potency of Gen2 leptin mutants, proteins purified from *E. coli* (Gen 2 leptin; Gen 2 leptin mutant with N82K; Gen 2 leptin mutant with S120A; Gen 2 leptin mutant with N82K and S120A) were serial diluted and assayed for their potency using leptin reporter cell line. The Gen2 leptin mutants were assessed for bioactivity using a cell-based signaling assay. The signaling assay using 293 epithelial cells overexpressing the human leptin receptor and containing a STAT3-responsive luciferase reporter gene. Fold induction of luciferase signal over non-treated control cells was calculated and plotted. IC50 of each sample were calculated with Prism. FIGS. 14A and 14B shows bioactivity of various Gen 2 leptin mutants, showing reduced bioactivity of N82K and S120A leptin mutants.

Figure 15A:
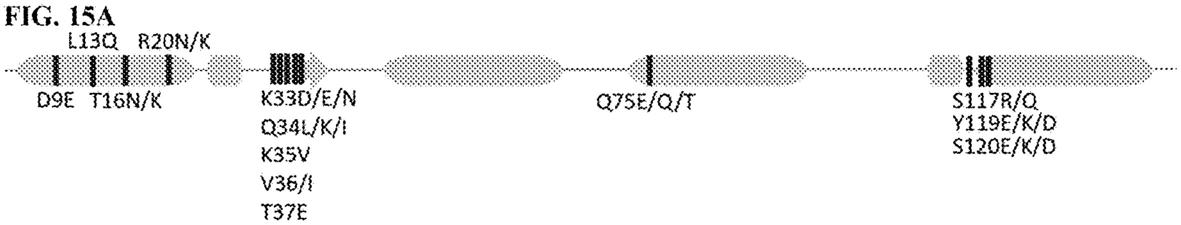
FIG. 15A provides non-binding (or reduced-binding) Gen2 leptin designs with residue locations and their possible substitutions.
Figure 15B:
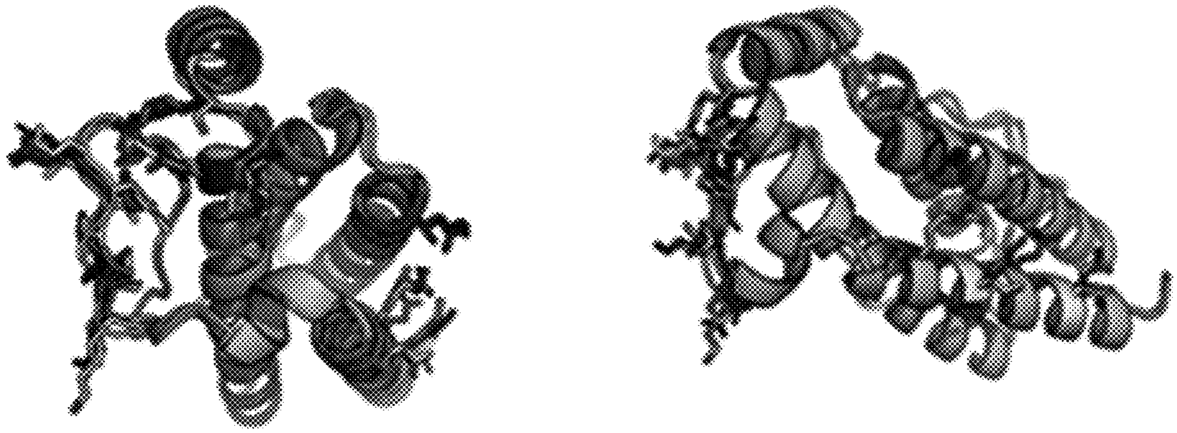
FIG. 15B provides a schematic of non-binding Gen2 regions.
Figures 15C, 15D:
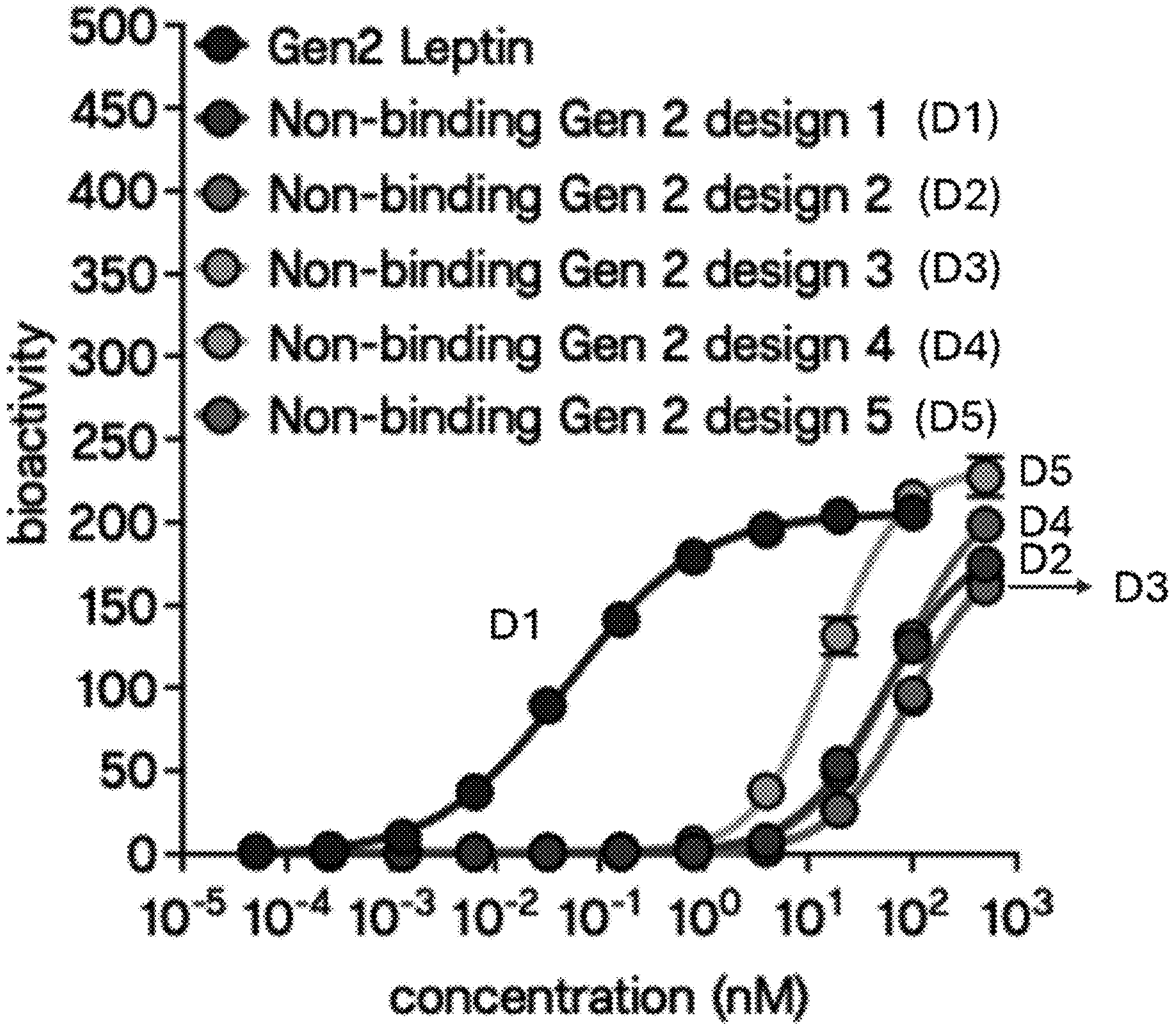
FIG. 15C provides bioactivity of various Gen2 leptin non-binding mutants; (1) PP8712-001; (2) PP8713-001; (3) PP8714-001; (4) PP8715-001; (5) PP8716-001, when compared to Gen 2 leptin (PP5867-117).
FIG. 15D provides IC50 values of five Gen 2 leptin non-binding mutants along with control.

Further, additional reduced-activity Gen 2 leptin mutants were generated using AI-guided sequence redesign allowing receptor binding regions to vary. The non-binding Gen2 leptin mutations started from Gen2 leptin. The previously fixed positions identified as potential receptor binding positions, were now positions for redesign, while keeping all other positions fixed. These include positions D9, L13, T16, R20, K33, Q34, K35, V36, T37, Q75, D85, L86, S117, Y119, S120, as presented in FIG. 15A. Sequence design was done using ProteinMPNN, then predictions of the structures were evaluated with AlphaFold2. Top 5 reduced binding interface designs were selected Table 7) based on comparable energies to Gen2 leptin, and poor predicted binding energies against the leptin receptors. To compare the potency of non-binding Gen2 leptin mutants, Gen 2 leptin and five non-binding Gen 2 leptin mutant proteins purified from *E. coli* were serial diluted and assayed for their potency using leptin reporter cell line. The generated designs were then assessed for bioactivity using a cell-based signaling assay described in previous examples. Fold induction of luciferase signal over non-treated control cells was calculated and plotted. IC50 of each sample were calculated with Prism. FIGS. 15C and 15D shows bioactivity of various reduced-binding mutants of Gen 2 leptin described in Table 7, indicating that reduced-binding Gen2 leptin mutants in the predicted receptor binding domains show no or minimal signaling.

TABLE 7

5 selected 'non-binding/reduced-binding" Gen 2 leptin mutants

| ID | Amino Acid | Substitutions (from Gen 2 leptin) |
|---|---|---|
| Non-binding Gen 2 design 1 | VPVEQIRKELETLIRKVITKIDTIPYVKEVSPDLKIEG LEFIPGTKEKITYTDADETLAIYQEILSLLPEPELQEI ALDLDNIRDLIRELAATKNCPLPRASGLPDREKLLE AIKERGEEVAVTTATKLKEFLEKLIEELKKDPGC (SEQ ID NO: 82) | D9E, T16K, R20K, K33D, Q34L, V36I, T37E, Q75E, S117R, Y119E, S120E |
| Non-binding Gen 2 design 2 | VPVEQIRKELETLIRNVITRIDTIPYVKEVSPEKVIEG LEFIPGTKEKITYTDADETLAIYQEILSLLPEPELQKI ALDLDNIRDLIRELAATKNCPLPRASGLPDREKLLE AIKERGKDVAVTTATKLKEFLEKLIEELKKDPGC (SEQ ID NO: 83) | D9E, T16N, K33E, Q34K, K35V, V36I, T37E, Q75K, S117R, Y119K, S120D |
| Non-binding Gen 2 design 3 | VPVEQIRKELETLIRNVITRIDTIPYVKEVSPDIVYE GLEFIPGTKEKITYTDADETLAIYQEILSLLPEPELQ QIALDLDNIRDLIRELAATKNCPLPRASGLPDREKL LEAIKEQGEKVAVTTATKLKEFLEKLIEELKKDPG C (SEQ ID NO: 84) | D9E, T16N, K33D, Q34I, K35V, V36Y, T37E, S117Q, Y119E, S120K |
| Non-binding Gen 2 design 4 | VPVEQIRKELETQIRNVITRIDTIPYVKEVSPNLKIE GLEFIPGTKEKITYTDADETLAIYQEILSLLPEPELQ TIALDLDNIRDLIRELAATKNCPLPRASGLPDREKL LEAIKERGDDVAVTTATKLKEFLEKLIEELKKDPG C (SEQ ID NO: 85) | D9E, L13Q, T16N, K33N, Q34L, V36I, T37E, Q75T, S117R, Y119D, S120D |
| Non-binding Gen 2 design 5 | VPVEQIRKELETLIRKVITQIDTIPYVKEVSPDLKIEG LEFIPGTKEKITYTDADETLAIYQEILSLLPEPELQQI ALDLDNIRDLIRELAATKNCPLPRASGLPDREKLLE AIKERGEEVAVTTATKLKEFLEKLIEELKKDPGC (SEQ ID NO: 86) | D9E, T16K, R20Q, K33D, Q34L, V36I, T37E, S117R, Y119E, S120E |

Example 13: Weight loss study of Gen 2 Leptin in comparison to WT *Spirulina* and Gen 1 Leptin Protocol 1: Pre-Study. Three days prior to study start (day-3), weight class specific animals were selected from the main CU Anschutz vivarium and brought up to the NORC lab satellite facility. The animals were weighed, and marked numerically for identification within their cages. The cages were also numbered according to their weight class and which lot of *Spirulina* they would be receiving. Animals went through 3 day acclimation period for adjustment to altered light system (lights out at 4 pm and lights on at 4 am), as well as increased temperature at 80 degrees Fahrenheit. All mice were weighed and food intake measured daily. At day-1 the qMRI was calibrated prior to use and baseline data was collected for every subject using the Echo qMRI.

Protocol 2: On-Study. Prior to entering the NORC lab satellite facility, treatment tubes and buffer were retrieved from the freezer. Resuspension was to occur no more than one hour prior to treatment in animals, due to the thickening process that naturally occurs which can increase gavage difficulty and accuracy. For group 1, using a 1000 μL pipette, 2000 μL of Milli-Q water was pipetted into a CaCO3 buffer tube, recapped, and gently inverted. For group 2, 2000 μL of PP5867-113 was pipetted into a CaCO3 buffer tube. For group 3, 400 μL of PP5867-113 and 1600 μL of MTRX-004 was pipetted into to the CaCO3 tube. For group 4, 2000 μL of PP5867-113 was pipetted into the $NaHCO_3$ tube. For group 6, add 2000 For group 6, add 2000 μL of MTRX-004 to the CaCO3 tube. Oral gavage needles and 1 mL disposable syringes were also collected and brought into the animal facility. Each cage had its food weighed, disposed of, and refilled. Every mouse within a cage was weighed, and then gavaged 200 μL of the solution according to the assignment in the study plan. PP5867-113 simply refers to a batch number (113) for the purified Gen 2 leptin, PP5867 (MBP_G4S_7Z3Q-ABC-006_6H).

Protocol 3: Post-Study/Sac On day-13, the Echo qMRI was calibrated and each mouse underwent a Day 13 qMR for comparative data. Each animal was assigned a liver and serum microcentrifuge tube. 1 mL syringes were prepped with EDTA to allow for blood collection without coagulation during blood drawing. Dry ice was collected to allow for flash freezing before analysis. Mice were weighed individually before being anesthetized with isoflurane. After sufficient level of anesthesia was reached, cervical dislocation was performed.

For serum collection, the thoracic area was aseptically prepped with alcohol before a 1 mL syringe with a 25-gauge needle was inserted for cardiac puncture and resulting exsanguination. The needle was removed to prevent hemolysis, and blood was then expelled into a SST microtainer and arranged into a separate tube rack. After 30 minutes, the SST microtainers were spun down @ 8000 rpm for 5 m in a refrigerated centrifuge and serum transferred to their corresponding microcentrifuge tubes. These tubes were then organized in a shipment box and labeled as serum.

For liver collections, an incision was made down the midline of the abdomen, where a ~0.5 cm section of the large liver lobe was excised and placed into its respected microtainer tube placed into the dry ice container. After complete collection of all subjects, the SST microtainers were spun down and serum transferred to their corresponding microcentrifuge tubes. These tubes were then organized in a shipment box and labeled as serum. The liver tubes were removed from dry ice and organized by group number into a shipment box and labeled as livers. Liver section was performed according to the method found in Lanaspa et al. (J Clin Invest. 2018; 128 (6): 2226-2238).

Statistical Analysis. For example: All results are expressed as the mean±standard deviation as calculated by Excel software (Microsoft version number, Renton, WA). IC50 values were calculated using GraphPad Prism (version number, GraphPad Software Inc, San Diego, CA).

This study was completed demonstrating efficacy of the leptin-expressing *Spirulina* biomass in promoting weight loss in mice. Obese DIO mice (8 mice per cohort) were dosed once daily at lights out with an oral gavage of WT *Spirulina* control (10 mg), *Spirulina* (10 mg) expressing Gen 1 leptin, and *Spirulina* (10 mg) expressing Gen 2 leptin in 0.16 M sodium bicarbonate solution for 14 days. C57Bl/6J mice fed DIO (60% fat) diet prior to initiation of treatment. At acclimatization diet transitioned to 45% fat. Cut-off weight for enrollment in the study was ≥45 g. Acclimatization proceeded for 5 days in an 80° F./40% humidity, 4 am/4 pm day/night cycle room. Mice were group housed. Treatment gavage was performed 30 minutes prior to lights out (4 pm). EchoMRI, liver sections collected, and terminal blood draw were performed at 14 days. Body weight was measured once daily, and food intake was continuously measured using mice housed in BioDaq cages.

Figure 16A:
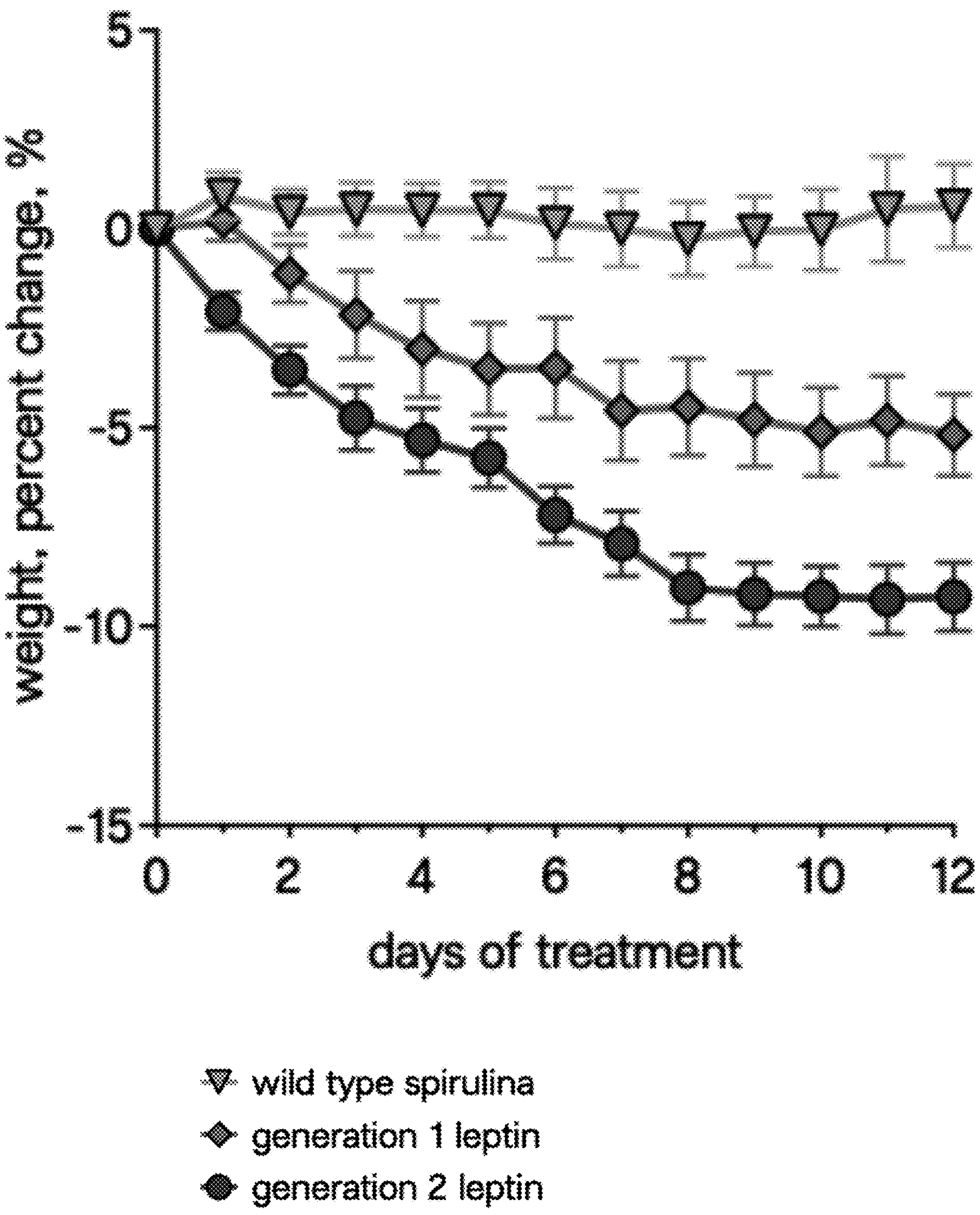
FIG. 16A provides baseline-corrected percent change in body weight over 12 days of treatment when WT *Spirulina* (control), *Spirulina* expressing Gen 1 leptin (SP2334), and *Spirulina* expressing Gen 2 leptin (SP3967; PP5867) were delivered to diet-induced obese (DIO) mice by gavage in 0.16 M sodium bicarbonate solution.
Figure 16B:
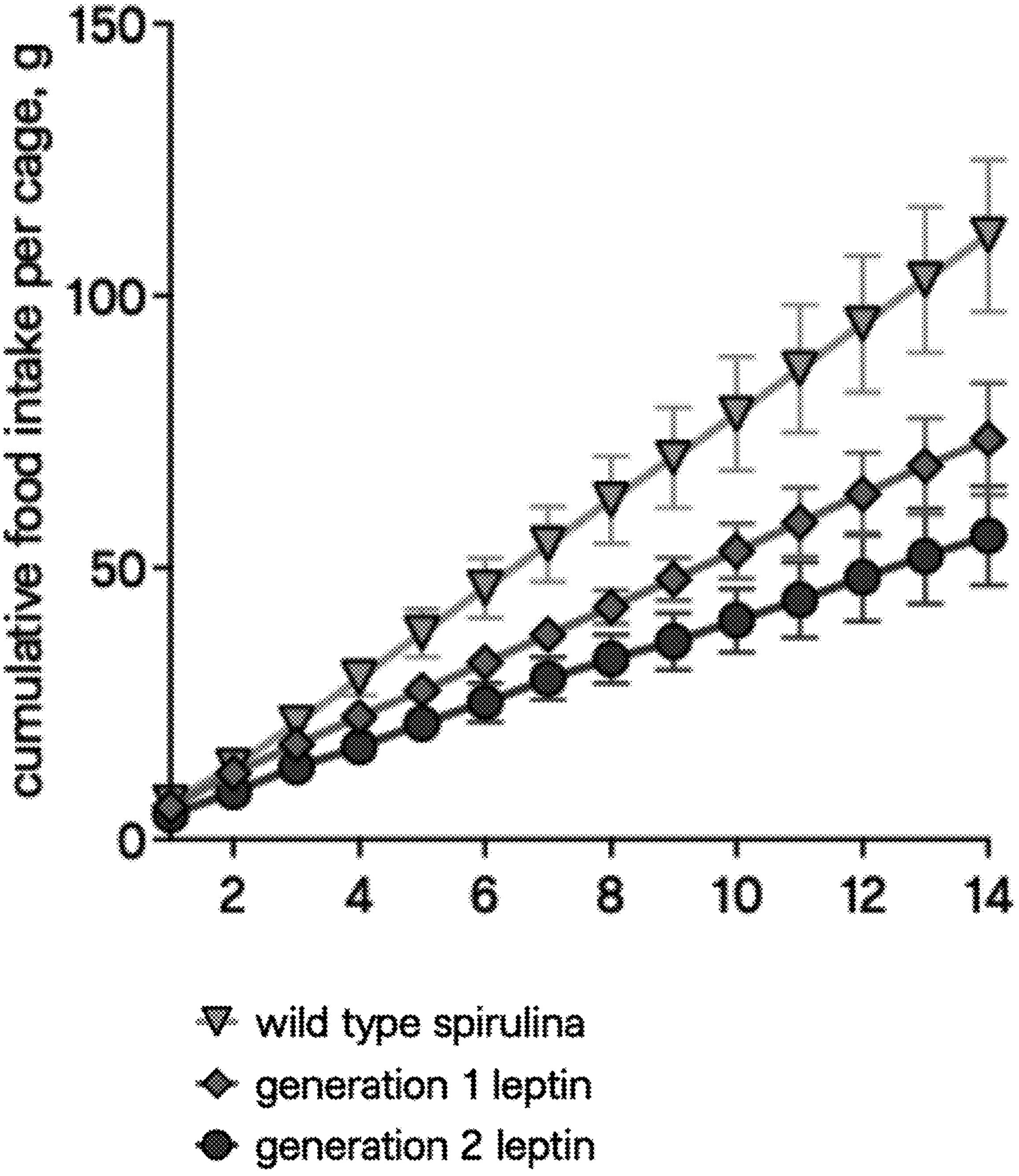
FIG. 16B provides cumulative food intake per cage in grams over 14 days of treatment when WT *Spirulina* (control), *Spirulina* expressing Gen 1 leptin (SP2334), and *Spirulina* expressing Gen 2 leptin (SP3967; PP5867) delivered to diet-induced obese (DIO) mice by gavage in 0.16 M sodium bicarbonate solution.
Figure 16C:
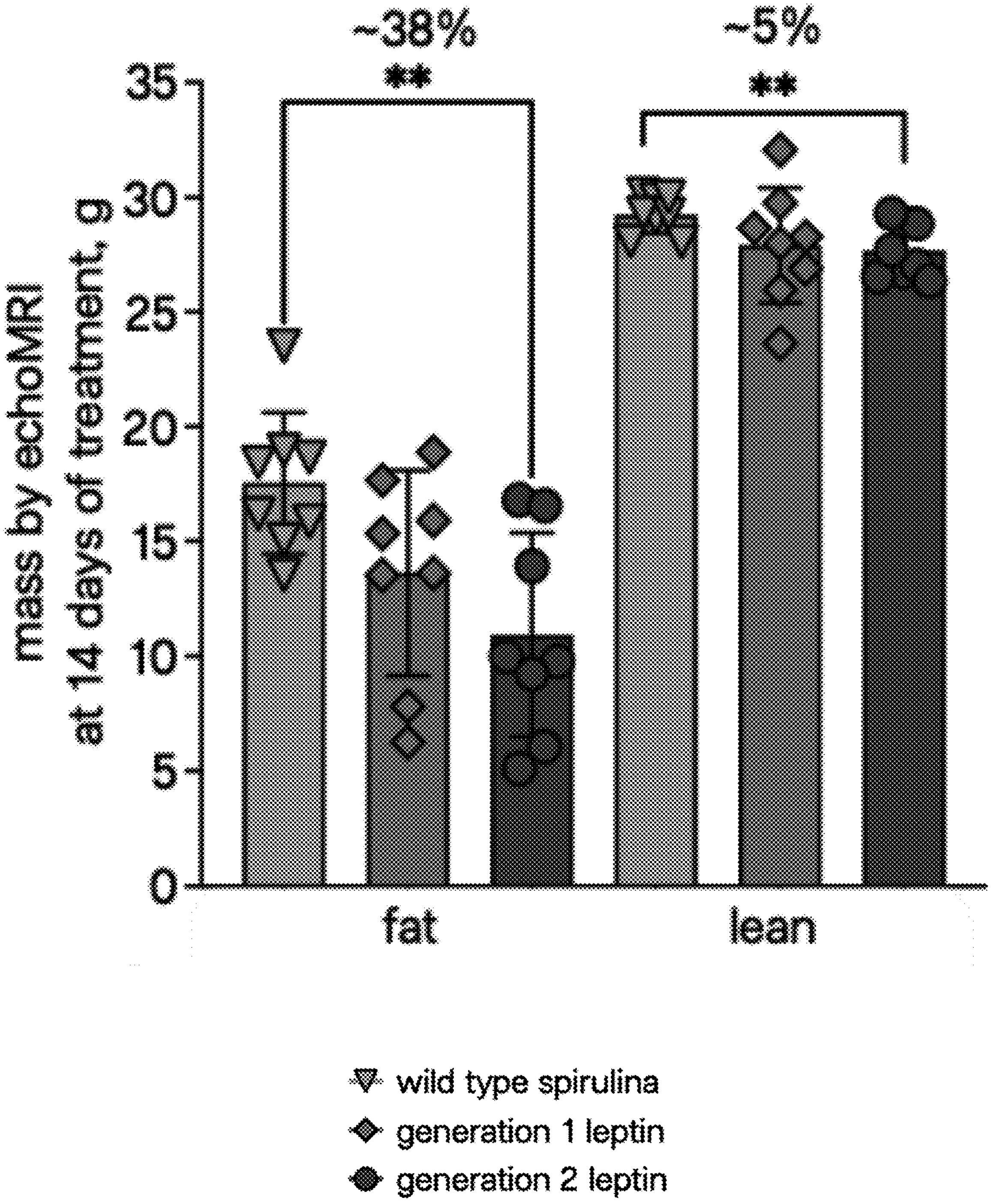
FIG. 16C provides body mass difference between control and treatment groups in fat and lean tissue as measured by echo MRI when WT *Spirulina* (control), *Spirulina* expressing Gen 1 leptin (SP2334), and *Spirulina* expressing Gen 2 leptin (SP3967; PP5867) delivered to diet-induced obese (DIO) mice by gavage in 0.16 M sodium bicarbonate solution.
Figure 16D:
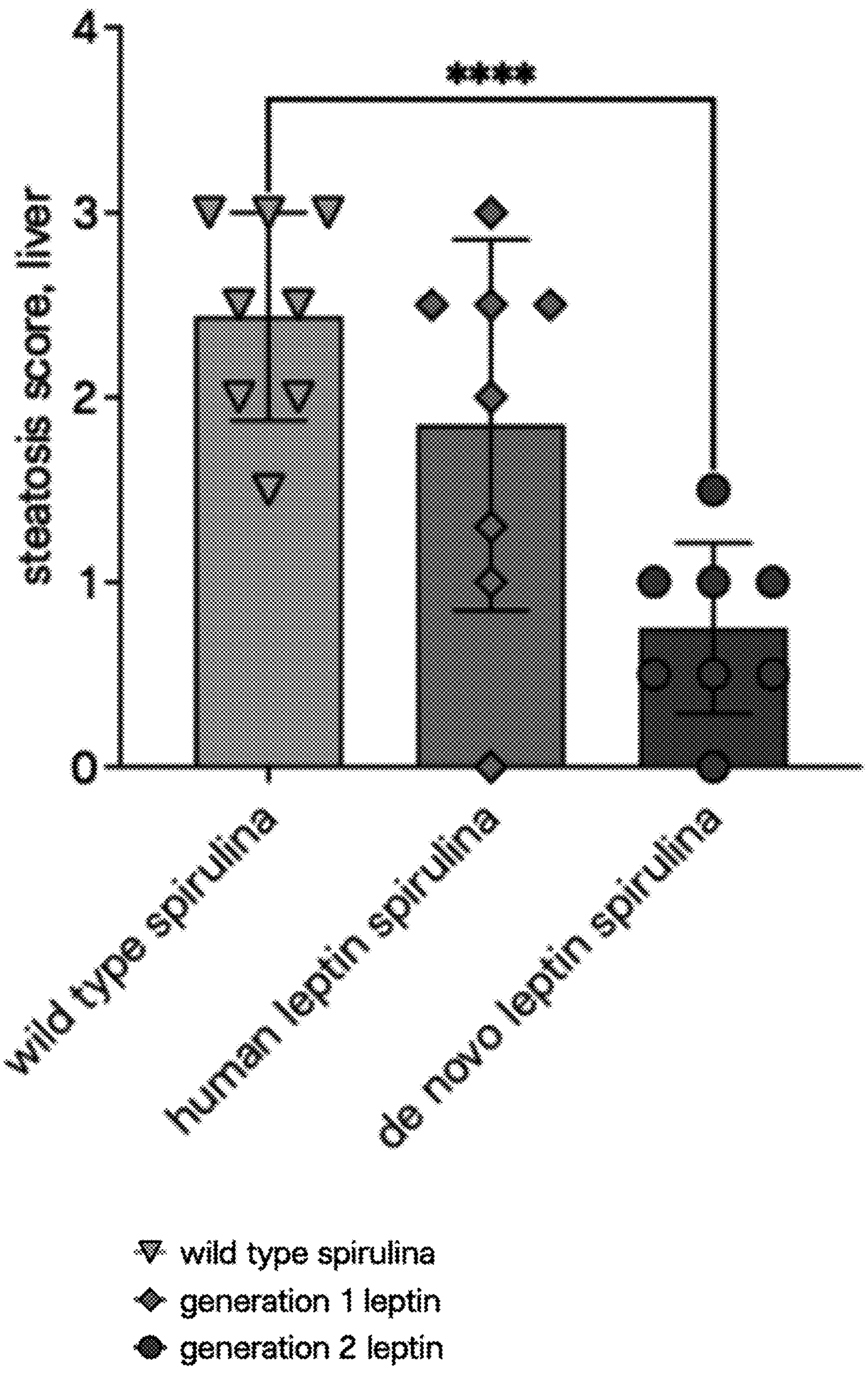
FIG. 16D provides liver histology steatosis score at conclusion of treatment when WT *Spirulina* (control), *Spirulina* expressing Gen 1 leptin (SP2334; human leptin *Spirulina*), and *Spirulina* expressing Gen 2 leptin (SP3967; PP5867; de novo leptin *Spirulina*) delivered to diet-induced obese (DIO) mice by gavage in 0.16 M sodium bicarbonate solution.

FIG. 16A shows the baseline-corrected percent change in body weight over 12 days of treatment. The body weight of mice fed with the *Spirulina* expressing GEN 2 leptin was reduced about 10% and the *Spirulina* expressing GEN 1 leptin was reduced about 5% over 12 days of treatment, while the wild type *Spirulina* did not cause any body weight loss over the same period. FIG. 16B shows cumulative food intake per cage in grams over 14 days of treatment. When comparing the wild type *Spirulina*, both *Spirulina* expressing Gen 1 and Gen 2 leptin, respectively, caused at least half of food intake over 14 days, which would be one of the causes for losing body loss Gen 2 leptin treatment groups had lower cumulative food intake than Gen 1. FIG. 16C shows body mass difference between control and treatment groups in fat and lean tissue as measured by echo MRI. Where there were no significant changes in lean (about 5%), significant loss of fat in mice fed with *Spirulina* expressing Gen 1 and Gen 2 leptins, respectively. Especially, about 38% fat reduction was observed in the mice fed with the *Spirulina* expressing Gen 2 leptin, in comparison with the mice fed with the wild type *Spirulina*. FIG. 16D shows liver histology steatosis score at conclusion of treatment. Similar to body weight and fat loss, steatosis score was significantly reduced in mice fed with *Spirulina* expressing Gen 1 or Gen 2 leptin. Gen 2 leptin expressing *Spirulina* had the lowest steatosis score among test groups.

Figure 17A:
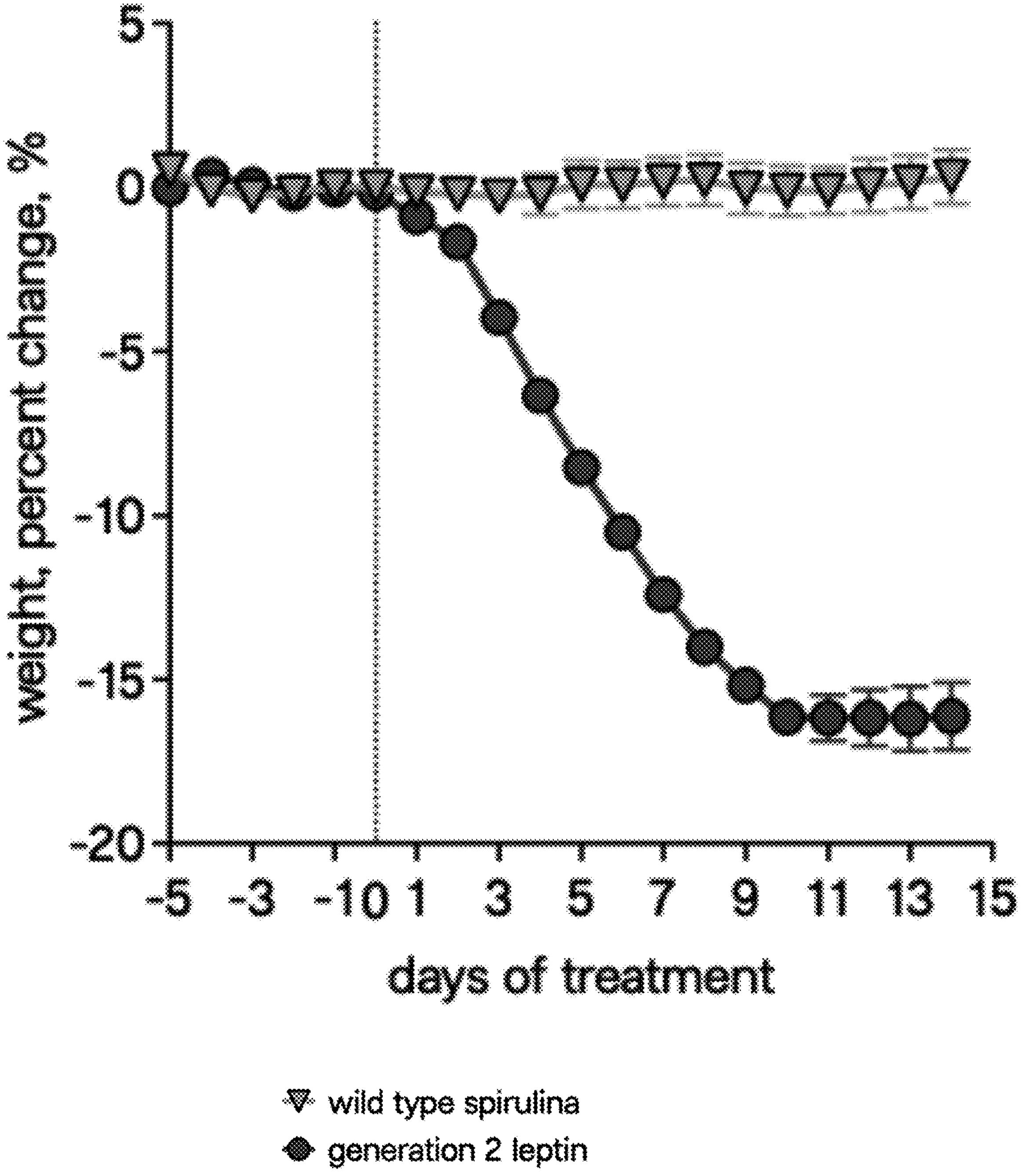
FIG. 17A provides baseline corrected percent change in body weight over 14 days of treatment when WT *Spirulina* (control and *Spirulina* expressing Gen 2 leptin (SP3967; PP5867) delivered to diet-induced obese (DIO) mice by gavage in 60 mM calcium carbonate solution.
Figure 17B:
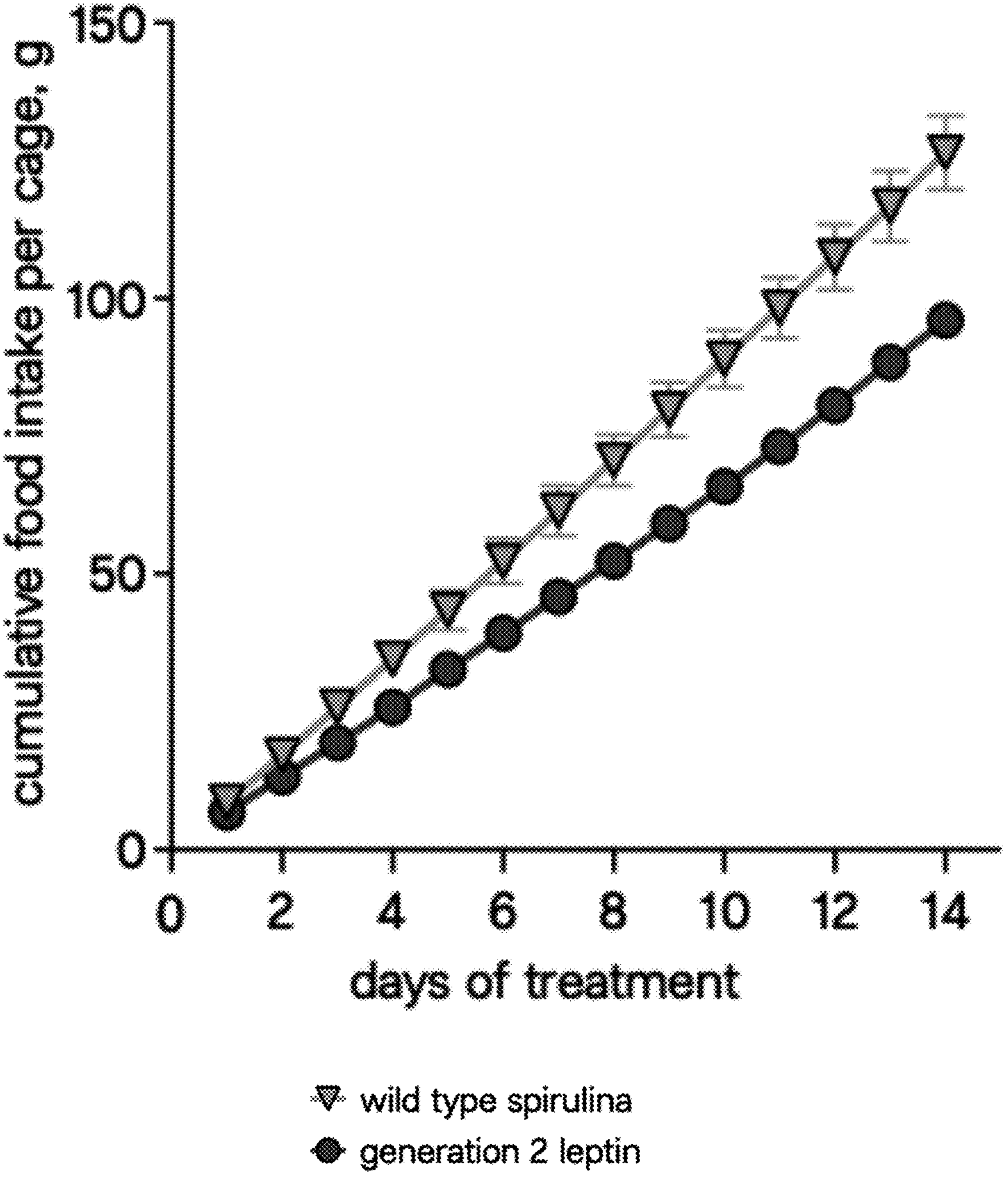
FIG. 17B provides cumulative food intake per cage in grams over 14 days of treatment when WT *Spirulina* (control and *Spirulina* expressing Gen 2 leptin (SP3967; PP5867) delivered to diet-induced obese (DIO) mice by gavage in 60 mM calcium carbonate solution.
Figure 17C:
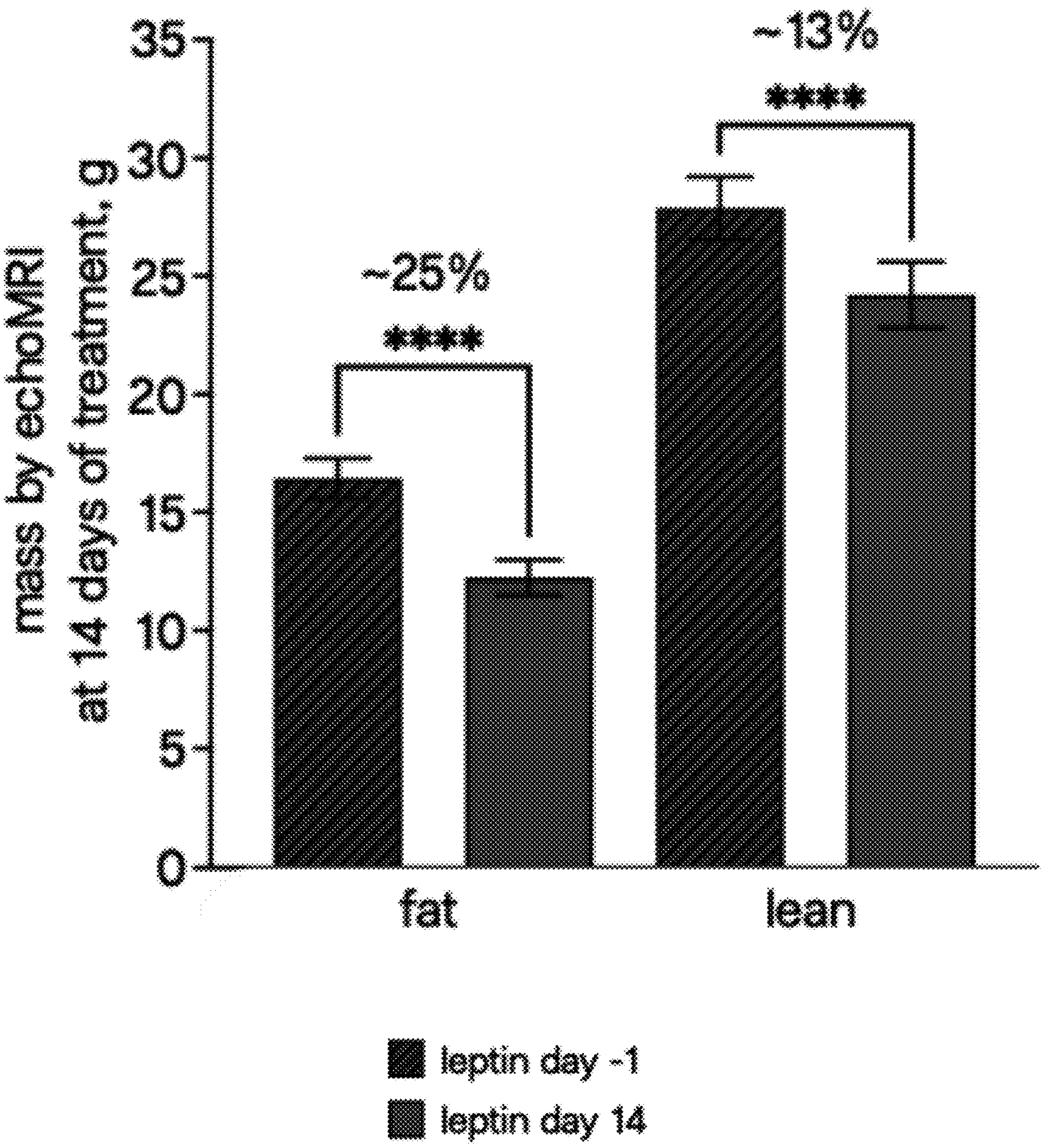
FIG. 17C provides body mass difference between day-1 and day 14 of treatment as measured by echo MRI when WT *Spirulina* (control and *Spirulina* expressing Gen 2 leptin (SP3967; PP5867) delivered to diet-induced obese (DIO) mice by gavage in 60 mM calcium carbonate solution.

Additionally, similar experiments were conducted using a different gavage buffer (60 mM calcium carbonate solution) instead of 0.16M sodium bicarbonate solution. C57Bl/6J mice fed DIO (60% fat) diet prior to initiation of treatment. At acclimatization diet transitioned to 45% fat. Cut-off weight for enrollment in the study was ≥45 g. Acclimatization proceeded for 5 days in an 80° F./40% humidity, 4 am/4 pm day/night cycle room. Mice were group housed. Treatment gavage was performed 30 minutes prior to lights out (4 pm). EchoMRI was performed at 14 days. FIGS. 17A-17C present the results of body weight loss, food intake, and body mass change when the *Spirulina* was delivered by gavage in 60 mM calcium carbonate. The general trend of the results are similar when using the gavage buffer either 0.16M sodium bicarbonate solution or 60 mM calcium carbonate solution.

Figure 18A:
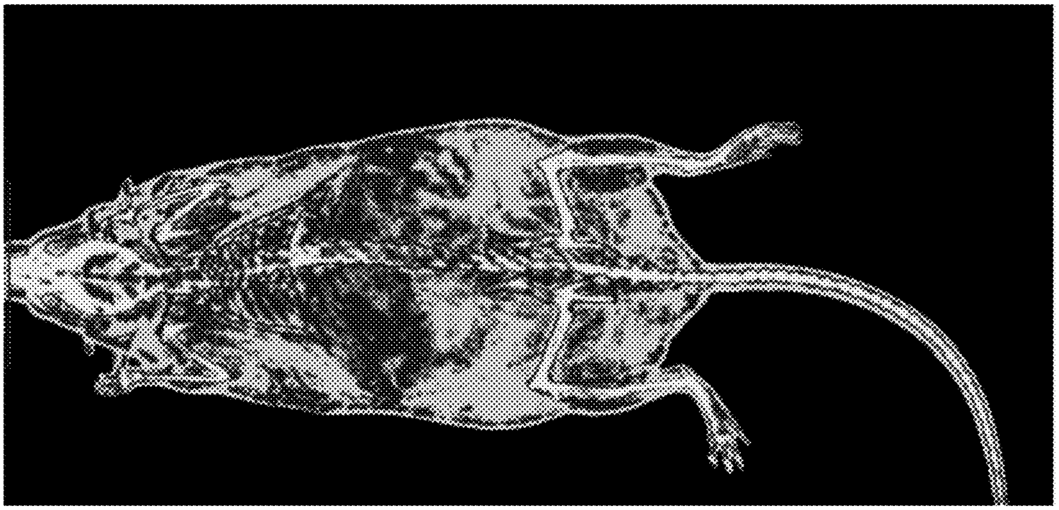
FIG. 18A provides DEXA scan of control mouse.
Figure 18B:
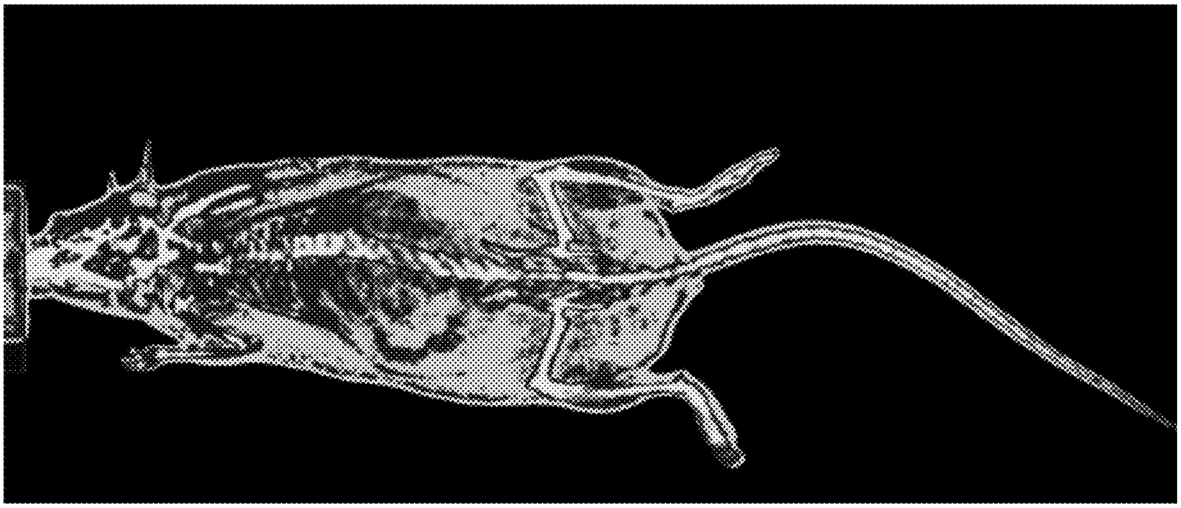
FIG. 18B provides DEXA scan of treated mouse.

FIGS. 18A and 18B shows examples of control and treated mice imaged in the DEXA scanner. The treated mice was fed with *Spirulina* expressing Gen 2 leptin. MRI images of darker grey color indicates lean biomass, lighter grey color indicates fat biomass, which were quantified and presented, for example, FIGS. 6L, 16C, and 17C.

Further Numbered Embodiments of the Disclosure

Other subject matters contemplated by the present disclosure is set out in the following numbered embodiments.

Numbered Embodiments 1

1. A composition comprising a therapeutically effective dose of a leptin receptor agonist for weight loss and/or weight maintenance when orally administered to an individual in need thereof, wherein after administration the leptin receptor agonist acts locally in the individual's gastrointestinal tissues, and wherein the leptin receptor agonist is not systemically bioavailable.

2. The composition of embodiment 1, wherein after oral administration the leptin receptor agonist is systemically bioavailable in the blood of the individual in an amount less than 0.05% of the administered dose.

3. The composition of embodiment 1, wherein the leptin receptor agonist is a small molecule, protein, or peptide.

4. The composition of embodiment 1, wherein the composition comprises a drug delivery vehicle comprising a nanoparticle, nanoemulsion, nanostructure, nanocarrier, nanogel, nanocapsule, nanomaterial, nanovesicle, and combinations thereof.

5. The composition of embodiment 1, wherein the composition comprises a drug delivery vehicle comprising a polyacrylamide, polyacrylate, chitosan, micelle, polymersome, dendrimer, liposome, polylactic acid (PLA), polyglutamic acid (PGA), poly(lactic-glycolic acid) (PLGA), virus, bacteriophage, bacteria-derived lipid vesicle, RNA nanoparticle, RNA vesicle, and combinations thereof.

6. The composition of embodiment 1, wherein the composition comprises a drug delivery vehicle comprising eukaryotic cells, parts of a eukaryotic organism, eukaryotic organisms, or prokaryotic cells.

7. The composition of embodiment 6, wherein the prokaryotic cells are bacterial cells.

8. The composition of embodiment 7, wherein the bacterial cells are *Escherichia coli* cells.

9. The composition of embodiment 6, wherein the eukaryotic cells are selected from the group consisting of filamentous fungi cells, yeast cells, algal cells, and plant cells.

10. The composition of embodiment 9, wherein the yeast is *Saccharomyces cerevisiae* or *Pichia pastoris.*

11. The composition of embodiment 9, wherein the alga is a *Cyanobacterium.*

12. The composition of embodiment 11, wherein the *Cyanobacterium* is *Spirulina.*

13. The composition of embodiment 6, wherein the drug delivery vehicle is cells that have been genetically engineered to express a leptin receptor agonist.

14. The composition of embodiment 13, wherein the genetically engineered cells are prepared by spray-drying, vacuum belt drying, fluidized bed drying, or lyophilization before administration.

15. The composition of embodiment 13, wherein prior to administration the genetically engineered cells undergo a simple lysis and tangential-flow filtration step to separate the leptin receptor agonist from cell membranes.

16. The composition of embodiment 13, wherein the genetically engineered cells in the composition are dead cells.

17. The composition of embodiment 13, wherein a portion of or all of the genetically engineered cells are further genetically engineered to express a protease inhibitor and/or a proteinase inhibitor.

18. The composition of embodiment 13, wherein the leptin receptor agonist is a leptin protein or therapeutically active fragment thereof.

19. The composition of embodiment 18 wherein the leptin protein or therapeutically active fragment thereof is a wild-type leptin, modified wild-type leptin, mutant version of wild-type leptin, or combinations thereof.

20. The composition of embodiment 19, wherein the modified wild-type leptin or mutant version of a wild-type leptin have increased stability compared to the wild-type leptin.

21. The composition of embodiment 19, wherein the modified wild-type leptin or mutant version of a wild-type leptin have improved packing energies and/or binding energies compared to the corresponding wild-type leptin.

22. The composition of embodiment 19, wherein the modified wild-type leptin or mutant version of a wild-type leptin have increased binding to receptors in gastrointestinal tissues when compared to the corresponding wild-type leptin.

23. The composition of embodiment 19, wherein the modified wild-type leptin is an engineered variant of leptin selected from the group consisting of the amino acid sequences listed in Table 2 and Table 4, and sequences with about 80%, or about 90%, or more sequence similarity to the amino acid sequences listed in Table 2 and Table 4.

24. The composition of embodiment 1, wherein the composition does not further include an added permeability enhancer and/or absorption enhancer isolated from their native sources or made recombinantly or synthetically prior to being added to the oral composition.

25. The composition of embodiment 1, wherein the composition further comprises a protease inhibitor and/or proteinase inhibitor.

26. The composition of embodiment 25, wherein the protease inhibitor is soybean trypsin inhibitor.

27. The composition of embodiment 1, wherein the individual is overweight.

28. The composition of embodiment 1, wherein the individual is obese.

29. The composition of embodiment 1, wherein the individual is a human.

30. The composition of embodiment 1, wherein the individual is an animal.

31. The composition of embodiment 30, wherein the animal is selected from the group consisting of a cat, dog, horse, mouse, rat, rabbit, guinea pig, and pig.

32. The composition of embodiment 1, wherein the leptin receptor agonist is protected from degradation during gastric transit.

33. The composition of embodiment 32, wherein the protection is provided by physical devices, robotic pills, microneedle pills or capsules, blended excipients, tablet coatings, enteric capsules, co-delivery with soluble leptin receptor, and combinations thereof.

34. The composition of embodiment 32, wherein the protection is provided by a *Spirulina*-expressed leptin.

35. The composition of embodiment 1, wherein the leptin receptor agonist is provided in a dose insufficient to induce weight loss if it were injected into the individual, wherein the individual is obese and the obesity is not caused by a leptin deficiency.

36. A method comprising orally administering a therapeutically effective dose of a leptin receptor agonist for weight loss and/or weight maintenance to an individual in need thereof, wherein after administration the leptin receptor agonist acts locally in the individual's gastrointestinal tissues, and wherein the leptin receptor agonist is not systemically bioavailable.

37. The method of embodiment 36, wherein after oral administration the leptin receptor agonist is systemically bioavailable in the blood of the individual in an amount less than 0.05% of the administered dose.

38. The method of embodiment 36, wherein the leptin receptor agonist is a small molecule, protein, or peptide.

39. The method of embodiment 36, wherein the composition comprises a drug delivery vehicle comprising a nanoparticle, nanoemulsion, nanostructure, nanocarrier, nanogel, nanocapsule, nanomaterial, nanovesicle, and combinations thereof.

40. The method of embodiment 36, wherein the composition comprises a drug delivery vehicle comprising a polyacrylamide, polyacrylate, chitosan, micelle, polymersome, dendrimer, liposome, polylactic acid (PLA), polyglutamic acid (PGA), poly(lactic-glycolic acid) (PLGA), virus, bacteriophage, bacteria-derived lipid vesicle, RNA nanoparticle, RNA vesicle, and combinations thereof.

41. The method of embodiment 36, wherein the composition comprises a drug delivery vehicle comprising eukaryotic cells, part of a eukaryotic organism, a eukaryotic organism, or prokaryotic cells.

42. The method of embodiment 41, wherein the prokaryotic cells are bacterial cells.

43. The method of embodiment 42, wherein the bacterial cells are *Escherichia coli* cells.

44. The method of embodiment 41, wherein the eukaryotic cells are from the group consisting of filamentous fungi cells, yeast cells, algal cells, and plant cells.

45. The method of embodiment 44, wherein the yeast is *Saccharomyces cerevisiae* or *Pichia pastoris*.

46. The method of embodiment 44, wherein the alga is a *Cyanobacterium*.

47. The method of embodiment 46, wherein the *Cyanobacterium* is *Spirulina*.

48. The method of embodiment 41, wherein the drug delivery vehicle is cells that have been genetically engineered to express a leptin receptor agonist.

49. The method of embodiment 48, wherein the genetically engineered cells are prepared by spray-drying before administration.

50. The method of embodiment 48, wherein prior to administration the genetically engineered cells undergo a simple lysis and tangential-flow filtration step to separate the leptin receptor agonist from cell membranes.

51. The method of embodiment 48, wherein the genetically engineered cells in the composition are dead cells.

52. The method of embodiment 48, wherein a portion of or all of the genetically engineered cells are further genetically engineered to express a protease inhibitor and/or a proteinase inhibitor.

53. The method of embodiment 48, wherein the leptin receptor agonist is a leptin protein or therapeutically active fragment thereof.

54. The method of embodiment 53, wherein the leptin protein or therapeutically active fragment thereof is a wildtype leptin, modified wild-type leptin, mutant version of wild-type leptin, or combinations thereof.

55. The method of embodiment 54, wherein the modified wild-type leptin or mutant version of a wild-type leptin have increased stability compared to the wild-type leptin.

56. The method of embodiment 54, wherein the modified wild-type leptin or mutant version of a wild-type leptin have improved packing energies and/or binding energies compared to the corresponding wild-type leptin.

57. The method of embodiment 54, wherein the modified wild-type leptin or mutant version of a wild-type leptin have increased binding to receptors in gastrointestinal tissues when compared to the corresponding wild-type leptin.

58. The method of embodiment 54, wherein the modified wild-type leptin is an engineered variant of leptin selected from the group consisting of the amino acid sequences listed in Table 2 and Table 4, and sequences with about 80%, or about 90%, or more sequence similarity to the amino acid sequences listed in Table 2 and Table 4.

59. The method of embodiment 36, wherein the composition does not further include an added permeability enhancer and/or absorption enhancer isolated from their native sources or made recombinantly or synthetically prior to being added to the oral composition.

60. The method of embodiment 36, wherein the composition further comprises a protease inhibitor and/or proteinase inhibitor.

61. The method of embodiment 36, wherein the protease inhibitor is soybean trypsin inhibitor.

62. The method of embodiment 36, wherein the individual is overweight.

63. The method of embodiment 36, wherein the individual is obese.

64. The method of embodiment 36, wherein the individual is a human.

65. The method of embodiment 36, wherein the individual is an animal.

66. The method of embodiment 65, wherein the animal is selected from the group consisting of a cat, dog, horse, mouse, rat, rabbit, guinea pig, and pig.

67. The method of embodiment 36, wherein the leptin receptor agonist is protected from degradation during gastric transit.

68. The method of embodiment 67, wherein the protection is provided by physical devices, robotic pills, microneedle pills or capsules, blended excipients, tablet coatings, enteric capsules, co-delivery with soluble leptin receptor, and combinations thereof.

69. The method of embodiment 36, wherein the leptin receptor agonist is provided in a dose insufficient to induce weight loss if it were injected into the individual, wherein the individual is obese and the obesity is not caused by a leptin deficiency.

70. A composition comprising a therapeutically effective amount of leptin for weight loss and/or weight maintenance when orally administered to a person or animal in need thereof, wherein the orally delivered leptin is at a dose insufficient to induce weight loss if it were injected into the individual.

71. A method comprising orally administering a therapeutically effective amount of leptin for weight loss and/or weight maintenance to a person or animal in need thereof, wherein the orally administered leptin is at a dose insufficient to induce weight loss if it were injected into the individual.

72. A composition comprising a therapeutically effective amount of an engineered variant of leptin for weight loss and/or weight maintenance when parenterally delivered to a person or animal in need thereof, wherein the engineered variant of leptin has increased stability compared to wild-type leptin.

73. A method comprising parenterally administering a therapeutically effective amount of an engineered variant of leptin for weight loss and/or weight maintenance delivered to a person or animal in need thereof, wherein the engineered variant of leptin has increased stability compared to wild-type leptin.

74. A composition comprising a therapeutically effective amount of an engineered variant of leptin for systemic glucose reduction when orally or parenterally delivered to a person or animal in need.

75. A method comprising orally or parenterally delivering a composition comprising a therapeutically effective amount of an engineered variant of leptin for systemic glucose reduction to a person or animal in need.

76. A composition comprising an effective amount of an orally delivered leptin composition to induce weight loss in an individual who is overweight or obese, wherein the leptin is protected from degradation during gastric transit.

77. A method comprising orally delivering an effective amount of a leptin composition to induce weight loss in an individual who is overweight or obese, wherein the leptin is protected from degradation during gastric transit.

78. The method of embodiment 77, wherein the method further comprises administering a second composition before, during, or after delivering the orally delivered leptin, wherein the second composition is selected from the group consisting of amylin, cholecystokinin (CCK), a GLP-1 agonist, glucagon, gastric inhibitory polypeptide (GIP) luminal CCK-releasing factor (LCRF), *Akkermansia muciniphila* protein P9, and a CG-1 inhibitor.

79. The method of embodiment 78, wherein the second composition is delivered orally or parenterally.

80. The method of embodiment 77, wherein the leptin is orally delivered after the individual ceases administration of a GLP-1 agonist.

81. The method of embodiment 77, wherein the leptin is orally delivered after the individual finishes dieting.

82. The method of embodiment 77, wherein the leptin is orally delivered after the individual undergoes bariatric surgery.

83. The method of embodiment 77, wherein the composition comprises cells genetically engineered to express the leptin.

84. The method of embodiment 83, wherein the leptin is expressed intracellularly in the genetically engineered cells.

85. The method of embodiment 83, wherein the genetically engineered cells are prepared by spray-drying.

86. The method of embodiment 83, wherein prior to administration the genetically engineered cells undergo a simple lysis and tangential-flow filtration step to separate the leptin from cell membranes.

87. The method of embodiment 83, wherein the genetically engineered cells in the oral composition are dead cells.

88. The method of embodiment 83, wherein the genetically engineered cells are further genetically engineered to express a protease inhibitor and/or a proteinase inhibitor.

89. The method of embodiment 83, wherein the cells are bacteria cells.

90. The method of embodiment 89, wherein the bacteria cells are Cyanobacteria cells.

91. The method of embodiment 90, wherein the Cyanobacteria cells are *Spirulina* cells.

92. A recombinant leptin with increased binding energy to receptors in GI tissues as compared to a non-recombinant, control leptin following oral administration to an individual.

93. The recombinant leptin of embodiment 92, wherein the recombinant leptin is not systemically available following the oral administration to the individual.

94. A method of treating obesity in an individual comprising orally administering the recombinant leptin of embodiment 92 or embodiment 93 to an individual.

95. The method of embodiment 94, wherein the individual being administered the recombinant leptin has a greater weight loss over a set time period as compared to an individual administered a non-recombinant, control leptin.

96. The method of embodiment 94 or embodiment 95, wherein the administration of the recombinant leptin results in no evidence of malaise in the individual as compared to an individual not receiving the recombinant leptin.

97. The method of embodiment 94, embodiment 95, or embodiment 96, wherein the individual is a lean individual.

98. The method of embodiment 94, embodiment 95, or embodiment 96, wherein the individual is an obese individual.

99. A recombinant *Spirulina* cell comprising an exogenous sequence encoding leptin.

100. The recombinant *Spirulina* cell of embodiment 99, wherein the exogenous sequence encoding the leptin is genomically integrated into the *Spirulina* cell genome.

101. The recombinant *Spirulina* cell of embodiment 100, wherein the genomic integration is within a neutral genomic region.

102. The recombinant *Spirulina* cell of embodiment 100, wherein the integration is accomplished without using markers.

103. The recombinant *Spirulina* cell of embodiment 101, wherein the neutral genomic region is the kanamycin aminoglycoside acetyltransferase.

104. The recombinant *Spirulina* cell of any one of embodiments 99-103, wherein the leptin is mammalian leptin.

105. The recombinant *Spirulina* cell of embodiment 104, wherein the mammalian leptin is non-human.

106. The recombinant *Spirulina* cell of embodiment 105, wherein the mammalian leptin is human.

107. The recombinant *Spirulina* cell of embodiment 106, wherein the human leptin is wildtype.

108. The recombinant *Spirulina* cell of embodiment 107, wherein the wildtype human leptin comprises a valine-to-methionine polymorphism at position 94.

109. The recombinant *Spirulina* cell of embodiment 106, wherein the human leptin is a leptin mimetic.

110. The recombinant *Spirulina* cell of embodiment 109, wherein the leptin mimetic comprises a sequence selected from the group consisting of the leptin sequences listed in Table 2 and Table 4, and sequences with about 80%, or about 90%, or more sequence similarity to the amino acid sequences listed in Table 2 and Table 4.

111. The recombinant *Spirulina* cell of any one of embodiments 99-110, wherein the *Spirulina* is of a species selected from the group consisting of: *A. amethystine, A. ardissonei, A. argentina, A. balkrishnanii, A. baryana, A. boryana, A. braunii, A. breviarticulata, A. brevis, A. curta, A. desikacharyiensis, A. funiformis, A. fusiformis, A. ghannae, A. gigantean, A. gomontiana, A. gomontiana* var. *crassa, A. indica, A. jenneri* var. *platensis, A. jenneri* Stizenberger, *A. jenneri* f. *purpurea, A. joshii, A. khannae, A. laxa, A. laxissima, A. laxissima, A. leopoliensis, A. major, A. margaritae, A. massartii, A. massartii* var. *indica, A. maxima, A. meneghiniana, A. miniata* var. *constricta, A. miniata, A. miniata* f. *acutissima, A. neapolitana, A. nordstedtii, A. oceanica*, A. *okensis, A. pellucida, A. platensis, A. platensis* var. non-*constricta, A. platensis* f. *granulate, A. platensis* f. *minor, A. platensis* var. *tenuis, A. santannae, A. setchellii, A. skujae, A. spirulinoides* f. *tenuis, A. spirulinoides, A. subsalsa, A. subtilissima, A. tenuis, A. tenuissima*, and *A. versicolor.*

112. The recombinant *Spirulina* cell of embodiment 111, wherein the *Spirulina* is the *A. platensis.*

113. A population of *Spirulina*, comprising: the recombinant *Spirulina* cell of any one of embodiments 99-112.

114. The population of embodiment 113, wherein the population is formulated for oral administration.

115. The population of embodiment 113 or embodiment 114, wherein the population comprises at least about $1\times10^5$ cells, or at least about $1\times10^7$ cells, or at least about $1\times10^9$ cells.

116. The population of any one of embodiments 113-115, further comprising an excipient.

117. A food supplement composition comprising the recombinant *Spirulina* cell of any one of embodiments 99-112 or the population of any one of embodiments 113-116.

118. A nutraceutical composition comprising the recombinant *Spirulina* cell of any one of embodiments 99-112 or the population of any one of embodiments 113-116.

119. A vector comprising a nucleic acid sequence encoding for leptin, wherein the sequence comprises at least 80% identity, or at least 90% identity to any one of the nucleic acid sequences selected from the group consisting of the leptin sequences listed in Table 2 and Table 4.

120. A vector comprising a nucleic acid sequence encoding for a leptin with an amino acid sequence which comprises at least 80% identity or 90% identity to any one of the amino acid sequences selected from the group consisting of the amino acid sequences listed in Table 2 and Table 4.

121. The vector of embodiment 120, wherein the sequence encodes protein pp 2054 produced by *Spirulina* strain SP2334.

122. The vector of any one of embodiments 119-121, wherein the vector further comprises a native *Spirulina* promoter.

123. The vector of embodiment 122, wherein the native *Spirulina* promoter is pCPC600.

124. The vector of any one of embodiments 119-123, wherein the sequence encoding for leptin is flanked by a pair of homology arms.

125. The vector of embodiment 124, wherein the homology arms comprise a sequence homologous to a neutral site in the *Spirulina* genome.

126. The vector of embodiment 125, wherein the neutral site further comprises a portion of a kanamycin aminoglycoside acetyltransferase gene.

127. A kit, comprising:

the recombinant *Spirulina* cell of any one of embodiments 91-112;

the population of any one of embodiments 113-116;

the food supplement of embodiment 117;

the nutraceutical of embodiment 118; and/or the vector of any one of embodiments 119-126.

128. The kit of embodiment 127, further comprising instructions for use thereof.

129. A method of making a recombinant *Spirulina* cell, the method comprising: introducing into a wild type *Spirulina* cell the vector of any one of embodiments 119-126, thereby generating a recombinant *Spirulina* cell.

130. The method of embodiment 129, further comprising culturing the recombinant *Spirulina* cell thereby generating a population of recombinant *Spirulina* cells.

131. The method of embodiment 130, wherein the culturing comprises antibiotic selection.

132. The method of embodiment 131, wherein the antibiotic is kanamycin.

133. The method of any one of embodiments 129-132, wherein the method further comprises drying the recombinant *Spirulina* cell.

134. A method of sustaining weight in a subject, the method comprising: administering recombinant *Spirulina* to the subject in need, wherein the recombinant *Spirulina* comprises an exogenous leptin sequence, thereby sustaining the weight in the subject in need.

135. The method of embodiment 133, wherein the weight is a normal weight as determined by body mass index.

136. The method of embodiment 133, wherein the weight is overweight as determined by body mass index.

137. A method of treatment, comprising: administering recombinant *Spirulina* to a subject having a body mass index beyond a normal weight, wherein the recombinant *Spirulina* comprises an exogenous leptin sequence, and wherein the administration is continued until the body mass index returns to normal.

138. The method of any one of embodiments 134-137, wherein the exogenous sequence encoding the leptin is genomically integrated into the *Spirulina* cell genome.

139. The method of embodiment 138, wherein the genomic integration is within a neutral genomic region.

140. The method of embodiment 139, wherein the neutral genomic region is kanamycin aminoglycoside acetyltransferase.

141. The method of any one of embodiments 134-140, wherein the leptin is mammalian leptin.

142. The method of embodiment 141, wherein the mammalian leptin is non-human.

143. The method of embodiment 142, wherein the mammalian leptin is human.

144. The method of embodiment 143, wherein the human leptin is wildtype.

Numbered Embodiments 2

1. A composition comprising a therapeutically effective dose of a leptin receptor agonist for weight loss and/or weight maintenance when orally administered to an individual in need thereof, wherein after administration the leptin receptor agonist acts locally in the individual's gastrointestinal tissues, and wherein the leptin receptor agonist is not systemically bioavailable.

2. The composition of embodiment 1, wherein after oral administration the leptin receptor agonist is systemically bioavailable in the blood of the individual in an amount less than 0.05% of the administered dose.

3. The composition of embodiment 1, wherein the leptin receptor agonist is a small molecule, protein, or peptide.

4. The composition of embodiment 1, wherein the composition comprises a drug delivery vehicle comprising a nanoparticle, nanoemulsion, nanostructure, nanocarrier, nanogel, nanocapsule, nanomaterial, nanovesicle, and combinations thereof.

5. The composition of embodiment 1, wherein the composition comprises a drug delivery vehicle comprising a polyacrylamide, polyacrylate, chitosan, micelle, polymersome, dendrimer, liposome, polylactic acid (PLA), polyglutamic acid (PGA), poly(lactic-glycolic acid) (PLGA), virus, bacteriophage, bacteria-derived lipid vesicle, RNA nanoparticle, RNA vesicle, and combinations thereof.

6. The composition of embodiment 1, wherein the composition comprises a drug delivery vehicle comprising eukaryotic cells, parts of a eukaryotic organism, eukaryotic organisms, or prokaryotic cells.

7. The composition of embodiment 6, wherein the prokaryotic cells are bacterial cells.

8. The composition of embodiment 7, wherein the bacterial cells are *Escherichia coli* cells.

9. The composition of embodiment 6, wherein the eukaryotic cells are selected from the group consisting of filamentous fungi cells, yeast cells, algal cells, and plant cells.

10. The composition of embodiment 9, wherein the yeast is *Saccharomyces cerevisiae* or *Pichia pastoris.*

11. The composition of embodiment 9, wherein the alga is a *Cyanobacterium.*

12. The composition of embodiment 11, wherein the *Cyanobacterium* is *Spirulina.*

13. The composition of embodiment 6, wherein the drug delivery vehicle is cells that have been genetically engineered to express a leptin receptor agonist.

14. The composition of embodiment 13, wherein the genetically engineered cells are prepared by spray-drying, vacuum belt drying, fluidized bed drying, or lyophilization before administration.

15. The composition of embodiment 13, wherein prior to administration the genetically engineered cells undergo a simple lysis and tangential-flow filtration step to separate the leptin receptor agonist from cell membranes.

16. The composition of embodiment 13, wherein the genetically engineered cells in the composition are dead cells.

17. The composition of embodiment 13, wherein a portion of or all of the genetically engineered cells are further genetically engineered to express a protease inhibitor and/or a proteinase inhibitor.

18. The composition of embodiment 13, wherein the leptin receptor agonist is a leptin protein or therapeutically active fragment thereof.

19. The composition of embodiment 18, wherein the leptin protein or therapeutically active fragment thereof is a wild-type leptin, modified wild-type leptin, mutant version of wild-type leptin, or combinations thereof.

20. The composition of embodiment 19, wherein the modified wild-type leptin or mutant version of a wild-type leptin has increased stability compared to the wild-type leptin.

21. The composition of embodiment 19, wherein the modified wild-type leptin or mutant version of a wild-type leptin has improved packing energies and/or binding energies compared to the corresponding wild-type leptin.

22. The composition of embodiment 19, wherein the modified wild-type leptin or mutant version of a wild-type leptin has increased binding to receptors in gastrointestinal tissues when compared to the corresponding wild-type leptin.

23. The composition of embodiment 19, wherein the modified wild-type leptin is an engineered variant of leptin selected from the group consisting of the amino acid sequences listed in Table 2 and Table 4, and sequences with about 80%, or about 90%, or more sequence similarity to the amino acid sequences listed in Table 2 and Table 4.

24. The composition of embodiment 1, wherein the composition does not further include an added permeability enhancer and/or absorption enhancer isolated from their native sources or made recombinantly or synthetically prior to being added to the oral composition.

25. The composition of embodiment 1, wherein the composition further comprises a protease inhibitor and/or proteinase inhibitor.

26. The composition of embodiment 25, wherein the protease inhibitor is soybean trypsin inhibitor.

27. The composition of embodiment 1, wherein the individual is overweight.

28. The composition of embodiment 1, wherein the individual is obese.

29. The composition of embodiment 1, wherein the individual is a human.

30. The composition of embodiment 1, wherein the individual is an animal.

31. The composition of embodiment 30, wherein the animal is selected from the group consisting of a cat, dog, horse, mouse, rat, rabbit, guinea pig, and pig.

32. The composition of embodiment 1, wherein the leptin receptor agonist is protected from degradation during gastric transit.

33. The composition of embodiment 32, wherein the protection is provided by physical devices, robotic pills, microneedle pills or capsules, blended excipients, tablet coatings, enteric capsules, co-delivery with soluble leptin receptor, and combinations thereof.

34. The composition of embodiment 32, wherein the protection is provided by a *Spirulina*-expressed leptin.

35. The composition of embodiment 1, wherein the leptin receptor agonist is provided in a dose insufficient to induce weight loss if it were injected into the individual, wherein the individual is obese and the obesity is not caused by a leptin deficiency.

36. The recombinant leptin receptor agonist of embodiment 35, wherein at least 60%, 65%, 70%, 75%, 80%, 85%, 90%, or 95% of the weight loss is body fat mass.

37. The recombinant leptin receptor agonist of embodiment 35 or 36, wherein less than 1%, 2%, 3%, 4%, 5%, 6%, 7%, 8%, 9%, 10%, 11%, 12%, 13%, 14%, 15%, 16%, 17%, 18%, or 19% of the weight loss is lean mass.

38. A method comprising orally administering a therapeutically effective dose of a leptin receptor agonist for weight loss and/or weight maintenance to an individual in need thereof, wherein after administration the leptin receptor agonist acts locally in the individual's gastrointestinal tissues, and wherein the leptin receptor agonist is not systemically bioavailable.

39. The method of embodiment 38, wherein after oral administration the leptin receptor agonist is systemically bioavailable in the blood of the individual in an amount less than 0.05% of the administered dose.

40. The method of embodiment 38, wherein the leptin receptor agonist is a small molecule, protein, or peptide.

41. The method of embodiment 38, wherein the composition comprises a drug delivery vehicle comprising a nanoparticle, nanoemulsion, nanostructure, nanocarrier, nanogel, nanocapsule, nanomaterial, nanovesicle, and combinations thereof.

42. The method of embodiment 38, wherein the composition comprises a drug delivery vehicle comprising a polyacrylamide, polyacrylate, chitosan, micelle, polymersome, dendrimer, liposome, polylactic acid (PLA), polyglutamic acid (PGA), poly(lactic-glycolic acid) (PLGA), virus, bacteriophage, bacteria-derived lipid vesicle, RNA nanoparticle, RNA vesicle, and combinations thereof.

43. The method of embodiment 38, wherein the composition comprises a drug delivery vehicle comprising eukaryotic cells, part of a eukaryotic organism, a eukaryotic organism, or prokaryotic cells.

44. The method of embodiment 43, wherein the prokaryotic cells are bacterial cells.

45. The method of embodiment 44, wherein the bacterial cells are *Escherichia coli* cells.

46. The method of embodiment 43, wherein the eukaryotic cells are from the group consisting of filamentous fungi cells, yeast cells, algal cells, and plant cells.

47. The method of embodiment 46, wherein the yeast is *Saccharomyces cerevisiae* or *Pichia pastoris.*

48. The method of embodiment 46, wherein the alga is a *Cyanobacterium.*

49. The method of embodiment 48, wherein the *Cyanobacterium* is *Spirulina.*

50. The method of embodiment 43, wherein the drug delivery vehicle is cells that have been genetically engineered to express a leptin receptor agonist.

51. The method of embodiment 50, wherein the genetically engineered cells are prepared by spray-drying or lyophilization before administration.

52. The method of embodiment 50, wherein prior to administration the genetically engineered cells undergo a simple lysis and tangential-flow filtration step to separate the leptin receptor agonist from cell membranes.

53. The method of embodiment 50, wherein the genetically engineered cells in the composition are dead cells.

54. The method of embodiment 50, wherein a portion of or all of the genetically engineered cells are further genetically engineered to express a protease inhibitor and/or a proteinase inhibitor.

55. The method of embodiment 50, wherein the leptin receptor agonist is a leptin protein or therapeutically active fragment thereof.

56. The method of embodiment 55, wherein the leptin protein or therapeutically active fragment thereof is a wild-type leptin, modified wild-type leptin, mutant version of wild-type leptin, or combinations thereof.

57. The method of embodiment 56, wherein the modified wild-type leptin or mutant version of a wild-type leptin has increased stability compared to the wild-type leptin.

58. The method of embodiment 56, wherein the modified wild-type leptin or mutant version of a wild-type leptin has improved packing energies and/or binding energies compared to the corresponding wild-type leptin.

59. The method of embodiment 56, wherein the modified wild-type leptin or mutant version of a wild-type leptin has increased binding to receptors in gastrointestinal tissues when compared to the corresponding wild-type leptin.

60. The method of embodiment 56, wherein the modified wild-type leptin is an engineered variant of leptin selected from the group consisting of the amino acid sequences listed in Table 2 and Table 4, and sequences with about 80%, or about 90%, or more sequence similarity to the amino acid sequences listed in Table 2 and Table 4.

61. The method of embodiment 38, wherein the composition does not further include an added permeability enhancer and/or absorption enhancer isolated from their native sources or made recombinantly or synthetically prior to being added to the oral composition.

62. The method of embodiment 38, wherein the composition further comprises a protease inhibitor and/or proteinase inhibitor.

63. The method of embodiment 38, wherein the protease inhibitor is soybean trypsin inhibitor.

64. The method of embodiment 38, wherein the individual is overweight.

65. The method of embodiment 38, wherein the individual is obese.

66. The method of embodiment 38, wherein the individual is a human.

67. The method of embodiment 38, wherein the individual is an animal.

68. The method of embodiment 67, wherein the animal is selected from the group consisting of a cat, dog, horse, mouse, rat, rabbit, guinea pig, and pig.

69. The method of embodiment 38, wherein the leptin receptor agonist is protected from degradation during gastric transit.

70. The method of embodiment 69, wherein the protection is provided by physical devices, robotic pills, microneedle pills or capsules, blended excipients, tablet coatings, enteric capsules, co-delivery with soluble leptin receptor, and combinations thereof.

71. The method of embodiment 38, wherein the leptin receptor agonist is provided in a dose insufficient to induce weight loss if it were injected into the individual, wherein the individual is obese and the obesity is not caused by a leptin deficiency.

72. A composition comprising a therapeutically effective amount of leptin for weight loss and/or weight maintenance when orally administered to a person or animal in need thereof, wherein the orally delivered leptin is at a dose insufficient to induce weight loss if it were injected into the individual.

73. A method comprising orally administering a therapeutically effective amount of leptin for weight loss and/or weight maintenance to a person or animal in need thereof, wherein the orally administered leptin is at a dose insufficient to induce weight loss if it were injected into the individual.

74. A composition comprising a therapeutically effective amount of an engineered variant of leptin for weight loss and/or weight maintenance when parenterally delivered to a person or animal in need thereof, wherein the engineered variant of leptin has increased stability compared to wild-type leptin.

75. A method comprising parenterally administering a therapeutically effective amount of an engineered variant of leptin for weight loss and/or weight maintenance delivered to a person or animal in need thereof, wherein the engineered variant of leptin has increased stability compared to wild-type leptin.

76. A composition comprising a therapeutically effective amount of an engineered variant of leptin for systemic glucose reduction when orally or parenterally delivered to a person or animal in need.

77. A method comprising orally or parenterally delivering a composition comprising a therapeutically effective amount of an engineered variant of leptin for systemic glucose reduction to a person or animal in need.

78. A composition comprising an effective amount of an orally delivered leptin composition to induce weight loss in an individual who is overweight or obese, wherein the leptin is protected from degradation during gastric transit.

79. A method comprising orally delivering an effective amount of a leptin composition to induce weight loss in an individual who is overweight or obese, wherein the leptin is protected from degradation during gastric transit.

80. The method of embodiment 79, wherein the method further comprises administering a second composition before, during, or after delivering the orally delivered leptin, wherein the second composition is selected from the group consisting of amylin, cholecystokinin (CCK), a GLP-1 agonist, glucagon, gastric inhibitory polypeptide (GIP) luminal CCK-releasing factor (LCRF), *Akkermansia muciniphila* protein P9, and a CG-1 inhibitor.

81. The method of embodiment 80, wherein the second composition is delivered orally or parenterally.

82. The method of embodiment 79, wherein the leptin is orally delivered after the individual ceases administration of a GLP-1 agonist.

83. The method of embodiment 79, wherein the leptin is orally delivered after the individual finishes dieting.

84. The method of embodiment 79, wherein the leptin is orally delivered after the individual undergoes bariatric surgery.

85. The method of embodiment 79, wherein the composition comprises cells genetically engineered to express the leptin.

86. The method of embodiment 85, wherein the leptin is expressed intracellularly in the genetically engineered cells.

87. The method of embodiment 85, wherein the genetically engineered cells are prepared by spray-drying.

88. The method of embodiment 85, wherein prior to administration the genetically engineered cells undergo a simple lysis and tangential-flow filtration step to separate the leptin from cell membranes.

89. The method of embodiment 85, wherein the genetically engineered cells in the oral composition are dead cells.

90. The method of embodiment 85, wherein the genetically engineered cells are further genetically engineered to express a protease inhibitor and/or a proteinase inhibitor.

91. The method of embodiment 85, wherein the cells are bacteria cells.

92. The method of embodiment 91, wherein the bacteria cells are Cyanobacteria cells.

93. The method of embodiment 92, wherein the Cyanobacteria cells are *Spirulina* cells.

94. A recombinant leptin with increased binding energy to receptors in GI tissues as compared to a non-recombinant, control leptin following oral administration to an individual.

95. The recombinant leptin of embodiment 94, wherein the recombinant leptin is not systemically available following the oral administration to the individual.

96. A method of reducing weight or treating obesity in an individual comprising orally administering the recombinant leptin of embodiment 94 or 95 to an individual.

97. The method of embodiment 96, wherein the individual being administered the recombinant leptin has a greater weight loss over a set time period as compared to an individual administered a non-recombinant, control leptin.

98. The method of embodiment 96, wherein the administration of the recombinant leptin results in no evidence of malaise in the individual as compared to an individual not receiving the recombinant leptin.

99. The method of embodiment 96 or 97, wherein the individual is a lean or overweight individual.

100. The method of embodiment 96 or 97, wherein the individual is an obese individual.

101. A recombinant *Spirulina* cell comprising an exogenous sequence encoding leptin.

102. The recombinant *Spirulina* cell of embodiment 101, wherein the exogenous sequence encoding the leptin is genomically integrated into the *Spirulina* cell genome.

103. The recombinant *Spirulina* cell of embodiment 102, wherein the genomic integration is within a neutral genomic region.

104. The recombinant *Spirulina* cell of embodiment 102, wherein the integration is accomplished without using markers.

105. The recombinant *Spirulina* cell of embodiment 103, wherein the neutral genomic region is the kanamycin aminoglycoside acetyltransferase.

106. The recombinant *Spirulina* cell of any one of embodiments 101-105, wherein the leptin is mammalian leptin.

107. The recombinant *Spirulina* cell of embodiment 106, wherein the mammalian leptin is non-human.

108. The recombinant *Spirulina* cell of embodiment 107, wherein the mammalian leptin is human.

109. The recombinant *Spirulina* cell of embodiment 108, wherein the human leptin is wildtype.

110. The recombinant *Spirulina* cell of embodiment 109, wherein the wildtype human leptin comprises a valine-to-methionine polymorphism at position 94.

111. The recombinant *Spirulina* cell of embodiment 108, wherein the human leptin is a leptin mimetic.

112. The recombinant *Spirulina* cell of embodiment 111, wherein the leptin mimetic comprises a sequence selected from the group consisting of the leptin sequences listed in Table 2 and Table 4, and sequences with about 80%, or about 90%, or more sequence similarity to the amino acid sequences listed in Table 2 and Table 4.

113. The recombinant *Spirulina* cell of any one of embodiments 101-112, wherein the *Spirulina* is of a species selected from the group consisting of: *A. amethystine, A. ardissonei, A. argentina, A. balkrishnanii, A. baryana, A. boryana, A. braunii, A. breviarticulata, A. brevis, A. curta, A. desikacharyiensis, A. funiformis, A. fusiformis, A. ghannae, A. gigantean, A. gomontiana, A. gomontiana* var. *crassa, A. indica, A. jenneri* var. *platensis, A. jenneri* Stizenberger, *A. jenneri* f. *purpurea, A. joshii, A. khannae, A. laxa, A. laxissima, A. laxissima, A. leopoliensis, A. major, A. margaritae, A. massartii, A. massartii* var. *indica, A. maxima, A. meneghiniana, A. miniata* var. *constricta, A. miniata, A. miniata* f. *acutissima, A. neapolitana, A. nordstedtii, A. oceanica, A. okensis, A. pellucida, A. platensis, A. platensis* var. non-*constricta, A. platensis* f. *granulate, A. platensis* f. *minor, A. platensis* var. *tenuis, A. santannae, A. setchellii, A. skujae, A. spirulinoides* f. *tenuis, A. spirulinoides, A. subsalsa, A. subtilissima, A. tenuis, A. tenuissima*, and *A. versicolor.*

114. The recombinant *Spirulina* cell of embodiment 113, wherein the *Spirulina* is the A. *platensis.*

115. A population of *Spirulina*, comprising: the recombinant *Spirulina* cell of any one of embodiments 101-114.

116. The population of embodiment 115, wherein the population is formulated for oral administration.

117. The population of embodiment 115 or 116, wherein the population comprises at least about $1\times10^5$ cells, or at least about $1\times10^7$ cells, or at least about $1\times10^9$ cells.

118. The population of any one of embodiments 115-117, further comprising an excipient.

119. A food supplement composition comprising the recombinant *Spirulina* cell of any one of embodiments 101-114 or the population of any one of embodiments 115-118.

120. A nutraceutical composition comprising the recombinant *Spirulina* cell of any one of embodiments 101-114 or the population of any one of embodiments 115-118.

121. A vector comprising a nucleic acid sequence encoding for leptin, wherein the sequence comprises at least 80% identity, or at least 90% identity to any one of the nucleic acid sequences selected from the group consisting of the leptin sequences listed in Table 2 and Table 4.

122. A vector comprising a nucleic acid sequence encoding for a leptin with an amino acid sequence which comprises at least 80% identity or 90% identity to any one of the amino acid sequences selected from the group consisting of the amino acid sequences listed in Table 2 and Table 4.

123. The vector of embodiment 122, wherein the sequence encodes protein pp 2054 produced by *Spirulina* strain SP2334.

124. The vector of any one of embodiments 121-123, wherein the vector further comprises a native *Spirulina* promoter.

125. The vector of embodiment 124, wherein the native *Spirulina* promoter is pCPC600.

126. The vector of any one of embodiments 121-125, wherein the sequence encoding for leptin is flanked by a pair of homology arms.

127. The vector of embodiment 126, wherein the homology arms comprise a sequence homologous to a neutral site in the *Spirulina* genome.

128. The vector of embodiment 127, wherein the neutral site further comprises a portion of a kanamycin aminoglycoside acetyltransferase gene.

129. A kit, comprising:

the recombinant *Spirulina* cell of any one of embodiments 101-114;

the population of any one of embodiments 115-118;

the food supplement of embodiment 119;

the nutraceutical of embodiment 120; and/or the vector of any one of embodiments 121-128.

130. The kit of embodiment 129, further comprising instructions for use thereof.

131. A method of making a recombinant *Spirulina* cell, the method comprising: introducing into a wild type *Spirulina* cell the vector of any one of embodiments 121-128, thereby generating a recombinant *Spirulina* cell.

132. The method of embodiment 131, further comprising culturing the recombinant *Spirulina* cell thereby generating a population of recombinant *Spirulina* cells.

133. The method of embodiment 132, wherein the culturing comprises antibiotic selection.

134. The method of embodiment 133, wherein the antibiotic is kanamycin.

135. The method of any one of embodiments 131-134, wherein the method further comprises drying the recombinant *Spirulina* cell.

136. A method of sustaining weight in a subject, the method comprising: administering recombinant *Spirulina* to the subject in need, wherein the recombinant *Spirulina* comprises an exogenous leptin sequence, thereby sustaining the weight in the subject in need.

137. The method of embodiment 136, wherein the weight is a normal weight as determined by body mass index.

138. The method of embodiment 136, wherein the weight is overweight as determined by body mass index.

139. A method of treatment, comprising: administering recombinant *Spirulina* to a subject having a body mass index beyond a normal weight, wherein the recombinant *Spirulina* comprises an exogenous leptin sequence, and wherein the administration is continued until the body mass index returns to normal.

140. The method of any one of embodiments 136-139, wherein the exogenous sequence encoding the leptin is genomically integrated into the *Spirulina* cell genome.

141. The method of embodiment 140, wherein the genomic integration is within a neutral genomic region.

142. The method of embodiment 141, wherein the neutral genomic region is kanamycin aminoglycoside acetyltransferase.

143. The method of any one of embodiments 136-142, wherein the leptin is mammalian leptin.

144. The method of embodiment 143, wherein the mammalian leptin is non-human.

145. The method of embodiment 144, wherein the mammalian leptin is human.

146. The method of embodiment 145, wherein the human leptin is wildtype.

147. A recombinant leptin receptor agonist comprising an amino acid substitution at a position selected from the group consisting of Q4, K5, V6, T10, I17, V18, N22, S25, T27, S32, D40, L49, L51, K53, M54, T66, S67, S70, R71, 174, S77, N78, L83, H88, H97, T106, A116, T121, V124, A125, Q130, S132, and Q139, wherein the positions are determined by alignment with SEQ ID NO: 63.

148. The recombinant leptin receptor agonist of embodiment 147, wherein the recombinant leptin receptor agonist comprises an amino acid substitution at a position selected from the group consisting of Q4, V6, 117, V18, N22, D40, L49, T66, L83, H88, and Q139.

149. The recombinant leptin receptor agonist of any one of embodiments 147-148, wherein the recombinant leptin receptor agonist comprises an amino acid substitution at a position selected from the group consisting of K5, T10, S25, T27, S32, L51, K53, M54, S67, S70, R71, 174, S77, N78, H97, T106, A116, T121, V124, A125, Q130, and $132.

150. The recombinant leptin receptor agonist of any one of embodiments 147-149, wherein the recombinant leptin receptor agonist comprises an amino acid substitution selected from the group consisting of Q4E, K5Q, V6I, T10L, I17V, V18I, N22D, S25P, T27V, S32P, D40E, L49I, L51Y, K53D, M54A, T66S, S67L, S70E, R71P, I74Q, S77A, N78L, L83I, H88R, H97P, T106D, A116E, T121V, V124T, A125T, Q130K, S132F, and Q139E.

151. The recombinant leptin receptor agonist of any one of embodiments 147-150, wherein the recombinant leptin receptor agonist comprises an amino acid substitution selected from the group consisting of Q4E, V6I, I17V, V18I, N22D, D40E, L49I, T66S, L83I, H88R, and Q139E.

152. The recombinant leptin receptor agonist of any one of embodiments 147-151, wherein the recombinant leptin receptor agonist comprises an amino acid substitution selected from the group consisting of K5Q, T10L, S25P, T27V, S32P, L51Y, K53D, M54A, S67L, S70E, R71P, 174Q, S77A, N78L, H97P, T106D, A116E, T121V, V124T, A125T, Q130K, and S132F.

153. The recombinant leptin receptor agonist of any one of embodiments 147-149, wherein the recombinant leptin receptor agonist comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 amino acid substitutions at the recited positions.

154. The recombinant leptin receptor agonist of any one of embodiments 147-149, wherein the recombinant leptin receptor agonist comprises amino acid substitutions at all of the recited positions.

155. The recombinant leptin receptor agonist of any one of embodiments 150-152, wherein the recombinant leptin receptor agonist comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 of the recited amino acid substitutions.

156. The recombinant leptin receptor agonist of any one of embodiments 150-152, wherein the recombinant leptin receptor agonist comprises all of the recited amino acid substitutions.

157. The recombinant leptin receptor agonist of any one of embodiments 147-156, wherein the recombinant leptin receptor agonist comprises an amino acid sequence having at least about 80%, 81%, 82%, 83%, 84% 85%, 86%, 87%, 88%, 89%, 90%, 91%, 92%, 93%, 94%, 95%, 96%, 97%, 98%, or 99% sequence identity with an amino acid sequence selected from Table 4.

158. The recombinant leptin receptor agonist of any one of embodiments 147-156, wherein the recombinant leptin receptor agonist comprises an amino acid sequence selected from Table 4.

159. The recombinant leptin receptor agonist of any one of embodiments 147-156, wherein the recombinant leptin receptor agonist comprises an amino acid sequence having at least about 80%, 81%, 82%, 83%, 84% 85%, 86%, 87%, 88%, 89%, 90%, 91%, 92%, 93%, 94%, 95%, 96%, 97%, 98%, or 99% sequence identity with a sequence selected from the group consisting of SEQ ID NO: 22, 52, 53, 54, 55, 56, 57, 58, 59, 60, 61, 62, 63, and 64.

160. The recombinant leptin receptor agonist of any one of embodiments 147-156, wherein the recombinant leptin receptor agonist comprises an amino acid sequence selected from the group consisting of SEQ ID NO: 22, 52, 53, 54, 55, 56, 57, 58, 59, 60, 61, 62, 63, and 64.

161. A recombinant leptin receptor agonist comprises an amino acid sequence having at least about 80%, 81%, 82%, 83%, 84% 85%, 86%, 87%, 88%, 89%, 90%, 91%, 92%, 93%, 94%, 95%, 96%, 97%, 98%, or 99% sequence identity with a sequence selected from the group consisting of SEQ ID NO: 22, 52, 53, 54, 55, 56, 57, 58, 59, 60, 61, 62, and 64

162. The recombinant leptin receptor agonist of embodiment 161, wherein the recombinant leptin receptor agonist comprises an amino acid selected from the group consisting of 4E, 5Q, 61, 10L, 17V, 18I, 22D, 25P, 27V, 32P, 40E, 49I, 51Y, 53D, 54A, 66S, 67L, 70E, 71P, 74Q, 77A, 78L, 83I, 88R, 97P, 106D, 116E, 121V, 124T, 125T, 130K, 132F, and 139E, wherein the positions are determined by alignment with a sequence selected from the group consisting of SEQ ID NO: 22, 52, 53, 54, 55, 56, 57, 58, 59, 60, 61, 62, and 64.

163. The recombinant leptin receptor agonist of embodiment 162, wherein the recombinant leptin receptor agonist comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 of the amino acids selected from the group consisting of 4E, 5Q, 6I, 10L, 17V, 18I, 22D, 25P, 27V, 32P, 40E, 49I, 51Y, 53D, 54A, 66S, 67L, 70E, 71P, 74Q, 77A, 78L, 83I, 88R, 97P, 106D, 116E, 121V, 124T, 125T, 130K, 132F, and 139E.

164. The recombinant leptin receptor agonist of any one of embodiments 162-163, wherein the recombinant leptin receptor agonist comprises all of the amino acids selected from the group consisting of 4E, 5Q, 6I, 10L, 17V, 18I, 22D, 25P, 27V, 32P, 40E, 49I, 51Y, 53D, 54A, 66S, 67L, 70E, 71P, 74Q, 77A, 78L, 83I, 88R, 97P, 106D, 116E, 121V, 124T, 125T, 130K, 132F, and 139E.

165. The recombinant leptin receptor agonist of any one of embodiments 161-164, wherein the recombinant leptin receptor agonist comprises an amino acid selected from the group consisting of D9, L13, T16, R20, K33, Q34, K35, V36, T37, Q75, D85, L86, S117, Y119, and $120.

166. The recombinant leptin receptor agonist of embodiment 161-165, wherein the recombinant leptin receptor agonist comprises at least 2, 3, 4, 5, 6, 7, 8, 9, 10, 11, 12, 13, 14, or 15 of the amino acids selected from the group consisting of D9, L13, T16, R20, K33, Q34, K35, V36, T37, Q75, D85, L86, S117, Y119, and S120.

167. The recombinant leptin receptor agonist of any one of embodiments 161-166, wherein the recombinant leptin receptor agonist comprises all of the amino acids selected from the group consisting of D9, L13, T16, R20, K33, Q34, K35, V36, T37, Q75, D85, L86, S117, Y119, and S120.

168. The recombinant leptin receptor agonist of any one of embodiments 147-167, wherein the recombinant leptin receptor is not SEQ ID NO: 63.

169. The recombinant leptin receptor agonist of any one of embodiments 147-168, wherein the recombinant leptin receptor agonist does not comprise a substitution at an activity-reducing position selected from the group consisting of D9, L13, T16, R20, K33, Q34, K35, V36, T37, Q75, D85, L86, S117, Y119, and $120.

170. The recombinant leptin receptor agonist of any one of embodiments 147-168, wherein the recombinant leptin receptor agonist comprises fewer than 15, 14, 13, 12, 11, 10, 9, 8, 7, 6, 5, 4, 3, 2, or 1 substitutions at an activity-reducing position selected from the group consisting of D9, L13, T16, R20, K33, Q34, K35, V36, T37, Q75, D85, L86, S117, Y119, and $120.

171. The recombinant leptin receptor agonist of any one of embodiments 147-168, wherein the recombinant leptin receptor agonist does not comprise any substitutions at positions selected from the group consisting of D9, L13, T16, R20, K33, Q34, K35, V36, T37, Q75, D85, L86, S117, Y119, and S120.

172. The recombinant leptin receptor agonist of any one of embodiments 147-171, wherein the recombinant leptin receptor agonist is comprised within a chimeric protein, said chimeric protein comprising a protein fusion partner.

173. The recombinant leptin receptor agonist of embodiment 172, wherein the protein fusion partner is N-terminally translationally fused to the recombinant leptin receptor agonist.

174. The recombinant leptin receptor agonist of embodiment 172, wherein the protein fusion partner is C-terminally translationally fused to the recombinant leptin receptor agonist.

175. The recombinant leptin receptor agonist of any one of embodiments 172-174, wherein the protein fusion partner is a protein purification tag or solubility enhancer.

176. The recombinant leptin receptor agonist of embodiment 175, wherein the protein purification tag or solubility enhancer is selected from the group consisting of a maltose binding protein (MBP), thioredoxin (TRX), a histidine tag, a green fluorescent protein (GFP), a glutathione S-transferase (GST), a FLAG tag, a Strep tag, and a HA tag.

177. The recombinant leptin receptor agonist of embodiment 175, wherein the solubility enhancer is MBP.

178. The recombinant leptin receptor agonist of any one of embodiments 172-177, wherein the protein fusion partner and the recombinant leptin receptor agonist are connected via a peptide linker.

179. The recombinant leptin receptor agonist of embodiment 178, wherein the peptide linker is a glycine-rich linker, a proline-rich linker, a serine-rich linker, or a protease-cleavable linker.

180. The recombinant leptin receptor agonist of embodiment 178, wherein the peptide linker is a G4S linker.

181. The recombinant leptin receptor agonist of any one of embodiments 147-180, wherein the recombinant leptin receptor agonist induces when administered to an overweight animal compared to an unmodified, wild-type, or non-recombinant leptin.

182. The recombinant leptin receptor agonist of embodiment 181, wherein at least 60%, 65%, 70%, 75%, 80%, 85%, 90%, or 95% of the weight loss is body fat mass.

183. The recombinant leptin receptor agonist of embodiment 181 or 182, wherein less than 1%, 2%, 3%, 4%, 5%, 6%, 7%, 8%, 9%, 10%, 11%, 12%, 13%, 14%, 15%, 16%, 17%, 18%, or 19% of the weight loss is lean mass.

184. The recombinant leptin receptor agonist of any one of embodiments 147-180, wherein the recombinant leptin receptor agonist results in a lower food intake by an overweight animal receiving the recombinant leptin receptor agonist compared to an unmodified, wild-type, or non-recombinant leptin.

185. The recombinant leptin receptor agonist of any one of embodiments 147-181, wherein the recombinant leptin receptor agonist exhibits reduced dimerization or aggregation when expressed in a recombinant host compared to an unmodified or wild-type leptin expressed in the same recombinant host.

186. The recombinant leptin receptor agonist of any one of embodiments 147-185, wherein the recombinant leptin receptor agonist expresses at higher levels in a recombinant host compared to an unmodified or wild-type leptin expressed in the same recombinant host under similar conditions.

187. The recombinant leptin receptor agonist of embodiment 186, wherein the recombinant leptin receptor agonist expresses at higher levels in *E. coli* and/or *Spirulina.*

188. The recombinant leptin receptor agonist of any one of embodiments 147-187, wherein the recombinant leptin receptor agonist exhibits stronger binding (Lower $K_D$) to the human leptin receptor compared to an unmodified, wild-type, or non-recombinant leptin.

189. The recombinant leptin receptor agonist of any one of embodiments 147-188, wherein the recombinant leptin receptor agonist exhibits higher thermostability compared to an unmodified, wild-type, or non-recombinant leptin.

190. The recombinant leptin receptor agonist of embodiment 189, wherein the recombinant leptin receptor agonist exhibits higher bioactivity after exposure to a temperature of at least about 50 Celsius, at least about 70 Celsius, or at least about 90 Celsius.

191. The recombinant leptin receptor agonist of embodiment 189, wherein the recombinant leptin receptor agonist exhibits higher bioactivity after exposure to a temperature between about 50 Celsius and about 90 Celsius.

192. The recombinant leptin receptor agonist of embodiment 181 or 184, wherein the animal is selected from the group consisting of a cat, dog, horse, mouse, rat, rabbit, guinea pig, and pig.

193. The recombinant leptin receptor agonist of embodiment 181 or 184, wherein the animal is a primate.

194. The recombinant leptin receptor agonist of embodiment 181 or 184, wherein the animal is a human.

195. The recombinant leptin receptor agonist of any one of embodiments 147-191, wherein the recombinant leptin receptor agonist is expressed and/or comprised within a biological cell.

196. The recombinant leptin receptor agonist of embodiment 195, wherein the biological cell is a eukaryotic cell or prokaryotic cell.

197. The recombinant leptin receptor agonist of embodiment 195, wherein the biological cell is a prokaryotic cell.

198. The recombinant leptin receptor agonist of embodiment 195, wherein the biological cell is a eukaryotic cell.

199. The recombinant leptin receptor agonist of embodiment 195, wherein the biological cell is a bacterial cell.

200. The recombinant leptin receptor agonist of embodiment 195, wherein the biological cell is an *Escherichia coli* cell.

201. The recombinant leptin receptor agonist of embodiment 195, wherein the biological cell is a eukaryotic cell selected from the group consisting of a filamentous fungi cell, a yeast cell, an algal cell, and a plant cell.

202. The recombinant leptin receptor agonist of embodiment 201, wherein the yeast cell is *Saccharomyces cerevisiae* or *Pichia pastoris.*

203. The recombinant leptin receptor agonist of embodiment 195, wherein the biological cell is a *Cyanobacterium.*

204. The recombinant leptin receptor agonist of embodiment 203, wherein the *Cyanobacterium* is *Spirulina.*

205. The recombinant leptin receptor agonist of any one of embodiments 195-204, wherein the biological cell is genetically engineered to express the recombinant leptin receptor agonist.

206. The recombinant leptin receptor agonist of any one of embodiments 195-205, wherein the biological cells are desiccated, dried, lyophilized, and/or non-living.

207. The recombinant leptin receptor agonist of any one of embodiments 147-206, wherein the recombinant leptin receptor agonist is comprised within a composition that does not include any added permeability enhancer excipient and/or absorption enhancer excipient.

208. The recombinant leptin receptor agonist of any one of embodiments 147-207, wherein the recombinant leptin receptor agonist is comprised within a composition comprising a protease inhibitor and/or proteinase inhibitor.

209. The recombinant leptin receptor agonist of embodiment 208, wherein the protease inhibitor is soybean trypsin inhibitor.

210. The recombinant leptin receptor agonist of any one of embodiments 147-209, wherein the recombinant leptin receptor agonist is comprised within a composition comprising a second active composition selected from the group consisting of amylin, cholecystokinin (CCK), a GLP-1 agonist, glucagon, gastric inhibitory polypeptide (GIP), luminal CCK-releasing factor (LCRF), *Akkermansia muciniphila* protein P9, and a CG-1 inhibitor.

211. A method comprising orally administering a therapeutically effective dose of the recombinant leptin receptor agonist of any one of embodiments 147-210, to an individual in need thereof.

212. The method of embodiment 211, wherein the recombinant leptin receptor agonist acts locally in the individual's gastrointestinal tissues.

213. The method of any one of embodiments 211-212, wherein the recombinant leptin receptor agonist is systemically bioavailable in the individual's blood in an amount less than 0.05% of the administered dose.

214. The method of any one of embodiments 211-213, wherein the individual is an overweight individual.

215. The method of any one of embodiments 211-214, wherein the individual is an obese individual.

216. The method of any one of embodiments 211-215, wherein administration of the recombinant leptin receptor agonist results in weight loss.

217. The method of embodiment 216, wherein at least 60%, 65%, 70%, 75%, 80%, 85%, 90%, or 95% of the weight loss is body fat mass.

218. The method of embodiment 216 or 217, wherein less than 1%, 2%, 3%, 4%, 5%, 6%, 7%, 8%, 9%, 10%, 11%, 12%, 13%, 14%, 15%, 16%, 17%, 18%, or 19% of the weight loss is lean mass.

219. The method of any one of embodiments 211-216, wherein administration of the recombinant leptin receptor agonist results in systemic glucose reduction.

220. The method of any one of embodiments 211-219, wherein the method further comprises administering a second composition before, during, or after delivering the recombinant leptin receptor agonist, wherein the second composition is selected from the group consisting of amylin, cholecystokinin (CCK), a GLP-1 agonist, glucagon, gastric inhibitory polypeptide (GIP), luminal CCK-releasing factor (LCRF), *Akkermansia muciniphila* protein P9, and a CG-1 inhibitor.

221. The method of embodiment 220, wherein the recombinant leptin receptor agonist is orally delivered after the individual ceases administration of the GLP-1 agonist.

222. The method of any one of embodiments 220-221, wherein the recombinant leptin receptor agonist is orally delivered after the individual finishes dieting.

223. The method of any one of embodiments 220-222, wherein the recombinant leptin receptor agonist is orally delivered after the individual undergoes bariatric surgery.

Numbered Embodiments 3

1. A recombinant leptin receptor agonist comprises an amino acid sequence having at least about 90% sequence identity with SEQ ID NO: 56.

2. The recombinant leptin receptor agonist of embodiment 1, wherein the recombinant leptin receptor agonist comprises an activity improving amino acid selected from the group consisting of 4E, 5Q, 6I, 10L, 17V, 18I, 22D, 25P, 27V, 32P, 40E, 49I, 51Y, 53D, 54A, 66S, 67L, 70E, 71P, 74Q, 77A, 78L, 83I, 88R, 97P, 106D, 116E, 121V, 124T, 125T, 130K, 132F, and 139E, wherein the positions are determined by alignment with SEQ ID NO: 56.

3. The recombinant leptin receptor agonist of embodiment 2, wherein the recombinant leptin receptor agonist comprises at least 5 of the recited activity improving amino acids.

4. The recombinant leptin receptor agonist of embodiment 2, wherein the recombinant leptin receptor agonist comprises at least 10 of the recited activity improving amino acids.

5. The recombinant leptin receptor agonist of embodiment 2, wherein the recombinant leptin receptor agonist comprises at least 15 of the recited activity improving amino acids.

6. The recombinant leptin receptor agonist of embodiment 2, wherein the recombinant leptin receptor agonist comprises all of the recited activity improving amino acids.

7. The recombinant leptin receptor agonist of embodiment 1, wherein the recombinant leptin receptor agonist does not comprise an activity-reducing amino acid substitution selected from the group consisting of D9E, L13Q, T16N/K, R20N/K, K33D/E/N, Q34L/K/I, K35V, V36I, T37E, Q75E/Q/T, S117R/Q, Y119E/K/D, and S120E/K/D.

8. The recombinant leptin receptor agonist of embodiment 1, wherein the recombinant leptin receptor agonist does not comprise any activity-reducing amino acid substitution selected from the group consisting of D9E, L13Q, T16N/K, R20N/K, K33D/E/N, Q34L/K/I, K35V, V36I, T37E, Q75E/Q/T, S117R/Q, Y119E/K/D, and S120E/K/D.

9. The recombinant leptin receptor agonist of embodiment 1, wherein the recombinant leptin receptor agonist comprises an amino acid selected from the group consisting of D9, L13, T16, R20, K33, Q34, K35, V36, T37, Q75, D85, L86, S117, Y119, and S120.

10. The recombinant leptin receptor agonist of embodiment 1, wherein the recombinant leptin receptor agonist comprises at least 2, 3, 4, 5, 6, 7, 8, 9, 10, 11, 12, 13, 14, or 15 of the amino acids selected from the group consisting of D9, L13, T16, R20, K33, Q34, K35, V36, T37, Q75, D85, L86, S117, Y119, and S120.

11. The recombinant leptin receptor agonist of embodiment 1, wherein the recombinant leptin receptor agonist comprises all of the amino acids selected from the group consisting of D9, L13, T16, R20, K33, Q34, K35, V36, T37, Q75, D85, L86, S117, Y119, and S120.

12. The recombinant leptin receptor agonist of embodiment 1, wherein the recombinant leptin receptor agonist is comprised within a chimeric protein, said chimeric protein comprising a protein fusion partner.

13. The recombinant leptin receptor agonist of embodiment 12, wherein the protein fusion partner is N-terminally translationally fused to the recombinant leptin receptor agonist.

14. The recombinant leptin receptor agonist of embodiment 12, wherein the protein fusion partner is C-terminally translationally fused to the recombinant leptin receptor agonist.

15. The recombinant leptin receptor agonist of embodiment 12, wherein the protein fusion partner is a protein purification tag or solubility enhancer.

16. The recombinant leptin receptor agonist of embodiment 15, wherein the protein purification tag or solubility enhancer is selected from the group consisting of a maltose binding protein (MBP), thioredoxin (TRX), a histidine tag, a green fluorescent protein (GFP), a glutathione S-transferase (GST), a FLAG tag, a Strep tag, and a HA tag.

17. The recombinant leptin receptor agonist of embodiment 15, wherein the solubility enhancer is MBP.

18. The recombinant leptin receptor agonist of embodiment 1, wherein the recombinant leptin receptor agonist induces higher weight loss when administered to an overweight animal compared to SEQ ID NO: 63.

19. The recombinant leptin receptor agonist of embodiment 18, wherein at least 80% of the weight loss is body fat mass.

20. The recombinant leptin receptor agonist of embodiment 18, wherein less than 20% of the weight loss is lean mass.

21. The recombinant leptin receptor agonist of embodiment 1, wherein the recombinant leptin receptor agonist results in a lower food intake by an overweight animal receiving the recombinant leptin receptor agonist compared to SEQ ID NO: 63.

22. The recombinant leptin receptor agonist of embodiment 1, wherein the recombinant leptin receptor agonist exhibits higher thermostability compared to SEQ ID NO: 63.

23. The recombinant leptin receptor agonist of embodiment 18, wherein the animal is selected from the group consisting of a cat, dog, horse, mouse, rat, rabbit, guinea pig, and human.

24. The recombinant leptin receptor agonist of embodiment 1, wherein the recombinant leptin receptor agonist is comprised within a biological cell.

25. The recombinant leptin receptor agonist of embodiment 24, wherein the biological cell is an *Escherichia coli* cell.

26. The recombinant leptin receptor agonist of embodiment 24, wherein the biological cell is *Spirulina*.

27. The recombinant leptin receptor agonist of embodiment 1, wherein the recombinant leptin receptor agonist is comprised within a composition comprising a protease inhibitor and/or proteinase inhibitor.

28. A method comprising orally administering a therapeutically effective dose of the recombinant leptin receptor agonist of embodiment 1 to an individual in need thereof.

29. A recombinant leptin receptor agonist comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% sequence identity with a sequence selected from the group consisting of SEQ ID NO: 22, 52, 53, 54, 55, 56, 57, 58, 59, 60, 61, 62, and 64.

30. A recombinant leptin receptor agonist comprising an amino acid substitution at a position selected from the group consisting of Q4, K5, V6, T10, I17, V18, N22, S25, T27, S32, D40, L49, L51, K53, M54, T66, S67, S70, R71, 174, S77, N78, L83, H88, H97, T106, A116, T121, V124, A125, Q130, S132, and Q139, wherein the positions are determined by alignment with SEQ ID NO: 63.

Numbered Embodiments 4

1. A recombinant leptin receptor agonist comprising an amino acid substitution at a position selected from the group consisting of Q4, K5, V6, T10, I17, V18, N22, S25, T27, S32, D40, L49, L51, K53, M54, T66, S67, S70, R71, 174, S77, N78, L83, H88, H97, T106, A116, T121, V124, A125, Q130, S132, and Q139, wherein the positions are determined by alignment with SEQ ID NO: 63.

2. The recombinant leptin receptor agonist of embodiment 1, wherein the recombinant leptin receptor agonist comprises an amino acid substitution at a position selected from the group consisting of Q4, V6, 117, V18, N22, D40, L49, T66, L83, H88, and Q139.

3. The recombinant leptin receptor agonist of any one of embodiments 1-2, wherein the recombinant leptin receptor agonist comprises an amino acid substitution at a position selected from the group consisting of K5, T10, S25, T27, S32, L51, K53, M54, S67, S70, R71, 174, S77, N78, H97, T106, A116, T121, V124, A125, Q130, and S132.

4. The recombinant leptin receptor agonist of any one of embodiments 1-3, wherein the recombinant leptin receptor agonist comprises an amino acid substitution selected from the group consisting of Q4E, K5Q, V6I, T10L, I17V, V18I, N22D, S25P, T27V, S32P, D40E, L49I, L51Y, K53D, M54A, T66S, S67L, S70E, R71P, I74Q, S77A, N78L, L83I, H88R, H97P, T106D, A116E, T121V, V124T, A125T, Q130K, S132F, and Q139E.

5. The recombinant leptin receptor agonist of any one of embodiments 1-4, wherein the recombinant leptin receptor agonist comprises an amino acid substitution selected from the group consisting of Q4E, V6I, I17V, V18I, N22D, D40E, L491, T66S, L83I, H88R, and Q139E.

6. The recombinant leptin receptor agonist of any one of embodiments 1-5, wherein the recombinant leptin receptor agonist comprises an amino acid substitution selected from the group consisting of K5Q, T10L, S25P, T27V, S32P, L51Y, K53D, M54A, S67L, S70E, R71P, 174Q, S77A, N78L, H97P, T106D, A116E, T121V, V124T, A125T, Q130K, and S132F.

7. The recombinant leptin receptor agonist of any one of embodiments 1-3, wherein the recombinant leptin receptor agonist comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 amino acid substitutions at the recited positions.

8. The recombinant leptin receptor agonist of any one of embodiments 1-3, wherein the recombinant leptin receptor agonist comprises amino acid substitutions at all of the recited positions.

9. The recombinant leptin receptor agonist of any one of embodiments 4-6, wherein the recombinant leptin receptor agonist comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 of the recited amino acid substitutions.

10. The recombinant leptin receptor agonist of any one of embodiments 4-6, wherein the recombinant leptin receptor agonist comprises all of the recited amino acid substitutions.

11. The recombinant leptin receptor agonist of any one of embodiments 1-10, wherein the recombinant leptin receptor agonist comprises an amino acid sequence having at least about 80%, 81%, 82%, 83%, 84% 85%, 86%, 87%, 88%, 89%, 90%, 91%, 92%, 93%, 94%, 95%, 96%, 97%, 98%, or 99% sequence identity with an amino acid sequence selected from Table 4.

12. The recombinant leptin receptor agonist of any one of embodiments 1-10, wherein the recombinant leptin receptor agonist comprises an amino acid sequence selected from Table 4.

13. The recombinant leptin receptor agonist of any one of embodiments 1-10, wherein the recombinant leptin receptor agonist comprises an amino acid sequence having at least about 80%, 81%, 82%, 83%, 84% 85%, 86%, 87%, 88%, 89%, 90%, 91%, 92%, 93%, 94%, 95%, 96%, 97%, 98%, or 99% sequence identity with a sequence selected from the group consisting of SEQ ID NO: 22, 52, 53, 54, 55, 56, 57, 58, 59, 60, 61, 62, 64, 70, 71, 72, 73, 74, 75, 76, 77, 78, 79, 80, 81.

14. The recombinant leptin receptor agonist of any one of embodiments 1-10, wherein the recombinant leptin receptor agonist comprises an amino acid sequence selected from the group consisting of SEQ ID NO: 22, 52, 53, 54, 55, 56, 57, 58, 59, 60, 61, 62, 63, and 64.

15. A recombinant leptin receptor agonist comprises an amino acid sequence having at least about 80%, 81%, 82%, 83%, 84% 85%, 86%, 87%, 88%, 89%, 90%, 91%, 92%, 93%, 94%, 95%, 96%, 97%, 98%, or 99% sequence identity with a sequence selected from the group consisting of SEQ ID NO: 22, 52, 53, 54, 55, 56, 57, 58, 59, 60, 61, 62, 64, 70, 71, 72, 73, 74, 75, 76, 77, 78, 79, 80, 81.

16. The recombinant leptin receptor agonist of embodiment 15, wherein the recombinant leptin receptor agonist comprises an amino acid selected from the group consisting of 4E, 5Q, 6I, 10L, 17V, 18I, 22D, 25P, 27V, 32P, 40E, 49I, 51Y, 53D, 54A, 66S, 67L, 70E, 71P, 74Q, 77A, 78L, 831, 88R, 97P, 106D, 116E, 121V, 124T, 125T, 130K, 132F, and 139E, wherein the positions are determined by alignment with an sequence selected from the group consisting of SEQ ID NO: 22, 52, 53, 54, 55, 56, 57, 58, 59, 60, 61, 62, and 64.

17. The recombinant leptin receptor agonist of embodiment 16, wherein the recombinant leptin receptor agonist comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 of the amino acids selected from the group consisting of 4E, 5Q, 6I, 10L, 17V, 18I, 22D, 25P, 27V, 32P, 40E, 49I, 51Y, 53D, 54A, 66S, 67L, 70E, 71P, 74Q, 77A, 78L, 83I, 88R, 97P, 106D, 116E, 121V, 124T, 125T, 130K, 132F, and 139E. 18. The recombinant leptin receptor agonist of any one of embodiments 16-17, wherein the recombinant leptin receptor agonist comprises all of the of the amino acids selected from the group consisting of 4E, 5Q, 6I, 10L, 17V, 18I, 22D, 25P, 27V, 32P, 40E, 49I, 51Y, 53D, 54A, 66S, 67L, 70E, 71P, 74Q, 77A, 78L, 83I, 88R, 97P, 106D, 116E, 121V, 124T, 125T, 130K, 132F, and 139E.

19. The recombinant leptin receptor agonist of any one of embodiments 15-18, wherein the recombinant leptin receptor agonist comprises an amino acid selected from the group consisting of D9, L13, T16, R20, K33, Q34, K35, V36, T37, Q75, D85, L86, S117, Y119, and $120.

20. The recombinant leptin receptor agonist of embodiment 15-19, wherein the recombinant leptin receptor agonist comprises at least 2, 3, 4, 5, 6, 7, 8, 9, 10, 11, 12, 13, 14, or 15 of the amino acids selected from the group consisting of D9, L13, T16, R20, K33, Q34, K35, V36, T37, Q75, D85, L86, S117, Y119, and S120.

21. The recombinant leptin receptor agonist of any one of embodiments 15-20, wherein the recombinant leptin receptor agonist comprises all of the amino acids selected from the group consisting of D9, L13, T16, R20, K33, Q34, K35, V36, T37, Q75, D85, L86, S117, Y119, and S120.

22. The recombinant leptin receptor agonist of any one of embodiments 1-21, wherein the recombinant leptin receptor is not SEQ ID NO: 63.

23. The recombinant leptin receptor agonist of any one of embodiments 1-22, wherein the recombinant leptin receptor agonist does not comprise a substitution at an activity-reducing position selected from the group consisting of D9, L13, T16, R20, K33, Q34, K35, V36, T37, Q75, D85, L86, S117, Y119, and S120.

24. The recombinant leptin receptor agonist of any one of embodiments 1-22, wherein the recombinant leptin receptor agonist comprises fewer than 15, 14, 13, 12, 11, 10, 9, 8, 7, 6, 5, 4, 3, 2, or 1 substitutions at an activity-reducing position selected from the group consisting of D9, L13, T16, R20, K33, Q34, K35, V36, T37, Q75, D85, L86, S117, Y119, and S120.

25. The recombinant leptin receptor agonist of any one of embodiments 1-22, wherein the recombinant leptin receptor agonist does not comprise any substitutions at positions selected from the group consisting of D9, L13, T16, R20, K33, Q34, K35, V36, T37, Q75, D85, L86, S117, Y119, and S120.

26. The recombinant leptin receptor agonist of any one of embodiments 1-25, wherein the recombinant leptin receptor agonist is comprised within a chimeric protein, said chimeric protein comprising a protein fusion partner.

27. The recombinant leptin receptor agonist of embodiment 26, wherein the protein fusion partner is N-terminally translationally fused to the recombinant leptin receptor agonist.

28. The recombinant leptin receptor agonist of embodiment 26, wherein the protein fusion partner is C-terminally translationally fused to the recombinant leptin receptor agonist.

29. The recombinant leptin receptor agonist of any one of embodiments 26-28, wherein the protein fusion partner is a protein purification tag or solubility enhancer.

30. The recombinant leptin receptor agonist of embodiment 29, wherein the protein purification tag is selected from the group consisting of a maltose binding protein (MBP), a histidine tag, a green fluorescent protein (GFP), a glutathione S-transferase (GST), a FLAG tag, a Strep tag, and a HA tag.

31. The recombinant leptin receptor agonist of embodiment 29, wherein the protein purification tag is MBP.

32. The recombinant leptin receptor agonist of any one of embodiments 26-31, wherein the protein fusion partner and the recombinant leptin receptor agonist are connected via a peptide linker.

33. The recombinant leptin receptor agonist of embodiment 32, wherein the peptide linker is a glycine-rich linker, a proline-rich linker, a serine-rich linker, or a protease-cleavable linker.

34. The recombinant leptin receptor agonist of embodiment 32, wherein the peptide linker is a G4S linker.

35. The recombinant leptin receptor agonist of any one of embodiments 1-34, wherein the recombinant leptin receptor agonist induces higher weight loss when administered to an overweight animal compared to an unmodified, wild-type, or non-recombinant leptin.

36. The recombinant leptin receptor agonist of embodiment 35, wherein at least 60%, 65%, 70%, 75%, 80%, 85%, 90%, or 95% of the weight loss is body fat mass.

37. The recombinant leptin receptor agonist of embodiment 35 or 36, wherein less than 1%, 2%, 3%, 4%, 5%, 6%, 7%, 8%, 9%, 10%, 11%, 12%, 13%, 14%, 15%, 16%, 17%, 18%, or 19% of the weight loss is lean mass.

38. The recombinant leptin receptor agonist of any one of embodiments 1-34, wherein the recombinant leptin receptor agonist results in a lower food intake by an overweight animal receiving the recombinant leptin receptor agonist compared to an unmodified, wild-type, or non-recombinant leptin.

39. The recombinant leptin receptor agonist of any one of embodiments 1-35, wherein the recombinant leptin receptor agonist exhibits reduced dimerization or aggregation when expressed in a recombinant host compared to an unmodified or wild-type leptin expressed in the same recombinant host.

40. The recombinant leptin receptor agonist of any one of embodiments 1-39, wherein the recombinant leptin receptor agonist expresses at higher levels in a recombinant host compared to an unmodified or wild-type leptin expressed in the same recombinant host under similar conditions.

41. The recombinant leptin receptor agonist of embodiment 40, wherein the recombinant leptin receptor agonist expresses at higher levels in *E. Coli* and/or *Spirulina.*

42. The recombinant leptin receptor agonist of any one of embodiments 1-41, wherein the recombinant leptin receptor agonist exhibits stronger binding (Lower $K_D$) to the human leptin receptor compared to an unmodified, wild-type, or non-recombinant leptin.

43. The recombinant leptin receptor agonist of any one of embodiments 1-42, wherein the recombinant leptin receptor agonist exhibits higher thermostability compared to an unmodified, wild-type, or non-recombinant leptin.

44. The recombinant leptin receptor agonist of embodiment 43, wherein the recombinant leptin receptor agonist exhibits higher bioactivity after exposure to a temperature of at least about 50 Celsius, at least about 70 Celsius, or at least about 90 Celsius.

45. The recombinant leptin receptor agonist of embodiment 43, wherein the recombinant leptin receptor agonist exhibits higher bioactivity after exposure to a temperature between about 50 Celsius and about 90 Celsius.

46. The recombinant leptin receptor agonist of embodiment 35 or 38, wherein the animal is selected from the group consisting of a cat, dog, horse, mouse, rat, rabbit, guinea pig, and pig.

47. The recombinant leptin receptor agonist of embodiment 35 or 38, wherein the animal is a primate.

48. The recombinant leptin receptor agonist of embodiment 35 or 38, wherein the animal is a human.

49. The recombinant leptin receptor agonist of any one of embodiments 1-45, wherein the recombinant leptin receptor agonist is expressed and/or comprised within a biological cell.

50. The recombinant leptin receptor agonist of embodiment 49, wherein the biological cell is a eukaryotic cell or prokaryotic cell.

51. The recombinant leptin receptor agonist of embodiment 49, wherein the biological cell is a prokaryotic cell.

52. The recombinant leptin receptor agonist of embodiment 49, wherein the biological cell is a eukaryotic cell.

53. The recombinant leptin receptor agonist of embodiment 49, wherein the biological cell is a bacterial cell.

54. The recombinant leptin receptor agonist of embodiment 49, wherein the biological cell is an *Escherichia coli* cell.

55. The recombinant leptin receptor agonist of embodiment 49, wherein the biological cell is a eukaryotic cell selected from the group consisting of a filamentous fungi cell, a yeast cell, an algal cell, and a plant cell.

56. The recombinant leptin receptor agonist of embodiment 55, wherein the yeast cell is *Saccharomyces cerevisiae* or *Pichia pastoris.*

57. The recombinant leptin receptor agonist of embodiment 49, wherein the biological cell is a *Cyanobacterium.*

58. The recombinant leptin receptor agonist of embodiment 57, wherein the *Cyanobacterium* is *Spirulina.*

59. The recombinant leptin receptor agonist of any one of embodiments 49-58, wherein the biological cell is genetically engineered to express the recombinant leptin receptor agonist.

60. The recombinant leptin receptor agonist of any one of embodiments 49-59, wherein the biological cells are desiccated, dried, lyophilized, and/or non-living.

61. The recombinant leptin receptor agonist of any one of embodiments 1-60, wherein the recombinant leptin receptor agonist is comprised within a composition that does not include any added permeability enhancer excipient and/or absorption enhancer excipient.

62. The recombinant leptin receptor agonist of any one of embodiments 1-61, wherein the recombinant leptin receptor agonist is comprised within a composition comprising a protease inhibitor and/or proteinase inhibitor.

63. The recombinant leptin receptor agonist of embodiment 62, wherein the protease inhibitor is soybean trypsin inhibitor.

64. The recombinant leptin receptor agonist of any one of embodiments 1-63, wherein the recombinant leptin receptor agonist is comprised within a composition comprising a second active composition selected from the group consisting of amylin, cholecystokinin (CCK), a GLP-1 agonist, glucagon, gastric inhibitory polypeptide (GIP), luminal CCK-releasing factor (LCRF), *Akkermansia muciniphila* protein P9, and a CG-1 inhibitor.

65. A method comprising orally administering a therapeutically effective dose of the recombinant leptin receptor agonist of any one of embodiments 1-64, to an individual in need thereof.

66. The method of embodiment 65, wherein the recombinant leptin receptor agonist acts locally in the individual's gastrointestinal tissues.

67. The method of any one of embodiments 65-66, wherein the recombinant leptin receptor agonist is systemically bioavailable in the individual's blood in an amount less than 0.05% of the administered dose.

68. The method of any one of embodiments 65-67, wherein the individual is an overweight individual.

69. The method of any one of embodiments 65-68, wherein the individual is an obese individual.

70. The method of any one of embodiments 65-69, wherein administration of the recombinant leptin receptor agonist results in weight loss.

71. The method of embodiment 70, wherein at least 60%, 65%, 70%, 75%, 80%, 85%, 90%, or 95% of the weight loss is body fat mass.

72. The method of embodiment 70 or 71, wherein less than 1%, 2%, 3%, 4%, 5%, 6%, 7%, 8%, 9%, 10%, 11%, 12%, 13%, 14%, 15%, 16%, 17%, 18%, or 19% of the weight loss is lean mass.

73. The method of any one of embodiments 65-70, wherein administration of the recombinant leptin receptor agonist results in systemic glucose reduction.

74. The method of any one of embodiments 65-73, wherein the method further comprises administering a second composition before, during, or after delivering the recombinant leptin receptor agonist, wherein the second composition is selected from the group consisting of amylin, cholecystokinin (CCK), a GLP-1 agonist, glucagon, gastric inhibitory polypeptide (GIP), luminal CCK-releasing factor (LCRF), *Akkermansia muciniphila* protein P9, and a CG-1 inhibitor. 75. The method of embodiment 74, wherein the recombinant leptin receptor agonist is orally delivered after the individual ceases administration of the GLP-1 agonist.

76. The method of any one of embodiments 74-75, wherein the recombinant leptin receptor agonist is orally delivered after the individual finishes dieting.

77. The method of any one of embodiments 74-76, wherein the recombinant leptin receptor agonist is orally delivered after the individual undergoes bariatric surgery.

INCORPORATION BY REFERENCE

All references, articles, publications, patents, patent publications, and patent applications cited herein within the above text and/or cited below are incorporated by reference in their entireties for all purposes. All literature and similar materials cited in this application, including patents, patent applications, articles, books, treatises, and Internet web pages are expressly incorporated by reference in their entirety for any purpose. When definitions of terms in incorporated references appear to differ from the definitions provided in this application, the definition provided in this application shall control.

However, mention of any reference, article, publication, patent, patent publication, and patent application cited herein is not, and should not be taken as acknowledgment or any form of suggestion that they constitute valid prior art or form part of the common general knowledge in any country in the world.

SEQUENCE LISTING

```
Sequence total quantity: 91
SEQ ID NO: 1           moltype = DNA  length = 2225
FEATURE                Location/Qualifiers
source                 1..2225
                       mol_type = other DNA
                       organism = synthetic construct
SEQUENCE: 1
gtgttggggc tgacttttgc tgccttgttg gggggggcga ttttaactga ggtcactttt  60
tcttggccgg gattggctaa tcgcttgtat gaggctatcc gtctgcggga ttatcccacg  120
gttcaagggg tggtggtatt tttggccgtt attgtggtgg cggctagttt ggcgatcgat  180
attttgaatg cttgtattga cccacggatt cgctattaat tccctgtcag aaaatatact  240
tagttattaa tacttagtta tttttcttaa taaattttaa caaaccaaag ggcgttggca  300
gtgtataaag gatatttgaa ggggtgagaa ggaaggcgaa tgttgattta tgaagtttga  360
ttaacatttg tatcaaaata taaaattctt ctcataaacc ctgtacaatc ttttaagatt  420
tcggaaagtg ttctaggata ctgaagaaat gaaccacggg gcaattgtta aaagcctttg  480
tcgatggttc gccccggaag gggtcttagg aggtgacacc gatggattga ttgtcgtgat  540
cattcatggt gtgtccaatc ccaactcaac tctaagcaag tcaacaagta ggagataaat  600
ctatgaaaat cgaagaaggt aaactggtaa tctggattaa cggcgataaa ggctataacg  660
gactcgctga agtcggtaag aaattcgaga aagataccgg aattaaagtc accgttgagc  720
atccggataa actggaagag aaattcccac aggttgcggc aactggcgat ggccctgaca  780
ttatcttctg ggcacacgac cgctttggtg gctacgctca atctggcctg ttggctgaaa  840
tcaccccgga caaagcgttc caggacaagc tgtatccgtt tacctgggat gccgtacgtt  900
acaacggcaa gctgattgct tacccgatcg ctgttgaagc gttatcgctg atttataaca  960
aagatctgct gccgaacccg ccaaaaacct gggaagagat cccggcgctg gataaagaac  1020
tgaaagcgaa aggtaagagc gcgctgatgt tcaacctgca agaaccgtac ttcacctggc  1080
cgctgattgc tgctgacggg ggttatgcgt tcaagtatga aaacggcaag tacgacatta  1140
aagacgtggg cgtggataac gctggcgcga aagcgggtct gaccttcctg gttgacctga  1200
ttaaaaacaa acacatgaat gcagacaccg attactccat cgcagaagct gcctttaata  1260
aaggcgaaac agcgatgacc atcaacggcc cgtgggcatg gtccaacatc gacaccagca  1320
aagtgaatta tggtgtaacg gtactgccga ccttcaaggg tcaaccatcc aaaccgttcg  1380
ttggcgtgct gagcgcaggt attaacgccg ccagtccgaa caaagagctg gcaaaagagt  1440
tcctcgaaaa ctatctgctg actgatgaag gtctggaagc ggttaataaa gacaaaccgc  1500
tgggtgccgt agcgctgaag tcttacgagg aagagttggc gaaagatcca cgtattgccg  1560
ccactatgga aaacgcccag aaaggtgaaa tcatgccgaa catcccgcag atgtccgctt  1620
tctggtatgc cgtgcgtact gcggtgatca acgccgccag cggtcgtcag actgtcgatg  1680
aagccctgaa agacgcgcag acttccggcg gaggtggagg ctcaaaaggc ggtggaggta  1740
gcgctggagg cgtaccgatc cagaaagtgc aggacgacac caagacgctg attaaaacaa  1800
ttgtcactcg tattaatgac atttcacaca cccagtccgt gagctcgaaa cagaaagtaa  1860
ccggtctgga ttttatcccg ggcctacatc caatactgac gctctcgaag atggatcaga  1920
ctcttgcagt gtatcagcag attcttacct ccatgccttc tcgtaacatg atccaaattt  1980
ctaatgatct tgaaaacctg cgcgacttac tgcatgttct ggcgttctca aaaagctgtc  2040
acttgccgtg ggccagtggt ttagaaacgc tggatagtct gggaggcgtg ttggaggcga  2100
gcggctacag caccgaagtc gttgctctgt cgcgcttgca agggagctta caggatatgc  2160
tctggcaact ggatctgagc cccggctgct caagcggcgg tagtcaccat caccaccatc  2220
actaa                                                             2225
```

```
SEQ ID NO: 2            moltype = DNA  length = 2227
FEATURE                 Location/Qualifiers
source                  1..2227
                        mol_type = other DNA
                        organism = synthetic construct
SEQUENCE: 2
gtgttggggc tgacttttgc tgccttgttg gggggggcga ttttaactga ggtcactttt  60
tcttggccgg gattggctaa tcgcttgtat gaggctatcc gtctgcggga ttatcccacg  120
gttcaagggg tggtggtatt tttggccgtt attgtggtgg cggctagttt ggcgatcgat  180
attttgaatg cttgtattga cccacggatt cgctattaat tccctgtcag aaaatatact  240
tagttattaa tacttagtta tttttcttaa taaattttaa caaaccaaag ggcgttggca  300
gtgtataaag gatatttgaa ggggtgagaa ggaaggcgaa tgttgattta tgaagtttga  360
ttaacatttg tatcaaaata taaaattctt ctcataaacc ctgtacaatc ttttaagatt  420
tcggaaagtg ttctaggata ctgaagaaat gaaccacggg gcaattgtta aaagcctttg  480
tcgatggttc gccccggaag gggtcttagg aggtgacacc gatggattga ttgtcgtgat  540
cattcatggt gtgtccaatc ccaactcaac tctaagcaag tcaacaagta ggagataaat  600
catgaaaatc gaagaaggta aactggtaat ctggattaac ggcgataaag gctataacgg  660
actcgctgaa gtcggtaaga aattcgagaa agataccgga attaaagtca ccgttgagca  720
tccggataaa ctggaagaga aattcccaca ggttgcggca actggcgatg gccctgacat  780
tatcttctgg gcacacgacc gctttggtgg ctacgctcaa tctggcctgt tggctgaaat  840
caccccggac aaagcgttcc aggacaagct gtatccgttt acctgggatg ccgtacgtta  900
caacggcaag ctgattgctt acccgatcgc tgttgaagcg ttatcgctga tttataacaa  960
agatctgctg ccgaacccgc caaaaacctg ggaagagatc ccggcgctgg ataaagaact  1020
gaaagcgaaa ggtaagagcg cgctgatgtt caacctgcaa gaaccgtact tcacctggcc  1080
gctgattgct gctgacgggg gttatgcgtt caagtatgaa aacggcaagt acgacattaa  1140
agacgtgggc gtggataacg ctggcgcgaa agcgggtctg accttcctgg ttgacctgat  1200
taaaaacaaa cacatgaatg cagacaccga ttactccatc gcagaagctg cctttaataa  1260
aggcgaaaca gcgatgacca tcaacggccc gtgggcatgg tccaacatcg acaccagcaa  1320
agtgaattat ggtgtaacgg tactgccgac cttcaagggt caaccatcca aaccgttcgt  1380
tggcgtgctg agcgcaggta ttaacgccgc cagtccgaac aaagagctgg caaaagagtt  1440
cctcgaaaac tatctgctga ctgatgaagg tctggaagcg gttaataaag acaaaccgct  1500
gggtgccgta gcgctgaagt cttacgagga agagttggcg aaagatccac gtattgccgc  1560
cactatggaa aacgcccaga aaggtgaaat catgccgaac atcccgcaga tgtccgcttt  1620
ctggtatgcc gtgcgtactg cggtgatcaa cgccgccagc ggtcgtcaga ctgtcgatga  1680
agccctgaaa gacgcgcaga cttccggcgg aggtggaggc tcaaaaggcg gtggaggtag  1740
cgctggannn nnnnnnnnnn nnnnnnnnnn nnnnnnnnnn nnnnnnnnnn nnnnnnnnnn  1800
nnnnnnnnnn nnnnnnnnnn nnnnnnnnnn nnnnnnnnnn nnnnnnnnnn nnnnnnnnnn  1860
nnnnnnnnnn nnnnnnnnnn nnnnnnnnnn nnnnnnnnnn nnnnnnnnnn nnnnnnnnnn  1920
nnnnnnnnnn nnnnnnnnnn nnnnnnnnnn nnnnnnnnnn nnnnnnnnnn nnnnnnnnnn  1980
nnnnnnnnnn nnnnnnnnnn nnnnnnnnnn nnnnnnnnnn nnnnnnnnnn nnnnnnnnnn  2040
nnnnnnnnnn nnnnnnnnnn nnnnnnnnnn nnnnnnnnnn nnnnnnnnnn nnnnnnnnnn  2100
nnnnnnnnnn nnnnnnnnnn nnnnnnnnnn nnnnnnnnnn nnnnnnnnnn nnnnnnnnnn  2160
nnnnnnnnnn nnnnnnnnnn nnnnnnnnnn nnnnnnnggc ggtagtcacc atcaccacca  2220
tcactaa                                                            2227

SEQ ID NO: 3            moltype =   length =
SEQUENCE: 3
000

SEQ ID NO: 4            moltype =   length =
SEQUENCE: 4
000

SEQ ID NO: 5            moltype =   length =
SEQUENCE: 5
000

SEQ ID NO: 6            moltype = AA  length = 146
FEATURE                 Location/Qualifiers
source                  1..146
                        mol_type = protein
                        organism = synthetic construct
SEQUENCE: 6
VPIQKVIDDT KTLIKTILTR INDISYTQSV SAKQRVTGLD FIPGLHPILS LSKMLQTLAF  60
YQQVLLSLPS QLVLQIANDL ENLRDLLILL AQSKNCQLPD TSNLKKPESL DDILRNSLYS  120
IEVVALSRLQ IVLQDILQQL DHDPDC                                       146

SEQ ID NO: 7            moltype = AA  length = 146
FEATURE                 Location/Qualifiers
source                  1..146
                        mol_type = protein
                        organism = synthetic construct
SEQUENCE: 7
VPIQKVFDDT KTLIKTILTR INDISYTQSV SAKQRVTGLD FIPGLHPILS LSKMLQTLAF  60
YQQVLLSLPS QLVLQIANDL ENLRDLLHLL AFSKNCSLPD TSNLQKPESL DEVLRNSLYS  120
IEVVALSRLQ ISLQDILQQL DVDPEC                                       146

SEQ ID NO: 8            moltype = AA  length = 146
FEATURE                 Location/Qualifiers
```

```
source                  1..146
                        mol_type = protein
                        organism = synthetic construct
SEQUENCE: 8
VPIQKVQDDT KTLIKVILTR INTLQYTQEV SSKLIVFGLD FIPGLEPILS LSKMLQTLAV  60
YQQVLLSLPS EDVLQIAADL ENLRLLLHLL AQSKNCQLPD TSNLKKPESL DEILRNSLYS  120
IEVVALSRLQ GSLLIILQQL DHDPDC                                       146

SEQ ID NO: 9            moltype = AA  length = 146
FEATURE                 Location/Qualifiers
source                  1..146
                        mol_type = protein
                        organism = synthetic construct
SEQUENCE: 9
MPIEEVRKNT KTLIKTIITK IDTIPYVQDV SPEITVTGLD FIPGDKPITS LSEAVLTLTR  60
YRQVLLSLPD PETQQIALDL DNLIELFREL AASKGCTLPD PSNLATPPEL AEVLKDSEFA  120
VYVTALTKLK KNLENILKEL EKDLAC                                       146

SEQ ID NO: 10           moltype = AA  length = 146
FEATURE                 Location/Qualifiers
source                  1..146
                        mol_type = protein
                        organism = synthetic construct
SEQUENCE: 10
RPLEQVRRDL KTLIKTIITK IDTIPYVQDV NPDITVTGLD FIPGNRPITS LSEAKKTLTK  60
YVQVLESLDD PETQEIALDL KNVIELIDEL AKSRGCTLPD TSTLEKDPRL EEVKKDSEFA  120
ITTTALRNLK INLEIILKEL ERDPAC                                       146

SEQ ID NO: 11           moltype = AA  length = 146
FEATURE                 Location/Qualifiers
source                  1..146
                        mol_type = protein
                        organism = synthetic construct
SEQUENCE: 11
VPIEKVREDL KTLIKTIIKK IDTIPEVQDV SPEITVTGLD FIPGNEPINS LSEAVLTLTR  60
YRQVLESLDD PETQQIALDL QNLIELLKEL AKEKGCTLPD PSNLKKPEEL EKVLEDAEFA  120
VRVTALTNLK KNLENILKVL ETDPAC                                       146

SEQ ID NO: 12           moltype = AA  length = 146
FEATURE                 Location/Qualifiers
source                  1..146
                        mol_type = protein
                        organism = synthetic construct
SEQUENCE: 12
VPIQKVQDDT KTLIKTIITR INDISHTQSV SSKVKVTGLD FIPGRHPILT LSKMDQTLAV  60
YQQILTSMPD PNVIQIANDL ENLRDLLHVL AFSKSCPLPW ASGLETLDSL RKVLEASLYS  120
TEVVALSRLQ GVLQDMLKQL DLSPGC                                       146

SEQ ID NO: 13           moltype = AA  length = 146
FEATURE                 Location/Qualifiers
source                  1..146
                        mol_type = protein
                        organism = synthetic construct
SEQUENCE: 13
VPIQKVQDDT KTLIKTIITR INDISHTQSV SSKVKVTGLD FIPGRHPILT LSKMDQTLAV  60
YQQILESMPD PNVIQIANDL ENLRDLLHVL AFSKSCPLPW ASGLETLDSL RKVLEASLYS  120
TEVVALSRLQ GVLQDMLKQL DLSPGC                                       146

SEQ ID NO: 14           moltype = AA  length = 146
FEATURE                 Location/Qualifiers
source                  1..146
                        mol_type = protein
                        organism = synthetic construct
SEQUENCE: 14
VPIQKVFDDT KTLIKTIITR INTIEHTQSV SSKIKVTGLD FIPGLQPILT LSKMDQTLAV  60
YQQILLSMPV PLVIQIAADL ENLRLLLHLL AKSKNCPLPW ASGLEDEDML RRVLEASLYS  120
TEVVTLLRLQ GVLLQMLEQL DLSPGC                                       146

SEQ ID NO: 15           moltype = AA  length = 146
FEATURE                 Location/Qualifiers
source                  1..146
                        mol_type = protein
                        organism = synthetic construct
SEQUENCE: 15
VPLEKIREDT KTLIRTIITR IDQIPYVADV SPKQKVTGLD FIPGTKDKYT YSDFAATLAK  60
YREILSATDD PELQQIALDL DNLIDLIREL AKSKGCPLPE ATGLPDPEKL KEALKESGYS  120
VEVETARKLK AFLEKALEEL EKDPGC                                       146

SEQ ID NO: 16           moltype = AA  length = 146
```

```
FEATURE                 Location/Qualifiers
source                  1..146
                        mol_type = protein
                        organism = synthetic construct
SEQUENCE: 16
VPEEQIRNDL KTLTKTIITR IDQIPAVKEV SPKQKVTGLE IIPGTKDKYT FTDMSATLAV  60
YREIFSMLDE PEVQQIALDL DNLIDLIKEL AKTKGCPLPE AKGVADKAKI EELIKESGYS  120
VYVTTATNLK AVLEKFIKEL EKDPGC                                       146

SEQ ID NO: 17           moltype = AA  length = 146
FEATURE                 Location/Qualifiers
source                  1..146
                        mol_type = protein
                        organism = synthetic construct
SEQUENCE: 17
VPVEQIRKDL ETLIRTVITR IDTIPYVKEV SPKQKVTGLE FIPGTKEKIT YTDADETLAI  60
YQEILSLLPE PELQQIALDL DNIRDLIREL AATKNCPLPR ASGLPDREKL LEAIKESGYS  120
VAVTTATKLK EFLEKLIEEL KKDPGC                                       146

SEQ ID NO: 18           moltype = DNA  length = 1101
FEATURE                 Location/Qualifiers
source                  1..1101
                        mol_type = other DNA
                        organism = synthetic construct
SEQUENCE: 18
atgaaaatcg aagaaggtaa actggtaatc tggattaacg gcgataaagg ctataacgga  60
ctcgctgaag tcggtaagaa attcgagaaa gataccggaa ttaaagtcac cgttgagcat  120
ccggataaac tggaagagaa attcccacag gttgcggcaa ctggcgatgg ccctgacatt  180
atcttctggg cacacgaccg ctttggtggc tacgctcaat ctggcctgtt ggctgaaatc  240
accccggaca aagcgttcca ggacaagctg tatccgttta cctgggatgc cgtacgttac  300
aacggcaagc tgattgctta cccgatcgct gttgaagcgt tatcgctgat ttataacaaa  360
gatctgctgc cgaacccgcc aaaaacctgg gaagagatcc cggcgctgga taaagaactg  420
aaagcgaaag gtaagagcgc gctgatgttc aacctgcaag aaccgtactt cacctggccg  480
ctgattgctg ctgacggggg ttatgcgttc aagtatgaaa acggcaagta cgacattaaa  540
gacgtgggcg tggataacgc tggcgcgaaa gcgggtctga ccttcctggt tgacctgatt  600
aaaaacaaac acatgaatgc agacaccgat tactccatcg cagaagctgc ctttaataaa  660
ggcgaaacag cgatgaccat caacggcccg tgggcatggt ccaacatcga caccagcaaa  720
gtgaattatg gtgtaacggt actgccgacc ttcaagggtc aaccatccaa accgttcgtt  780
ggcgtgctga gcgcaggtat taacgccgcc agtccgaaca aagagctggc aaaagagttc  840
ctcgaaaact atctgctgac tgatgaaggt ctggaagcgg ttaataaaga caaaccgctg  900
ggtgccgtag cgctgaagtc ttacgaggaa gagttggcga aagatccacg tattgccgcc  960
actatggaaa acgcccagaa aggtgaaatc atgccgaaca tcccgcagat gtccgctttc  1020
tggtatgccg tgcgtactgc ggtgatcaac gccgccagcg gtcgtcagac tgtcgatgaa  1080
gccctgaaag acgcgcagac t                                            1101

SEQ ID NO: 19           moltype = DNA  length = 42
FEATURE                 Location/Qualifiers
source                  1..42
                        mol_type = other DNA
                        organism = synthetic construct
SEQUENCE: 19
tccggcggag gtggaggctc aaaaggcggt ggaggtagcg ct                     42

SEQ ID NO: 20           moltype = DNA  length = 450
FEATURE                 Location/Qualifiers
source                  1..450
                        mol_type = other DNA
                        organism = synthetic construct
SEQUENCE: 20
ggaggcgtac cgatccagaa agtgcaggac gacaccaaga cgctgattaa aacaattgtc  60
actcgtatta atgacatttc acacacccag tccgtgagct cgaaacagaa agtaaccggt  120
ctggatttta tcccgggcct acatccaata ctgacgctct cgaagatgga tcagactctt  180
gcagtgtatc agcagattct tacctccatg ccttctcgta acatgatcca aatttctaat  240
gatcttgaaa acctgcgcga cttactgcat gttctggcgt tctcaaaaag ctgtcacttg  300
ccgtgggcca gtggtttaga aacgctggat agtctgggag gcgtgttgga ggcgagcggc  360
tacagcaccg aagtcgttgc tctgtcgcgc ttgcaaggga gcttacagga tatgctctgg  420
caactggatc tgagccccgg ctgctcaagc                                   450

SEQ ID NO: 21           moltype = DNA  length = 601
FEATURE                 Location/Qualifiers
source                  1..601
                        mol_type = other DNA
                        organism = synthetic construct
SEQUENCE: 21
gtgttggggc tgacttttgc tgccttgttg gggggggcga ttttaactga ggtcactttt  60
tcttggccgg gattggctaa tcgcttgtat gaggctatcc gtctgcggga ttatcccacg  120
gttcaagggg tggtggtatt tttggccgtt attgtggtgg cggctagttt ggcgatcgat  180
attttgaatg cttgtattga cccacggatt cgctattaat tccctgtcag aaaatatact  240
tagttattaa tacttagtta tttttcttaa taaattttaa caaaccaaag ggcgttggca  300
```

```
gtgtataaag gatatttgaa ggggtgagaa ggaaggcgaa tgttgattta tgaagtttga  360
ttaacatttg tatcaaaata taaaattctt ctcataaacc ctgtacaatc ttttaagatt  420
tcggaaagtg ttctaggata ctgaagaaat gaaccacggg gcaattgtta aaagcctttg  480
tcgatggttc gccccggaag gggtcttagg aggtgacacc gatggattga ttgtcgtgat  540
cattcatggt gtgtccaatc ccaactcaac tctaagcaag tcaacaagta ggagataaat  600
c                                                                  601

SEQ ID NO: 22          moltype = AA  length = 146
FEATURE                Location/Qualifiers
source                 1..146
                       mol_type = protein
                       organism = synthetic construct
SEQUENCE: 22
VPIQKVQDDT KTLIKTIITR INDISHTQSV SSKVKVTGLD FIPGRHPILT LSKMDQTLAV  60
YQQILTSMPD PNVIQIANDL ENLRDLLHVL AFSKSCPLPW ASGLETLDSL RKVLEASLYS  120
TEVVALSRLQ GVLQDMLKQL DLSPGC                                       146

SEQ ID NO: 23          moltype = DNA  length = 438
FEATURE                Location/Qualifiers
source                 1..438
                       mol_type = other DNA
                       organism = synthetic construct
SEQUENCE: 23
gtgccgatcc aaaaagtcca ggacgatact aaaacactaa ttaaaacgat tatcacacgt  60
attaatgaca tctcccatac tcagagcgtc tcctctaagg ttaaggtcac cggactggac  120
tttattccag gtcgccaccc tatcctaaca ttatctaaga tggatcagac cctagccgtg  180
tatcaacaga tcctgacttc catgccagac ccaaacgtga tccaaattgc aaatgacctg  240
gagaacctcc gagatttact acacgtgcta gcgtttagca aaagctgtcc cctcccgtgg  300
gcgagcggat tggaaacgct cgatagcttg cgaaaggttc tcgaagcgag cctatactcc  360
acggaggtcg tagccttatc tcgtttacaa ggagtgctgc aggacatgct aaagcagctc  420
gacctatctc ccggatgc                                                438

SEQ ID NO: 24          moltype = DNA  length = 438
FEATURE                Location/Qualifiers
source                 1..438
                       mol_type = other DNA
                       organism = synthetic construct
SEQUENCE: 24
gtacccattc aaaaggtcca agatgacact aaaaccttga ttaagacgat catcacacgg  60
atcaatgata tttcccatac ccagagcgta agctctaaag ttaaggtgac gggcttggat  120
ttcattcctg gccgtcatcc tatcttgacc ttgagcaaga tggatcagac actagccgtc  180
tatcagcaga tcctagaatc catgcccgac cccaatgtca tccaaatcgc gaatgacctc  240
gagaatttac gtgacctact gcatgtattg gctttctcta aatcttgccc tctcccctgg  300
gctagcggac tggaaacgct agacagcctc cggaaggtgc tggaggccag cttatactct  360
acagaggtcg tagctttaag ccgcctacaa ggtgtgctac aggatatgct gaagcaatta  420
gatctcagcc ccggatgc                                                438

SEQ ID NO: 25          moltype = DNA  length = 438
FEATURE                Location/Qualifiers
source                 1..438
                       mol_type = other DNA
                       organism = synthetic construct
SEQUENCE: 25
gtacccatcc aaaaggtgtt tgatgacacg aaaacactga tcaagactat tatcacacgg  60
attaacacta tcgagcacac tcaaagtgtt agctccaaga ttaaggttac ggggttagac  120
ttcattccgg gactacagcc gatcctaaca ctgtctaaaa tggaccaaac gctagctgtg  180
taccagcaga ttctattgag tatgccggtt ccgttagtca tccaaatcgc cgctgaccta  240
gagaacctgc gtttgctcct ccatctgctc gcgaagagta aaaattgtcc tctgccctgg  300
gcgagcggac tggaagatga agatatgcta cggcgcgtgc tggaagcaag tttatattcc  360
actgaagtcg tgacgttgct acgcctgcaa ggtgtcttac tacaaatgct agagcagcta  420
gacttgagcc cagggtgt                                                438

SEQ ID NO: 26          moltype = DNA  length = 438
FEATURE                Location/Qualifiers
source                 1..438
                       mol_type = other DNA
                       organism = synthetic construct
SEQUENCE: 26
gtcccgttgg agaaaattcg tgaggacaca aagacattga ttcggaccat tatcactcgg  60
attgatcaaa tcccttacgt cgcagatgtc agcccgaagc agaaggtcac agggctcgat  120
ttcattcccg gaactaaaga caaatacaca tatagcgatt ttgcagcgac attagccaaa  180
taccgtgaaa tcttatctgc tactgacgat cctgaactac aacaaatcgc attggatttg  240
gataatttaa ttgatctaat tcgggagttg gcaaagagca aggggtgtcc gttaccagaa  300
gccacggggt tgccagatcc ggaaaaacta aaggaggcat taaaagaatc cggatatagt  360
gtcgaagtag agacggcacg aaaactcaaa gcattcctgg agaaggcgct agaagagtta  420
gaaaaagatc caggttgc                                                438

SEQ ID NO: 27          moltype = DNA  length = 438
FEATURE                Location/Qualifiers
```

```
source                  1..438
                        mol_type = other DNA
                        organism = synthetic construct
SEQUENCE: 27
gtccctgaag aacaaattcg gaatgattta aaaaccctca ctaagacgat tatcacgcgc  60
atcgatcaga tcccggctgt taaagaagtg agccccaagc agaaggtgac cgggctggaa  120
attatccccg gaacaaaaga taaatatacg tttacagaca tgagtgcgac gctggcggtc  180
taccgtgaga ttttctctat gctcgacgaa ccagaggttc agcaaattgc actcgatctc  240
gataatttga tcgacctcat caaagaacta gcgaagacaa agggttgccc actacccgag  300
gcgaagggcg tagccgacaa ggccaaaatt gaggagctga ttaaggaaag tggttactcc  360
gtttatgtga caacagcaac aaatttgaag gctgtgctcg aaaagttcat taaagagcta  420
gaaaaagatc ccggttgc                                                438

SEQ ID NO: 28           moltype = DNA  length = 438
FEATURE                 Location/Qualifiers
source                  1..438
                        mol_type = other DNA
                        organism = synthetic construct
SEQUENCE: 28
gtccccgtag agcaaatccg aaaggatctc gagacactga tccggaccgt catcacacgt  60
attgatacaa tcccctacgt taaggaggta agcccaaagc aaaaagtcac cggcctggaa  120
tttattcctg gtacaaaaga gaaaatcaca tataccgatg ctgacgaaac cttggcaatt  180
tatcaagaga ttctaagtct attgccggaa ccggagttac aacaaattgc actggacttg  240
gataatatcc gggacctcat tcgcgagctg gcggccacca agaattgccc tctacctcgt  300
gccagtggtt tacccgaccg agagaagctg ctcgaggcta tcaaggagag tggatacagt  360
gtagctgtca ccacagcgac taagttaaag gagttcttgg aaaagctaat tgaggagttg  420
aagaaggacc ccggatgt                                                438

SEQ ID NO: 29           moltype = DNA  length = 438
FEATURE                 Location/Qualifiers
source                  1..438
                        mol_type = other DNA
                        organism = synthetic construct
SEQUENCE: 29
gtaccaatcc agaaggtaat tgatgatact aaaactctaa ttaaaaccat tctaactcgt  60
attaatgaca tcagttatac acagagtgtt agtgccaaac aacgtgtgac cggattggac  120
ttcatcccgg gcttacatcc gatcttgtcc ttgtctaaga tgctccagac attagctttt  180
tatcaacagg tcttgctatc tttaccatcc caattagtcc tccagatcgc caatgattta  240
gagaatctac gcgatttact gatcctccta gcccagagta agaactgcca actgcccgat  300
actagtaatc taaagaagcc cgagagctta gacgacattt tgcgtaatag tttatatagc  360
attgaggtcg tcgcactgtc tcgtttgcaa attgtcttgc aggatattct acagcaactc  420
gatcacgatc ctgattgc                                                438

SEQ ID NO: 30           moltype = DNA  length = 438
FEATURE                 Location/Qualifiers
source                  1..438
                        mol_type = other DNA
                        organism = synthetic construct
SEQUENCE: 30
gtgcctattc agaaggtgtt cgatgacacg aaaacactaa tcaagacaat tctgacgcgc  60
atcaatgaca tctcctacac tcaatccgtt tccgcgaagc agcgcgtcac gggtctggat  120
tttatccctg gcctccatcc catcttgagc ctgtccaaga tgttacaaac attggcgttc  180
taccaacagg tgctgttaag tttaccctcc caactcgtgt tgcaaattgc gaatgatctc  240
gagaacttac gcgacttgct acatctgtta gcattcagca agaactgcag cttgccagat  300
acctccaacc tacagaagcc cgagtctttg gatgaagtat tgcgcaacag cctgtatagt  360
attgaggtcg tcgctctgtc tcgcttacaa atcagcctcc aggacatcct acaacagttg  420
gacgtggacc ctgagtgt                                                438

SEQ ID NO: 31           moltype = DNA  length = 438
FEATURE                 Location/Qualifiers
source                  1..438
                        mol_type = other DNA
                        organism = synthetic construct
SEQUENCE: 31
gtccctattc agaaagtaca ggatgatacc aaaacgctca tcaaagttat tttaacacgt  60
attaacaccc tacaatatac gcaagaagta tccagcaagc tgatcgtctt tggcctggat  120
tttattccag gtttagaacc catcttgtcc ttgagcaaaa tgctgcagac cttagcggtg  180
tatcaacagg ttttgctgag cttaccaagt gaggacgtac tgcaaatcgc tgcagacttg  240
gaaaacttgc gcctactcct gcatctatta gcgcagagta aaaactgtca attacctgac  300
acttctaatc tcaaaaaacc ggagagtctc gatgaaatcc tccgtaacag tctctatagt  360
attgaagttg ttgcactaag tcgcctccag ggttccctcc taatcatctt gcaacaactc  420
gaccacgacc ccgattgt                                                438

SEQ ID NO: 32           moltype = DNA  length = 438
FEATURE                 Location/Qualifiers
source                  1..438
                        mol_type = other DNA
                        organism = synthetic construct
SEQUENCE: 32
```

```
atgcctattg aggaagtccg aaagaacact aaaacactca tcaaaaccat tattacgaag  60
atcgatacga tcccttacgt gcaggacgtg tctccagaga ttacagttac tggcctcgac  120
ttcattcccg gcgacaaacc catcacatcc ttgtccgagg cagtactcac gttgacgcgc  180
taccggcaag ttctcctgtc cctgcccgat ccggaaactc agcaaattgc tctggatcta  240
gacaatctca tcgaactctt ccgtgaattg gcggccagca aaggttgtac cctcccagat  300
cccagcaacc tagccacacc gcccgagctg gcggaagtgc tgaaggatag cgaatttgca  360
gtctacgtta ccgctctaac gaagttaaag aaaaacctag agaacatcct gaaggaatta  420
gagaaggacc tcgcgtgt                                              438

SEQ ID NO: 33          moltype = DNA  length = 438
FEATURE                Location/Qualifiers
source                 1..438
                       mol_type = other DNA
                       organism = synthetic construct
SEQUENCE: 33
cgtccactcg aacaagtacg ccgtgatctc aagacgctga ttaaaacgat tatcaccaag  60
attgatacga tcccctacgt acaggatgtg aaccctgata ttactgtcac tgggctagac  120
tttattcctg gcaaccgacc tatcacgagt ttgagtgaag ctaagaaaac cctcacaaag  180
tacgtccaag ttttggagag tttagacgac cccgaaaccc aagaaatcgc cttagattta  240
aaaaacgtga tcgagttaat tgacgagtta gcgaagagcc ggggctgcac gttgcccgat  300
acttccaccc tagaaaagga tccgcgactc gaagaggtca agaaagacag tgagtttgcg  360
attacgacga cggccctgcg aaacttaaag attaacttgg agattattct aaaagagtta  420
gaacgcgatc cggcctgc                                              438

SEQ ID NO: 34          moltype = DNA  length = 438
FEATURE                Location/Qualifiers
source                 1..438
                       mol_type = other DNA
                       organism = synthetic construct
SEQUENCE: 34
gttcctatcg aaaaagtccg ggaggatcta aaaacactaa tcaagaccat catcaagaag  60
attgatacta tcccagaagt tcaggatgtg tccccagaga tcacggtgac gggattggat  120
tttattccgg gcaacgaacc cattaattct ctaagcgaag ctgtattaac cctcacgcgg  180
tatcgccaag tactagagtc tctagatgat ccagaaacgc agcagattgc cttagacttg  240
cagaatttaa ttgaactgtt aaaagaatta gcaaaggaaa agggatgcac attgcccgat  300
cctagtaacc taaaaaagcc ggaagagctg gaaaaggtac tggaagacgc cgagttcgct  360
gttcgtgtaa ccgctctcac aaacctaaag aaaaatttgg agaacattct gaaagttctc  420
gaaacagacc cagcctgt                                              438

SEQ ID NO: 35          moltype = DNA  length = 438
FEATURE                Location/Qualifiers
source                 1..438
                       mol_type = other DNA
                       organism = synthetic construct
SEQUENCE: 35
gtaccgatcc agaaagtgca ggacgacacc aagacgctga ttaaaacaat tgtcactcgt  60
attaatgaca tttcacacac ccagtccgtg agctcgaaac agaaagtaac cggtctggat  120
tttatcccgg gcctacatcc aatactgacg ctctcgaaga tggatcagac tcttgcagtg  180
tatcagcaga ttcttacctc catgccttct cgtaacatga tccaaatttc taatgatctt  240
gaaaacctgc gcgacttact gcatgttctg gcgttctcaa aaagctgtca cttgccgtgg  300
gccagtggtt tagaaacgct ggatagtctg ggaggcgtgt tggaggcgag cggctacagc  360
accgaagtcg ttgctctgtc gcgcttgcaa gggagcttac aggatatgct ctggcaactg  420
gatctgagcc ccggctgc                                              438

SEQ ID NO: 36          moltype = DNA  length = 438
FEATURE                Location/Qualifiers
source                 1..438
                       mol_type = other DNA
                       organism = synthetic construct
SEQUENCE: 36
gtnccnatnc agaaagtncn ngatgatacn aaaacactna ttaagacnat tatcacncgn  60
attaatnana tcccntacac ncaggangtn agcncnaagc tnaangtnac nggnctggan  120
tttattccng gcnnncaacc natcntnacn ttgaccaana tggnncagac nctngcnntn  180
tatcancaga ttctnnnnnc nntnccngan ccngangtnc tncaaattgc nnnngatctn  240
ganaatntnc gcganctnct ncangtntta gcgnagagna agagntgccc nctnccngan  300
gcnagnggnc tagaaaagcn nganannctn gangaggtnn tgnanganag cgnatatncn  360
attgangtcg tngcnctnnc ncgcttacaa gnnntcctnc agaanatnct nnagcagctn  420
gannnngacc ccggntgc                                              438

SEQ ID NO: 37          moltype = DNA  length = 1004
FEATURE                Location/Qualifiers
source                 1..1004
                       mol_type = other DNA
                       organism = synthetic construct
SEQUENCE: 37
tatgggggag gattttatga tcggatgttg agtcagtctg agtggtctaa aattcctacg  60
gtgggaattg tgtttgcggc cgccagggtg gatactctcc ctagggatag ttgggaccag  120
cctttggcgg cggtttgtac agaggagggt atatgggagt ttccaaaata acttctggtg  180
ggggggcaaa ttatcgggcg atcgccactt atatggtatt aattgctata gcgatcgcta  240
```

-continued

```
tgctatttcc cctattttgg ttggtgggaa ctgcctttaa atcccctacc gaaaacatct  300
ttcaggttcc cccccagttt attccaaggg aacctacttt cactaatttt gtcagagttt  360
ggcaaaccaa tccctttggt cgctatttat ttaatagtac cctcgtcgcc cttttaaccg  420
tcggattaaa tctgctattt tgttccttgg cggcctatcc tttggcgcgc ttaaactttt  480
ggggtcgcga ttttctccta agtgcgatcg tttccaccat catgataccc tttcagattg  540
tcatgattcc cctgtatatt ctagcagtac agttaggatt aagaaatact tatttaggca  600
ttatttttcc atctttagcc tccgcttttg gcatctttct attgcgacag gcatttatgg  660
gagttcccaa agagttagaa gaagccgcca gaattgatgg ctgttcagaa ttagggattt  720
ggtggcatat tatgatcccc tcagtccgtc ccgccttaat gaccttagcc atttttgtat  780
ttatcgggtc ttggagtgat ttctctggc ccttaattgt agtcgatcgc ccagaatatt  840
ataccatccc tttaggcgtg gcaaatctag ccggaacttt ttctctcgat tggcggatag  900
tcgccgccgg ttccgtcatt tctatcgctc ctgtgttact actattttta atcgtacaac  960
ggtatattgt gcctacagat acagctacgg gggttaaagg ttga                   1004

SEQ ID NO: 38          moltype = DNA  length = 1020
FEATURE                Location/Qualifiers
source                 1..1020
                       mol_type = other DNA
                       organism = synthetic construct
SEQUENCE: 38
ggaatcatga atcatcccac aactaagcat caaaaaatta catcctgtta ctggggaatt  60
tctgaactac ctgggttaga tacaggtaat attaaactcc tgaatcaatg tggtattgaa  120
aacacccagc aactgctcac gcgcgggagt aataatgcta ataaaatcgc cttatctaac  180
caactaggta tcaacatcag agatatcagt aaatgggtcg caatgtccga cttagccagg  240
gttcccagta ttggctatca atattgtggt gtccttttgc atagtggcgt aagttcagtt  300
aaccaactat ctcagatgtc tattcaacaa ctgcataaac agattttacg gctctatgta  360
ggaaccttgc aatctcgcca actctgtcca tctgttgatg tcatccaaac ctggattaaa  420
caagctaaaa ttttgcataa aattaattaa taattactag atgaaatcat gaatttttcc  480
gaagatttgc gacaaaatgc accagccacc gaaagaaacc gcgaacctat tttagaggtc  540
ttaaaaaggg tgttgcccgc cacgggaacc gttttagaag tagccagcgg cacaggacaa  600
cacgcggttt tttttgctcc ccgtctctcc cctaggcggt ggctaccttc cgacccgcaa  660
cctttgttac aacagagtat taaagcatgg caaattcatt caccttcaga taatctttac  720
cctcccctac agttaaatgt agaagctaat ccttggccag tggaagggaa tgatttaccc  780
tgggaattat cggaatttcc catcactgct attgtagcaa ttaacctgat tcatatttcg  840
ccttggtcgg cttgtgaagg gttaatggcg ggaagcgatc gcattttgaa accgggggga  900
attttatatc tctatggacc ctataaaata gctggaaaac acaccgcacc tagtaacgct  960
tcctttgatg aatatttgcg aacttctaac cctaagtggg gtgtcagaaa ccttgatgat  1020

SEQ ID NO: 39          moltype = DNA  length = 7553
FEATURE                Location/Qualifiers
source                 1..7553
                       mol_type = other DNA
                       organism = synthetic construct
SEQUENCE: 39
ggaatcatga atcatcccac aactaagcat caaaaaatta catcctgtta ctggggaatt  60
tctgaactac ctgggttaga tacaggtaat attaaactcc tgaatcaatg tggtattgaa  120
aacacccagc aactgctcac gcgcgggagt aataatgcta ataaaatcgc cttatctaac  180
caactaggta tcaacatcag agatatcagt aaatgggtcg caatgtccga cttagccagg  240
gttcccagta ttggctatca atattgtggt gtccttttgc atagtggcgt aagttcagtt  300
aaccaactat ctcagatgtc tattcaacaa ctgcataaac agattttacg gctctatgta  360
ggaaccttgc aatctcgcca actctgtcca tctgttgatg tcatccaaac ctggattaaa  420
caagctaaaa ttttgcataa aattaattaa taattactag atgaaatcat gaatttttcc  480
gaagatttgc gacaaaatgc accagccacc gaaagaaacc gcgaacctat tttagaggtc  540
ttaaaaaggg tgttgcccgc cacgggaacc gttttagaag tagccagcgg cacaggacaa  600
cacgcggttt tttttgctcc ccgtctctcc cctaggcggt ggctaccttc cgacccgcaa  660
cctttgttac aacagagtat taaagcatgg caaattcatt caccttcaga taatctttac  720
cctcccctac agttaaatgt agaagctaat ccttggccag tggaagggaa tgatttaccc  780
tgggaattat cggaatttcc catcactgct attgtagcaa ttaacctgat tcatatttcg  840
ccttggtcgg cttgtgaagg gttaatggcg ggaagcgatc gcattttgaa accgggggga  900
attttatatc tctatggacc ctataaaata gctggaaaac acaccgcacc tagtaacgct  960
tcctttgatg aatatttgcg aacttctaac cctaagtggg gtgtcagaaa ccttgatgat  1020
tcacatacgc ggccgcctgg gccttgagct cgaatttcct gcattaatga atcggccaac  1080
gcgcggggag aggcggtttg cgtattgggc gctcttccgc ttcctcgctc actgactcgc  1140
tgcgctcggt cgttcggctg cggcgagcgg tatcagctca ctcaaaggcg gtaatacggt  1200
tatccacaga atcaggggat aacgcaggaa agaacatgtg agcaaaaggc cagcaaaagg  1260
ccaggaaccg taaaaatagc ggagtgtata ctggcttact atgttggcac tgatgagggt  1320
gtcagtgaag tgcttcatgt ggcaggagaa aaaaggctgc accggtgcgt cagcagaata  1380
tgtgatacag gatatattcc gcttcctcgc tcactgactc gctacgctcg gtcgttcgac  1440
tgcggcgagc ggaaatggct tacgaacggg gcggagattt cctggaagat gccaggaaga  1500
tacttaacag ggaagtgaga gggccgcggc aaagccgttt ttccataggc tccgcccccc  1560
tgacaagcat cacgaaatct gacgctcaaa tcagtggtgg cgaaacccga caggactata  1620
aagataccag gcgtttcccc ctggcggctc cctcgtgcgc tctcctgttc ctgcctttcg  1680
gtttaccggt gtcattccgc tgttatggcc gcgtttgtct cattccacgc ctgacactca  1740
gttccgggta ggcagttcgc tccaagctgg actgtatgca cgaacccccc attcagtccg  1800
accgctgcgc cttatccggt aactatcgtc ttgagtccaa cccggaaaga catgcaaaag  1860
caccactggc agcagccact ggtaattgat ttagaggagt tagtcttgaa gtcatgcgcc  1920
ggttaaggct aaactgaaag gacaagtttt ggtgactgcg ctcctccaag ccagttacct  1980
cggttcaaag agttggtagc tcagagaacc ttcgaaaaac cgccctgcaa ggcggttttt  2040
tcgttttcag agcaagagat tacgcgcaga ccaaaacgat ctcaagaaga tcatcttatt  2100
```

-continued

```
aagattatca aaaaggatct tcacctagat ccttttaaat taaaaatgaa gttttaaatc  2160
aatctaaagt atatatgagt aaacttggtc tgacagttac caatgcttaa tcagtgaggc  2220
acctatctca gcgatctgtc tatttcgttc atccatagtt gcctgactcc ccgtcgtgta  2280
gataactacg atacgggagg gcttaccatc tggccccagt gctgcaatga taccgcggga  2340
cccacgctca ccggctccag atttatcagc aataaaccag ccagccggaa gggccgagcg  2400
cagaagtggt cctgcaactt tatccgcctc catccagtct attaattgtt gccgggaagc  2460
tagagtaagt agttcgccag ttaatagttt gcgcaacgtt gttgccattg ctacaggcat  2520
cgtggtgtca cgctcgtcgt ttggtatggc ttcattcagc tccggttccc aacgatcaag  2580
gcgagttaca tgatccccca tgttgtgcaa aaaagcggtt agctccttcg gtcctccgat  2640
cgttgtcaga agtaagttgg ccgcagtgtt atcactcatg gttatggcag cactgcataa  2700
ttctcttact gtcatgccat ccgtaagatg cttttctgtg actggtgagt actcaaccaa  2760
gtcattctga gaatagtgta tgcggcgacc gagttgctct tgcccggcgt caatacggga  2820
taataccgcg ccacatagca gaactttaaa agtgctcatc attggaaaac gttcttcggg  2880
gcgaaaactc tcaaggatct taccgctgtt gagatccagt tcgatgtaac ccactcgtgc  2940
acccaactga tcttcagcat cttttacttt caccagcgtt tctgggtgag caaaaacagg  3000
aaggcaaaat gccgcaaaaa agggaataag ggcgacacgg aaatgttgaa tactcatact  3060
cttccttttt caatattatt gaagcattta tcagggttat tgtctcatga gcggatacat  3120
atttgaatgt atttagaaaa ataaacaaat aggggttccg cgcacatttc cccgaaaagt  3180
gccacctgac gtctaagaaa ccattattat catgacatta acctataaaa ataggcgtat  3240
cacgaggccc tttcgtctcg cgcgtttcgg tgatgacggt gaaaacctct gacacatgca  3300
gctcccggag acggtcacag cttgtctgta agcggatgcc aagcttgcat gcctgcaggt  3360
ggcgcgccta tgggggagga ttttatgatc ggatgttgag tcagtctgag tggtctaaaa  3420
ttcctacggt gggaattgtg tttgcggccg ccagggtgga tactctccct agggatagtt  3480
gggaccagcc tttggcggcg gtttgtacag aggagggtat atgggagttt ccaaaataac  3540
ttctggtggg ggggcaaatt atcgggcgat cgccacttat atggtattaa ttgctatagc  3600
gatcgctatg ctatttcccc tattttggtt ggtgggaact gcctttaaat cccctaccga  3660
aaacatcttt caggttcccc cccagtttat tccaagggaa cctactttca ctaattttgt  3720
cagagtttgg caaaccaatc cctttggtcg ctatttattt aatagtaccc tcgtcgccct  3780
tttaaccgtc ggattaaatc tgctattttg ttccttggcg gcctatcctt tggcgcgctt  3840
aaacttttgg ggtcgcgatt ttctcctaag tgcgatcgtt tccaccatca tgataccctt  3900
tcagattgtc atgattcccc tgtatattct agcagtacag ttaggattaa gaaatactta  3960
tttaggcatt atttttccat ctttagcctc cgcttttggc atctttctat tgcgacaggc  4020
atttatggga gttcccaaag agttagaaga agccgccaga attgatggct gttcagaatt  4080
agggatttgg tggcatatta tgatcccctc agtccgtccc gccttaatga ccttagccat  4140
ttttgtattt atcgggtctt ggagtgattt tctctggccc ttaattgtag tcgatcgccc  4200
agaatattat accatccctt taggcgtggc aaatctagcc ggaacttttt ctctcgattg  4260
gcggatagtc gccgccggtt ccgtcatttc tatcgctcct gtgttactac tatttttaat  4320
cgtacaacgg tatattgtgc ctacagatac agctacgggg gttaaaggtt gaatgaggat  4380
tattaatctc agtcctaata atcaaaatca tatccaccag gcggcgactt tattagtcgc  4440
agaatttcgg gaaaattggc cgaatgcttg gccgacttat gaacgtggtt tagccgaggt  4500
tatggagtct tttggcgacg atagagttaa tctagtcgcc gtcgatgaaa atgataatct  4560
tctaggctgg attggtggta ttagccaata tcaaggccat gtttgggaat tacatccttt  4620
ggtagtcaaa agcgattatc aagggttagg aatagggcga aaattggtcg ccaatttaga  4680
ggattatgtc cgctcacaag gagggttaac cttatggttg ggtaccgatg acgaaaataa  4740
tttaacctcc ctatctggtg tcgaattata cccccatttt ttggaaaata ttgctaacat  4800
aaaaaaccat ggtcgtcatc cctatgaatt ttatcagaaa tgcggttttg tgattatggg  4860
agtagtcccc gatgctaacg gtatcgggaa acctgatatt ttgatggcta aatctctgag  4920
aattgacaat catcctaaat ccaactgaat gttgtcagtt aagtttatag ggctgctatg  4980
gtatgataaa aaaatccccc cagcagttgg gggggaatga ttaattaggt attgaattgg  5040
ttaaattgga ggtgtgttgg ggctgacttt tgctgccttg ttgggggggg cgattttaac  5100
tgaggtcact ttttcttggc cgggattggc taatcgcttg tatgaggcta tccgtctgcg  5160
ggattatccc acggttcaag ggtggtggt atttttggcc gttattgtgg tggcggctag  5220
tttggcgatc gatattttga atgcttgtat tgacccacgg attcgctatt aattccctgt  5280
cagaaaatat acttagttat taatacttag ttatttttct taataaattt taacaaacca  5340
aagggcgttg gcagtgtata aaggatattt gaaggggtga gaaggaaggc gaatgttgat  5400
ttatgaagtt tgattaacat ttgtatcaaa atataaaatt cttctcataa accctgtaca  5460
atcttttaag atttcggaaa gtgttctagg atactgaaga aatgaaccac ggggcaattg  5520
ttaaaagcct ttgtcgatgg ttcgccccgg aaggggtctt aggaggtgac accgatggat  5580
tgattgtcgt gatcattcat ggtgtgtcca atcccaactc aactctaagc aagtcaacaa  5640
gtaggagata aatctatgaa aatcgaagaa ggtaaactgg taatctggat taacggcgat  5700
aaaggctata acggactcgc tgaagtcggt aagaaattcg agaaagatac cggaattaaa  5760
gtcaccgttg agcatccgga taaactggaa gagaaattcc cacaggttgc ggcaactggc  5820
gatggccctg acattatctt ctgggcacac gaccgctttg gtggctacgc tcaatctggc  5880
ctgttggctg aaatcacccc ggacaaagcg ttccaggaca agctgtatcc gtttacctgg  5940
gatgccgtac gttacaacgg caagctgatt gcttacccga tcgctgttga agcgttatcg  6000
ctgatttata acaaagatct gctgccgaac ccgccaaaaa cctgggaaga gatcccggcg  6060
ctggataaag aactgaaagc gaaaggtaag agcgcgctga tgttcaacct gcaagaaccg  6120
tacttcacct ggccgctgat tgctgctgac gggggttatg cgttcaagta tgaaaacggc  6180
aagtacgaca ttaaagacgt gggcgtggat aacgctggcg cgaaagcggg tctgaccttc  6240
ctggttgacc tgattaaaaa caaacacatg aatgcagaca ccgattactc catcgcagaa  6300
gctgccttta ataaaggcga aacagcgatg accatcaacg gcccgtgggc atggtccaac  6360
atcgacacca gcaaagtgaa ttatggtgta acggtactgc cgaccttcaa gggtcaacca  6420
tccaaaccgt tcgttggcgt gctgagcgca ggtattaacg ccgccagtcc gaacaaagag  6480
ctggcaaaag agttcctcga aaactatctg ctgactgatg aaggtctgga agcggttaat  6540
aaagacaaac cgctgggtgc cgtagcgctg aagtcttacg aggaagagtt ggcgaaagat  6600
ccacgtattg ccgccactat ggaaaacgcc cagaaaggtg aaatcatgcc gaacatcccg  6660
cagatgtccg ctttctggta tgccgtgcgt actgcggtga tcaacgccgc cagcggtcgt  6720
cagactgtcg atgaagccct gaaagacgcg cagacttccg gcggaggtgg aggctcaaaa  6780
ggcggtggag gtagcgctgg aggcgtaccg atccagaaag tgcaggacga caccaagacg  6840
```

```
ctgattaaaa caattgtcac tcgtattaat gacatttcac acacccagtc cgtgagctcg  6900
aaacagaaag taaccggtct ggattttatc ccgggcctac atccaatact gacgctctcg  6960
aagatggatc agactcttgc agtgtatcag cagattctta cctccatgcc ttctcgtaac  7020
atgatccaaa tttctaatga tcttgaaaac ctgcgcgact tactgcatgt tctggcgttc  7080
tcaaaaagct gtcacttgcc gtgggccagt ggtttagaaa cgctggatag tctgggaggc  7140
gtgttggagg cgagcggcta cagcaccgaa gtcgttgctc tgtcgcgctt gcaagggagc  7200
ttacaggata tgctctggca actggatctg agccccggct gctcaagcgg cggtagtcac  7260
catcaccacc atcactaaca gccaaataaa acgaaaggct cagtcgaaag actgggcctt  7320
tcgttttatc tgttgtttgt cggtgaacgc tctcctgagt aggacaaatc cgccgggagc  7380
ggatttgaac gttgcgaagc aacggcccgg agggtggcgg gcaggacgcc cgccataaac  7440
tgccaggcat caaattaagc agaaggccat cctgacggat ggcctttttg cgtttctaca  7500
aactccggat ccggccggct tgaagacagt agcgtaagag ttgacattaa tgc         7553

SEQ ID NO: 40          moltype = DNA  length = 7550
FEATURE                Location/Qualifiers
source                 1..7550
                       mol_type = other DNA
                       organism = synthetic construct
SEQUENCE: 40
ggaatcatga atcatcccac aactaagcat caaaaaatta catcctgtta ctggggaatt  60
tctgaactac ctgggttaga tacaggtaat attaaactcc tgaatcaatg tggtattgaa  120
aacacccagc aactgctcac gcgcgggagt aataatgcta ataaaatcgc cttatctaac  180
caactaggta tcaacatcag agatatcagt aaatgggtcg caatgtccga cttagccagg  240
gttcccagta ttggctatca atattgtggt gtccttttgc atagtggcgt aagttcagtt  300
aaccaactat ctcagatgtc tattcaacaa ctgcataaac agattttacg gctctatgta  360
ggaaccttgc aatctcgcca actctgtcca tctgttgatg tcatccaaac ctggattaaa  420
caagctaaaa ttttgcataa aattaattaa taattactag atgaaatcat gaatttttcc  480
gaagatttgc gacaaaatgc accagccacc gaaagaaacc gcgaacctat tttagaggtc  540
ttaaaaaggg tgttgcccgc cacgggaacc gttttagaag tagccagcgg cacaggacaa  600
cacgcggttt tttttgctcc ccgtctctcc cctaggcggt ggctaccttc cgacccgcaa  660
cctttgttac aacagagtat taaagcatgg caaattcatt caccttcaga taatctttac  720
cctcccctac agttaaatgt agaagctaat ccttggccag tggaagggaa tgatttaccc  780
tgggaattat cggaatttcc catcactgct attgtagcaa ttaacctgat tcatatttcg  840
ccttggtcgg cttgtgaagg gttaatggcg ggaagcgatc gcattttgaa accgggggga  900
attttatatc tctatggacc ctataaaata gctggaaaac acaccgcacc tagtaacgct  960
tcctttgatg aatatttgcg aacttctaac cctaagtggg gtgtcagaaa ccttgatgat  1020
tcacatacgc ggccgcctgg gccttgagct cgaatttcct gcattaatga atcggccaac  1080
gcgcggggag aggcggtttg cgtattgggc gctcttccgc ttcctcgctc actgactcgc  1140
tgcgctcggt cgttcggctg cggcgagcgg tatcagctca ctcaaaggcg gtaatacggt  1200
tatccacaga atcaggggat aacgcaggaa agaacatgtg agcaaaaggc cagcaaaagg  1260
ccaggaaccg taaaaatagc ggagtgtata ctggcttact atgttggcac tgatgagggt  1320
gtcagtgaag tgcttcatgt ggcaggagaa aaaaggctgc accggtgcgt cagcagaata  1380
tgtgatacag gatatattcc gcttcctcgc tcactgactc gctacgctcg gtcgttcgac  1440
tgcggcgagc ggaaatggct tacgaacggg gcggagattt cctggaagat gccaggaaga  1500
tacttaacag ggaagtgaga gggccgcggc aaagccgttt ttccataggc tccgcccccc  1560
tgacaagcat cacgaaatct gacgctcaaa tcagtggtgg cgaaacccga caggactata  1620
aagataccag gcgtttcccc ctggcggctc cctcgtgcgc tctcctgttc ctgcctttcg  1680
gtttaccggt gtcattccgc tgttatggcc gcgtttgtct cattccacgc ctgacactca  1740
gttccgggta ggcagttcgc tccaagctgg actgtatgca cgaacccccc attcagtccg  1800
accgctgcgc cttatccggt aactatcgtc ttgagtccaa cccggaaaga catgcaaaag  1860
caccactggc agcagccact ggtaattgat ttagaggagt tagtcttgaa gtcatgcgcc  1920
ggttaaggct aaactgaaag gacaagtttt ggtgactgcg ctcctccaag ccagttacct  1980
cggttcaaag agttggtagc tcagagaacc ttcgaaaaac cgccctgcaa ggcggttttt  2040
tcgttttcag agcaagagat tacgcgcaga ccaaaacgat ctcaagaaga tcatcttatt  2100
aagattatca aaaaggatct tcacctagat ccttttaaat taaaaatgaa gttttaaatc  2160
aatctaaagt atatatgagt aaacttggtc tgacagttac caatgcttaa tcagtgaggc  2220
acctatctca gcgatctgtc tatttcgttc atccatagtt gcctgactcc ccgtcgtgta  2280
gataactacg atacgggagg gcttaccatc tggccccagt gctgcaatga taccgcggga  2340
cccacgctca ccggctccag atttatcagc aataaaccag ccagccggaa gggccgagcg  2400
cagaagtggt cctgcaactt tatccgcctc catccagtct attaattgtt gccgggaagc  2460
tagagtaagt agttcgccag ttaatagttt gcgcaacgtt gttgccattg ctacaggcat  2520
cgtggtgtca cgctcgtcgt ttggtatggc ttcattcagc tccggttccc aacgatcaag  2580
gcgagttaca tgatccccca tgttgtgcaa aaaagcggtt agctccttcg gtcctccgat  2640
cgttgtcaga agtaagttgg ccgcagtgtt atcactcatg gttatggcag cactgcataa  2700
ttctcttact gtcatgccat ccgtaagatg cttttctgtg actggtgagt actcaaccaa  2760
gtcattctga gaatagtgta tgcggcgacc gagttgctct tgcccggcgt caatacggga  2820
taataccgcg ccacatagca gaactttaaa agtgctcatc attggaaaac gttcttcggg  2880
gcgaaaactc tcaaggatct taccgctgtt gagatccagt tcgatgtaac ccactcgtgc  2940
acccaactga tcttcagcat cttttacttt caccagcgtt tctgggtgag caaaaacagg  3000
aaggcaaaat gccgcaaaaa agggaataag ggcgacacgg aaatgttgaa tactcatact  3060
cttccttttt caatattatt gaagcattta tcagggttat tgtctcatga gcggatacat  3120
atttgaatgt atttagaaaa ataaacaaat aggggttccg cgcacatttc cccgaaaagt  3180
gccacctgac gtctaagaaa ccattattat catgacatta acctataaaa ataggcgtat  3240
cacgaggccc tttcgtctcg cgcgtttcgg tgatgacggt gaaaacctct gacacatgca  3300
gctcccggag acggtcacag cttgtctgta agcggatgcc aagcttgcat gcctgcaggt  3360
ggcgcgccta tgggggagga ttttatgatc ggatgttgag tcagtctgag tggtctaaaa  3420
ttcctacggt gggaattgtg tttgcggccg ccagggtgga tactctccct agggatagtt  3480
gggaccagcc tttggcggcg gtttgtacag aggagggtat atgggagttt ccaaaataac  3540
ttctggtggg ggggcaaatt atcgggcgat cgccacttat atggtattaa ttgctatagc  3600
```

```
gatcgctatg ctatttcccc tattttggtt ggtgggaact gcctttaaat cccctaccga  3660
aaacatcttt caggttcccc cccagtttat tccaagggaa cctactttca ctaattttgt  3720
cagagtttgg caaaccaatc cctttggtcg ctatttattt aatagtaccc tcgtcgccct  3780
tttaaccgtc ggattaaatc tgctattttg ttccttggcg gcctatcctt tggcgcgctt  3840
aaacttttgg ggtcgcgatt ttctcctaag tgcgatcgtt tccaccatca tgataccctt  3900
tcagattgtc atgattcccc tgtatattct agcagtacag ttaggattaa gaaatactta  3960
tttaggcatt atttttccat ctttagcctc cgcttttggc atctttctat tgcgacaggc  4020
atttatggga gttcccaaag agttagaaga agccgccaga attgatggct gttcagaatt  4080
agggatttgg tggcatatta tgatcccctc agtccgtccc gccttaatga ccttagccat  4140
ttttgtattt atcgggtctt ggagtgattt tctctggccc ttaattgtag tcgatcgccc  4200
agaatattat accatccctt taggcgtggc aaatctagcc ggaacttttt ctctcgattg  4260
gcggatagtc gccgccggtt ccgtcatttc tatcgctcct gtgttactac tatttttaat  4320
cgtacaacgg tatattgtgc ctacagatac agctacgggg gttaaaggtt gaatgaggat  4380
tattaatctc agtcctaata atcaaaatca tatccaccag gcggcgactt tattagtcgc  4440
agaatttcgg gaaaattggc cgaatgcttg gccgacttat gaacgtggtt tagccgaggt  4500
tatggagtct tttggcgacg atagagttaa tctagtcgcc gtcgatgaaa atgataatct  4560
tctaggctgg attggtggta ttagccaata tcaaggccat gtttgggaat tacatccttt  4620
ggtagtcaaa agcgattatc aagggttagg aatagggcga aaattggtcg ccaatttaga  4680
ggattatgtc cgctcacaag gagggttaac cttatggttg ggtaccgatg acgaaaataa  4740
tttaacctcc ctatctggtg tcgaattata cccccatttt ttggaaaata ttgctaacat  4800
aaaaaaccat ggtcgtcatc cctatgaatt ttatcagaaa tgcggttttg tgattatggg  4860
agtagtcccc gatgctaacg gtatcgggaa acctgatatt ttgatggcta aatctctgag  4920
aattgacaat catcctaaat ccaactgaat gttgtcagtt aagtttatag ggctgctatg  4980
gtatgataaa aaaatccccc cagcagttgg gggggaatga ttaattaggt attgaattgg  5040
ttaaattgga ggtgtgttgg ggctgacttt tgctgccttg ttgggggggg cgattttaac  5100
tgaggtcact ttttcttggc cgggattggc taatcgcttg tatgaggcta tccgtctgcg  5160
ggattatccc acggttcaag ggggtggtggt atttttggcc gttattgtgg tggcggctag  5220
tttggcgatc gatattttga atgcttgtat tgacccacgg attcgctatt aattccctgt  5280
cagaaaatat acttagttat taatacttag ttatttttct taataaattt taacaaacca  5340
aagggcgttg gcagtgtata aaggatattt gaaggggtga gaaggaaggc gaatgttgat  5400
ttatgaagtt tgattaacat ttgtatcaaa atataaaatt cttctcataa accctgtaca  5460
atcttttaag atttcggaaa gtgttctagg atactgaaga aatgaaccac ggggcaattg  5520
ttaaaagcct ttgtcgatgg ttcgccccgg aagggtctt aggaggtgac accgatggat  5580
tgattgtcgt gatcattcat ggtgtgtcca atcccaactc aactctaagc aagtcaacaa  5640
gtaggagata aatctatgaa aatcgaagaa ggtaaactgg taatctggat taacggcgat  5700
aaaggctata acggactcgc tgaagtcggt aagaaattcg agaaagatac cggaattaaa  5760
gtcaccgttg agcatccgga taaactggaa gagaaattcc cacaggttgc ggcaactggc  5820
gatggccctg acattatctt ctgggcacac gaccgctttg gtggctacgc tcaatctggc  5880
ctgttggctg aaatcacccc ggacaaagcg ttccaggaca agctgtatcc gtttacctgg  5940
gatgccgtac gttacaacgg caagctgatt gcttacccga tcgctgttga agcgttatcg  6000
ctgatttata acaaagatct gctgccgaac ccgccaaaaa cctgggaaga gatcccggcg  6060
ctggataaag aactgaaagc gaaaggtaag agcgcgctga tgttcaacct gcaagaaccg  6120
tacttcacct ggccgctgat tgctgctgac gggggttatg cgttcaagta tgaaaacggc  6180
aagtacgaca ttaaagacgt gggcgtggat aacgctggcg cgaaagcggg tctgaccttc  6240
ctggttgacc tgattaaaaa caaacacatg aatgcagaca ccgattactc catcgcagaa  6300
gctgccttta ataaaggcga aacagcgatg accatcaacg gcccgtgggc atggtccaac  6360
atcgacacca gcaaagtgaa ttatggtgta acggtactgc cgaccttcaa gggtcaacca  6420
tccaaaccgt tcgttggcgt gctgagcgca ggtattaacg ccgccagtcc gaacaaagag  6480
ctggcaaaag agttcctcga aaactatctg ctgactgatg aaggtctgga agcggttaat  6540
aaagacaaac cgctgggtgc cgtagcgctg aagtcttacg aggaagagtt ggcgaaagat  6600
ccacgtattg ccgccactat ggaaaacgcc cagaaaggtg aaatcatgcc gaacatcccg  6660
cagatgtccg ctttctggta tgccgtgcgt actgcggtga tcaacgccgc cagcggtcgt  6720
cagactgtcg atgaagccct gaaagacgcg cagacttccg gcggaggtgg aggctcaaaa  6780
ggcggtggag gtagcgctgg agtaccaatc cagaaggtaa ttgatgatac taaaactcta  6840
attaaaacca ttctaactcg tattaatgac atcagttata cacagagtgt tagtgccaaa  6900
caacgtgtga ccggattgga cttcatcccg ggcttacatc cgatcttgtc cttgtctaag  6960
atgctccaga cattagcttt ttatcaacag gtcttgctat ctttaccatc ccaattagtc  7020
ctccagatcg ccaatgattt agagaatcta cgcgatttac tgatcctcct agcccagagt  7080
aagaactgcc aactgcccga tactagtaat ctaaagaagc ccgagagctt agacgacatt  7140
ttgcgtaata gtttatatag cattgaggtc gtcgcactgt ctcgtttgca aattgtcttg  7200
caggatattc tacagcaact cgatcacgat cctgattgct caagcggcgg tagtcaccat  7260
caccaccatc actaacagcc aaataaaacg aaaggctcag tcgaaagact gggcctttcg  7320
ttttatctgt tgtttgtcgg tgaacgctct cctgagtagg acaaatccgc cgggagcgga  7380
tttgaacgtt gcgaagcaac ggcccggagg gtggcgggca ggacgcccgc cataaactgc  7440
caggcatcaa attaagcaga aggccatcct gacggatggc ctttttgcgt ttctacaaac  7500
tccggatccg gccggcttga agacagaatg gtatcagtaa ggtgaaatgc             7550
```

```
SEQ ID NO: 41           moltype = DNA  length = 7550
FEATURE                 Location/Qualifiers
source                  1..7550
                        mol_type = other DNA
                        organism = synthetic construct
SEQUENCE: 41
ggaatcatga atcatcccac aactaagcat caaaaaatta catcctgtta ctggggaatt  60
tctgaactac ctgggttaga tacaggtaat attaaactcc tgaatcaatg tggtattgaa  120
aacacccagc aactgctcac gcgcgggagt aataatgcta ataaaatcgc cttatctaac  180
caactaggta tcaacatcag agatatcagt aaatgggtcg caatgtccga cttagccagg  240
gttcccagta ttggctatca atattgtggt gtccttttgc atagtggcgt aagttcagtt  300
aaccaactat ctcagatgtc tattcaacaa ctgcataaac agattttacg gctctatgta  360
```

-continued

```
ggaaccttgc aatctcgcca actctgtcca tctgttgatg tcatccaaac ctggattaaa  420
caagctaaaa ttttgcataa aattaattaa taattactag atgaaatcat gaatttttcc  480
gaagatttgc gacaaaatgc accagccacc gaaagaaacc gcgaacctat tttagaggtc  540
ttaaaaaggg tgttgcccgc cacgggaacc gttttagaag tagccagcgg cacaggacaa  600
cacgcggttt tttttgctcc ccgtctctcc cctaggcggt ggctaccttc cgacccgcaa  660
cctttgttac aacagagtat taaagcatgg caaattcatt caccttcaga taatctttac  720
cctcccctac agttaaatgt agaagctaat ccttggccag tggaagggaa tgatttaccc  780
tgggaattat cggaatttcc catcactgct attgtagcaa ttaacctgat tcatatttcg  840
ccttggtcgg cttgtgaagg gttaatggcg ggaagcgatc gcattttgaa accgggggga  900
attttatatc tctatggacc ctataaaata gctggaaaac acaccgcacc tagtaacgct  960
tcctttgatg aatatttgcg aacttctaac cctaagtggg gtgtcagaaa ccttgatgat  1020
tcacatacgc ggccgcctgg gccttgagct cgaatttcct gcattaatga atcggccaac  1080
gcgcggggag aggcggtttg cgtattgggc gctcttccgc ttcctcgctc actgactcgc  1140
tgcgctcggt cgttcggctg cggcgagcgg tatcagctca ctcaaaggcg gtaatacggt  1200
tatccacaga atcaggggat aacgcaggaa agaacatgtg agcaaaaggc cagcaaaagg  1260
ccaggaaccg taaaaatagc ggagtgtata ctggcttact atgttggcac tgatgagggt  1320
gtcagtgaag tgcttcatgt ggcaggagaa aaaaggctgc accggtgcgt cagcagaata  1380
tgtgatacag gatatattcc gcttcctcgc tcactgactc gctacgctcg gtcgttcgac  1440
tgcggcgagc ggaaatggct tacgaacggg gcggagattt cctggaagat gccaggaaga  1500
tacttaacag ggaagtgaga gggccgcggc aaagccgttt ttccataggc tccgcccccc  1560
tgacaagcat cacgaaatct gacgctcaaa tcagtggtgg cgaaacccga caggactata  1620
aagataccag gcgtttcccc ctggcggctc cctcgtgcgc tctcctgttc ctgcctttcg  1680
gtttaccggt gtcattccgc tgttatggcc gcgtttgtct cattccacgc ctgacactca  1740
gttccgggta ggcagttcgc tccaagctgg actgtatgca cgaacccccc attcagtccg  1800
accgctgcgc cttatccggt aactatcgtc ttgagtccaa cccggaaaga catgcaaaag  1860
caccactggc agcagccact ggtaattgat ttagaggagt tagtcttgaa gtcatgcgcc  1920
ggttaaggct aaactgaaag gacaagtttt ggtgactgcg ctcctccaag ccagttacct  1980
cggttcaaag agttggtagc tcagagaacc ttcgaaaaac cgccctgcaa ggcggttttt  2040
tcgttttcag agcaagagat tacgcgcaga ccaaaacgat ctcaagaaga tcatcttatt  2100
aagattatca aaaaggatct tcacctagat ccttttaaat taaaaatgaa gttttaaatc  2160
aatctaaagt atatatgagt aaacttggtc tgacagttac caatgcttaa tcagtgaggc  2220
acctatctca gcgatctgtc tatttcgttc atccatagtt gcctgactcc ccgtcgtgta  2280
gataactacg atacgggagg gcttaccatc tggccccagt gctgcaatga taccgcggga  2340
cccacgctca ccggctccag atttatcagc aataaaccag ccagccggaa gggccgagcg  2400
cagaagtggt cctgcaactt tatccgcctc catccagtct attaattgtt gccgggaagc  2460
tagagtaagt agttcgccag ttaatagttt gcgcaacgtt gttgccattg ctacaggcat  2520
cgtggtgtca cgctcgtcgt ttggtatggc ttcattcagc tccggttccc aacgatcaag  2580
gcgagttaca tgatccccca tgttgtgcaa aaaagcggtt agctccttcg gtcctccgat  2640
cgttgtcaga agtaagttgg ccgcagtgtt atcactcatg gttatggcag cactgcataa  2700
ttctcttact gtcatgccat ccgtaagatg cttttctgtg actggtgagt actcaaccaa  2760
gtcattctga gaatagtgta tgcggcgacc gagttgctct tgcccggcgt caatacggga  2820
taataccgcg ccacatagca gaactttaaa agtgctcatc attggaaaac gttcttcggg  2880
gcgaaaactc tcaaggatct taccgctgtt gagatccagt tcgatgtaac ccactcgtgc  2940
acccaactga tcttcagcat cttttacttt caccagcgtt tctgggtgag caaaaacagg  3000
aaggcaaaat gccgcaaaaa agggaataag ggcgacacgg aaatgttgaa tactcatact  3060
cttccttttt caatattatt gaagcattta tcagggttat tgtctcatga gcggatacat  3120
atttgaatgt atttagaaaa ataaacaaat aggggttccg cgcacatttc cccgaaaagt  3180
gccacctgac gtctaagaaa ccattattat catgacatta acctataaaa ataggcgtat  3240
cacgaggccc tttcgtctcg cgcgtttcgg tgatgacggt gaaaacctct gacacatgca  3300
gctcccggag acggtcacag cttgtctgta agcggatgcc aagcttgcat gcctgcaggt  3360
ggcgcgccta tgggggagga ttttatgatc ggatgttgag tcagtctgag tggtctaaaa  3420
ttcctacggt gggaattgtg tttgcggccg ccagggtgga tactctccct agggatagtt  3480
gggaccagcc tttggcggcg gtttgtacag aggagggtat atgggagttt ccaaaataac  3540
ttctggtggg ggggcaaatt atcgggcgat cgccacttat atggtattaa ttgctatagc  3600
gatcgctatg ctatttcccc tattttggtt ggtgggaact gcctttaaat cccctaccga  3660
aaacatcttt caggttcccc cccagtttat tccaagggaa cctactttca ctaattttgt  3720
cagagtttgg caaaccaatc cctttggtcg ctatttattt aatagtaccc tcgtcgccct  3780
tttaaccgtc ggattaaatc tgctattttg ttccttggcg gcctatcctt tggcgcgctt  3840
aaacttttgg ggtcgcgatt ttctcctaag tgcgatcgtt tccaccatca tgataccctt  3900
tcagattgtc atgattcccc tgtatattct agcagtacag ttaggattaa gaaatactta  3960
tttaggcatt atttttccat ctttagcctc cgcttttggc atctttctat tgcgacaggc  4020
atttatggga gttcccaaag agttagaaga agccgccaga attgatggct gttcagaatt  4080
agggatttgg tggcatatta tgatcccctc agtccgtccc gccttaatga ccttagccat  4140
ttttgtattt atcgggtctt ggagtgattt tctctggccc ttaattgtag tcgatcgccc  4200
agaatattat accatccctt taggcgtggc aaatctagcc ggaacttttt ctctcgattg  4260
gcggatagtc gccgccggtt ccgtcatttc tatcgctcct gtgttactac tatttttaat  4320
cgtacaacgg tatattgtgc ctacagatac agctacgggg gttaaaggtt gaatgaggat  4380
tattaatctc agtcctaata atcaaaatca tatccaccag gcggcgactt tattagtcgc  4440
agaatttcgg gaaaattggc cgaatgcttg gccgacttat gaacgtggtt tagccgaggt  4500
tatggagtct tttggcgacg atagagttaa tctagtcgcc gtcgatgaaa atgataatct  4560
tctaggctgg attggtggta ttagccaata tcaaggccat gtttgggaat tacatccttt  4620
ggtagtcaaa agcgattatc aagggttagg aatagggcga aaattggtcg ccaatttaga  4680
ggattatgtc cgctcacaag gagggttaac cttatggttg ggtaccgatg acgaaaataa  4740
tttaacctcc ctatctggtg tcgaattata cccccatttt ttggaaaata ttgctaacat  4800
aaaaaaccat ggtcgtcatc cctatgaatt ttatcagaaa tgcggttttg tgattatggg  4860
agtagtcccc gatgctaacg gtatcgggaa acctgatatt ttgatggcta aatctctgag  4920
aattgacaat catcctaaat ccaactgaat gttgtcagtt aagtttatag ggctgctatg  4980
gtatgataaa aaatccccc cagcagttgg gggggaatga ttaattaggt attgaattgg  5040
ttaaattgga ggtgtgttgg ggctgacttt tgctgccttg ttgggggggg cgattttaac  5100
```

```
tgaggtcact ttttcttggc cgggattggc taatcgcttg tatgaggcta tccgtctgcg  5160
ggattatccc acggttcaag ggtggtggt atttttggcc gttattgtgg tggcggctag  5220
tttggcgatc gatattttga atgcttgtat tgacccacgg attcgctatt aattccctgt  5280
cagaaaatat acttagttat taatacttag ttatttttct taataaattt taacaaacca  5340
aagggcgttg gcagtgtata aaggatattt gaaggggtga gaaggaaggc gaatgttgat  5400
ttatgaagtt tgattaacat ttgtatcaaa atataaaatt cttctcataa accctgtaca  5460
atcttttaag atttcggaaa gtgttctagg atactgaaga aatgaaccac ggggcaattg  5520
ttaaaagcct ttgtcgatgg ttcgccccgg aaggggtctt aggaggtgac accgatggat  5580
tgattgtcgt gatcattcat ggtgtgtcca atcccaactc aactctaagc aagtcaacaa  5640
gtaggagata aatctatgaa aatcgaagaa ggtaaactgg taatctggat taacggcgat  5700
aaaggctata acggactcgc tgaagtcggt aagaaattcg agaaagatac cggaattaaa  5760
gtcaccgttg agcatccgga taaactggaa gagaaattcc cacaggttgc ggcaactggc  5820
gatggccctg acattatctt ctgggcacac gaccgctttg gtggctacgc tcaatctggc  5880
ctgttggctg aaatcacccc ggacaaagcg ttccaggaca agctgtatcc gtttacctgg  5940
gatgccgtac gttacaacgg caagctgatt gcttacccga tcgctgttga agcgttatcg  6000
ctgatttata acaaagatct gctgccgaac ccgccaaaaa cctgggaaga gatcccggcg  6060
ctggataaag aactgaaagc gaaaggtaag agcgcgctga tgttcaacct gcaagaaccg  6120
tacttcacct ggccgctgat tgctgctgac gggggttatg cgttcaagta tgaaaacggc  6180
aagtacgaca ttaaagacgt gggcgtggat aacgctggcg cgaaagcggg tctgaccttc  6240
ctggttgacc tgattaaaaa caaacacatg aatgcagaca ccgattactc catcgcagaa  6300
gctgccttta ataaaggcga aacagcgatg accatcaacg gcccgtgggc atggtccaac  6360
atcgacacca gcaaagtgaa ttatggtgta acggtactgc cgaccttcaa gggtcaacca  6420
tccaaaccgt tcgttggcgt gctgagcgca ggtattaacg ccgccagtcc gaacaaagag  6480
ctggcaaaag agttcctcga aaactatctg ctgactgatg aaggtctgga agcggttaat  6540
aaagacaaac cgctgggtgc cgtagcgctg aagtcttacg aggaagagtt ggcgaaagat  6600
ccacgtattg ccgccactat ggaaaacgcc cagaaaggtg aaatcatgcc gaacatcccg  6660
cagatgtccg ctttctggta tgccgtgcgt actgcggtga tcaacgccgc cagcggtcgt  6720
cagactgtcg atgaagccct gaaagacgcg cagacttccg gcggaggtgg aggctcaaaa  6780
ggcggtggag gtagcgctgg agtgcctatt cagaaggtgt tcgatgacac gaaaacacta  6840
atcaagacaa ttctgacgcg catcaatgac atctcctaca ctcaatccgt ttccgcgaag  6900
cagcgcgtca cgggtctgga ttttatccct ggcctccatc ccatcttgag cctgtccaag  6960
atgttacaaa cattggcgtt ctaccaacag gtgctgttaa gtttaccctc ccaactcgtg  7020
ttgcaaattg cgaatgatct cgagaactta cgcgacttgc tacatctgtt agcattcagc  7080
aagaactgca gcttgccaga tacctccaac ctacagaagc ccgagtcttt ggatgaagta  7140
ttgcgcaaca gcctgtatag tattgaggtc gtcgctctgt ctcgcttaca aatcagcctc  7200
caggacatcc tacaacagtt ggacgtggac cctgagtgtt caagcggcgg tagtcaccat  7260
caccaccatc actaacagcc aaataaaacg aaaggctcag tcgaaagact gggcctttcg  7320
ttttatctgt tgtttgtcgg tgaacgctct cctgagtagg acaaatccgc cgggagcgga  7380
tttgaacgtt gcgaagcaac ggcccggagg gtggcgggca ggacgcccgc cataaactgc  7440
caggcatcaa attaagcaga aggccatcct gacggatggc ctttttgcgt ttctacaaac  7500
tccggatccg gccggcttga agacaggtgg cgtgtgaccc gcgataatgc             7550

SEQ ID NO: 42           moltype = DNA  length = 7550
FEATURE                 Location/Qualifiers
source                  1..7550
                        mol_type = other DNA
                        organism = synthetic construct
SEQUENCE: 42
ggaatcatga atcatcccac aactaagcat caaaaaatta catcctgtta ctggggaatt  60
tctgaactac ctgggttaga tacaggtaat attaaactcc tgaatcaatg tggtattgaa  120
aacacccagc aactgctcac gcgcgggagt aataatgcta ataaaatcgc cttatctaac  180
caactaggta tcaacatcag agatatcagt aaatgggtcg caatgtccga cttagccagg  240
gttcccagta ttggctatca atattgtggt gtccttttgc atagtggcgt aagttcagtt  300
aaccaactat ctcagatgtc tattcaacaa ctgcataaac agattttacg gctctatgta  360
ggaaccttgc aatctcgcca actctgtcca tctgttgatg tcatccaaac ctggattaaa  420
caagctaaaa ttttgcataa aattaattaa taattactag atgaaatcat gaattttttcc  480
gaagatttgc gacaaaatgc accagccacc gaaagaaacc gcgaacctat tttagaggtc  540
ttaaaaaggg tgttgcccgc cacgggaacc gttttagaag tagccagcgg cacaggacaa  600
cacgcggttt tttttgctcc ccgtctctcc cctaggcggt ggctacctcc cgacccgcaa  660
cctttgttac aacagagtat taaagcatgg caaattcatt caccttcaga taatctttac  720
cctcccctac agttaaatgt agaagctaat ccttggccag tggaagggaa tgatttaccc  780
tgggaattat cggaatttcc catcactgct attgtagcaa ttaacctgat tcatatttcg  840
ccttggtcgg cttgtgaagg gttaatggcg ggaagcgatc gcattttgaa accgggggga  900
attttatatc tctatggacc ctataaaata gctggaaaac acaccgcacc tagtaacgct  960
tcctttgatg aatatttgcg aacttctaac cctaagtggg gtgtcagaaa ccttgatgat  1020
tcacatacgc ggccgcctgg gccttgagct cgaatttcct gcattaatga atcggccaac  1080
gcgcggggag aggcggtttg cgtattgggc gctcttccgc ttcctcgctc actgactcgc  1140
tgcgctcggt cgttcggctg cggcgagcgg tatcagctca ctcaaaggcg gtaatacggt  1200
tatccacaga atcaggggat aacgcaggaa agaacatgtg agcaaaaggc cagcaaaagg  1260
ccaggaaccg taaaaatagc ggagtgtata ctggcttact atgttggcac tgatgagggt  1320
gtcagtgaag tgcttcatgt ggcaggagaa aaaaggctgc accggtgcgt cagcagaata  1380
tgtgatacag gatatattcc gcttcctcgc tcactgactc gctacgctcg gtcgttcgac  1440
tgcggcgagc ggaaatggct tacgaacggg gcggagattt cctggaagat gccaggaaga  1500
tacttaacag ggaagtgaga gggccgcggc aaagccgttt ttccataggc tccgcccccc  1560
tgacaagcat cacgaaatct gacgctcaaa tcagtggtgg cgaaacccga caggactata  1620
aagataccag gcgtttcccc ctggcggctc cctcgtgcgc tctcctgttc ctgcctttcg  1680
gtttaccggt gtcattccgc tgttatggcc gcgtttgtct cattccacgc ctgacactca  1740
gttccgggta ggcagttcgc tccaagctgg actgtatgca cgaacccccc attcagtccg  1800
accgctgcgc cttatccggt aactatcgtc ttgagtccaa cccggaaaga catgcaaaag  1860
```

```
caccactggc agcagccact ggtaattgat ttagaggagt tagtcttgaa gtcatgcgcc  1920
ggttaaggct aaactgaaag gacaagtttt ggtgactgcg ctcctccaag ccagttacct  1980
cggttcaaag agttggtagc tcagagaacc ttcgaaaaac cgccctgcaa ggcggttttt  2040
tcgttttcag agcaagagat tacgcgcaga ccaaaacgat ctcaagaaga tcatcttatt  2100
aagattatca aaaaggatct tcacctagat ccttttaaat taaaaatgaa gttttaaatc  2160
aatctaaagt atatatgagt aaacttggtc tgacagttac caatgcttaa tcagtgaggc  2220
acctatctca gcgatctgtc tatttcgttc atccatagtt gcctgactcc ccgtcgtgta  2280
gataactacg atacgggagg gcttaccatc tggccccagt gctgcaatga taccgcggga  2340
cccacgctca ccggctccag atttatcagc aataaaccag ccagccggaa gggccgagcg  2400
cagaagtggt cctgcaactt tatccgcctc catccagtct attaattgtt gccgggaagc  2460
tagagtaagt agttcgccag ttaatagttt gcgcaacgtt gttgccattg ctacaggcat  2520
cgtggtgtca cgctcgtcgt ttggtatggc ttcattcagc tccggttccc aacgatcaag  2580
gcgagttaca tgatccccca tgttgtgcaa aaaagcggtt agctccttcg gtcctccgat  2640
cgttgtcaga agtaagttgg ccgcagtgtt atcactcatg gttatggcag cactgcataa  2700
ttctcttact gtcatgccat ccgtaagatg cttttctgtg actggtgagt actcaaccaa  2760
gtcattctga gaatagtgta tgcggcgacc gagttgctct tgcccggcgt caatacggga  2820
taataccgcg ccacatagca gaactttaaa agtgctcatc attggaaaac gttcttcggg  2880
gcgaaaactc tcaaggatct taccgctgtt gagatccagt tcgatgtaac ccactcgtgc  2940
acccaactga tcttcagcat cttttacttt caccagcgtt tctgggtgag caaaaacagg  3000
aaggcaaaat gccgcaaaaa agggaataag ggcgacacgg aaatgttgaa tactcatact  3060
cttccttttt caatattatt gaagcattta tcagggttat tgtctcatga gcggatacat  3120
atttgaatgt atttagaaaa ataaacaaat aggggttccg cgcacatttc cccgaaaagt  3180
gccacctgac gtctaagaaa ccattattat catgacatta acctataaaa ataggcgtat  3240
cacgaggccc tttcgtctcg cgcgtttcgg tgatgacggt gaaaacctct gacacatgca  3300
gctcccggag acggtcacag cttgtctgta agcggatgcc aagcttgcat gcctgcaggt  3360
ggcgcgccta tgggggagga ttttatgatc ggatgttgag tcagtctgag tggtctaaaa  3420
ttcctacggt gggaattgtg tttgcggccg ccagggtgga tactctccct agggatagtt  3480
gggaccagcc tttggcggcg gtttgtacag aggagggtat atgggagttt ccaaaataac  3540
ttctggtggg ggggcaaatt atcgggcgat cgccacttat atggtattaa ttgctatagc  3600
gatcgctatg ctatttcccc tattttggtt ggtgggaact gcctttaaat cccctaccga  3660
aaacatcttt caggttcccc cccagtttat tccaagggaa cctactttca ctaattttgt  3720
cagagtttgg caaaccaatc cctttggtcg ctatttattt aatagtaccc tcgtcgccct  3780
tttaaccgtc ggattaaatc tgctattttg ttccttggcg gcctatcctt tggcgcgctt  3840
aaacttttgg ggtcgcgatt ttctcctaag tgcgatcgtt tccaccatca tgataccctt  3900
tcagattgtc atgattcccc tgtatattct agcagtacag ttaggattaa gaaatactta  3960
tttaggcatt atttttccat ctttagcctc cgcttttggc atctttctat tgcgacaggc  4020
atttatggga gttcccaaag agttagaaga agccgccaga attgatggct gttcagaatt  4080
agggatttgg tggcatatta tgatcccctc agtccgtccc gccttaatga ccttagccat  4140
ttttgtattt atcgggtctt ggagtgattt tctctggccc ttaattgtag tcgatcgccc  4200
agaatattat accatccctt taggcgtggc aaatctagcc ggaacttttt ctctcgattg  4260
gcggatagtc gccgccggtt ccgtcatttc tatcgctcct gtgttactac tattttttaat  4320
cgtacaacgg tatattgtgc ctacagatac agctacgggg gttaaaggtt gaatgaggat  4380
tattaatctc agtcctaata atcaaaatca tatccaccag gcggcgactt tattagtcgc  4440
agaatttcgg gaaaattggc cgaatgcttg gccgacttat gaacgtggtt tagccgaggt  4500
tatggagtct tttggcgacg atagagttaa tctagtcgcc gtcgatgaaa atgataatct  4560
tctaggctgg attggtggta ttagccaata tcaaggccat gtttgggaat tacatccttt  4620
ggtagtcaaa agcgattatc aagggttagg aatagggcga aaattggtcg ccaatttaga  4680
ggattatgtc cgctcacaag gagggttaac cttatggttg ggtaccgatg acgaaaataa  4740
tttaacctcc ctatctggtg tcgaattata cccccatttt ttggaaaata ttgctaacat  4800
aaaaaaccat ggtcgtcatc cctatgaatt ttatcagaaa tgcggttttg tgattatggg  4860
agtagtcccc gatgctaacg gtatcgggaa acctgatatt ttgatggcta aatctctgag  4920
aattgacaat catcctaaat ccaactgaat gttgtcagtt aagtttatag ggctgctatg  4980
gtatgataaa aaaatccccc cagcagttgg gggggaatga ttaattaggt attgaattgg  5040
ttaaattgga ggtgtgttgg ggctgacttt tgctgccttg ttggggggggg cgattttaac  5100
tgaggtcact ttttcttggc cgggattggc taatcgcttg tatgaggcta tccgtctgcg  5160
ggattatccc acggttcaag ggtggtggt atttttggcc gttattgtgg tggcggctag  5220
tttggcgatc gatattttga atgcttgtat tgacccacgg attcgctatt aattccctgt  5280
cagaaaatat acttagttat taatacttag ttattttttct taataaattt taacaaacca  5340
aagggcgttg gcagtgtata aaggatattt gaaggggtga gaaggaaggc gaatgttgat  5400
ttatgaagtt tgattaacat ttgtatcaaa atataaaatt cttctcataa accctgtaca  5460
atcttttaag atttcggaaa gtgttctagg atactgaaga aatgaaccac ggggcaattg  5520
ttaaaagcct ttgtcgatgg ttcgccccgg aaggggtctt aggaggtgac accgatggat  5580
tgattgtcgt gatcattcat ggtgtgtcca atcccaactc aactctaagc aagtcaacaa  5640
gtaggagata aatctatgaa aatcgaagaa ggtaaactgg taatctggat taacggcgat  5700
aaaggctata acggactcgc tgaagtcggt aagaaattcg agaaagatac cggaattaaa  5760
gtcaccgttg agcatccgga taaactggaa gagaaattcc cacaggttgc ggcaactggc  5820
gatggccctg acattatctt ctgggcacac gaccgctttg gtggctacgc tcaatctggc  5880
ctgttggctg aaatcacccc ggacaaagcg ttccaggaca agctgtatcc gtttacctgg  5940
gatgccgtac gttacaacgg caagctgatt gcttacccga tcgctgttga agcgttatcg  6000
ctgatttata acaaagatct gctgccgaac ccgccaaaaa cctgggaaga gatcccggcg  6060
ctggataaag aactgaaagc gaaaggtaag agcgcgctga tgttcaacct gcaagaaccg  6120
tacttcacct ggccgctgat tgctgctgac gggggttatg cgttcaagta tgaaaacggc  6180
aagtacgaca ttaaagacgt gggcgtggat aacgctggcg cgaaagcggg tctgaccttc  6240
ctggttgacc tgattaaaaa caaacacatg aatgcagaca ccgattactc catcgcagaa  6300
gctgccttta ataaaggcga aacagcgatg accatcaacg gcccgtgggc atggtccaac  6360
atcgacacca gcaaagtgaa ttatggtgta acggtactgc cgaccttcaa gggtcaacca  6420
tccaaaccgt tcgttggcgt gctgagcgca ggtattaacg ccgccagtcc gaacaaagag  6480
ctggcaaaag agttcctcga aaactatctg ctgactgatg aaggtctgga agcggttaat  6540
aaagacaaac cgctgggtgc cgtagcgctg aagtcttacg aggaagagtt ggcgaaagat  6600
```

```
ccacgtattg ccgccactat ggaaaacgcc cagaaaggtg aaatcatgcc gaacatcccg  6660
cagatgtccg ctttctggta tgccgtgcgt actgcggtga tcaacgccgc cagcggtcgt  6720
cagactgtcg atgaagccct gaaagacgcg cagacttccg gcggaggtgg aggctcaaaa  6780
ggcggtggag gtagcgctgg agtccctatt cagaaagtac aggatgatac caaaacgctc  6840
atcaaagtta ttttaacacg tattaacacc ctacaatata cgcaagaagt atccagcaag  6900
ctgatcgtct ttggcctgga ttttattcca ggtttagaac ccatcttgtc cttgagcaaa  6960
atgctgcaga ccttagcggt gtatcaacag gttttgctga gcttaccaag tgaggacgta  7020
ctgcaaatcg ctgcagactt ggaaaacttg cgcctactcc tgcatctatt agcgcagagt  7080
aaaaactgtc aattacctga cacttctaat ctcaaaaaac cggagagtct cgatgaaatc  7140
ctccgtaaca gtctctatag tattgaagtt gttgcactaa gtcgcctcca gggttccctc  7200
ctaatcatct tgcaacaact cgaccacgac cccgattgtt caagcggcgg tagtcaccat  7260
caccaccatc actaacagcc aaataaaacg aaaggctcag tcgaaagact gggcctttcg  7320
ttttatctgt tgtttgtcgg tgaacgctct cctgagtagg acaaatccgc cgggagcgga  7380
tttgaacgtt gcgaagcaac ggcccggagg gtggcgggca ggacgcccgc cataaactgc  7440
caggcatcaa attaagcaga aggccatcct gacggatggc ctttttgcgt ttctacaaac  7500
tccggatccg gccggcttga agacagcatg agcgatgcga ccgataatgc             7550
```

```
SEQ ID NO: 43           moltype = DNA  length = 7550
FEATURE                 Location/Qualifiers
source                  1..7550
                        mol_type = other DNA
                        organism = synthetic construct
SEQUENCE: 43
ggaatcatga atcatcccac aactaagcat caaaaaatta catcctgtta ctggggaatt  60
tctgaactac ctgggttaga tacaggtaat attaaactcc tgaatcaatg tggtattgaa  120
aacacccagc aactgctcac gcgcgggagt aataatgcta ataaaatcgc cttatctaac  180
caactaggta tcaacatcag agatatcagt aaatgggtcg caatgtccga cttagccagg  240
gttcccagta ttggctatca atattgtggt gtccttttgc atagtggcgt aagttcagtt  300
aaccaactat ctcagatgtc tattcaacaa ctgcataaac agattttacg gctctatgta  360
ggaaccttgc aatctcgcca actctgtcca tctgttgatg tcatccaaac ctggattaaa  420
caagctaaaa ttttgcataa aattaattaa taattactag atgaaatcat gaatttttcc  480
gaagatttgc gacaaaatgc accagccacc gaaagaaacc gcgaacctat tttagaggtc  540
ttaaaaaggg tgttgcccgc cacgggaacc gttttagaag tagccagcgg cacaggacaa  600
cacgcggttt tttttgctcc ccgtctctcc cctaggcggt ggctaccttc cgacccgcaa  660
cctttgttac aacagagtat taaagcatgg caaattcatt caccttcaga taatctttac  720
cctcccctac agttaaatgt agaagctaat ccttggccag tggaagggaa tgatttaccc  780
tggaattat cggaatttcc catcactgct attgtagcaa ttaacctgat tcatatttcg  840
ccttggtcgg cttgtgaagg gttaatggcg ggaagcgatc gcattttgaa accgggggga  900
attttatatc tctatggacc ctataaaata gctggaaaac acaccgcacc tagtaacgct  960
tcctttgatg aatatttgcg aacttctaac cctaagtggg gtgtcagaaa ccttgatgat  1020
tcacatacgc ggccgcctgg gccttgagct cgaatttcct gcattaatga atcggccaac  1080
gcgcggggag aggcggtttg cgtattgggc gctcttccgc ttcctcgctc actgactcgc  1140
tgcgctcggt cgttcggctg cggcgagcgg tatcagctca ctcaaaggcg gtaatacggt  1200
tatccacaga atcaggggat aacgcaggaa agaacatgtg agcaaaaggc cagcaaaagg  1260
ccaggaaccg taaaaatagc ggagtgtata ctggcttact atgttggcac tgatgagggt  1320
gtcagtgaag tgcttcatgt ggcaggagaa aaaaggctgc accggtgcgt cagcagaata  1380
tgtgatacag gatatattcc gcttcctcgc tcactgactc gctacgctcg gtcgttcgac  1440
tgcggcgagc ggaaatggct tacgaacggg gcggagattt cctggaagat gccaggaaga  1500
tacttaacag ggaagtgaga gggccgcggc aaagccgttt ttccataggc tccgcccccc  1560
tgacaagcat cacgaaatct gacgctcaaa tcagtggtgg cgaaacccga caggactata  1620
aagataccag gcgtttcccc ctggcggctc cctcgtgcgc tctcctgttc ctgcctttcg  1680
gtttaccggt gtcattccgc tgttatggcc gcgtttgtct cattccacgc ctgacactca  1740
gttccgggta ggcagttcgc tccaagctgg actgtatgca cgaacccccc attcagtccg  1800
accgctgcgc cttatccggt aactatcgtc ttgagtccaa cccggaaaga catgcaaaag  1860
caccactggc agcagccact ggtaattgat ttagaggagt tagtcttgaa gtcatgcgcc  1920
ggttaaggct aaactgaaag gacaagtttt ggtgactgcg ctcctccaag ccagttacct  1980
cggttcaaag agttggtagc tcagagaacc ttcgaaaaac cgccctgcaa ggcggttttt  2040
tcgttttcag agcaagagat tacgcgcaga ccaaaacgat ctcaagaaga tcatcttatt  2100
aagattatca aaaaggatct tcacctagat ccttttaaat taaaaatgaa gttttaaatc  2160
aatctaaagt atatatgagt aaacttggtc tgacagttac caatgcttaa tcagtgaggc  2220
acctatctca gcgatctgtc tatttcgttc atccatagtt gcctgactcc ccgtcgtgta  2280
gataactacg atacgggagg gcttaccatc tggccccagt gctgcaatga taccgcggga  2340
cccacgctca ccggctccag atttatcagc aataaaccag ccagccggaa gggccgagcg  2400
cagaagtggt cctgcaactt tatccgcctc catccagtct attaattgtt gccgggaagc  2460
tagagtaagt agttcgccag ttaatagttt gcgcaacgtt gttgccattg ctacaggcat  2520
cgtggtgtca cgctcgtcgt ttggtatggc ttcattcagc tccggttccc aacgatcaag  2580
gcgagttaca tgatccccca tgttgtgcaa aaaagcggtt agctccttcg gtcctccgat  2640
cgttgtcaga agtaagttgg ccgcagtgtt atcactcatg gttatggcag cactgcataa  2700
ttctcttact gtcatgccat ccgtaagatg cttttctgtg actggtgagt actcaaccaa  2760
gtcattctga gaatagtgta tgcggcgacc gagttgctct tgcccggcgt caatacggga  2820
taataccgcg ccacatagca gaactttaaa agtgctcatc attggaaaac gttcttcggg  2880
gcgaaaactc tcaaggatct taccgctgtt gagatccagt tcgatgtaac ccactcgtgc  2940
acccaactga tcttcagcat cttttacttt caccagcgtt tctgggtgag caaaaacagg  3000
aaggcaaaat gccgcaaaaa agggaataag ggcgacacgg aaatgttgaa tactcatact  3060
cttccttttt caatattatt gaagcattta tcagggttat tgtctcatga gcggatacat  3120
atttgaatgt atttagaaaa ataaacaaat aggggttccg cgcacatttc cccgaaaagt  3180
gccacctgac gtctaagaaa ccattattat catgacatta acctataaaa ataggcgtat  3240
cacgaggccc tttcgtctcg cgcgtttcgg tgatgacggt gaaaacctct gacacatgca  3300
gctcccggag acggtcacag cttgtctgta agcggatgcc aagcttgcat gcctgcaggt  3360
```

```
ggcgcgccta tgggggagga ttttatgatc ggatgttgag tcagtctgag tggtctaaaa  3420
ttcctacggt gggaattgtg tttgcggccg ccagggtgga tactctccct agggatagtt  3480
gggaccagcc tttggcggcg gtttgtacag aggagggtat atgggagttt ccaaaataac  3540
ttctggtggg ggggcaaatt atcgggcgat cgccacttat atggtattaa ttgctatagc  3600
gatcgctatg ctatttcccc tattttggtt ggtgggaact gcctttaaat cccctaccga  3660
aaacatcttt caggttcccc cccagtttat tccaagggaa cctactttca ctaattttgt  3720
cagagtttgg caaaccaatc cctttggtcg ctatttattt aatagtaccc tcgtcgccct  3780
tttaaccgtc ggattaaatc tgctattttg ttccttggcg gcctatcctt tggcgcgctt  3840
aaacttttgg ggtcgcgatt ttctcctaag tgcgatcgtt tccaccatca tgataccctt  3900
tcagattgtc atgattcccc tgtatattct agcagtacag ttaggattaa gaaatactta  3960
tttaggcatt atttttccat ctttagcctc cgcttttggc atctttctat tgcgacaggc  4020
atttatggga gttcccaaag agttagaaga agccgccaga attgatggct gttcagaatt  4080
agggatttgg tggcatatta tgatcccctc agtccgtccc gccttaatga ccttagccat  4140
ttttgtattt atcgggtctt ggagtgattt tctctggccc ttaattgtag tcgatcgccc  4200
agaatattat accatccctt taggcgtggc aaatctagcc ggaacttttt ctctcgattg  4260
gcggatagtc gccgccggtt ccgtcatttc tatcgctcct gtgttactac tatttttaat  4320
cgtacaacgg tatattgtgc ctacagatac agctacgggg gttaaaggtt gaatgaggat  4380
tattaatctc agtcctaata atcaaaatca tatccaccag gcggcgactt tattagtcgc  4440
agaatttcgg gaaaattggc cgaatgcttg gccgacttat gaacgtggtt tagccgaggt  4500
tatggagtct tttggcgacg atagagttaa tctagtcgcc gtcgatgaaa atgataatct  4560
tctaggctgg attggtggta ttagccaata tcaaggccat gtttgggaat tacatccttt  4620
ggtagtcaaa agcgattatc aagggttagg aatagggcga aaattggtcg ccaatttaga  4680
ggattatgtc cgctcacaag gagggttaac cttatggttg ggtaccgatg acgaaaataa  4740
tttaacctcc ctatctggtg tcgaattata cccccatttt ttggaaaata ttgctaacat  4800
aaaaaaccat ggtcgtcatc cctatgaatt ttatcagaaa tgcggttttg tgattatggg  4860
agtagtcccc gatgctaacg gtatcgggaa acctgatatt ttgatggcta aatctctgag  4920
aattgacaat catcctaaat ccaactgaat gttgtcagtt aagtttatag ggctgctatg  4980
gtatgataaa aaaatccccc cagcagttgg gggggaatga ttaattaggt attgaattgg  5040
ttaaattgga ggtgtgttgg ggctgacttt tgctgccttg ttgggggggg cgattttaac  5100
tgaggtcact ttttcttggc cgggattggc taatcgcttg tatgaggcta tccgtctgcg  5160
ggattatccc acggttcaag gggtggtggt atttttggcc gttattgtgg tggcggctag  5220
tttggcgatc gatattttga atgcttgtat tgacccacgg attcgctatt aattccctgt  5280
cagaaaatat acttagttat taatacttag ttatttttct taataaattt taacaaacca  5340
aagggcgttg gcagtgtata aaggatattt gaaggggtga gaaggaaggc gaatgttgat  5400
ttatgaagtt tgattaacat ttgtatcaaa atataaaatt cttctcataa accctgtaca  5460
atcttttaag atttcggaaa gtgttctagg atactgaaga aatgaaccac ggggcaattg  5520
ttaaaagcct ttgtcgatgg ttcgccccgg aaggggtctt aggaggtgac accgatggat  5580
tgattgtcgt gatcattcat ggtgtgtcca atcccaactc aactctaagc aagtcaacaa  5640
gtaggagata aatctatgaa aatcgaagaa ggtaaactgg taatctggat taacggcgat  5700
aaaggctata acggactcgc tgaagtcggt aagaaattcg agaaagatac cggaattaaa  5760
gtcaccgttg agcatccgga taaactggaa gagaaattcc cacaggttgc ggcaactggc  5820
gatggccctg acattatctt ctgggcacac gaccgctttg gtggctacgc tcaatctggc  5880
ctgttggctg aaatcacccc ggacaaagcg ttccaggaca agctgtatcc gtttacctgg  5940
gatgccgtac gttacaacgg caagctgatt gcttacccga tcgctgttga agcgttatcg  6000
ctgatttata acaaagatct gctgccgaac ccgccaaaaa cctgggaaga gatcccggcg  6060
ctggataaag aactgaaagc gaaaggtaag agcgcgctga tgttcaacct gcaagaaccg  6120
tacttcacct ggccgctgat tgctgctgac gggggttatg cgttcaagta tgaaaacggc  6180
aagtacgaca ttaaagacgt gggcgtggat aacgctggcg cgaaagcggg tctgaccttc  6240
ctggttgacc tgattaaaaa caaacacatg aatgcagaca ccgattactc catcgcagaa  6300
gctgccttta ataaaggcga aacagcgatg accatcaacg gcccgtgggc atggtccaac  6360
atcgacacca gcaaagtgaa ttatggtgta acggtactgc cgaccttcaa gggtcaacca  6420
tccaaaccgt tcgttggcgt gctgagcgca ggtattaacg ccgccagtcc gaacaaagag  6480
ctggcaaaag agttcctcga aaactatctg ctgactgatg aaggtctgga agcggttaat  6540
aaagacaaac cgctgggtgc cgtagcgctg aagtcttacg aggaagagtt ggcgaaagat  6600
ccacgtattg ccgccactat ggaaaacgcc cagaaaggtg aaatcatgcc gaacatcccg  6660
cagatgtccg ctttctggta tgccgtgcgt actgcggtga tcaacgccgc cagcggtcgt  6720
cagactgtcg atgaagccct gaaagacgcg cagacttccg gcggaggtgg aggctcaaaa  6780
ggcggtggag gtagcgctgg aatgcctatt gaggaagtcc gaaagaacac taaaacactc  6840
atcaaaacca ttattacgaa gatcgatacg atcccttacg tgcaggacgt gtctccagag  6900
attacagtta ctggcctcga cttcattccc ggcgacaaac ccatcacatc cttgtccgag  6960
gcagtactca cgttgacgcg ctaccggcaa gttctcctgt ccctgcccga tccggaaact  7020
cagcaaattg ctctggatct agacaatctc atcgaactct tccgtgaatt ggcggccagc  7080
aaaggttgta ccctcccaga tcccagcaac ctagccacac cgcccgagct ggcggaagtg  7140
ctgaaggata gcgaatttgc agtctacgtt accgctctaa cgaagttaaa gaaaaaccta  7200
gagaacatcc tgaaggaatt agagaaggac ctcgcgtgtt caagcggcgg tagtcaccat  7260
caccaccatc actaacagcc aaataaaacg aaaggctcag tcgaaagact gggcctttcg  7320
ttttatctgt tgtttgtcgg tgaacgctct cctgagtagg acaaatccgc cgggagcgga  7380
tttgaacgtt gcgaagcaac ggcccggagg gtggcgggca ggacgcccgc cataaactgc  7440
caggcatcaa attaagcaga aggccatcct gacggatggc ctttttgcgt ttctacaaac  7500
tccggatccg gccggcttga agacagcgtg gggatgcggg gacacaatgc             7550
```

```
SEQ ID NO: 44          moltype = DNA  length = 7550
FEATURE                Location/Qualifiers
source                 1..7550
                       mol_type = other DNA
                       organism = synthetic construct
SEQUENCE: 44
ggaatcatga atcatcccac aactaagcat caaaaaatta catcctgtta ctggggaatt  60
tctgaactac ctgggttaga tacaggtaat attaaactcc tgaatcaatg tggtattgaa  120
```

```
aacacccagc aactgctcac gcgcgggagt aataatgcta ataaaatcgc cttatctaac  180
caactaggta tcaacatcag agatatcagt aaatgggtcg caatgtccga cttagccagg  240
gttcccagta ttggctatca atattgtggt gtccttttgc atagtggcgt aagttcagtt  300
aaccaactat ctcagatgtc tattcaacaa ctgcataaac agattttacg gctctatgta  360
ggaaccttgc aatctcgcca actctgtcca tctgttgatg tcatccaaac ctggattaaa  420
caagctaaaa ttttgcataa aattaattaa taattactag atgaaatcat gaatttttcc  480
gaagatttgc gacaaaatgc accagccacc gaaagaaacc gcgaacctat tttagaggtc  540
ttaaaaaggg tgttgcccgc cacgggaacc gttttagaag tagccagcgg cacaggacaa  600
cacgcggttt tttttgctcc ccgtctctcc cctaggcggt ggctaccttc cgacccgcaa  660
cctttgttac aacagagtat taaagcatgg caaattcatt caccttcaga taatctttac  720
cctcccctac agttaaatgt agaagctaat ccttggccag tggaagggaa tgatttaccc  780
tgggaattat cggaatttcc catcactgct attgtagcaa ttaacctgat tcatatttcg  840
ccttggtcgg cttgtgaagg gttaatggcg ggaagcgatc gcattttgaa accgggggga  900
attttatatc tctatggacc ctataaaata gctggaaaac acaccgcacc tagtaacgct  960
tcctttgatg aatatttgcg aacttctaac cctaagtggg gtgtcagaaa ccttgatgat  1020
tcacatacgc ggccgcctgg gccttgagct cgaatttcct gcattaatga atcggccaac  1080
gcgcggggag aggcggtttg cgtattgggc gctcttccgc ttcctcgctc actgactcgc  1140
tgcgctcggt cgttcggctg cggcgagcgg tatcagctca ctcaaaggcg gtaatacggt  1200
tatccacaga atcaggggat aacgcaggaa agaacatgtg agcaaaaggc cagcaaaagg  1260
ccaggaaccg taaaaatagc ggagtgtata ctggcttact atgttggcac tgatgagggt  1320
gtcagtgaag tgcttcatgt ggcaggagaa aaaaggctgc accggtgcgt cagcagaata  1380
tgtgatacag gatatattcc gcttcctcgc tcactgactc gctacgctcg gtcgttcgac  1440
tgcggcgagc ggaaatggct tacgaacggg gcggagattt cctggaagat gccaggaaga  1500
tacttaacag ggaagtgaga gggccgcggc aaagccgttt ttccataggc tccgcccccc  1560
tgacaagcat cacgaaatct gacgctcaaa tcagtggtgg cgaaacccga caggactata  1620
aagataccag gcgtttcccc ctggcggctc cctcgtgcgc tctcctgttc ctgcctttcg  1680
gtttaccggt gtcattccgc tgttatggcc gcgtttgtct cattccacgc ctgacactca  1740
gttccgggta ggcagttcgc tccaagctgg actgtatgca cgaacccccc attcagtccg  1800
accgctgcgc cttatccggt aactatcgtc ttgagtccaa cccggaaaga catgcaaaag  1860
caccactggc agcagccact ggtaattgat ttagaggagt tagtcttgaa gtcatgcgcc  1920
ggttaaggct aaactgaaag gacaagtttt ggtgactgcg ctcctccaag ccagttacct  1980
cggttcaaag agttggtagc tcagagaacc ttcgaaaaac cgccctgcaa ggcggttttt  2040
tcgttttcag agcaagagat tacgcgcaga ccaaaacgat ctcaagaaga tcatcttatt  2100
aagattatca aaaaggatct tcacctagat ccttttaaat taaaaatgaa gttttaaatc  2160
aatctaaagt atatatgagt aaacttggtc tgacagttac caatgcttaa tcagtgaggc  2220
acctatctca gcgatctgtc tatttcgttc atccatagtt gcctgactcc ccgtcgtgta  2280
gataactacg atacgggagg gcttaccatc tggccccagt gctgcaatga taccgcggga  2340
cccacgctca ccggctccag atttatcagc aataaaccag ccagccggaa gggccgagcg  2400
cagaagtggt cctgcaactt tatccgcctc catccagtct attaattgtt gccgggaagc  2460
tagagtaagt agttcgccag ttaatagttt gcgcaacgtt gttgccattg ctacaggcat  2520
cgtggtgtca cgctcgtcgt ttggtatggc ttcattcagc tccggttccc aacgatcaag  2580
gcgagttaca tgatccccca tgttgtgcaa aaaagcggtt agctccttcg gtcctccgat  2640
cgttgtcaga agtaagttgg ccgcagtgtt atcactcatg gttatggcag cactgcataa  2700
ttctcttact gtcatgccat ccgtaagatg cttttctgtg actggtgagt actcaaccaa  2760
gtcattctga gaatagtgta tgcggcgacc gagttgctct tgcccggcgt caatacggga  2820
taataccgcg ccacatagca gaactttaaa agtgctcatc attggaaaac gttcttcggg  2880
gcgaaaactc tcaaggatct taccgctgtt gagatccagt tcgatgtaac ccactcgtgc  2940
acccaactga tcttcagcat cttttacttt caccagcgtt tctgggtgag caaaaacagg  3000
aaggcaaaat gccgcaaaaa agggaataag ggcgacacgg aaatgttgaa tactcatact  3060
cttccttttt caatattatt gaagcattta tcagggttat tgtctcatga gcggatacat  3120
atttgaatgt atttagaaaa ataaacaaat aggggttccg cgcacatttc cccgaaaagt  3180
gccacctgac gtctaagaaa ccattattat catgacatta acctataaaa ataggcgtat  3240
cacgaggccc tttcgtctcg cgcgtttcgg tgatgacggt gaaaacctct gacacatgca  3300
gctcccggag acggtcacag cttgtctgta agcggatgcc aagcttgcat gcctgcaggt  3360
ggcgcgccta tgggggagga ttttatgatc ggatgttgag tcagtctgag tggtctaaaa  3420
ttcctacggt gggaattgtg tttgcggccg ccagggtgga tactctccct agggatagtt  3480
gggaccagcc tttggcggcg gtttgtacag aggagggtat atgggagttt ccaaaataac  3540
ttctggtggg ggggcaaatt atcgggcgat cgccacttat atggtattaa ttgctatagc  3600
gatcgctatg ctatttcccc tattttggtt ggtgggaact gcctttaaat cccctaccga  3660
aaacatcttt caggttcccc cccagtttat tccaagggaa cctactttca ctaattttgt  3720
cagagtttgg caaaccaatc cctttggtcg ctatttattt aatagtaccc tcgtcgccct  3780
tttaaccgtc ggattaaatc tgctattttg ttccttggcg gcctatcctt tggcgcgctt  3840
aaacttttgg ggtcgcgatt ttctcctaag tgcgatcgtt tccaccatca tgatacccttt 3900
tcagattgtc atgattcccc tgtatattct agcagtacag ttaggattaa gaaatactta  3960
tttaggcatt atttttccat ctttagcctc cgcttttggc atctttctat tgcgacaggc  4020
atttatggga gttcccaaag agttagaaga agccgccaga attgatggct gttcagaatt  4080
agggatttgg tggcatatta tgatcccctc agtccgtccc gccttaatga ccttagccat  4140
ttttgtattt atcgggtctt ggagtgattt tctctggccc ttaattgtag tcgatcgccc  4200
agaatattat accatccctt taggcgtggc aaatctagcc ggaacttttt ctctcgattg  4260
gcggatagtc gccgccggtt ccgtcatttc tatcgctcct gtgttactac tatttttaat  4320
cgtacaacgg tatattgtgc ctacagatac agctacgggg gttaaaggtt gaatgaggat  4380
tattaatctc agtcctaata atcaaaatca tatccaccag gcggcgactt tattagtcgc  4440
agaatttcgg gaaaattggc cgaatgcttg gccgacttat gaacgtggtt tagccgaggt  4500
tatggagtct tttggcgacg atagagttaa tctagtcgcc gtcgatgaaa atgataatct  4560
tctaggctgg attggtggta ttagccaata tcaaggccat gtttgggaat tacatccttt  4620
ggtagtcaaa agcgattatc aagggttagg aatagggcga aaattggtcg ccaatttaga  4680
ggattatgtc cgctcacaag gagggttaac cttatggttg ggtaccgatg acgaaaataa  4740
tttaacctcc ctatctggtg tcgaattata cccccatttt ttggaaaata ttgctaacat  4800
aaaaaaccat ggtcgtcatc cctatgaatt ttatcagaaa tgcggttttg tgattatggg  4860
```

```
agtagtcccc gatgctaacg gtatcgggaa acctgatatt ttgatggcta aatctctgag  4920
aattgacaat catcctaaat ccaactgaat gttgtcagtt aagtttatag ggctgctatg  4980
gtatgataaa aaaatccccc cagcagttgg gggggaatga ttaattaggt attgaattgg  5040
ttaaattgga ggtgtgttgg ggctgacttt tgctgccttg ttgggggggg cgattttaac  5100
tgaggtcact ttttcttggc cggattggc  taatcgcttg tatgaggcta tccgtctgcg  5160
ggattatccc acggttcaag ggtggtggt  atttttggcc gttattgtgg tggcggctag  5220
tttggcgatc gatattttga atgcttgtat tgacccacgg attcgctatt aattccctgt  5280
cagaaaatat acttagttat taatacttag ttattttttct taataaattt taacaaacca  5340
aagggcgttg gcagtgtata aaggatattt gaaggggtga gaaggaaggc gaatgttgat  5400
ttatgaagtt tgattaacat ttgtatcaaa atataaaatt cttctcataa accctgtaca  5460
atcttttaag atttcggaaa gtgttctagg atactgaaga aatgaaccac ggggcaattg  5520
ttaaaagcct ttgtcgatgg ttcgccccgg aaggggtctt aggaggtgac accgatggat  5580
tgattgtcgt gatcattcat ggtgtgtcca atcccaactc aactctaagc aagtcaacaa  5640
gtaggagata aatctatgaa aatcgaagaa ggtaaactgg taatctggat taacggcgat  5700
aaaggctata acggactcgc tgaagtcggt aagaaattcg agaaagatac cggaattaaa  5760
gtcaccgttg agcatccgga taaactggaa gagaaattcc cacaggttgc ggcaactggc  5820
gatggccctg acattatctt ctgggcacac gaccgctttg gtggctacgc tcaatctggc  5880
ctgttggctg aaatcacccc ggacaaagcg ttccaggaca agctgtatcc gtttacctgg  5940
gatgccgtac gttacaacgg caagctgatt gcttacccga tcgctgttga agcgttatcg  6000
ctgatttata acaaagatct gctgccgaac ccgccaaaaa cctgggaaga gatcccggcg  6060
ctggataaag aactgaaagc gaaaggtaag agcgcgctga tgttcaacct gcaagaaccg  6120
tacttcacct ggccgctgat tgctgctgac gggggttatg cgttcaagta tgaaaacggc  6180
aagtacgaca ttaaagacgt gggcgtggat aacgctggcg cgaaagcggg tctgaccttc  6240
ctggttgacc tgattaaaaa caaacacatg aatgcagaca ccgattactc catcgcagaa  6300
gctgccttta ataaaggcga aacagcgatg accatcaacg gcccgtgggc atggtccaac  6360
atcgacacca gcaaagtgaa ttatggtgta acggtactgc cgaccttcaa gggtcaacca  6420
tccaaaccgt tcgttggcgt gctgagcgca ggtattaacg ccgccagtcc gaacaaagag  6480
ctggcaaaag agttcctcga aaactatctg ctgactgatg aaggtctgga agcggttaat  6540
aaagacaaac cgctgggtgc cgtagcgctg aagtcttacg aggaagagtt ggcgaaagat  6600
ccacgtattg ccgccactat ggaaaacgcc cagaaaggtg aaatcatgcc gaacatcccg  6660
cagatgtccg ctttctggta tgccgtgcgt actgcggtga tcaacgccgc cagcggtcgt  6720
cagactgtcg atgaagccct gaaagacgcg cagacttccg gcggaggtgg aggctcaaaa  6780
ggcggtggag gtagcgctgg acgtccactc gaacaagtac gccgtgatct caagacgctg  6840
attaaaacga ttatcaccaa gattgatacg atcccctacg tacaggatgt gaaccctgat  6900
attactgtca ctgggctaga ctttattcct ggcaaccgac ctatcacgag tttgagtgaa  6960
gctaagaaaa ccctcacaaa gtacgtccaa gttttggaga gtttagacga ccccgaaacc  7020
caagaaatcg ccttagattt aaaaaacgtg atcgagttaa ttgacgagtt agcgaagagc  7080
cggggctgca cgttgcccga tacttccacc ctagaaaagg atccgcgact cgaagaggtc  7140
aagaaagaca gtgagtttgc gattacgacg acggccctgc gaaacttaaa gattaacttg  7200
gagattattc taaaagagtt agaacgcgat ccggcctgct caagcggcgg tagtcaccat  7260
caccaccatc actaacagcc aaataaaacg aaaggctcag tcgaaagact gggcctttcg  7320
ttttatctgt tgtttgtcgg tgaacgctct cctgagtagg acaaatccgc cgggagcgga  7380
tttgaacgtt gcgaagcaac ggcccggagg gtggcgggca ggacgcccgc cataaactgc  7440
caggcatcaa attaagcaga aggccatcct gacggatggc ctttttgcgt ttctacaaac  7500
tccggatccg gccggcttga agacagcatc tcggataggt tctggaatgc             7550
```

```
SEQ ID NO: 45          moltype = DNA  length = 7550
FEATURE                Location/Qualifiers
source                 1..7550
                       mol_type = other DNA
                       organism = synthetic construct
SEQUENCE: 45
ggaatcatga atcatcccac aactaagcat caaaaaatta catcctgtta ctggggaatt  60
tctgaactac ctgggttaga tacaggtaat attaaactcc tgaatcaatg tggtattgaa  120
aacacccagc aactgctcac gcgcgggagt aataatgcta ataaaatcgc cttatctaac  180
caactaggta tcaacatcag agatatcagt aaatgggtcg caatgtccga cttagccagg  240
gttcccagta ttggctatca atattgtggt gtccttttgc atagtggcgt aagttcagtt  300
aaccaactat ctcagatgtc tattcaacaa ctgcataaac agattttacg gctctatgta  360
ggaaccttgc aatctcgcca actctgtcca tctgttgatg tcatccaaac ctggattaaa  420
caagctaaaa ttttgcataa aattaattaa taattactag atgaaatcat gaatttttcc  480
gaagatttgc gacaaaatgc accagccacc gaaagaaacc gcgaacctat tttagaggtc  540
ttaaaaaggg tgttgcccgc cacgggaacc gttttagaag tagccagcgg cacaggacaa  600
cacgcggttt tttttgctcc ccgtctctcc cctaggcggt ggctaccttc cgacccgcaa  660
cctttgttac aacagagtat taaagcatgg caaattcatt caccttcaga taatctttac  720
cctcccctac agttaaatgt agaagctaat ccttggccag tggaagggaa tgatttaccc  780
tgggaattat cggaatttcc catcactgct attgtagcaa ttaacctgat tcatatttcg  840
ccttggtcgg cttgtgaagg gttaatggcg ggaagcgatc gcattttgaa accgggggga  900
attttatatc tctatggacc ctataaaata gctggaaaac acaccgcacc tagtaacgct  960
tcctttgatg aatatttgcg aacttctaac cctaagtggg gtgtcagaaa ccttgatgat  1020
tcacatacgc ggccgcctgg gccttgagct cgaatttcct gcattaatga atcggccaac  1080
gcgcggggag aggcggtttg cgtattgggc gctcttccgc ttcctcgctc actgactcgc  1140
tgcgctcggt cgttcggctg cggcgagcgg tatcagctca ctcaaaggcg gtaatacggt  1200
tatccacaga atcaggggat aacgcaggaa agaacatgtg agcaaaaggc cagcaaaagg  1260
ccaggaaccg taaaaatagc ggagtgtata ctggcttact atgttggcac tgatgagggt  1320
gtcagtgaag tgcttcatgt ggcaggagaa aaaaggctgc accggtgcgt cagcagaata  1380
tgtgatacag gatatattcc gcttcctcgc tcactgactc gctacgctcg gtcgttcgac  1440
tgcggcgagc ggaaatggct tacgaacggg gcggagattt cctggaagat gccaggaaga  1500
tacttaacag ggaagtgaga gggccgcggc aaagccgttt ttccataggc tccgcccccc  1560
tgacaagcat cacgaaatct gacgctcaaa tcagtggtgg cgaaacccga caggactata  1620
```

```
aagataccag gcgtttcccc ctggcggctc cctcgtgcgc tctcctgttc ctgcctttcg  1680
gtttaccggt gtcattccgc tgttatggcc gcgtttgtct cattccacgc ctgacactca  1740
gttccgggta ggcagttcgc tccaagctgg actgtatgca cgaacccccc attcagtccg  1800
accgctgcgc cttatccggt aactatcgtc ttgagtccaa cccggaaaga catgcaaaag  1860
caccactggc agcagccact ggtaattgat ttagaggagt tagtcttgaa gtcatgcgcc  1920
ggttaaggct aaactgaaag gacaagtttt ggtgactgcg ctcctccaag ccagttacct  1980
cggttcaaag agttggtagc tcagagaacc ttcgaaaaac cgccctgcaa ggcggttttt  2040
tcgttttcag agcaagagat tacgcgcaga ccaaaacgat ctcaagaaga tcatcttatt  2100
aagattatca aaaaggatct tcacctagat ccttttaaat taaaaatgaa gttttaaatc  2160
aatctaaagt atatatgagt aaacttggtc tgacagttac caatgcttaa tcagtgaggc  2220
acctatctca gcgatctgtc tatttcgttc atccatagtt gcctgactcc ccgtcgtgta  2280
gataactacg atacgggagg gcttaccatc tggccccagt gctgcaatga taccgcggga  2340
cccacgctca ccggctccag atttatcagc aataaaccag ccagccggaa gggccgagcg  2400
cagaagtggt cctgcaactt tatccgcctc catccagtct attaattgtt gccgggaagc  2460
tagagtaagt agttcgccag ttaatagttt gcgcaacgtt gttgccattg ctacaggcat  2520
cgtggtgtca cgctcgtcgt ttggtatggc ttcattcagc tccggttccc aacgatcaag  2580
gcgagttaca tgatccccca tgttgtgcaa aaaagcggtt agctccttcg gtcctccgat  2640
cgttgtcaga agtaagttgg ccgcagtgtt atcactcatg gttatggcag cactgcataa  2700
ttctcttact gtcatgccat ccgtaagatg cttttctgtg actggtgagt actcaaccaa  2760
gtcattctga gaatagtgta tgcggcgacc gagttgctct tgcccggcgt caatacggga  2820
taataccgcg ccacatagca gaactttaaa agtgctcatc attggaaaac gttcttcggg  2880
gcgaaaactc tcaaggatct taccgctgtt gagatccagt tcgatgtaac ccactcgtgc  2940
acccaactga tcttcagcat cttttacttt caccagcgtt tctgggtgag caaaaacagg  3000
aaggcaaaat gccgcaaaaa agggaataag ggcgacacgg aaatgttgaa tactcatact  3060
cttccttttt caatattatt gaagcattta tcagggttat tgtctcatga gcggatacat  3120
atttgaatgt atttagaaaa ataaacaaat aggggttccg cgcacatttc cccgaaaagt  3180
gccacctgac gtctaagaaa ccattattat catgacatta acctataaaa ataggcgtat  3240
cacgaggccc tttcgtctcg cgcgtttcgg tgatgacggt gaaaacctct gacacatgca  3300
gctcccggag acggtcacag cttgtctgta agcggatgcc aagcttgcat gcctgcaggt  3360
ggcgcgccta tgggggagga ttttatgatc ggatgttgag tcagtctgag tggtctaaaa  3420
ttcctacggt gggaattgtg tttgcggccg ccagggtgga tactctccct agggatagtt  3480
gggaccagcc tttggcggcg gtttgtacag aggagggtat atgggagttt ccaaaataac  3540
ttctggtggg ggggcaaatt atcgggcgat cgccacttat atggtattaa ttgctatagc  3600
gatcgctatg ctatttcccc tattttggtt ggtgggaact gcctttaaat cccctaccga  3660
aaacatcttt caggttcccc cccagtttat tccaagggaa cctactttca ctaattttgt  3720
cagagtttgg caaaccaatc cctttggtcg ctatttattt aatagtaccc tcgtcgccct  3780
tttaaccgtc ggattaaatc tgctattttg ttccttggcg gcctatcctt tggcgcgctt  3840
aaacttttgg ggtcgcgatt ttctcctaag tgcgatcgtt tccaccatca tgataccctt  3900
tcagattgtc atgattcccc tgtatattct agcagtacag ttaggattaa gaaatactta  3960
tttaggcatt atttttccat ctttagcctc cgcttttggc atctttctat tgcgacaggc  4020
atttatggga gttcccaaag agttagaaga agccgccaga attgatggct gttcagaatt  4080
agggatttgg tggcatatta tgatcccctc agtccgtccc gccttaatga ccttagccat  4140
ttttgtattt atcgggtctt ggagtgattt tctctggccc ttaattgtag tcgatcgccc  4200
agaatattat accatccctt taggcgtggc aaatctagcc ggaacttttt ctctcgattg  4260
gcggatagtc gccgccggtt ccgtcatttc tatcgctcct gtgttactac tatttttaat  4320
cgtacaacgg tatattgtgc ctacagatac agctacgggg gttaaaggtt gaatgaggat  4380
tattaatctc agtcctaata atcaaaatca tatccaccag gcggcgactt tattagtcgc  4440
agaatttcgg gaaaattggc cgaatgcttg gccgacttat gaacgtggtt tagccgaggt  4500
tatggagtct tttggcgacg atagagttaa tctagtcgcc gtcgatgaaa atgataatct  4560
tctaggctgg attggtggta ttagccaata tcaaggccat gtttgggaat tacatccttt  4620
ggtagtcaaa agcgattatc aagggttagg aatagggcga aaattggtcg ccaatttaga  4680
ggattatgtc cgctcacaag gagggttaac cttatggttg ggtaccgatg acgaaaataa  4740
tttaacctcc ctatctggtg tcgaattata cccccatttt ttggaaaata ttgctaacat  4800
aaaaaaccat ggtcgtcatc cctatgaatt ttatcagaaa tgcggttttg tgattatggg  4860
agtagtcccc gatgctaacg gtatcgggaa acctgatatt ttgatggcta aatctctgag  4920
aattgacaat catcctaaat ccaactgaat gttgtcagtt aagtttatag ggctgctatg  4980
gtatgataaa aaaatccccc cagcagttgg gggggaatga ttaattaggt attgaattgg  5040
ttaaattgga ggtgtgttgg ggctgacttt tgctgccttg ttgggggggg cgattttaac  5100
tgaggtcact ttttcttggc cgggattggc taatcgcttg tatgaggcta tccgtctgcg  5160
ggattatccc acggttcaag ggcggtggt atttttggcc gttattgtgg tggcggctag  5220
tttggcgatc gatattttga atgcttgtat tgacccacgg attcgctatt aattccctgt  5280
cagaaaatat acttagttat taatacttag ttatttttct taataaattt taacaaacca  5340
aagggcgttg gcagtgtata aaggatattt gaaggggtga gaaggaaggc gaatgttgat  5400
ttatgaagtt tgattaacat ttgtatcaaa atataaaatt cttctcataa accctgtaca  5460
atcttttaag atttcggaaa gtgttctagg atactgaaga aatgaaccac ggggcaattg  5520
ttaaaagcct ttgtcgatgg ttcgccccgg aaggggtctt aggaggtgac accgatggat  5580
tgattgtcgt gatcattcat ggtgtgtcca atcccaactc aactctaagc aagtcaacaa  5640
gtaggagata aatctatgaa aatcgaagaa ggtaaactgg taatctggat taacggcgat  5700
aaaggctata acggactcgc tgaagtcggt aagaaattcg agaaagatac cggaattaaa  5760
gtcaccgttg agcatccgga taaactggaa gagaaattcc cacaggttgc ggcaactggc  5820
gatggccctg acattatctt ctgggcacac gaccgctttg gtggctacgc tcaatctggc  5880
ctgttggctg aaatcacccc ggacaaagcg ttccaggaca agctgtatcc gtttacctgg  5940
gatgccgtac gttacaacgg caagctgatt gcttacccga tcgctgttga agcgttatcg  6000
ctgatttata acaaagatct gctgccgaac ccgccaaaaa cctgggaaga gatcccggcg  6060
ctggataaag aactgaaagc gaaaggtaag agcgcgctga tgttcaacct gcaagaaccg  6120
tacttcacct ggccgctgat tgctgctgac gggggttatg cgttcaagta tgaaaacggc  6180
aagtacgaca ttaaagacgt gggcgtggat aacgctggcg cgaaagcggg tctgaccttc  6240
ctggttgacc tgattaaaaa caaacacatg aatgcagaca ccgattactc catcgcagaa  6300
gctgccttta ataaaggcga aacagcgatg accatcaacg gcccgtgggc atggtccaac  6360
```

```
atcgacacca gcaaagtgaa ttatggtgta acggtactgc cgaccttcaa gggtcaacca  6420
tccaaaccgt tcgttggcgt gctgagcgca ggtattaacg ccgccagtcc gaacaaagag  6480
ctggcaaaag agttcctcga aaactatctg ctgactgatg aaggtctgga agcggttaat  6540
aaagacaaac cgctgggtgc cgtagcgctg aagtcttacg aggaagagtt ggcgaaagat  6600
ccacgtattg ccgccactat ggaaaacgcc cagaaaggtg aaatcatgcc gaacatcccg  6660
cagatgtccg ctttctggta tgccgtgcgt actgcggtga tcaacgccgc cagcggtcgt  6720
cagactgtcg atgaagccct gaaagacgcg cagacttccg gcggaggtgg aggctcaaaa  6780
ggcggtggag gtagcgctgg agttcctatc gaaaaagtcc gggaggatct aaaaacacta  6840
atcaagacca tcatcaagaa gattgatact atcccagaag ttcaggatgt gtccccagag  6900
atcacggtga cgggattgga ttttattccg ggcaacgaac ccattaattc tctaagcgaa  6960
gctgtattaa ccctcacgcg gtatcgccaa gtactagagt ctctagatga tccagaaacg  7020
cagcagattg ccttagactt gcagaattta attgaactgt taaaagaatt agcaaaggaa  7080
aagggatgca cattgcccga tcctagtaac ctaaaaaagc cggaagagct ggaaaaggta  7140
ctggaagacg ccgagttcgc tgttcgtgta accgctctca caaacctaaa gaaaaatttg  7200
gagaacattc tgaaagttct cgaaacagac ccagcctgtt caagcggcgg tagtcaccat  7260
caccaccatc actaacagcc aaataaaacg aaaggctcag tcgaaagact gggcctttcg  7320
ttttatctgt tgtttgtcgg tgaacgctct cctgagtagg acaaatccgc cgggagcgga  7380
tttgaacgtt gcgaagcaac ggcccggagg gtggcgggca ggacgcccgc cataaactgc  7440
caggcatcaa attaagcaga aggccatcct gacggatggc ctttttgcgt ttctacaaac  7500
tccggatccg gccggcttga agacagcaca catgggtcac gtacaaatgc             7550

SEQ ID NO: 46          moltype = DNA  length = 7550
FEATURE                Location/Qualifiers
source                 1..7550
                       mol_type = other DNA
                       organism = synthetic construct
SEQUENCE: 46
ggaatcatga atcatcccac aactaagcat caaaaaatta catcctgtta ctggggaatt  60
tctgaactac ctgggttaga tacaggtaat attaaactcc tgaatcaatg tggtattgaa  120
aacacccagc aactgctcac gcgcgggagt aataatgcta ataaaatcgc cttatctaac  180
caactaggta tcaacatcag agatatcagt aaatgggtcg caatgtccga cttagccagg  240
gttcccagta ttggctatca atattgtggt gtccttttgc atagtggcgt aagttcagtt  300
aaccaactat ctcagatgtc tattcaacaa ctgcataaac agattttacg gctctatgta  360
ggaaccttgc aatctcgcca actctgtcca tctgttgatg tcatccaaac ctggattaaa  420
caagctaaaa ttttgcataa aattaattaa taattactag atgaaatcat gaatttttcc  480
gaagatttgc gacaaaatgc accagccacc gaaagaaacc gcgaacctat tttagaggtc  540
ttaaaaaggg tgttgcccgc cacgggaacc gttttagaag tagccagcgg cacaggacaa  600
cacgcggttt tttttgctcc ccgtctctcc cctaggcggt ggctaccttc cgacccgcaa  660
cctttgttac aacagagtat taaagcatgg caaattcatt caccttcaga taatctttac  720
cctcccctac agttaaatgt agaagctaat ccttggccag tggaagggaa tgatttaccc  780
tgggaattat cggaatttcc catcactgct attgtagcaa ttaacctgat tcatatttcg  840
ccttggtcgg cttgtgaagg gttaatggcg ggaagcgatc gcattttgaa accgggggga  900
attttatatc tctatggacc ctataaaata gctggaaaac acaccgcacc tagtaacgct  960
tcctttgatg aatatttgcg aacttctaac cctaagtggg gtgtcagaaa ccttgatgat  1020
tcacatacgc ggccgcctgg gccttgagct cgaatttcct gcattaatga atcggccaac  1080
gcgcggggag aggcggtttg cgtattgggc gctcttccgc ttcctcgctc actgactcgc  1140
tgcgctcggt cgttcggctg cggcgagcgg tatcagctca ctcaaaggcg gtaatacggt  1200
tatccacaga atcaggggat aacgcaggaa agaacatgtg agcaaaaggc cagcaaaagg  1260
ccaggaaccg taaaaatagc ggagtgtata ctggcttact atgttggcac tgatgagggt  1320
gtcagtgaag tgcttcatgt ggcaggagaa aaaaggctgc accggtgcgt cagcagaata  1380
tgtgatacag gatatattcc gcttcctcgc tcactgactc gctacgctcg gtcgttcgac  1440
tgcggcgagc ggaaatggct tacgaacggg gcggagattt cctggaagat gccaggaaga  1500
tacttaacag ggaagtgaga gggccgcggc aaagccgttt ttccataggc tccgcccccc  1560
tgacaagcat cacgaaatct gacgctcaaa tcagtggtgg cgaaacccga caggactata  1620
aagataccag gcgtttcccc ctggcggctc cctcgtgcgc tctcctgttc ctgcctttcg  1680
gtttaccggt gtcattccgc tgttatggcc gcgtttgtct cattccacgc ctgacactca  1740
gttccgggta ggcagttcgc tccaagctgg actgtatgca cgaacccccc attcagtccg  1800
accgctgcgc cttatccggt aactatcgtc ttgagtccaa cccggaaaga catgcaaaag  1860
caccactggc agcagccact ggtaattgat ttagaggagt tagtcttgaa gtcatgcgcc  1920
ggttaaggct aaactgaaag gacaagtttt ggtgactgcg ctcctccaag ccagttacct  1980
cggttcaaag agttggtagc tcagagaacc ttcgaaaaac cgccctgcaa ggcggttttt  2040
tcgttttcag agcaagagat tacgcgcaga ccaaaacgat ctcaagaaga tcatcttatt  2100
aagattatca aaaaggatct tcacctagat ccttttaaat taaaaatgaa gttttaaatc  2160
aatctaaagt atatatgagt aaacttggtc tgacagttac caatgcttaa tcagtgaggc  2220
acctatctca gcgatctgtc tatttcgttc atccatagtt gcctgactcc ccgtcgtgta  2280
gataactacg atacgggagg gcttaccatc tggccccagt gctgcaatga taccgcggga  2340
cccacgctca ccggctccag atttatcagc aataaaccag ccagccggaa gggccgagcg  2400
cagaagtggt cctgcaactt tatccgcctc catccagtct attaattgtt gccgggaagc  2460
tagagtaagt agttcgccag ttaatagttt gcgcaacgtt gttgccattg ctacaggcat  2520
cgtggtgtca cgctcgtcgt ttggtatggc ttcattcagc tccggttccc aacgatcaag  2580
gcgagttaca tgatccccca tgttgtgcaa aaaagcggtt agctccttcg gtcctccgat  2640
cgttgtcaga agtaagttgg ccgcagtgtt atcactcatg gttatggcag cactgcataa  2700
ttctcttact gtcatgccat ccgtaagatg cttttctgtg actggtgagt actcaaccaa  2760
gtcattctga gaatagtgta tgcggcgacc gagttgctct tgcccggcgt caatacggga  2820
taataccgcg ccacatagca gaactttaaa agtgctcatc attggaaaac gttcttcggg  2880
gcgaaaactc tcaaggatct taccgctgtt gagatccagt tcgatgtaac ccactcgtgc  2940
acccaactga tcttcagcat cttttacttt caccagcgtt tctgggtgag caaaaacagg  3000
aaggcaaaat gccgcaaaaa agggaataag ggcgacacgg aaatgttgaa tactcatact  3060
cttccttttt caatattatt gaagcattta tcagggttat tgtctcatga gcggatacat  3120
```

```
atttgaatgt atttagaaaa ataaacaaat aggggttccg cgcacatttc cccgaaaagt  3180
gccacctgac gtctaagaaa ccattattat catgacatta acctataaaa ataggcgtat  3240
cacgaggccc tttcgtctcg cgcgtttcgg tgatgacggt gaaaacctct gacacatgca  3300
gctcccggag acggtcacag cttgtctgta agcggatgcc aagcttgcat gcctgcaggt  3360
ggcgcgccta tgggggagga ttttatgatc ggatgttgag tcagtctgag tggtctaaaa  3420
ttcctacggt gggaattgtg tttgcggccg ccagggtgga tactctccct agggatagtt  3480
gggaccagcc tttggcggcg gtttgtacag aggagggtat atgggagttt ccaaaataac  3540
ttctggtggg ggggcaaatt atcgggcgat cgccacttat atggtattaa ttgctatagc  3600
gatcgctatg ctatttcccc tattttggtt ggtgggaact gcctttaaat cccctaccga  3660
aaacatcttt caggttcccc cccagtttat tccaagggaa cctactttca ctaattttgt  3720
cagagtttgg caaaccaatc cctttggtcg ctatttattt aatagtaccc tcgtcgccct  3780
tttaaccgtc ggattaaatc tgctattttg ttccttggcg gcctatcctt tggcgcgctt  3840
aaacttttgg ggtcgcgatt ttctcctaag tgcgatcgtt tccaccatca tgataccctt  3900
tcagattgtc atgattcccc tgtatattct agcagtacag ttaggattaa gaaatactta  3960
tttaggcatt atttttccat ctttagcctc cgcttttggc atctttctat tgcgacaggc  4020
atttatggga gttcccaaag agttagaaga agccgccaga attgatggct gttcagaatt  4080
agggatttgg tggcatatta tgatcccctc agtccgtccc gccttaatga ccttagccat  4140
ttttgtattt atcgggtctt ggagtgattt tctctggccc ttaattgtag tcgatcgccc  4200
agaatattat accatccctt taggcgtggc aaatctagcc ggaacttttt ctctcgattg  4260
gcggatagtc gccgccggtt ccgtcatttc tatcgctcct gtgttactac tatttttaat  4320
cgtacaacgg tatattgtgc ctacagatac agctacgggg gttaaaggtt gaatgaggat  4380
tattaatctc agtcctaata atcaaaatca tatccaccag gcggcgactt tattagtcgc  4440
agaatttcgg gaaaattggc cgaatgcttg gccgacttat gaacgtggtt tagccgaggt  4500
tatggagtct tttggcgacg atagagttaa tctagtcgcc gtcgatgaaa atgataatct  4560
tctaggctgg attggtggta ttagccaata tcaaggccat gtttgggaat tacatccttt  4620
ggtagtcaaa agcgattatc aagggttagg aatagggcga aaattggtcg ccaatttaga  4680
ggattatgtc cgctcacaag gagggttaac cttatggttg ggtaccgatg acgaaaataa  4740
tttaacctcc ctatctggtg tcgaattata cccccatttt ttggaaaata ttgctaacat  4800
aaaaaaccat ggtcgtcatc cctatgaatt ttatcagaaa tgcggttttg tgattatggg  4860
agtagtcccc gatgctaacg gtatcgggaa acctgatatt ttgatggcta aatctctgag  4920
aattgacaat catcctaaat ccaactgaat gttgtcagtt aagtttatag ggctgctatg  4980
gtatgataaa aaaatccccc cagcagttgg gggggaatga ttaattaggt attgaattgg  5040
ttaaattgga ggtgtgttgg ggctgacttt tgctgccttg ttgggggggg cgattttaac  5100
tgaggtcact ttttcttggc cgggattggc taatcgcttg tatgaggcta tccgtctgcg  5160
ggattatccc acggttcaag gggtggtggt atttttggcc gttattgtgg tggcggctag  5220
tttggcgatc gatattttga atgcttgtat tgacccacgg attcgctatt aattccctgt  5280
cagaaaatat acttagttat taatacttag ttatttttct taataaattt taacaaacca  5340
aagggcgttg gcagtgtata aaggatattt gaaggggtga gaaggaaggc gaatgttgat  5400
ttatgaagtt tgattaacat ttgtatcaaa atataaaatt cttctcataa accctgtaca  5460
atcttttaag atttcggaaa gtgttctagg atactgaaga aatgaaccac ggggcaattg  5520
ttaaaagcct ttgtcgatgg ttcgccccgg aaggggtctt aggaggtgac accgatggat  5580
tgattgtcgt gatcattcat ggtgtgtcca atcccaactc aactctaagc aagtcaacaa  5640
gtaggagata aatctatgaa aatcgaagaa ggtaaactgg taatctggat taacggcgat  5700
aaaggctata acggactcgc tgaagtcggt aagaaattcg agaaagatac cggaattaaa  5760
gtcaccgttg agcatccgga taaactggaa gagaaattcc cacaggttgc ggcaactggc  5820
gatggccctg acattatctt ctgggcacac gaccgctttg gtggctacgc tcaatctggc  5880
ctgttggctg aaatcacccc ggacaaagcg ttccaggaca agctgtatcc gtttacctgg  5940
gatgccgtac gttacaacgg caagctgatt gcttacccga tcgctgttga agcgttatcg  6000
ctgatttata acaaagatct gctgccgaac ccgccaaaaa cctgggaaga gatcccggcg  6060
ctggataaag aactgaaagc gaaaggtaag agcgcgctga tgttcaacct gcaagaaccg  6120
tacttcacct ggccgctgat tgctgctgac gggggttatg cgttcaagta tgaaaacggc  6180
aagtacgaca ttaaagacgt gggcgtggat aacgctggcg cgaaagcggg tctgaccttc  6240
ctggttgacc tgattaaaaa caaacacatg aatgcagaca ccgattactc catcgcagaa  6300
gctgccttta ataaaggcga aacagcgatg accatcaacg gcccgtgggc atggtccaac  6360
atcgacacca gcaaagtgaa ttatggtgta acggtactgc cgaccttcaa gggtcaacca  6420
tccaaaccgt tcgttggcgt gctgagcgca ggtattaacg ccgccagtcc gaacaaagag  6480
ctggcaaaag agttcctcga aaactatctg ctgactgatg aaggtctgga agcggttaat  6540
aaagacaaac cgctgggtgc cgtagcgctg aagtcttacg aggaagagtt ggcgaaagat  6600
ccacgtattg ccgccactat ggaaaacgcc cagaaaggtg aaatcatgcc gaacatcccg  6660
cagatgtccg ctttctggta tgccgtgcgt actgcggtga tcaacgccgc cagcggtcgt  6720
cagactgtcg atgaagccct gaaagacgcg cagacttccg gcggaggtgg aggctcaaaa  6780
ggcggtggag gtagcgctgg agtgccgatc caaaaagtcc aggacgatac taaaacacta  6840
attaaaacga ttatcacacg tattaatgac atctcccata ctcagagcgt ctcctctaag  6900
gttaaggtca ccggactgga ctttattcca ggtcgccacc ctatcctaac attatctaag  6960
atggatcaga ccctagccgt gtatcaacag atcctgactt ccatgccaga cccaaacgtg  7020
atccaaattg caaatgacct ggagaacctc cgagatttac tacacgtgct agcgtttagc  7080
aaaagctgtc ccctcccgtg ggcgagcgga ttggaaacgc tcgatagctt gcgaaaggtt  7140
ctcgaagcga gcctatactc cacggaggtc gtagccttat ctcgtttaca aggagtgctg  7200
caggacatgc taaagcagct cgacctatct cccggatgct caagcggcgg tagtcaccat  7260
caccaccatc actaacagcc aaataaaacg aaaggctcag tcgaaagact gggcctttcg  7320
ttttatctgt tgtttgtcgg tgaacgctct cctgagtagg acaaatccgc cgggagcgga  7380
tttgaacgtt gcgaagcaac ggcccggagg gtggcgggca ggacgcccgc cataaactgc  7440
caggcatcaa attaagcaga aggccatcct gacggatggc ctttttgcgt ttctacaaac  7500
tccggatccg gccggcttga agacagtagt gcacgcctcg aggttaatgc             7550
```

```
SEQ ID NO: 47          moltype = DNA  length = 7550
FEATURE                Location/Qualifiers
source                 1..7550
                       mol_type = other DNA
```

```
                         organism = synthetic construct
SEQUENCE: 47
ggaatcatga atcatcccac aactaagcat caaaaaatta catcctgtta ctggggaatt  60
tctgaactac ctgggttaga tacaggtaat attaaactcc tgaatcaatg tggtattgaa  120
aacacccagc aactgctcac gcgcgggagt aataatgcta ataaaatcgc cttatctaac  180
caactaggta tcaacatcag agatatcagt aaatgggtcg caatgtccga cttagccagg  240
gttcccagta ttggctatca atattgtggt gtccttttgc atagtggcgt aagttcagtt  300
aaccaactat ctcagatgtc tattcaacaa ctgcataaac agattttacg gctctatgta  360
ggaaccttgc aatctcgcca actctgtcca tctgttgatg tcatccaaac ctggattaaa  420
caagctaaaa ttttgcataa aattaattaa taattactag atgaaatcat gaatttttcc  480
gaagatttgc gacaaaatgc accagccacc gaaagaaacc gcgaacctat tttagaggtc  540
ttaaaaaggg tgttgcccgc cacgggaacc gttttagaag tagccagcgg cacaggacaa  600
cacgcggttt tttttgctcc ccgtctctcc cctaggcggt ggctaccttc cgacccgcaa  660
cctttgttac aacagagtat taaagcatgg caaattcatt caccttcaga taatctttac  720
cctcccctac agttaaatgt agaagctaat ccttggccag tggaagggaa tgatttaccc  780
tgggaattat cggaatttcc catcactgct attgtagcaa ttaacctgat tcatatttcg  840
ccttggtcgg cttgtgaagg gttaatggcg ggaagcgatc gcattttgaa accgggggga  900
attttatatc tctatggacc ctataaaata gctggaaaac acaccgcacc tagtaacgct  960
tcctttgatg aatatttgcg aacttctaac cctaagtggg gtgtcagaaa ccttgatgat  1020
tcacatacgc ggccgcctgg gccttgagct cgaatttcct gcattaatga atcggccaac  1080
gcgcggggag aggcggtttg cgtattgggc gctcttccgc ttcctcgctc actgactcgc  1140
tgcgctcggt cgttcggctg cggcgagcgg tatcagctca ctcaaaggcg gtaatacggt  1200
tatccacaga atcaggggat aacgcaggaa agaacatgtg agcaaaaggc cagcaaaagg  1260
ccaggaaccg taaaaatagc ggagtgtata ctggcttact atgttggcac tgatgagggt  1320
gtcagtgaag tgcttcatgt ggcaggagaa aaaaggctgc accggtgcgt cagcagaata  1380
tgtgatacag gatatattcc gcttcctcgc tcactgactc gctacgctcg gtcgttcgac  1440
tgcggcgagc ggaaatggct tacgaacggg gcggagattt cctggaagat gccaggaaga  1500
tacttaacag ggaagtgaga gggccgcggc aaagccgttt ttccataggc tccgcccccc  1560
tgacaagcat cacgaaatct gacgctcaaa tcagtggtgg cgaaacccga caggactata  1620
aagataccag gcgtttcccc ctggcggctc cctcgtgcgc tctcctgttc ctgcctttcg  1680
gtttaccggt gtcattccgc tgttatggcc gcgtttgtct cattccacgc ctgacactca  1740
gttccgggta ggcagttcgc tccaagctgg actgtatgca cgaacccccc attcagtccg  1800
accgctgcgc cttatccggt aactatcgtc ttgagtccaa cccggaaaga catgcaaaag  1860
caccactggc agcagccact ggtaattgat ttagaggagt tagtcttgaa gtcatgcgcc  1920
ggttaaggct aaactgaaag gacaagtttt ggtgactgcg ctcctccaag ccagttacct  1980
cggttcaaag agttggtagc tcagagaacc ttcgaaaaac cgccctgcaa ggcggttttt  2040
tcgttttcag agcaagagat tacgcgcaga ccaaaacgat ctcaagaaga tcatcttatt  2100
aagattatca aaaaggatct tcacctagat ccttttaaat taaaaatgaa gttttaaatc  2160
aatctaaagt atatatgagt aaacttggtc tgacagttac caatgcttaa tcagtgaggc  2220
acctatctca gcgatctgtc tatttcgttc atccatagtt gcctgactcc ccgtcgtgta  2280
gataactacg atacgggagg gcttaccatc tggccccagt gctgcaatga taccgcggga  2340
cccacgctca ccggctccag atttatcagc aataaaccag ccagccggaa gggccgagcg  2400
cagaagtggt cctgcaactt tatccgcctc catccagtct attaattgtt gccgggaagc  2460
tagagtaagt agttcgccag ttaatagttt gcgcaacgtt gttgccattg ctacaggcat  2520
cgtggtgtca cgctcgtcgt ttggtatggc ttcattcagc tccggttccc aacgatcaag  2580
gcgagttaca tgatccccca tgttgtgcaa aaaagcggtt agctccttcg gtcctccgat  2640
cgttgtcaga agtaagttgg ccgcagtgtt atcactcatg gttatggcag cactgcataa  2700
ttctcttact gtcatgccat ccgtaagatg cttttctgtg actggtgagt actcaaccaa  2760
gtcattctga gaatagtgta tgcggcgacc gagttgctct tgcccggcgt caatacggga  2820
taataccgcg ccacatagca gaactttaaa agtgctcatc attggaaaac gttcttcggg  2880
gcgaaaactc tcaaggatct taccgctgtt gagatccagt tcgatgtaac ccactcgtgc  2940
acccaactga tcttcagcat cttttacttt caccagcgtt tctgggtgag caaaaacagg  3000
aaggcaaaat gccgcaaaaa agggaataag ggcgacacgg aaatgttgaa tactcatact  3060
cttccttttt caatattatt gaagcattta tcagggttat tgtctcatga gcggatacat  3120
atttgaatgt atttagaaaa ataaacaaat aggggttccg cgcacatttc cccgaaaagt  3180
gccacctgac gtctaagaaa ccattattat catgacatta acctataaaa ataggcgtat  3240
cacgaggccc tttcgtctcg cgcgtttcgg tgatgacggt gaaaacctct gacacatgca  3300
gctcccggag acggtcacag cttgtctgta agcggatgcc aagcttgcat gcctgcaggt  3360
ggcgcgccta tggggagga ttttatgatc ggatgttgag tcagtctgag tggtctaaaa  3420
ttcctacggt gggaattgtg tttgcggccg ccagggtgga tactctccct agggatagtt  3480
gggaccagcc tttggcggcg gtttgtacag aggagggtat atgggagttt ccaaaataac  3540
ttctggtggg ggggcaaatt atcgggcgat cgccacttat atggtattaa ttgctatagc  3600
gatcgctatg ctatttcccc tattttggtt ggtgggaact gcctttaaat cccctaccga  3660
aaacatcttt caggttcccc cccagtttat tccaagggaa cctactttca ctaattttgt  3720
cagagtttgg caaaccaatc cctttggtcg ctatttattt aatagtaccc tcgtcgccct  3780
tttaaccgtc ggattaaatc tgctattttg ttccttggcg gcctatcctt tggcgcgctt  3840
aaacttttgg ggtcgcgatt ttctcctaag tgcgatcgtt tccaccatca tgataccctt  3900
tcagattgtc atgattcccc tgtatattct agcagtacag ttaggattaa gaaatactta  3960
tttaggcatt atttttccat ctttagcctc cgcttttggc atctttctat tgcgacaggc  4020
atttatggga gttcccaaag agttagaaga agccgccaga attgatggct gttcagaatt  4080
agggatttgg tggcatatta tgatcccctc agtccgtccc gccttaatga ccttagccat  4140
ttttgtattt atcgggtctt ggagtgattt tctctggccc ttaattgtag tcgatcgccc  4200
agaatattat accatcccctt taggcgtggc aaatctagcc ggaacttttt ctctcgattg  4260
gcggatagtc gccgccggtt ccgtcatttc tatcgctcct gtgttactac tatttttaat  4320
cgtacaacgg tatattgtgc ctacagatac agctacgggg gttaaaggtt gaatgaggat  4380
tattaatctc agtcctaata atcaaaatca tatccaccag gcggcgactt tattagtcgc  4440
agaatttcgg gaaaattggc cgaatgcttg gccgacttat gaacgtggtt tagccgaggt  4500
tatggagtct tttggcgacg atagagttaa tctagtcgcc gtcgatgaaa atgataatct  4560
tctaggctgg attggtggta ttagccaata tcaaggccat gtttgggaat tacatccttt  4620
```

```
ggtagtcaaa agcgattatc aagggttagg aatagggcga aaattggtcg ccaatttaga  4680
ggattatgtc cgctcacaag gagggttaac cttatggttg ggtaccgatg acgaaaataa  4740
tttaacctcc ctatctggtg tcgaattata cccccatttt ttggaaaata ttgctaacat  4800
aaaaaaccat ggtcgtcatc cctatgaatt ttatcagaaa tgcggttttg tgattatggg  4860
agtagtcccc gatgctaacg gtatcgggaa acctgatatt ttgatggcta aatctctgag  4920
aattgacaat catcctaaat ccaactgaat gttgtcagtt aagtttatag ggctgctatg  4980
gtatgataaa aaaatccccc cagcagttgg gggggaatga ttaattaggt attgaattgg  5040
ttaaattgga ggtgtgttgg ggctgacttt tgctgccttg ttggggggggg cgattttaac  5100
tgaggtcact ttttcttggc cgggattggc taatcgcttg tatgaggcta tccgtctgcg  5160
ggattatccc acggttcaag gggtggtggt atttttggcc gttattgtgg tggcggctag  5220
tttggcgatc gatattttga atgcttgtat tgacccacgg attcgctatt aattccctgt  5280
cagaaaatat acttagttat taatacttag ttatttttct taataaattt taacaaacca  5340
aagggcgttg gcagtgtata aaggatattt gaaggggtga gaaggaaggc gaatgttgat  5400
ttatgaagtt tgattaacat ttgtatcaaa atataaaatt cttctcataa accctgtaca  5460
atcttttaag atttcggaaa gtgttctagg atactgaaga aatgaaccac ggggcaattg  5520
ttaaaagcct ttgtcgatgg ttcgccccgg aaggggtctt aggaggtgac accgatggat  5580
tgattgtcgt gatcattcat ggtgtgtcca atcccaactc aactctaagc aagtcaacaa  5640
gtaggagata aatctatgaa aatcgaagaa ggtaaactgg taatctggat taacggcgat  5700
aaaggctata acggactcgc tgaagtcggt aagaaattcg agaaagatac cggaattaaa  5760
gtcaccgttg agcatccgga taaactggaa gagaaattcc cacaggttgc ggcaactggc  5820
gatggccctg acattatctt ctgggcacac gaccgctttg gtggctacgc tcaatctggc  5880
ctgttggctg aaatcacccc ggacaaagcg ttccaggaca agctgtatcc gtttacctgg  5940
gatgccgtac gttacaacgg caagctgatt gcttacccga tcgctgttga agcgttatcg  6000
ctgatttata acaaagatct gctgccgaac ccgccaaaaa cctgggaaga gatcccggcg  6060
ctggataaag aactgaaagc gaaaggtaag agcgcgctga tgttcaacct gcaagaaccg  6120
tacttcacct ggccgctgat tgctgctgac ggggggttatg cgttcaagta tgaaaacggc  6180
aagtacgaca ttaaagacgt gggcgtggat aacgctggcg cgaaagcggg tctgaccttc  6240
ctggttgacc tgattaaaaa caaacacatg aatgcagaca ccgattactc catcgcagaa  6300
gctgccttta ataaaggcga aacagcgatg accatcaacg gcccgtgggc atggtccaac  6360
atcgacacca gcaaagtgaa ttatggtgta acggtactgc cgaccttcaa gggtcaacca  6420
tccaaaccgt tcgttggcgt gctgagcgca ggtattaacg ccgccagtcc gaacaaagag  6480
ctggcaaaag agttcctcga aaactatctg ctgactgatg aaggtctgga agcggttaat  6540
aaagacaaac cgctgggtgc cgtagcgctg aagtcttacg aggaagagtt ggcgaaagat  6600
ccacgtattg ccgccactat ggaaaacgcc cagaaaggtg aaatcatgcc gaacatcccg  6660
cagatgtccg ctttctggta tgccgtgcgt actgcggtga tcaacgccgc cagcggtcgt  6720
cagactgtcg atgaagccct gaaagacgcg cagacttccg gcggaggtgg aggctcaaaa  6780
ggcggtggag gtagcgctgg agtacccatt caaaaggtcc aagatgacac taaaaccttg  6840
attaagacga tcatcacacg gatcaatgat atttcccata cccagagcgt aagctctaaa  6900
gttaaggtga cgggcttgga tttcattcct ggccgtcatc ctatcttgac cttgagcaag  6960
atggatcaga cactagccgt ctatcagcag atcctagaat ccatgcccga ccccaatgtc  7020
atccaaatcg cgaatgacct cgagaattta cgtgacctac tgcatgtatt ggctttctct  7080
aaatcttgcc ctctccccctg ggctagcgga ctggaaacgc tagacagcct ccggaaggtg  7140
ctggaggcca gcttatactc tacagaggtc gtagctttaa gccgcctaca aggtgtgcta  7200
caggatatgc tgaagcaatt agatctcagc cccggatgct caagcggcgg tagtcaccat  7260
caccaccatc actaacagcc aaataaaacg aaaggctcag tcgaaagact gggcctttcg  7320
ttttatctgt tgtttgtcgg tgaacgctct cctgagtagg acaaatccgc cgggagcgga  7380
tttgaacgtt gcgaagcaac ggcccggagg gtggcgggca ggacgcccgc cataaactgc  7440
caggcatcaa attaagcaga aggccatcct gacggatggc ctttttgcgt ttctacaaac  7500
tccggatccg gccggcttga agacagtgtg ccggcgtgct ttggcaatgc             7550
```

```
SEQ ID NO: 48           moltype = DNA  length = 7550
FEATURE                 Location/Qualifiers
source                  1..7550
                        mol_type = other DNA
                        organism = synthetic construct
SEQUENCE: 48
ggaatcatga atcatcccac aactaagcat caaaaaatta catcctgtta ctggggaatt  60
tctgaactac ctgggttaga tacaggtaat attaaactcc tgaatcaatg tggtattgaa  120
aacacccagc aactgctcac gcgcgggagt aataatgcta ataaaatcgc cttatctaac  180
caactaggta tcaacatcag agatatcagt aaatgggtcg caatgtccga cttagccagg  240
gttcccagta ttggctatca atattgtggt gtccttttgc atagtggcgt aagttcagtt  300
aaccaactat ctcagatgtc tattcaacaa ctgcataaac agattttacg gctctatgta  360
ggaaccttgc aatctcgcca actctgtcca tctgttgatg tcatccaaac ctggattaaa  420
caagctaaaa ttttgcataa aattaattaa taattactag atgaaatcat gaatttttcc  480
gaagatttgc gacaaaatgc accagccacc gaaagaaacc gcgaacctat tttagaggtc  540
ttaaaaaggg tgttgcccgc cacgggaacc gttttagaag tagccagcgg cacaggacaa  600
cacgcggttt tttttgctcc ccgtctctcc cctaggcggt ggctaccttc cgacccgcaa  660
cctttgttac aacagagtat taaagcatgg caaattcatt caccttcaga taatctttac  720
cctcccctac agttaaatgt agaagctaat ccttggccag tggaagggaa tgatttaccc  780
tgggaattat cggaatttcc catcactgct attgtagcaa ttaacctgat tcatatttcg  840
ccttggtcgg cttgtgaagg gttaatggcg ggaagcgatc gcattttgaa accgggggga  900
attttatatc tctatggacc ctataaaata gctggaaaac acaccgcacc tagtaacgct  960
tcctttgatg aatatttgcg aacttctaac cctaagtggg gtgtcagaaa ccttgatgat  1020
tcacatacgc ggccgcctgg gccttgagct cgaatttcct gcattaatga atcggccaac  1080
gcgcggggag aggcggtttg cgtattgggc gctcttccgc ttcctcgctc actgactcgc  1140
tgcgctcggt cgttcggctg cggcgagcgg tatcagctca ctcaaaggcg gtaatacggt  1200
tatccacaga atcaggggat aacgcaggaa agaacatgtg agcaaaaggc cagcaaaagg  1260
ccaggaaccg taaaaatagc ggagtgtata ctggcttact atgttggcac tgatgagggt  1320
gtcagtgaag tgcttcatgt ggcaggagaa aaaaggctgc accggtgcgt cagcagaata  1380
```

-continued

```
tgtgatacag gatatattcc gcttcctcgc tcactgactc gctacgctcg gtcgttcgac  1440
tgcggcgagc ggaaatggct tacgaacggg gcggagattt cctggaagat gccaggaaga  1500
tacttaacag ggaagtgaga gggccgcggc aaagccgttt ttccataggc tccgcccccc  1560
tgacaagcat cacgaaatct gacgctcaaa tcagtggtgg cgaaacccga caggactata  1620
aagataccag gcgtttcccc ctggcggctc cctcgtgcgc tctcctgttc ctgcctttcg  1680
gtttaccggt gtcattccgc tgttatggcc gcgtttgtct cattccacgc ctgacactca  1740
gttccgggta ggcagttcgc tccaagctgg actgtatgca cgaacccccc attcagtccg  1800
accgctgcgc cttatccggt aactatcgtc ttgagtccaa cccggaaaga catgcaaaag  1860
caccactggc agcagccact ggtaattgat ttagaggagt tagtcttgaa gtcatgcgcc  1920
ggttaaggct aaactgaaag gacaagtttt ggtgactgcg ctcctccaag ccagttacct  1980
cggttcaaag agttggtagc tcagagaacc ttcgaaaaac cgccctgcaa ggcggttttt  2040
tcgttttcag agcaagagat tacgcgcaga ccaaaacgat ctcaagaaga tcatcttatt  2100
aagattatca aaaaggatct tcacctagat ccttttaaat taaaaatgaa gttttaaatc  2160
aatctaaagt atatatgagt aaacttggtc tgacagttac caatgcttaa tcagtgaggc  2220
acctatctca gcgatctgtc tatttcgttc atccatagtt gcctgactcc ccgtcgtgta  2280
gataactacg atacgggagg gcttaccatc tggccccagt gctgcaatga taccgcggga  2340
cccacgctca ccggctccag atttatcagc aataaaccag ccagccggaa gggccgagcg  2400
cagaagtggt cctgcaactt tatccgcctc catccagtct attaattgtt gccgggaagc  2460
tagagtaagt agttcgccag ttaatagttt gcgcaacgtt gttgccattg ctacaggcat  2520
cgtggtgtca cgctcgtcgt ttggtatggc ttcattcagc tccggttccc aacgatcaag  2580
gcgagttaca tgatccccca tgttgtgcaa aaaagcggtt agctccttcg gtcctccgat  2640
cgttgtcaga agtaagttgg ccgcagtgtt atcactcatg gttatggcag cactgcataa  2700
ttctcttact gtcatgccat ccgtaagatg cttttctgtg actggtgagt actcaaccaa  2760
gtcattctga gaatagtgta tgcggcgacc gagttgctct tgcccggcgt caatacggga  2820
taataccgcg ccacatagca gaactttaaa agtgctcatc attggaaaac gttcttcggg  2880
gcgaaaactc tcaaggatct taccgctgtt gagatccagt tcgatgtaac ccactcgtgc  2940
acccaactga tcttcagcat cttttacttt caccagcgtt tctgggtgag caaaaacagg  3000
aaggcaaaat gccgcaaaaa agggaataag ggcgacacgg aaatgttgaa tactcatact  3060
cttccttttt caatattatt gaagcattta tcagggttat tgtctcatga gcggatacat  3120
atttgaatgt atttagaaaa ataaacaaat aggggttccg cgcacatttc cccgaaaagt  3180
gccacctgac gtctaagaaa ccattattat catgacatta acctataaaa ataggcgtat  3240
cacgaggccc tttcgtctcg cgcgtttcgg tgatgacggt gaaaacctct gacacatgca  3300
gctcccggag acggtcacag cttgtctgta agcggatgcc aagcttgcat gcctgcaggt  3360
ggcgcgccta tgggggagga ttttatgatc ggatgttgag tcagtctgag tggtctaaaa  3420
ttcctacggt gggaattgtg tttgcggccg ccagggtgga tactctccct agggatagtt  3480
gggaccagcc tttggcggcg gtttgtacag aggagggtat atgggagttt ccaaaataac  3540
ttctggtggg ggggcaaatt atcgggcgat cgccacttat atggtattaa ttgctatagc  3600
gatcgctatg ctatttcccc tattttggtt ggtgggaact gcctttaaat cccctaccga  3660
aaacatcttt caggttcccc cccagtttat tccaagggaa cctactttca ctaattttgt  3720
cagagtttgg caaaccaatc cctttggtcg ctatttattt aatagtaccc tcgtcgccct  3780
tttaaccgtc ggattaaatc tgctattttg ttccttggcg gcctatcctt tggcgcgctt  3840
aaacttttgg ggtcgcgatt ttctcctaag tgcgatcgtt tccaccatca tgataccctt  3900
tcagattgtc atgattcccc tgtatattct agcagtacag ttaggattaa gaaatactta  3960
tttaggcatt atttttccat ctttagcctc cgcttttggc atctttctat tgcgacaggc  4020
atttatggga gttcccaaag agttagaaga agccgccaga attgatggct gttcagaatt  4080
agggatttgg tggcatatta tgatcccctc agtccgtccc gccttaatga ccttagccat  4140
ttttgtattt atcgggtctt ggagtgattt tctctggccc ttaattgtag tcgatcgccc  4200
agaatattat accatccctt taggcgtggc aaatctagcc ggaacttttt ctctcgattg  4260
gcggatagtc gccgccggtt ccgtcatttc tatcgctcct gtgttactac tatttttaat  4320
cgtacaacgg tatattgtgc ctacagatac agctacgggg gttaaaggtt gaatgaggat  4380
tattaatctc agtcctaata atcaaaatca tatccaccag gcggcgactt tattagtcgc  4440
agaatttcgg gaaaattggc cgaatgcttg gccgacttat gaacgtggtt tagccgaggt  4500
tatggagtct tttggcgacg atagagttaa tctagtcgcc gtcgatgaaa atgataatct  4560
tctaggctgg attggtggta ttagccaata tcaaggccat gtttgggaat tacatccttt  4620
ggtagtcaaa agcgattatc aagggttagg aatagggcga aaattggtcg ccaatttaga  4680
ggattatgtc cgctcacaag gagggttaac cttatggttg ggtaccgatg acgaaaataa  4740
tttaacctcc ctatctggtg tcgaattata cccccatttt ttggaaaata ttgctaacat  4800
aaaaaaccat ggtcgtcatc cctatgaatt ttatcagaaa tgcggttttg tgattatggg  4860
agtagtcccc gatgctaacg gtatcgggaa acctgatatt ttgatggcta aatctctgag  4920
aattgacaat catcctaaat ccaactgaat gttgtcagtt aagtttatag ggctgctatg  4980
gtatgataaa aaaatccccc cagcagttgg gggggaatga ttaattaggt attgaattgg  5040
ttaaattgga ggtgtgttgg ggctgacttt tgctgccttg ttgggggggg cgattttaac  5100
tgaggtcact ttttcttggc cgggattggc taatcgcttg tatgaggcta tccgtctgcg  5160
ggattatccc acggttcaag gggtggtggt atttttggcc gttattgtgg tggcggctag  5220
tttggcgatc gatattttga atgcttgtat tgacccacgg attcgctatt aattccctgt  5280
cagaaaatat acttagttat taatacttag ttatttttct taataaattt taacaaacca  5340
aagggcgttg gcagtgtata aaggatattt gaaggggtga gaaggaaggc gaatgttgat  5400
ttatgaagtt tgattaacat ttgtatcaaa atataaaatt cttctcataa accctgtaca  5460
atcttttaag atttcggaaa gtgttctagg atactgaaga aatgaaccac ggggcaattg  5520
ttaaaagcct ttgtcgatgg ttcgccccgg aaggggtctt aggaggtgac accgatggat  5580
tgattgtcgt gatcattcat ggtgtgtcca atcccaactc aactctaagc aagtcaacaa  5640
gtaggagata aatctatgaa aatcgaagaa ggtaaactgg taatctggat taacggcgat  5700
aaaggctata acggactcgc tgaagtcggt aagaaattcg agaaagatac cggaattaaa  5760
gtcaccgttg agcatccgga taaactggaa gagaaattcc cacaggttgc ggcaactggc  5820
gatggccctg acattatctt ctgggcacac gaccgctttg gtggctacgc tcaatctggc  5880
ctgttggctg aaatcacccc ggacaaagcg ttccaggaca agctgtatcc gtttacctgg  5940
gatgccgtac gttacaacgg caagctgatt gcttacccga tcgctgttga agcgttatcg  6000
ctgatttata acaaagatct gctgccgaac ccgccaaaaa cctgggaaga gatcccggcg  6060
ctggataaag aactgaaagc gaaaggtaag agcgcgctga tgttcaacct gcaagaaccg  6120
```

```
tacttcacct ggccgctgat tgctgctgac gggggttatg cgttcaagta tgaaaacggc  6180
aagtacgaca ttaaagacgt gggcgtggat aacgctggcg cgaaagcggg tctgaccttc  6240
ctggttgacc tgattaaaaa caaacacatg aatgcagaca ccgattactc catcgcagaa  6300
gctgccttta ataaaggcga aacagcgatg accatcaacg gcccgtgggc atggtccaac  6360
atcgacacca gcaaagtgaa ttatggtgta acggtactgc cgaccttcaa gggtcaacca  6420
tccaaaccgt tcgttggcgt gctgagcgca ggtattaacg ccgccagtcc gaacaaagag  6480
ctggcaaaag agttcctcga aaactatctg ctgactgatg aaggtctgga agcggttaat  6540
aaagacaaac cgctgggtgc cgtagcgctg aagtcttacg aggaagagtt ggcgaaagat  6600
ccacgtattg ccgccactat ggaaaacgcc cagaaaggtg aaatcatgcc gaacatcccg  6660
cagatgtccg ctttctggta tgccgtgcgt actgcggtga tcaacgccgc cagcggtcgt  6720
cagactgtcg atgaagccct gaaagacgcg cagacttccg gcggaggtgg aggctcaaaa  6780
ggcggtggag gtagcgctgg agtacccatc caaaaggtgt ttgatgacac gaaaacactg  6840
atcaagacta ttatcacacg gattaacact atcgagcaca ctcaaagtgt tagctccaag  6900
attaaggtta cggggttaga cttcattccg ggactacagc cgatcctaac actgtctaaa  6960
atggaccaaa cgctagctgt gtaccagcag attctattga gtatgccggt tccgttagtc  7020
atccaaatcg ccgctgacct agagaacctg cgtttgctcc tccatctgct cgcgaagagt  7080
aaaaattgtc ctctgccctg ggcgagcgga ctggaagatg aagatatgct acggcgcgtg  7140
ctggaagcaa gtttatattc cactgaagtc gtgacgttgc tacgcctgca aggtgtctta  7200
ctacaaatgc tagagcagct agacttgagc ccagggtgtt caagcggcgg tagtcaccat  7260
caccaccatc actaacagcc aaataaaacg aaaggctcag tcgaaagact gggcctttcg  7320
ttttatctgt tgtttgtcgg tgaacgctct cctgagtagg acaaatccgc cgggagcgga  7380
tttgaacgtt gcgaagcaac ggcccggagg gtggcgggca ggacgcccgc cataaactgc  7440
caggcatcaa attaagcaga aggccatcct gacggatggc ctttttgcgt ttctacaaac  7500
tccggatccg gccggcttga agacagggca ggttccgacc aaccgaatgc             7550
```

```
SEQ ID NO: 49          moltype = DNA  length = 7550
FEATURE                Location/Qualifiers
source                 1..7550
                       mol_type = other DNA
                       organism = synthetic construct
SEQUENCE: 49
ggaatcatga atcatcccac aactaagcat caaaaaatta catcctgtta ctggggaatt  60
tctgaactac ctgggttaga tacaggtaat attaaactcc tgaatcaatg tggtattgaa  120
aacacccagc aactgctcac gcgcgggagt aataatgcta ataaaatcgc cttatctaac  180
caactaggta tcaacatcag agatatcagt aaatgggtcg caatgtccga cttagccagg  240
gttcccagta ttggctatca atattgtggt gtcctttttgc atagtggcgt aagttcagtt  300
aaccaactat ctcagatgtc tattcaacaa ctgcataaac agattttacg gctctatgta  360
ggaaccttgc aatctcgcca actctgtcca tctgttgatg tcatccaaac ctggattaaa  420
caagctaaaa ttttgcataa aattaattaa taattactag atgaaatcat gaatttttcc  480
gaagatttgc gacaaaatgc accagccacc gaaagaaacc gcgaacctat tttagaggtc  540
ttaaaaaggg tgttgcccgc cacgggaacc gttttagaag tagccagcgg cacaggacaa  600
cacgcggttt tttttgctcc ccgtctctcc cctaggcggt ggctaccttc cgacccgcaa  660
cctttgttac aacagagtat taaagcatgg caaattcatt caccttcaga taatctttac  720
cctcccctac agttaaatgt agaagctaat ccttggccag tggaagggaa tgatttaccc  780
tgggaattat cggaatttcc catcactgct attgtagcaa ttaacctgat tcatatttcg  840
ccttggtcgg cttgtgaagg gttaatggcg ggaagcgatc gcattttgaa accgggggga  900
attttatatc tctatggacc ctataaaata gctggaaaac acaccgcacc tagtaacgct  960
tcctttgatg aatatttgcg aacttctaac cctaagtggg gtgtcagaaa ccttgatgat  1020
tcacatacgc ggccgcctgg gccttgagct cgaatttcct gcattaatga atcggccaac  1080
gcgcggggag aggcggtttg cgtattgggc gctcttccgc ttcctcgctc actgactcgc  1140
tgcgctcggt cgttcggctg cggcgagcgg tatcagctca ctcaaaggcg gtaatacggt  1200
tatccacaga atcaggggat aacgcaggaa agaacatgtg agcaaaaggc cagcaaaagg  1260
ccaggaaccg taaaaatagc ggagtgtata ctggcttact atgttggcac tgatgagggt  1320
gtcagtgaag tgcttcatgt ggcaggagaa aaaaggctgc accggtgcgt cagcagaata  1380
tgtgatacag gatatattcc gcttcctcgc tcactgactc gctacgctcg gtcgttcgac  1440
tgcggcgagc ggaaatggct tacgaacggg gcggagattt cctggaagat gccaggaaga  1500
tacttaacag ggaagtgaga gggccgcggc aaagccgttt ttccataggc tccgcccccc  1560
tgacaagcat cacgaaatct gacgctcaaa tcagtggtgg cgaaacccga caggactata  1620
aagataccag gcgtttcccc ctggcggctc cctcgtgcgc tctcctgttc ctgcctttcg  1680
gtttaccggt gtcattccgc tgttatggcc gcgtttgtct cattccacgc ctgacactca  1740
gttccgggta ggcagttcgc tccaagctgg actgtatgca cgaacccccc attcagtccg  1800
accgctgcgc cttatccggt aactatcgtc ttgagtccaa cccggaaaga catgcaaaag  1860
caccactggc agcagccact ggtaattgat ttagaggagt tagtcttgaa gtcatgcgcc  1920
ggttaaggct aaactgaaag gacaagtttt ggtgactgcg ctcctccaag ccagttacct  1980
cggttcaaag agttggtagc tcagagaacc ttcgaaaaac cgccctgcaa ggcggttttt  2040
tcgttttcag agcaagagat tacgcgcaga ccaaaacgat ctcaagaaga tcatcttatt  2100
aagattatca aaaaggatct tcacctagat ccttttaaat taaaaatgaa gttttaaatc  2160
aatctaaagt atatatgagt aaacttggtc tgacagttac caatgcttaa tcagtgaggc  2220
acctatctca gcgatctgtc tatttcgttc atccatagtt gcctgactcc ccgtcgtgta  2280
gataactacg atacgggagg gcttaccatc tggccccagt gctgcaatga taccgcggga  2340
cccacgctca ccggctccag atttatcagc aataaaccag ccagccggaa gggccgagcg  2400
cagaagtggt cctgcaactt tatccgcctc catccagtct attaattgtt gccgggaagc  2460
tagagtaagt agttcgccag ttaatagttt gcgcaacgtt gttgccattg ctacaggcat  2520
cgtggtgtca cgctcgtcgt ttggtatggc ttcattcagc tccggttccc aacgatcaag  2580
gcgagttaca tgatccccca tgttgtgcaa aaaagcggtt agctccttcg gtcctccgat  2640
cgttgtcaga agtaagttgg ccgcagtgtt atcactcatg gttatggcag cactgcataa  2700
ttctcttact gtcatgccat ccgtaagatg cttttctgtg actggtgagt actcaaccaa  2760
gtcattctga gaatagtgta tgcggcgacc gagttgctct tgcccggcgt caatacggga  2820
taataccgcg ccacatagca gaactttaaa agtgctcatc attggaaaac gttcttcggg  2880
```

```
gcgaaaactc tcaaggatct taccgctgtt gagatccagt tcgatgtaac ccactcgtgc  2940
acccaactga tcttcagcat cttttacttt caccagcgtt tctgggtgag caaaaacagg  3000
aaggcaaaat gccgcaaaaa agggaataag ggcgacacgg aaatgttgaa tactcatact  3060
cttccttttt caatattatt gaagcattta tcagggttat tgtctcatga gcggatacat  3120
atttgaatgt atttagaaaa ataaacaaat aggggttccg cgcacatttc cccgaaaagt  3180
gccacctgac gtctaagaaa ccattattat catgacatta acctataaaa ataggcgtat  3240
cacgaggccc tttcgtctcg cgcgtttcgg tgatgacggt gaaaacctct gacacatgca  3300
gctcccggag acggtcacag cttgtctgta agcggatgcc aagcttgcat gcctgcaggt  3360
ggcgcgccta tgggggagga ttttatgatc ggatgttgag tcagtctgag tggtctaaaa  3420
ttcctacggt gggaattgtg tttgcggccg ccagggtgga tactctccct agggatagtt  3480
gggaccagcc tttggcggcg gtttgtacag aggagggtat atgggagttt ccaaaataac  3540
ttctggtggg ggggcaaatt atcgggcgat cgccacttat atggtattaa ttgctatagc  3600
gatcgctatg ctatttcccc tattttggtt ggtgggaact gcctttaaat cccctaccga  3660
aaacatcttt caggttcccc cccagtttat tccaagggaa cctactttca ctaattttgt  3720
cagagtttgg caaaccaatc cctttggtcg ctatttattt aatagtaccc tcgtcgccct  3780
tttaaccgtc ggattaaatc tgctattttg ttccttggcg gcctatcctt tggcgcgctt  3840
aaactttttgg ggtcgcgatt ttctcctaag tgcgatcgtt tccaccatca tgataccctt  3900
tcagattgtc atgattcccc tgtatattct agcagtacag ttaggattaa gaaatactta  3960
tttaggcatt atttttccat ctttagcctc cgcttttggc atctttctat tgcgacaggc  4020
atttatggga gttcccaaag agttagaaga agccgccaga attgatggct gttcagaatt  4080
agggatttgg tggcatatta tgatcccctc agtccgtccc gccttaatga ccttagccat  4140
ttttgtattt atcgggtctt ggagtgattt tctctggccc ttaattgtag tcgatcgccc  4200
agaatattat accatccctt taggcgtggc aaatctagcc ggaacttttt ctctcgattg  4260
gcggatagtc gccgccggtt ccgtcatttc tatcgctcct gtgttactac tatttttaat  4320
cgtacaacgg tatattgtgc ctacagatac agctacgggg gttaaaggtt gaatgaggat  4380
tattaatctc agtcctaata atcaaaatca tatccaccag gcggcgactt tattagtcgc  4440
agaatttcgg gaaaattggc cgaatgcttg gccgacttat gaacgtggtt tagccgaggt  4500
tatggagtct tttggcgacg atagagttaa tctagtcgcc gtcgatgaaa atgataatct  4560
tctaggctgg attggtggta ttagccaata tcaaggccat gtttgggaat tacatccttt  4620
ggtagtcaaa agcgattatc aagggttagg aatagggcga aaattggtcg ccaatttaga  4680
ggattatgtc cgctcacaag gagggttaac cttatggttg ggtaccgatg acgaaaataa  4740
tttaacctcc ctatctggtg tcgaattata cccccatttt ttggaaaata ttgctaacat  4800
aaaaaaccat ggtcgtcatc cctatgaatt ttatcagaaa tgcggttttg tgattatggg  4860
agtagtcccc gatgctaacg gtatcgggaa acctgatatt ttgatggcta aatctctgag  4920
aattgacaat catcctaaat ccaactgaat gttgtcagtt aagtttatag ggctgctatg  4980
gtatgataaa aaaatccccc cagcagttgg gggggaatga ttaattaggt attgaattgg  5040
ttaaattgga ggtgtgttgg ggctgacttt tgctgccttg ttgggggggg cgattttaac  5100
tgaggtcact ttttcttggc cggattggc taatcgcttg tatgaggcta tccgtctgcg  5160
ggattatccc acggttcaag ggtggtggt atttttggcc gttattgtgg tggcggctag  5220
tttggcgatc gatattttga atgcttgtat tgacccacgg attcgctatt aattccctgt  5280
cagaaaatat acttagttat taatacttag ttatttttct taataaattt taacaaacca  5340
aagggcgttg gcagtgtata aaggatattt gaaggggtga gaaggaaggc gaatgttgat  5400
ttatgaagtt tgattaacat ttgtatcaaa atataaaatt cttctcataa accctgtaca  5460
atcttttaag atttcggaaa gtgttctagg atactgaaga aatgaaccac ggggcaattg  5520
ttaaaagcct ttgtcgatgg ttcgccccgg aaggggtctt aggaggtgac accgatggat  5580
tgattgtcgt gatcattcat ggtgtgtcca atcccaactc aactctaagc aagtcaacaa  5640
gtaggagata aatctatgaa aatcgaagaa ggtaaactgg taatctggat taacggcgat  5700
aaaggctata acggactcgc tgaagtcggt aagaaattcg agaaagatac cggaattaaa  5760
gtcaccgttg agcatccgga taaactggaa gagaaattcc cacaggttgc ggcaactggc  5820
gatggccctg acattatctt ctgggcacac gaccgctttg gtggctacgc tcaatctggc  5880
ctgttggctg aaatcacccc ggacaaagcg ttccaggaca agctgtatcc gtttacctgg  5940
gatgccgtac gttacaacgg caagctgatt gcttacccga tcgctgttga agcgttatcg  6000
ctgatttata acaaagatct gctgccgaac ccgccaaaaa cctgggaaga gatcccggcg  6060
ctggataaag aactgaaagc gaaaggtaag agcgcgctga tgttcaacct gcaagaaccg  6120
tacttcacct ggccgctgat tgctgctgac gggggttatg cgttcaagta tgaaaacggc  6180
aagtacgaca ttaaagacgt gggcgtggat aacgctggcg cgaaagcggg tctgaccttc  6240
ctggttgacc tgattaaaaa caaacacatg aatgcagaca ccgattactc catcgcagaa  6300
gctgccttta ataaaggcga aacagcgatg accatcaacg gcccgtgggc atggtccaac  6360
atcgacacca gcaaagtgaa ttatggtgta acggtactgc cgaccttcaa gggtcaacca  6420
tccaaaccgt tcgttggcgt gctgagcgca ggtattaacg ccgccagtcc gaacaaagag  6480
ctggcaaaag agttcctcga aaactatctg ctgactgatg aaggtctgga agcggttaat  6540
aaagacaaac cgctgggtgc cgtagcgctg aagtcttacg aggaagagtt ggcgaaagat  6600
ccacgtattg ccgccactat ggaaaacgcc cagaaaggtg aaatcatgcc gaacatcccg  6660
cagatgtccg ctttctggta tgccgtgcgt actgcggtga tcaacgccgc cagcggtcgt  6720
cagactgtcg atgaagccct gaaagacgcg cagacttccg gcggaggtgg aggctcaaaa  6780
ggcggtggag gtagcgctgg agtcccgttg gagaaaattc gtgaggacac aaagacattg  6840
attcggacca ttatcactcg gattgatcaa atcccttacg tcgcagatgt cagcccgaag  6900
cagaaggtca cagggctcga tttcattccc ggaactaaag acaaatacac atatagcgat  6960
tttgcagcga cattagccaa ataccgtgaa atcttatctg ctactgacga tcctgaacta  7020
caacaaatcg cattggattt ggataattta attgatctaa ttcgggagtt ggcaaagagc  7080
aaggggtgtc cgttaccaga agccacgggg ttgccagatc cggaaaaact aaaggaggca  7140
ttaaaagaat ccggatatag tgtcgaagta gagacggcac gaaaactcaa agcattcctg  7200
gagaaggcgc tagaagagtt agaaaaagat ccaggttgct caagcggcgg tagtcaccat  7260
caccaccatc actaacagcc aaataaaacg aaaggctcag tcgaaagact gggcctttcg  7320
ttttatctgt tgtttgtcgg tgaacgctct cctgagtagg acaaatccgc cgggagcgga  7380
tttgaacgtt gcgaagcaac ggcccggagg gtggcgggca ggacgcccgc cataaactgc  7440
caggcatcaa attaagcaga aggccatcct gacggatggc ctttttgcgt ttctacaaac  7500
tccggatccg gccggcttga agacagcaat ggggcgcgtg taatgaatgc              7550
```

```
SEQ ID NO: 50          moltype = DNA  length = 7550
FEATURE                Location/Qualifiers
source                 1..7550
                       mol_type = other DNA
                       organism = synthetic construct
SEQUENCE: 50
ggaatcatga atcatcccac aactaagcat caaaaaatta catcctgtta ctggggaatt  60
tctgaactac ctgggttaga tacaggtaat attaaactcc tgaatcaatg tggtattgaa  120
aacacccagc aactgctcac gcgcgggagt aataatgcta ataaaatcgc cttatctaac  180
caactaggta tcaacatcag agatatcagt aaatgggtcg caatgtccga cttagccagg  240
gttcccagta ttggctatca atattgtggt gtccttttgc atagtggcgt aagttcagtt  300
aaccaactat ctcagatgtc tattcaacaa ctgcataaac agattttacg gctctatgta  360
ggaaccttgc aatctcgcca actctgtcca tctgttgatg tcatccaaac ctggattaaa  420
caagctaaaa ttttgcataa aattaattaa taattactag atgaaatcat gaatttttcc  480
gaagatttgc gacaaaatgc accagccacc gaaagaaacc gcgaacctat tttagaggtc  540
ttaaaaaggg tgttgcccgc cacgggaacc gttttagaag tagccagcgg cacaggacaa  600
cacgcggttt tttttgctcc ccgtctctcc cctaggcggt ggctaccttc cgacccgcaa  660
cctttgttac aacagagtat taaagcatgg caaattcatt caccttcaga taatctttac  720
cctcccctac agttaaatgt agaagctaat ccttggccag tggaagggaa tgatttaccc  780
tgggaattat cggaatttcc catcactgct attgtagcaa ttaacctgat tcatatttcg  840
ccttggtcgg cttgtgaagg gttaatggcg ggaagcgatc gcattttgaa accgggggga  900
attttatatc tctatggacc ctataaaata gctggaaaac acaccgcacc tagtaacgct  960
tcctttgatg aatatttgcg aacttctaac cctaagtggg gtgtcagaaa ccttgatgat  1020
tcacatacgc ggccgcctgg gccttgagct cgaatttcct gcattaatga atcggccaac  1080
gcgcggggag aggcggtttg cgtattgggc gctcttccgc ttcctcgctc actgactcgc  1140
tgcgctcggt cgttcggctg cggcgagcgg tatcagctca ctcaaaggcg gtaatacggt  1200
tatccacaga atcaggggat aacgcaggaa agaacatgtg agcaaaaggc cagcaaaagg  1260
ccaggaaccg taaaaatagc ggagtgtata ctggcttact atgttggcac tgatgagggt  1320
gtcagtgaag tgcttcatgt ggcaggagaa aaaaggctgc accggtgcgt cagcagaata  1380
tgtgatacag gatatattcc gcttcctcgc tcactgactc gctacgctcg gtcgttcgac  1440
tgcggcgagc ggaaatggct tacgaacggg gcggagattt cctggaagat gccaggaaga  1500
tacttaacag ggaagtgaga gggccgcggc aaagccgttt ttccataggc tccgcccccc  1560
tgacaagcat cacgaaatct gacgctcaaa tcagtggtgg cgaaacccga caggactata  1620
aagataccag gcgtttcccc ctggcggctc cctcgtgcgc tctcctgttc ctgcctttcg  1680
gtttaccggt gtcattccgc tgttatggcc gcgtttgtct cattccacgc ctgacactca  1740
gttccgggta ggcagttcgc tccaagctgg actgtatgca cgaacccccc attcagtccg  1800
accgctgcgc cttatccggt aactatcgtc ttgagtccaa cccggaaaga catgcaaaag  1860
caccactggc agcagccact ggtaattgat ttagaggagt tagtcttgaa gtcatgcgcc  1920
ggttaaggct aaactgaaag gacaagtttt ggtgactgcg ctcctccaag ccagttacct  1980
cggttcaaag agttggtagc tcagagaacc ttcgaaaaac cgccctgcaa ggcggttttt  2040
tcgttttcag agcaagagat tacgcgcaga ccaaaacgat ctcaagaaga tcatcttatt  2100
aagattatca aaaaggatct tcacctagat ccttttaaat taaaaatgaa gttttaaatc  2160
aatctaaagt atatatgagt aaacttggtc tgacagttac caatgcttaa tcagtgaggc  2220
acctatctca gcgatctgtc tatttcgttc atccatagtt gcctgactcc ccgtcgtgta  2280
gataactacg atacgggagg gcttaccatc tggccccagt gctgcaatga taccgcggga  2340
cccacgctca ccggctccag atttatcagc aataaaccag ccagccggaa gggccgagcg  2400
cagaagtggt cctgcaactt tatccgcctc catccagtct attaattgtt gccgggaagc  2460
tagagtaagt agttcgccag ttaatagttt gcgcaacgtt gttgccattg ctacaggcat  2520
cgtggtgtca cgctcgtcgt ttggtatggc ttcattcagc tccggttccc aacgatcaag  2580
gcgagttaca tgatccccca tgttgtgcaa aaaagcggtt agctccttcg gtcctccgat  2640
cgttgtcaga agtaagttgg ccgcagtgtt atcactcatg gttatggcag cactgcataa  2700
ttctcttact gtcatgccat ccgtaagatg cttttctgtg actggtgagt actcaaccaa  2760
gtcattctga gaatagtgta tgcggcgacc gagttgctct tgcccggcgt caatacggga  2820
taataccgcg ccacatagca gaactttaaa agtgctcatc attggaaaac gttcttcggg  2880
gcgaaaactc tcaaggatct taccgctgtt gagatccagt tcgatgtaac ccactcgtgc  2940
acccaactga tcttcagcat cttttacttt caccagcgtt tctgggtgag caaaaacagg  3000
aaggcaaaat gccgcaaaaa agggaataag ggcgacacgg aaatgttgaa tactcatact  3060
cttccttttt caatattatt gaagcattta tcagggttat tgtctcatga gcggatacat  3120
atttgaatgt atttagaaaa ataaacaaat aggggttccg cgcacatttc cccgaaaagt  3180
gccacctgac gtctaagaaa ccattattat catgacatta acctataaaa ataggcgtat  3240
cacgaggccc tttcgtctcg cgcgtttcgg tgatgacggt gaaaacctct gacacatgca  3300
gctcccggag acggtcacag cttgtctgta agcggatgcc aagcttgcat gcctgcaggt  3360
ggcgcgccta tgggggagga ttttatgatc ggatgttgag tcagtctgag tggtctaaaa  3420
ttcctacggt gggaattgtg tttgcggccg ccagggtgga tactctccct agggatagtt  3480
gggaccagcc tttggcggcg gtttgtacag aggagggtat atgggagttt ccaaaataac  3540
ttctggtggg ggggcaaatt atcgggcgat cgccacttat atggtattaa ttgctatagc  3600
gatcgctatg ctatttcccc tattttggtt ggtgggaact gcctttaaat cccctaccga  3660
aaacatcttt caggttcccc cccagtttat tccaagggaa cctactttca ctaattttgt  3720
cagagtttgg caaaccaatc cctttggtcg ctatttattt aatagtaccc tcgtcgccct  3780
tttaaccgtc ggattaaatc tgctattttg ttccttggcg gcctatcctt tggcgcgctt  3840
aaacttttgg ggtcgcgatt ttctcctaag tgcgatcgtt tccaccatca tgataccctt  3900
tcagattgtc atgattcccc tgtatattct agcagtacag ttaggattaa gaaatactta  3960
tttaggcatt atttttccat ctttagcctc cgcttttggc atctttctat tgcgacaggc  4020
atttatggga gttcccaaag agttagaaga agccgccaga attgatggct gttcagaatt  4080
agggatttgg tggcatatta tgatcccctc agtccgtccc gccttaatga ccttagccat  4140
ttttgtattt atcgggtctt ggagtgattt tctctggccc ttaattgtag tcgatcgccc  4200
agaatattat accatccctt taggcgtggc aaatctagcc ggaacttttt ctctcgattg  4260
gcggatagtc gccgccggtt ccgtcatttc tatcgctcct gtgttactac tattttttaat  4320
cgtacaacgg tatattgtgc ctacagatac agctacgggg gttaaaggtt gaatgaggat  4380
```

```
tattaatctc agtcctaata atcaaaatca tatccaccag gcggcgactt tattagtcgc  4440
agaatttcgg gaaaattggc cgaatgcttg gccgacttat gaacgtggtt tagccgaggt  4500
tatggagtct tttggcgacg atagagttaa tctagtcgcc gtcgatgaaa atgataatct  4560
tctaggctgg attggtggta ttagccaata tcaaggccat gtttgggaat tacatccttt  4620
ggtagtcaaa agcgattatc aagggttagg aatagggcga aaattggtcg ccaatttaga  4680
ggattatgtc cgctcacaag gagggttaac cttatggttg ggtaccgatg acgaaaataa  4740
tttaacctcc ctatctggtg tcgaattata cccccatttt ttggaaaata ttgctaacat  4800
aaaaaaccat ggtcgtcatc cctatgaatt ttatcagaaa tgcggttttg tgattatggg  4860
agtagtcccc gatgctaacg gtatcgggaa acctgatatt ttgatggcta aatctctgag  4920
aattgacaat catcctaaat ccaactgaat gttgtcagtt aagtttatag ggctgctatg  4980
gtatgataaa aaaatccccc cagcagttgg gggggaatga ttaattaggt attgaattgg  5040
ttaaattgga ggtgtgttgg ggctgacttt tgctgccttg ttgggggggg cgattttaac  5100
tgaggtcact ttttcttggc cgggattggc taatcgcttg tatgaggcta tccgtctgcg  5160
ggattatccc acggttcaag gggtggtggt atttttggcc gttattgtgg tggcggctag  5220
tttggcgatc gatattttga atgcttgtat tgacccacgg attcgctatt aattccctgt  5280
cagaaaatat acttagttat taatacttag ttatttttct taataaattt taacaaacca  5340
aagggcgttg gcagtgtata aaggatattt gaaggggtga gaaggaaggc gaatgttgat  5400
ttatgaagtt tgattaacat ttgtatcaaa atataaaatt cttctcataa accctgtaca  5460
atcttttaag atttcggaaa gtgttctagg atactgaaga aatgaaccac ggggcaattg  5520
ttaaaagcct ttgtcgatgg ttcgccccgg aaggggtctt aggaggtgac accgatggat  5580
tgattgtcgt gatcattcat ggtgtgtcca atcccaactc aactctaagc aagtcaacaa  5640
gtaggagata aatctatgaa aatcgaagaa ggtaaactgg taatctggat taacggcgat  5700
aaaggctata acggactcgc tgaagtcggt aagaaattcg agaaagatac cggaattaaa  5760
gtcaccgttg agcatccgga taaactggaa gagaaattcc cacaggttgc ggcaactggc  5820
gatggccctg acattatctt ctgggcacac gaccgctttg gtggctacgc tcaatctggc  5880
ctgttggctg aaatcacccc ggacaaagcg ttccaggaca agctgtatcc gtttacctgg  5940
gatgccgtac gttacaacgg caagctgatt gcttacccga tcgctgttga agcgttatcg  6000
ctgatttata acaaagatct gctgccgaac ccgccaaaaa cctgggaaga gatcccggcg  6060
ctggataaag aactgaaagc gaaaggtaag agcgcgctga tgttcaacct gcaagaaccg  6120
tacttcacct ggccgctgat tgctgctgac gggggttatg cgttcaagta tgaaaacggc  6180
aagtacgaca ttaaagacgt gggcgtggat aacgctggcg cgaaagcggg tctgaccttc  6240
ctggttgacc tgattaaaaa caaacacatg aatgcagaca ccgattactc catcgcagaa  6300
gctgccttta ataaaggcga aacagcgatg accatcaacg gcccgtgggc atggtccaac  6360
atcgacacca gcaaagtgaa ttatggtgta acggtactgc cgaccttcaa gggtcaacca  6420
tccaaaccgt tcgttggcgt gctgagcgca ggtattaacg ccgccagtcc gaacaaagag  6480
ctggcaaaag agttcctcga aaactatctg ctgactgatg aaggtctgga agcggttaat  6540
aaagacaaac cgctgggtgc cgtagcgctg aagtcttacg aggaagagtt ggcgaaagat  6600
ccacgtattg ccgccactat ggaaaacgcc cagaaaggtg aaatcatgcc gaacatcccg  6660
cagatgtccg ctttctggta tgccgtgcgt actgcggtga tcaacgccgc cagcggtcgt  6720
cagactgtcg atgaagccct gaaagacgcg cagacttccg gcggaggtgg aggctcaaaa  6780
ggcggtggag gtagcgctgg agtccctgaa gaacaaattc ggaatgattt aaaaaccctc  6840
actaagacga ttatcacgcg catcgatcag atcccggctg ttaaagaagt gagccccaag  6900
cagaaggtga ccgggctgga aattatcccc ggaacaaaag ataaatatac gtttacagac  6960
atgagtgcga cgctggcggt ctaccgtgag attttctcta tgctcgacga accagaggtt  7020
cagcaaattg cactcgatct cgataatttg atcgacctca tcaaagaact agcgaagaca  7080
aagggttgcc cactacccga ggcgaagggc gtagccgaca aggccaaaat tgaggagctg  7140
attaaggaaa gtggttactc cgtttatgtg acaacagcaa caaatttgaa ggctgtgctc  7200
gaaaagttca ttaaagagct agaaaaagat cccggttgct caagcggcgg tagtcaccat  7260
caccaccatc actaacagcc aaataaaacg aaaggctcag tcgaaagact gggcctttcg  7320
ttttatctgt tgtttgtcgg tgaacgctct cctgagtagg acaaatccgc cgggagcgga  7380
tttgaacgtt gcgaagcaac ggcccggagg gtggcgggca ggacgcccgc cataaactgc  7440
caggcatcaa attaagcaga aggccatcct gacggatggc ctttttgcgt ttctacaaac  7500
tccggatccg gccggcttga agacagatac cgttccgccg tcaagaatgc             7550
```

```
SEQ ID NO: 51          moltype = DNA  length = 7550
FEATURE                Location/Qualifiers
source                 1..7550
                       mol_type = other DNA
                       organism = synthetic construct
SEQUENCE: 51
ggaatcatga atcatcccac aactaagcat caaaaaatta catcctgtta ctggggaatt  60
tctgaactac ctgggttaga tacaggtaat attaaactcc tgaatcaatg tggtattgaa  120
aacacccagc aactgctcac gcgcgggagt aataatgcta ataaaatcgc cttatctaac  180
caactaggta tcaacatcag agatatcagt aaatgggtcg caatgtccga cttagccagg  240
gttcccagta ttggctatca atattgtggt gtccttttgc atagtggcgt aagttcagtt  300
aaccaactat ctcagatgtc tattcaacaa ctgcataaac agattttacg gctctatgta  360
ggaaccttgc aatctcgcca actctgtcca tctgttgatg tcatccaaac ctggattaaa  420
caagctaaaa ttttgcataa aattaattaa taattactag atgaaatcat gaatttttcc  480
gaagatttgc gacaaaatgc accagccacc gaaagaaacc gcgaacctat tttagaggtc  540
ttaaaaaggg tgttgcccgc cacgggaacc gttttagaag tagccagcgg cacaggacaa  600
cacgcggttt tttttgctcc ccgtctctcc cctaggcggt ggctaccttc cgacccgcaa  660
cctttgttac aacagagtat taaagcatgg caaattcatt caccttcaga taatctttac  720
cctcccctac agttaaatgt agaagctaat ccttggccag tggaagggaa tgatttaccc  780
tgggaattat cggaatttcc catcactgct attgtagcaa ttaacctgat tcatatttcg  840
ccttggtcgg cttgtgaagg gttaatggcg ggaagcgatc gcattttgaa accgggggga  900
attttatatc tctatggacc ctataaaata gctggaaaac acaccgcacc tagtaacgct  960
tcctttgatg aatatttgcg aacttctaac cctaagtggg gtgtcagaaa ccttgatgat  1020
tcacatacgc ggccgcctgg gccttgagct cgaatttcct gcattaatga atcggccaac  1080
gcgcggggag aggcggtttg cgtattgggc gctcttccgc ttcctcgctc actgactcgc  1140
```

```
tgcgctcggt cgttcggctg cggcgagcgg tatcagctca ctcaaaggcg gtaatacggt  1200
tatccacaga atcaggggat aacgcaggaa agaacatgtg agcaaaaggc cagcaaaagg  1260
ccaggaaccg taaaaatagc ggagtgtata ctggcttact atgttggcac tgatgagggt  1320
gtcagtgaag tgcttcatgt ggcaggagaa aaaaggctgc accggtgcgt cagcagaata  1380
tgtgatacag gatatattcc gcttcctcgc tcactgactc gctacgctcg gtcgttcgac  1440
tgcggcgagc ggaaatggct tacgaacggg gcggagattt cctggaagat gccaggaaga  1500
tacttaacag ggaagtgaga gggccgcggc aaagccgttt ttccataggc tccgcccccc  1560
tgacaagcat cacgaaatct gacgctcaaa tcagtggtgg cgaaacccga caggactata  1620
aagataccag gcgtttcccc ctggcggctc cctcgtgcgc tctcctgttc ctgcctttcg  1680
gtttaccggt gtcattccgc tgttatggcc gcgtttgtct cattccacgc ctgacactca  1740
gttccgggta ggcagttcgc tccaagctgg actgtatgca cgaacccccc attcagtccg  1800
accgctgcgc cttatccggt aactatcgtc ttgagtccaa cccggaaaga catgcaaaag  1860
caccactggc agcagccact ggtaattgat ttagaggagt tagtcttgaa gtcatgcgcc  1920
ggttaaggct aaactgaaag gacaagtttt ggtgactgcg ctcctccaag ccagttacct  1980
cggttcaaag agttggtagc tcagagaacc ttcgaaaaac cgccctgcaa ggcggttttt  2040
tcgttttcag agcaagagat tacgcgcaga ccaaaacgat ctcaagaaga tcatcttatt  2100
aagattatca aaaaggatct tcacctagat ccttttaaat taaaaatgaa gttttaaatc  2160
aatctaaagt atatatgagt aaacttggtc tgacagttac caatgcttaa tcagtgaggc  2220
acctatctca gcgatctgtc tatttcgttc atccatagtt gcctgactcc ccgtcgtgta  2280
gataactacg atacgggagg gcttaccatc tggccccagt gctgcaatga taccgcggga  2340
cccacgctca ccggctccag atttatcagc aataaaccag ccagccggaa gggccgagcg  2400
cagaagtggt cctgcaactt tatccgcctc catccagtct attaattgtt gccgggaagc  2460
tagagtaagt agttcgccag ttaatagttt gcgcaacgtt gttgccattg ctacaggcat  2520
cgtggtgtca cgctcgtcgt ttggtatggc ttcattcagc tccggttccc aacgatcaag  2580
gcgagttaca tgatccccca tgttgtgcaa aaaagcggtt agctccttcg gtcctccgat  2640
cgttgtcaga agtaagttgg ccgcagtgtt atcactcatg gttatggcag cactgcataa  2700
ttctcttact gtcatgccat ccgtaagatg cttttctgtg actggtgagt actcaaccaa  2760
gtcattctga gaatagtgta tgcggcgacc gagttgctct tgcccggcgt caatacggga  2820
taataccgcg ccacatagca gaactttaaa agtgctcatc attggaaaac gttcttcggg  2880
gcgaaaactc tcaaggatct taccgctgtt gagatccagt tcgatgtaac ccactcgtgc  2940
acccaactga tcttcagcat cttttacttt caccagcgtt tctgggtgag caaaaacagg  3000
aaggcaaaat gccgcaaaaa agggaataag ggcgacacgg aaatgttgaa tactcatact  3060
cttccttttt caatattatt gaagcattta tcagggttat tgtctcatga gcggatacat  3120
atttgaatgt atttagaaaa ataaacaaat aggggttccg cgcacatttc cccgaaaagt  3180
gccacctgac gtctaagaaa ccattattat catgacatta acctataaaa ataggcgtat  3240
cacgaggccc tttcgtctcg cgcgtttcgg tgatgacggt gaaaacctct gacacatgca  3300
gctcccggag acggtcacag cttgtctgta agcggatgcc aagcttgcat gcctgcaggt  3360
ggcgcgccta tggggggagga ttttatgatc ggatgttgag tcagtctgag tggtctaaaa  3420
ttcctacggt gggaattgtg tttgcggccg ccagggtgga tactctccct agggatagtt  3480
gggaccagcc tttggcggcg gtttgtacag aggagggtat atgggagttt ccaaaataac  3540
ttctggtggg ggggcaaatt atcgggcgat cgccacttat atggtattaa ttgctatagc  3600
gatcgctatg ctatttcccc tattttggtt ggtgggaact gcctttaaat cccctaccga  3660
aaacatcttt caggttcccc cccagtttat tccaagggaa cctactttca ctaattttgt  3720
cagagtttgg caaaccaatc cctttggtcg ctatttattt aatagtaccc tcgtcgccct  3780
tttaaccgtc ggattaaatc tgctattttg ttccttggcg gcctatcctt tggcgcgctt  3840
aaacttttgg ggtcgcgatt ttctcctaag tgcgatcgtt tccaccatca tgataccctt  3900
tcagattgtc atgattcccc tgtatattct agcagtacag ttaggattaa gaaatactta  3960
tttaggcatt atttttccat ctttagcctc cgcttttggc atctttctat tgcgacaggc  4020
atttatggga gttcccaaag agttagaaga agccgccaga attgatggct gttcagaatt  4080
agggatttgg tggcatatta tgatcccctc agtccgtccc gccttaatga ccttagccat  4140
ttttgtattt atcgggtctt ggagtgattt tctctggccc ttaattgtag tcgatcgccc  4200
agaatattat accatccctt taggcgtggc aaatctagcc ggaacttttt ctctcgattg  4260
gcggatagtc gccgccggtt ccgtcatttc tatcgctcct gtgttactac tatttttaat  4320
cgtacaacgg tatattgtgc ctacagatac agctacgggg gttaaaggtt gaatgaggat  4380
tattaatctc agtcctaata atcaaaatca tatccaccag gcggcgactt tattagtcgc  4440
agaatttcgg gaaaattggc cgaatgcttg gccgacttat gaacgtggtt tagccgaggt  4500
tatggagtct tttggcgacg atagagttaa tctagtcgcc gtcgatgaaa atgataatct  4560
tctaggctgg attggtggta ttagccaata tcaaggccat gtttgggaat tacatccttt  4620
ggtagtcaaa agcgattatc aagggttagg aatagggcga aaattggtcg ccaatttaga  4680
ggattatgtc cgctcacaag gagggttaac cttatggttg ggtaccgatg acgaaaataa  4740
tttaacctcc ctatctggtg tcgaattata cccccatttt ttggaaaata ttgctaacat  4800
aaaaaaccat ggtcgtcatc cctatgaatt ttatcagaaa tgcggttttg tgattatggg  4860
agtagtcccc gatgctaacg gtatcgggaa acctgatatt ttgatggcta aatctctgag  4920
aattgacaat catcctaaat ccaactgaat gttgtcagtt aagtttatag ggctgctatg  4980
gtatgataaa aaaatccccc cagcagttgg gggggaatga ttaattaggt attgaattgg  5040
ttaaattgga ggtgtgttgg ggctgacttt tgctgccttg ttgggggggg cgattttaac  5100
tgaggtcact ttttcttggc cgggattggc taatcgcttg tatgaggcta tccgtctgcg  5160
ggattatccc acggttcaag ggtggtggt attttggcc gttattgtgg tggcggctag  5220
tttggcgatc gatattttga atgcttgtat tgacccacgg attcgctatt aattccctgt  5280
cagaaaatat acttagttat taatacttag ttatttttct taataaattt taacaaacca  5340
aagggcgttg gcagtgtata aaggatattt gaaggggtga gaaggaaggc gaatgttgat  5400
ttatgaagtt tgattaacat ttgtatcaaa atataaaatt cttctcataa accctgtaca  5460
atcttttaag atttcggaaa gtgttctagg atactgaaga aatgaaccac ggggcaattg  5520
ttaaaagcct ttgtcgatgg ttcgccccgg aaggggtctt aggaggtgac accgatggat  5580
tgattgtcgt gatcattcat ggtgtgtcca atcccaactc aactctaagc aagtcaacaa  5640
gtaggagata aatctatgaa aatcgaagaa ggtaaactgg taatctggat taacggcgat  5700
aaaggctata acggactcgc tgaagtcggt aagaaattcg agaaagatac cggaattaaa  5760
gtcaccgttg agcatccgga taaactggaa gagaaattcc cacaggttgc ggcaactggc  5820
gatggccctg acattatctt ctgggcacac gaccgctttg gtggctacgc tcaatctggc  5880
```

```
ctgttggctg aaatcacccc ggacaaagcg ttccaggaca agctgtatcc gtttacctgg  5940
gatgccgtac gttacaacgg caagctgatt gcttacccga tcgctgttga agcgttatcg  6000
ctgatttata acaaagatct gctgccgaac ccgccaaaaa cctgggaaga gatcccggcg  6060
ctggataaag aactgaaagc gaaaggtaag agcgcgctga tgttcaacct gcaagaaccg  6120
tacttcacct ggccgctgat tgctgctgac ggggttatg cgttcaagta tgaaaacggc  6180
aagtacgaca ttaaagacgt gggcgtggat aacgctggcg cgaaagcggg tctgaccttc  6240
ctggttgacc tgattaaaaa caaacacatg aatgcagaca ccgattactc catcgcagaa  6300
gctgccttta ataaaggcga aacagcgatg accatcaacg gcccgtgggc atggtccaac  6360
atcgacacca gcaaagtgaa ttatggtgta acggtactgc cgaccttcaa gggtcaacca  6420
tccaaaccgt tcgttggcgt gctgagcgca ggtattaacg ccgccagtcc gaacaaagag  6480
ctggcaaaag agttcctcga aaactatctg ctgactgatg aaggtctgga agcggttaat  6540
aaagacaaac cgctgggtgc cgtagcgctg aagtcttacg aggaagagtt ggcgaaagat  6600
ccacgtattg ccgccactat ggaaaacgcc cagaaaggtg aaatcatgcc gaacatcccg  6660
cagatgtccg ctttctggta tgccgtgcgt actgcggtga tcaacgccgc cagcggtcgt  6720
cagactgtcg atgaagccct gaaagacgcg cagacttccg gcggaggtgg aggctcaaaa  6780
ggcggtggag gtagcgctgg agtccccgta gagcaaatcc gaaaggatct cgagacactg  6840
atccggaccg tcatcacacg tattgataca atcccctacg ttaaggaggt aagcccaaag  6900
caaaaagtca ccggcctgga atttattcct ggtacaaaag agaaaatcac atataccgat  6960
gctgacgaaa ccttggcaat ttatcaagag attctaagtc tattgccgga accggagtta  7020
caacaaattg cactggactt ggataatatc cgggacctca ttcgcgagct ggcggccacc  7080
aagaattgcc ctctacctcg tgccagtggt ttacccgacc gagagaagct gctcgaggct  7140
atcaaggaga gtggatacag tgtagctgtc accacagcga ctaagttaaa ggagttcttg  7200
gaaaagctaa ttgaggagtt gaagaaggac cccggatgtt caagcggcgg tagtcaccat  7260
caccaccatc actaacagcc aaataaaacg aaaggctcag tcgaaagact gggcctttcg  7320
ttttatctgt tgtttgtcgg tgaacgctct cctgagtagg acaaatccgc cgggagcgga  7380
tttgaacgtt gcgaagcaac ggcccggagg gtggcgggca ggacgcccgc cataaactgc  7440
caggcatcaa attaagcaga aggccatcct gacggatggc ctttttgcgt ttctacaaac  7500
tccggatccg gccggcttga agacaggagt atttatcgga ctctcaatgc             7550

SEQ ID NO: 52          moltype = AA  length = 146
FEATURE                Location/Qualifiers
source                 1..146
                       mol_type = protein
                       organism = synthetic construct
SEQUENCE: 52
VPIQKVQDDT KTLIKTIITR INDISHTQSV SSKVKVTGLD FIPGRHPILT LSKMDQTLAV  60
YQQILESMPD PNVIQIANDL ENLRDLLHVL AFSKSCPLPW ASGLETLDSL RKVLEASLYS  120
TEVVALSRLQ GVLQDMLKQL DLSPGC                                      146

SEQ ID NO: 53          moltype = AA  length = 146
FEATURE                Location/Qualifiers
source                 1..146
                       mol_type = protein
                       organism = synthetic construct
SEQUENCE: 53
VPIQKVFDDT KTLIKTIITR INTIEHTQSV SSKIKVTGLD FIPGLQPILT LSKMDQTLAV  60
YQQILLSMPV PLVIQIAADL ENLRLLLHLL AKSKNCPLPW ASGLEDEDML RRVLEASLYS  120
TEVVTLLRLQ GVLLQMLEQL DLSPGC                                      146

SEQ ID NO: 54          moltype = AA  length = 146
FEATURE                Location/Qualifiers
source                 1..146
                       mol_type = protein
                       organism = synthetic construct
SEQUENCE: 54
VPLEKIREDT KTLIRTIITR IDQIPYVADV SPKQKVTGLD FIPGTKDKYT YSDFAATLAK  60
YREILSATDD PELQQIALDL DNLIDLIREL AKSKGCPLPE ATGLPDPEKL KEALKESGYS  120
VEVETARKLK AFLEKALEEL EKDPGC                                      146

SEQ ID NO: 55          moltype = AA  length = 146
FEATURE                Location/Qualifiers
source                 1..146
                       mol_type = protein
                       organism = synthetic construct
SEQUENCE: 55
VPEEQIRNDL KTLTKTIITR IDQIPAVKEV SPKQKVTGLE IIPGTKDKYT FTDMSATLAV  60
YREIFSMLDE PEVQQIALDL DNLIDLIKEL AKTKGCPLPE AKGVADKAKI EELIKESGYS  120
VYVTTATNLK AVLEKFIKEL EKDPGC                                      146

SEQ ID NO: 56          moltype = AA  length = 146
FEATURE                Location/Qualifiers
source                 1..146
                       mol_type = protein
                       organism = synthetic construct
SEQUENCE: 56
VPVEQIRKDL ETLIRTVITR IDTIPYVKEV SPKQKVTGLE FIPGTKEKIT YTDADETLAI  60
YQEILSLLPE PELQQIALDL DNIRDLIREL AATKNCPLPR ASGLPDREKL LEAIKESGYS  120
VAVTTATKLK EFLEKLIEEL KKDPGC                                      146
```

```
SEQ ID NO: 57          moltype = AA  length = 146
FEATURE                Location/Qualifiers
source                 1..146
                       mol_type = protein
                       organism = synthetic construct
SEQUENCE: 57
VPIQKVIDDT KTLIKTILTR INDISYTQSV SAKQRVTGLD FIPGLHPILS LSKMLQTLAF  60
YQQVLLSLPS QLVLQIANDL ENLRDLLILL AQSKNCQLPD TSNLKKPESL DDILRNSLYS  120
IEVVALSRLQ IVLQDILQQL DHDPDC                                       146

SEQ ID NO: 58          moltype = AA  length = 146
FEATURE                Location/Qualifiers
source                 1..146
                       mol_type = protein
                       organism = synthetic construct
SEQUENCE: 58
VPIQKVFDDT KTLIKTILTR INDISYTQSV SAKQRVTGLD FIPGLHPILS LSKMLQTLAF  60
YQQVLLSLPS QLVLQIANDL ENLRDLLHLL AFSKNCSLPD TSNLQKPESL DEVLRNSLYS  120
IEVVALSRLQ ISLQDILQQL DVDPEC                                       146

SEQ ID NO: 59          moltype = AA  length = 146
FEATURE                Location/Qualifiers
source                 1..146
                       mol_type = protein
                       organism = synthetic construct
SEQUENCE: 59
VPIQKVQDDT KTLIKVILTR INTLQYTQEV SSKLIVFGLD FIPGLEPILS LSKMLQTLAV  60
YQQVLLSLPS EDVLQIAADL ENLRLLLHLL AQSKNCQLPD TSNLKKPESL DEILRNSLYS  120
IEVVALSRLQ GSLLIILQQL DHDPDC                                       146

SEQ ID NO: 60          moltype = AA  length = 146
FEATURE                Location/Qualifiers
source                 1..146
                       mol_type = protein
                       organism = synthetic construct
SEQUENCE: 60
MPIEEVRKNT KTLIKTIITK IDTIPYVQDV SPEITVTGLD FIPGDKPITS LSEAVLTLTR  60
YRQVLLSLPD PETQQIALDL DNLIELFREL AASKGCTLPD PSNLATPPEL AEVLKDSEFA  120
VYVTALTKLK KNLENILKEL EKDLAC                                       146

SEQ ID NO: 61          moltype = AA  length = 146
FEATURE                Location/Qualifiers
source                 1..146
                       mol_type = protein
                       organism = synthetic construct
SEQUENCE: 61
RPLEQVRRDL KTLIKTIITK IDTIPYVQDV NPDITVTGLD FIPGNRPITS LSEAKKTLTK  60
YVQVLESLDD PETQEIALDL KNVIELIDEL AKSRGCTLPD TSTLEKDPRL EEVKKDSEFA  120
ITTTALRNLK INLEIILKEL ERDPAC                                       146

SEQ ID NO: 62          moltype = AA  length = 146
FEATURE                Location/Qualifiers
source                 1..146
                       mol_type = protein
                       organism = synthetic construct
SEQUENCE: 62
VPIEKVREDL KTLIKTIIKK IDTIPEVQDV SPEITVTGLD FIPGNEPINS LSEAVLTLTR  60
YRQVLESLDD PETQQIALDL QNLIELLKEL AKEKGCTLPD PSNLKKPEEL EKVLEDAEFA  120
VRVTALTNLK KNLENILKVL ETDPAC                                       146

SEQ ID NO: 63          moltype = AA  length = 146
FEATURE                Location/Qualifiers
source                 1..146
                       mol_type = protein
                       organism = synthetic construct
SEQUENCE: 63
VPIQKVQDDT KTLIKTIVTR INDISHTQSV SSKQKVTGLD FIPGLHPILT LSKMDQTLAV  60
YQQILTSMPS RNMIQISNDL ENLRDLLHVL AFSKSCHLPW ASGLETLDSL GGVLEASGYS  120
TEVVALSRLQ GSLQDMLWQL DLSPGC                                       146

SEQ ID NO: 64          moltype = AA  length = 147
FEATURE                Location/Qualifiers
source                 1..147
                       mol_type = protein
                       organism = synthetic construct
SEQUENCE: 64
GVPIQKVXDD TKTLIKTIIT RINXIXYTQX VSXKXKVTGL DFIPGXXPIL TLSKMXQTLA  60
XYQQILXSLP XPXVXQIAXD LENLRDLLXX LAXSKXCXLP XASGLXXXXX LXEVLXXSXY  120
SXEVVALXRL QXXLXXXLXQ LDXDPGC                                      147
```

```
SEQ ID NO: 65          moltype = AA  length = 367
FEATURE                Location/Qualifiers
source                 1..367
                       mol_type = protein
                       organism = synthetic construct
SEQUENCE: 65
MKIEEGKLVI WINGDKGYNG LAEVGKKFEK DTGIKVTVEH PDKLEEKFPQ VAATGDGPDI  60
IFWAHDRFGG YAQSGLLAEI TPDKAFQDKL YPFTWDAVRY NGKLIAYPIA VEALSLIYNK  120
DLLPNPPKTW EEIPALDKEL KAKGKSALMF NLQEPYFTWP LIAADGGYAF KYENGKYDIK  180
DVGVDNAGAK AGLTFLVDLI KNKHMNADTD YSIAEAAFNK GETAMTINGP WAWSNIDTSK  240
VNYGVTVLPT FKGQPSKPFV GVLSAGINAA SPNKELAKEF LENYLLTDEG LEAVNKDKPL  300
GAVALKSYEE ELAKDPRIAA TMENAQKGEI MPNIPQMSAF WYAVRTAVIN AASGRQTVDE  360
ALKDAQT                                                            367

SEQ ID NO: 66          moltype = AA  length = 14
FEATURE                Location/Qualifiers
source                 1..14
                       mol_type = protein
                       organism = synthetic construct
SEQUENCE: 66
SGGGGGSKGG GGSA                                                    14

SEQ ID NO: 67          moltype = AA  length = 150
FEATURE                Location/Qualifiers
source                 1..150
                       mol_type = protein
                       organism = synthetic construct
SEQUENCE: 67
GGVPIQKVQD DTKTLIKTIV TRINDISHTQ SVSSKQKVTG LDFIPGLHPI LTLSKMDQTL  60
AVYQQILTSM PSRNMIQISN DLENLRDLLH VLAFSKSCHL PWASGLETLD SLGGVLEASG  120
YSTEVVALSR LQGSLQDMLW QLDLSPGCSS                                   150

SEQ ID NO: 68          moltype =   length =
SEQUENCE: 68
000

SEQ ID NO: 69          moltype = AA  length = 147
FEATURE                Location/Qualifiers
source                 1..147
                       mol_type = protein
                       organism = synthetic construct
SEQUENCE: 69
GVPIQKVXDD TKTLIKTIIT RINXIXYTQX VSXKXKVTGL DFIPGXXPIL TLSKMXQTLA  60
XYQQILXSLP XPXVXQIAXD LENLRDLLXX LAXSKXCXLP XASGLXXXXX LXEVLXXSXY  120
SXEVVALXRL QXXLXXXLXQ LDXDPGC                                      147

SEQ ID NO: 70          moltype = AA  length = 147
FEATURE                Location/Qualifiers
source                 1..147
                       mol_type = protein
                       organism = synthetic construct
SEQUENCE: 70
GVPIQKVQDD TKTLIKTIIT RINDISHTQS VSSKVKVTGL DFIPGRHPIL TLSKMDQTLA  60
VYQQILESMP DPNVIQIAND LENLRDLLHV LAFSKSCPLP WASGLETLDS LRKVLEASLY  120
STEVVALSRL QGVLQDMLKQ LDLSPGC                                      147

SEQ ID NO: 71          moltype = AA  length = 147
FEATURE                Location/Qualifiers
source                 1..147
                       mol_type = protein
                       organism = synthetic construct
SEQUENCE: 71
GVPIQKVFDD TKTLIKTIIT RINTIEHTQS VSSKIKVTGL DFIPGLQPIL TLSKMDQTLA  60
VYQQILLSMP VPLVIQIAAD LENLRLLLHL LAKSKNCPLP WASGLEDEDM LRRVLEASLY  120
STEVVTLLRL QGVLLQMLEQ LDLSPGC                                      147

SEQ ID NO: 72          moltype = AA  length = 147
FEATURE                Location/Qualifiers
source                 1..147
                       mol_type = protein
                       organism = synthetic construct
SEQUENCE: 72
GVPLEKIRED TKTLIRTIIT RIDQIPYVAD VSPKQKVTGL DFIPGTKDKY TYSDFAATLA  60
KYREILSATD DPELQQIALD LDNLIDLIRE LAKSKGCPLP EATGLPDPEK LKEALKESGY  120
SVEVETARKL KAFLEKALEE LEKDPGC                                      147

SEQ ID NO: 73          moltype = AA  length = 147
FEATURE                Location/Qualifiers
```

```
source                  1..147
                        mol_type = protein
                        organism = synthetic construct
SEQUENCE: 73
GVPEEQIRND LKTLTKTIIT RIDQIPAVKE VSPKQKVTGL EIIPGTKDKY TFTDMSATLA  60
VYREIFSMLD EPEVQQIALD LDNLIDLIKE LAKTKGCPLP EAKGVADKAK IEELIKESGY  120
SVYVTTATNL KAVLEKFIKE LEKDPGC                                      147

SEQ ID NO: 74           moltype = AA  length = 147
FEATURE                 Location/Qualifiers
source                  1..147
                        mol_type = protein
                        organism = synthetic construct
SEQUENCE: 74
GVPVEQIRKD LETLIRTVIT RIDTIPYVKE VSPKQKVTGL EFIPGTKEKI TYTDADETLA  60
IYQEILSLLP EPELQQIALD LDNIRDLIRE LAATKNCPLP RASGLPDREK LLEAIKESGY  120
SVAVTTATKL KEFLEKLIEE LKKDPGC                                      147

SEQ ID NO: 75           moltype = AA  length = 147
FEATURE                 Location/Qualifiers
source                  1..147
                        mol_type = protein
                        organism = synthetic construct
SEQUENCE: 75
GVPIQKVIDD TKTLIKTILT RINDISYTQS VSAKQRVTGL DFIPGLHPIL SLSKMLQTLA  60
FYQQVLLSLP SQLVLQIAND LENLRDLLIL LAQSKNCQLP DTSNLKKPES LDDILRNSLY  120
SIEVVALSRL QIVLQDILQQ LDHDPDC                                      147

SEQ ID NO: 76           moltype = AA  length = 147
FEATURE                 Location/Qualifiers
source                  1..147
                        mol_type = protein
                        organism = synthetic construct
SEQUENCE: 76
GVPIQKVFDD TKTLIKTILT RINDISYTQS VSAKQRVTGL DFIPGLHPIL SLSKMLQTLA  60
FYQQVLLSLP SQLVLQIAND LENLRDLLHL LAFSKNCSLP DTSNLQKPES LDEVLRNSLY  120
SIEVVALSRL QISLQDILQQ LDVDPEC                                      147

SEQ ID NO: 77           moltype = AA  length = 147
FEATURE                 Location/Qualifiers
source                  1..147
                        mol_type = protein
                        organism = synthetic construct
SEQUENCE: 77
GVPIQKVQDD TKTLIKVILT RINTLQYTQE VSSKLIVFGL DFIPGLEPIL SLSKMLQTLA  60
VYQQVLLSLP SEDVLQIAAD LENLRLLLHL LAQSKNCQLP DTSNLKKPES LDEILRNSLY  120
SIEVVALSRL QGSLLIILQQ LDHDPDC                                      147

SEQ ID NO: 78           moltype = AA  length = 147
FEATURE                 Location/Qualifiers
source                  1..147
                        mol_type = protein
                        organism = synthetic construct
SEQUENCE: 78
GMPIEEVRKN TKTLIKTIIT KIDTIPYVQD VSPEITVTGL DFIPGDKPIT SLSEAVLTLT  60
RYRQVLLSLP DPETQQIALD LDNLIELFRE LAASKGCTLP DPSNLATPPE LAEVLKDSEF  120
AVYVTALTKL KKNLENILKE LEKDLAC                                      147

SEQ ID NO: 79           moltype = AA  length = 147
FEATURE                 Location/Qualifiers
source                  1..147
                        mol_type = protein
                        organism = synthetic construct
SEQUENCE: 79
GRPLEQVRRD LKTLIKTIIT KIDTIPYVQD VNPDITVTGL DFIPGNRPIT SLSEAKKTLT  60
KYVQVLESLD DPETQEIALD LKNVIELIDE LAKSRGCTLP DTSTLEKDPR LEEVKKDSEF  120
AITTTALRNL KINLEIILKE LERDPAC                                      147

SEQ ID NO: 80           moltype = AA  length = 147
FEATURE                 Location/Qualifiers
source                  1..147
                        mol_type = protein
                        organism = synthetic construct
SEQUENCE: 80
GVPIEKVRED LKTLIKTIIK KIDTIPEVQD VSPEITVTGL DFIPGNEPIN SLSEAVLTLT  60
RYRQVLESLD DPETQQIALD LQNLIELLKE LAKEKGCTLP DPSNLKKPEE LEKVLEDAEF  120
AVRVTALTNL KKNLENILKV LETDPAC                                      147

SEQ ID NO: 81           moltype = AA  length = 147
```

```
FEATURE                Location/Qualifiers
source                 1..147
                       mol_type = protein
                       organism = synthetic construct
SEQUENCE: 81
GVPIQKVQDD TKTLIKTIVT RINDISHTQS VSSKQKVTGL DFIPGLHPIL TLSKMDQTLA  60
VYQQILTSMP SRNMIQISND LENLRDLLHV LAFSKSCHLP WASGLETLDS LGGVLEASGY  120
STEVVALSRL QGSLQDMLWQ LDLSPGC                                     147

SEQ ID NO: 82          moltype = AA  length = 146
FEATURE                Location/Qualifiers
source                 1..146
                       mol_type = protein
                       organism = synthetic construct
SEQUENCE: 82
VPVEQIRKEL ETLIRKVITK IDTIPYVKEV SPDLKIEGLE FIPGTKEKIT YTDADETLAI  60
YQEILSLLPE PELQEIALDL DNIRDLIREL AATKNCPLPR ASGLPDREKL LEAIKERGEE  120
VAVTTATKLK EFLEKLIEEL KKDPGC                                      146

SEQ ID NO: 83          moltype = AA  length = 146
FEATURE                Location/Qualifiers
source                 1..146
                       mol_type = protein
                       organism = synthetic construct
SEQUENCE: 83
VPVEQIRKEL ETLIRNVITR IDTIPYVKEV SPEKVIEGLE FIPGTKEKIT YTDADETLAI  60
YQEILSLLPE PELQKIALDL DNIRDLIREL AATKNCPLPR ASGLPDREKL LEAIKERGKD  120
VAVTTATKLK EFLEKLIEEL KKDPGC                                      146

SEQ ID NO: 84          moltype = AA  length = 146
FEATURE                Location/Qualifiers
source                 1..146
                       mol_type = protein
                       organism = synthetic construct
SEQUENCE: 84
VPVEQIRKEL ETLIRNVITR IDTIPYVKEV SPDIVYEGLE FIPGTKEKIT YTDADETLAI  60
YQEILSLLPE PELQQIALDL DNIRDLIREL AATKNCPLPR ASGLPDREKL LEAIKEQGEK  120
VAVTTATKLK EFLEKLIEEL KKDPGC                                      146

SEQ ID NO: 85          moltype = AA  length = 146
FEATURE                Location/Qualifiers
source                 1..146
                       mol_type = protein
                       organism = synthetic construct
SEQUENCE: 85
VPVEQIRKEL ETQIRNVITR IDTIPYVKEV SPNLKIEGLE FIPGTKEKIT YTDADETLAI  60
YQEILSLLPE PELQTIALDL DNIRDLIREL AATKNCPLPR ASGLPDREKL LEAIKERGDD  120
VAVTTATKLK EFLEKLIEEL KKDPGC                                      146

SEQ ID NO: 86          moltype = AA  length = 146
FEATURE                Location/Qualifiers
source                 1..146
                       mol_type = protein
                       organism = synthetic construct
SEQUENCE: 86
VPVEQIRKEL ETLIRKVITQ IDTIPYVKEV SPDLKIEGLE FIPGTKEKIT YTDADETLAI  60
YQEILSLLPE PELQQIALDL DNIRDLIREL AATKNCPLPR ASGLPDREKL LEAIKERGEE  120
VAVTTATKLK EFLEKLIEEL KKDPGC                                      146

SEQ ID NO: 87          moltype = AA  length = 147
FEATURE                Location/Qualifiers
source                 1..147
                       mol_type = protein
                       organism = synthetic construct
SEQUENCE: 87
GVPIQKVQDD TKTLIKTIVT RINDISHTQS VSSKQKVTGL DFIPGLHPIL TLSKMDQTLA  60
VYQQILTSMP SRNMIQISND LENLRDLLHV LAFSKSCHLP WASGLETLDS LGGVLEASGY  120
STEVVALSRL QGSLQDMLWQ LDLSPGC                                     147

SEQ ID NO: 88          moltype = AA  length = 11
FEATURE                Location/Qualifiers
source                 1..11
                       mol_type = protein
                       organism = synthetic construct
SEQUENCE: 88
GGGGSKGGGG S                                                      11

SEQ ID NO: 89          moltype = AA  length = 6
FEATURE                Location/Qualifiers
```

-continued

```
source                  1..6
                        mol_type = protein
                        organism = synthetic construct
SEQUENCE: 89
HHHHHH                                                              6

SEQ ID NO: 90           moltype = AA  length = 5
FEATURE                 Location/Qualifiers
source                  1..5
                        mol_type = protein
                        organism = synthetic construct
SEQUENCE: 90
GGGGS                                                               5

SEQ ID NO: 91           moltype = AA  length = 8
FEATURE                 Location/Qualifiers
source                  1..8
                        mol_type = protein
                        organism = synthetic construct
SEQUENCE: 91
WSHPQFEK                                                            8
```

What is claimed is:

1. A recombinant leptin receptor agonist comprising an amino acid sequence having at least about 80% sequence identity with SEQ ID NO: 56.

2. The recombinant leptin receptor agonist of claim 1, wherein the recombinant leptin receptor agonist having at least about 80% sequence identity with SEQ ID NO: 56 comprises an activity improving amino acid selected from the group consisting of 4E, 5Q, 6I, 10L, 17V, 18I, 22D, 25P, 27V, 32P, 40E, 49I, 51Y, 53D, 54A, 66S, 67L, 70E, 71P, 74Q, 77A, 78L, 83I, 88R, 97P, 106D, 116E, 121V, 124T, 125T, 130K, 132F, 139E, and combinations thereof, wherein the positions are determined by alignment with SEQ ID NO: 56.

3. The recombinant leptin receptor agonist of claim 2, wherein the recombinant leptin receptor agonist comprises at least 5 of the recited activity improving amino acids.

4. The recombinant leptin receptor agonist of claim 2, wherein the recombinant leptin receptor agonist comprises at least 10 of the recited activity improving amino acids.

5. The recombinant leptin receptor agonist of claim 2, wherein the recombinant leptin receptor agonist comprises at least 15 of the recited activity improving amino acids.

6. The recombinant leptin receptor agonist of claim 2, wherein the recombinant leptin receptor agonist comprises all of the recited activity improving amino acids.

7. The recombinant leptin receptor agonist of claim 1, wherein the recombinant leptin receptor agonist does not comprise an activity-reducing amino acid substitution selected from the group consisting of D9E, L13Q, T16N, T16K, R20N, R20K, K33D, K33E, K33N, Q34L, Q34K, Q34I, K35V, V36I, T37E, Q75E, Q75T, S117R, S117Q, Y119E, Y119K, Y119D, S120E, S120K, and S120D.

8. The recombinant leptin receptor agonist of claim 1, wherein the recombinant leptin receptor agonist does not comprise any activity-reducing amino acid substitutions selected from the group consisting of D9E, L13Q, T16N, T16K, R20N, R20K, K33D, K33E, K33N, Q34L, Q34K, Q34I, K35V, V36I, T37E, Q75E, Q75T, S117R, S117Q, Y119E, Y119K, Y119D, S120E, S120K, and S120D.

9. The recombinant leptin receptor agonist of claim 1, wherein the recombinant leptin receptor agonist having at least about 80% sequence identity with SEQ ID NO: 56 comprises an amino acid selected from the group consisting of D9, L13, T16, R20, K33, Q34, K35, V36, T37, Q75, D85, L86, S117, Y119, and $120.

10. The recombinant leptin receptor agonist of claim 1, wherein the recombinant leptin receptor agonist having at least about 80% sequence identity with SEQ ID NO: 56 comprises at least 2, 3, 4, 5, 6, 7, 8, 9, 10, 11, 12, 13, 14, or 15 of the amino acids selected from the group consisting of D9, L13, T16, R20, K33, Q34, K35, V36, T37, Q75, D85, L86, S117, Y119, S120, and combination thereof.

11. The recombinant leptin receptor agonist of claim 1, wherein the recombinant leptin receptor agonist having at least about 80% sequence identity with SEQ ID NO: 56 comprises D9, L13, T16, R20, K33, Q34, K35, V36, T37, Q75, D85, L86, S117, Y119, and S120.

12. The recombinant leptin receptor agonist of claim 1, wherein the recombinant leptin receptor agonist is comprised within a chimeric protein, said chimeric protein comprising a protein fusion partner.

13. The recombinant leptin receptor agonist of claim 12, wherein the protein fusion partner is N-terminally translationally fused to the recombinant leptin receptor agonist.

14. The recombinant leptin receptor agonist of claim 12, wherein the protein fusion partner is C-terminally translationally fused to the recombinant leptin receptor agonist.

15. The recombinant leptin receptor agonist of claim 12, wherein the protein fusion partner is a protein purification tag or solubility enhancer.

16. The recombinant leptin receptor agonist of claim 15, wherein the protein purification tag or solubility enhancer is selected from the group consisting of a maltose binding protein (MBP), thioredoxin (TRX), a histidine tag, a green fluorescent protein (GFP), a glutathione S-transferase (GST), a FLAG tag, a tag comprising the amino acid peptide sequence of SEQ ID NO: 91 (WSHPQFEK), and a HA tag.

17. The recombinant leptin receptor agonist of claim 15, wherein the solubility enhancer is MBP.

18. The recombinant leptin receptor agonist of claim 1, wherein the recombinant leptin receptor agonist having at least about 80% sequence identity with SEQ ID NO: 56 induces higher weight loss when administered to an overweight animal compared to SEQ ID NO: 63.

19. The recombinant leptin receptor agonist of claim 18, wherein at least 80% of the weight loss is body fat mass.

20. The recombinant leptin receptor agonist of claim 18, wherein less than 20% of the weight loss is lean mass.

21. The recombinant leptin receptor agonist of claim 1, wherein the recombinant leptin receptor agonist having at least about 80% sequence identity with SEQ ID NO: 56 results in a lower food intake by an overweight animal receiving the recombinant leptin receptor agonist compared to SEQ ID NO: 63.

22. The recombinant leptin receptor agonist of claim 1, wherein the recombinant leptin receptor agonist having at least about 80% sequence identity with SEQ ID NO: 56 exhibits higher thermostability compared to SEQ ID NO: 63.

23. The recombinant leptin receptor agonist of claim 18, wherein the animal is a mouse.

24. The recombinant leptin receptor agonist of claim 1, wherein the recombinant leptin receptor agonist is comprised within a biological cell.

25. The recombinant leptin receptor agonist of claim 24, wherein the biological cell is an *Escherichia coli* cell.

26. The recombinant leptin receptor agonist of claim 24, wherein the biological cell is *Spirulina*.

27. The recombinant leptin receptor agonist of claim 1, wherein the recombinant leptin receptor agonist is comprised within a composition comprising a protease inhibitor and/or proteinase inhibitor.

28. A method comprising orally administering a therapeutically effective dose of the recombinant leptin receptor agonist of claim 1 to an individual in need thereof.

29. A recombinant leptin receptor agonist comprising an amino acid sequence having at least 95% sequence identity with a sequence selected from the group consisting of SEQ ID NO: 52, 53, 54, 55, 56, 57, 58, 59, 60, 61, 62, and 64.

* * * * *